US010002337B2

(12) United States Patent
Siddique et al.

(10) Patent No.: US 10,002,337 B2
(45) Date of Patent: Jun. 19, 2018

(54) METHOD FOR COLLABORATIVE SHOPPING

(75) Inventors: M. A. Sami Siddique, Mississauga (CA); Abida Raouf, Mississauga (CA); Abdul Aziz Raouf, Mississauga (CA); Jesse Smith, Madoc (CA)

(73) Assignee: DRESSBOT, INC., Toronto (CA)

( * ) Notice: Subject to any disclaimer, the term of this patent is extended or adjusted under 35 U.S.C. 154(b) by 685 days.

(21) Appl. No.: 13/612,593

(22) Filed: Sep. 12, 2012

(65) Prior Publication Data

US 2013/0066750 A1 Mar. 14, 2013

Related U.S. Application Data

(63) Continuation of application No. 12/409,074, filed on Mar. 23, 2009.

(60) Provisional application No. 61/064,716, filed on Mar. 21, 2008.

(51) Int. Cl.

| | |
|---|---|
| ***G06Q 30/00*** | (2012.01) |
| ***G06Q 10/06*** | (2012.01) |
| ***G06Q 20/12*** | (2012.01) |
| ***G06Q 20/20*** | (2012.01) |
| ***G06Q 20/40*** | (2012.01) |
| ***G06Q 30/02*** | (2012.01) |
| ***G06Q 30/06*** | (2012.01) |
| ***G06Q 50/24*** | (2012.01) |
| ***G06T 15/02*** | (2011.01) |
| ***G06T 17/00*** | (2006.01) |
| ***G06Q 40/00*** | (2012.01) |

(52) U.S. Cl.

CPC ......... *G06Q 10/0637* (2013.01); *G06Q 20/12* (2013.01); *G06Q 20/204* (2013.01); *G06Q 20/40* (2013.01); *G06Q 30/02* (2013.01); *G06Q 30/06* (2013.01); *G06Q 30/0601* (2013.01); *G06Q 40/12* (2013.12); *G06Q 50/24* (2013.01); *G06T 15/02* (2013.01); *G06T 17/00* (2013.01)

(58) Field of Classification Search

CPC .................................. G06Q 30/0601–30/0645
USPC ............................................... 705/26.1–27.2
See application file for complete search history.

(56) References Cited

U.S. PATENT DOCUMENTS

| | | | | |
|---|---|---|---|---|
| 6,901,379 | B1 * | 5/2005 | Balter | G06Q 30/0643 434/395 |
| 2002/0133247 | A1 | 9/2002 | Smith et al. | |
| 2002/0152163 | A1 | 10/2002 | Bezos et al. | |
| 2002/0194108 | A1 * | 12/2002 | Kitze | G06Q 30/0283 705/37 |
| 2003/0172092 | A1 | 9/2003 | Berger | |
| 2005/0043996 | A1 | 2/2005 | Silver | |
| 2005/0261970 | A1 | 11/2005 | Vucina et al. | |

(Continued)

OTHER PUBLICATIONS

Kujubu, L., & Nelson, M. (1999). The return of the shopping mall. InfoWorld, 21(5), 1(1). Retrieved from https://dialog.proquest.com/professional/docview/666570382?accountid=142257.*

*Primary Examiner* — Resha Desai

(74) *Attorney, Agent, or Firm* — Roberts Mlotkowski Safran Cole & Calderon P.C.; Jorie L. Stroup

(57) ABSTRACT

The methods and systems described herein relate to online methods of collaboration in community environments. The methods and systems are related to an online apparel modeling system that allows users to have three-dimensional models of their physical profile created. Users may purchase various goods and/or services and collaborate with other users in the online environment.

18 Claims, 128 Drawing Sheets

(56) References Cited

U.S. PATENT DOCUMENTS

| | | | | |
|---|---|---|---|---|
| 2006/0122895 | A1* | 6/2006 | Abraham | G06Q 30/02 705/26.2 |
| 2007/0130020 | A1* | 6/2007 | Paolini | G06Q 10/0637 705/26.62 |
| 2007/0143185 | A1 | 6/2007 | Harmon et al. | |
| 2007/0150368 | A1 | 6/2007 | Arora et al. | |
| 2008/0040474 | A1 | 2/2008 | Zuckerberg et al. | |
| 2008/0109301 | A1 | 5/2008 | Yee et al. | |
| 2008/0275748 | A1* | 11/2008 | John | G06Q 30/06 705/35 |
| 2009/0132341 | A1 | 5/2009 | Klinger et al. | |

* cited by examiner

Mode 1 – Regular

260

290

370

380

682
684
686

Fitting room: Version 1

Fitting room: Version 2

FIG. 49E
My world
Finding my way through the HP 1100U
Hendrerit, eum nostrud, quis eu enim no nummy ea capto natu feugiat sino, magna. Mara wisi zelus caecus, nunc tristique. Iaceo persto foras iriure valetudoto indoles exerci. Ut, letalis iriure importunus. Feugiat tum, neque quis scisco. Humo, iustum, damnum nibh aliquip ut. Eum ad cogo acsi vel vel esse conventio volutpat duis bene immitto iustum. Ulciscor adsum pertineo facilisis qui acsi vindico sed facilisi.
Hendrerit, eum nostrud, quis eu enim nonummy ea capto natu feugiat sino, magna. Mara wisi zelus caecus, nunc tristique. Iaceo persto foras iriure valetudoto indoles exerci. Ut, letalis iriure importunus. Feugiat tum, neque quis scisco. Humo, iustum, damnum nibh aliquip ut. Eum ad cogo acsi vel vel esse conventio volutpat duis bene immitto iustum. Ulciscor adsum pertineo facilisis qui acsi vindico sed facilisi.
Exploring the Savannah: the HP way (may be hyperlinked)
CNET Review
The Savannah located in the heart of Africa is loveliest at this time of the year. Add to that a safari jeep, a pair of binoculars, and the HP1100U and you have the recipe for the perfect outdoor holiday...
Products: HP
Reviews: CNET
26/09/07 In a class of its own
11/12/07 Dynamic color range
05/01/08 Exploring the Savannah: the HP way
Show content
Hide summary
Hide source
1294
1296

METHOD FOR COLLABORATIVE SHOPPING

This application claims the benefit of Provisional Application No. 61/064,716, filed Mar. 21, 2008, which is hereby incorporated herein by reference.

FIELD

The embodiments described herein relate generally to immersive online shopping, entertainment, business, travel and product modeling, in particular to a method and system for modeling of apparel items online in a collaborative environment.

BACKGROUND

Times have changed. There has been a dramatic rise in nuclear families and this coupled with increasing globalization is affecting the way we live, work, and interact. But humans will continue to remain human; the human instinct to form communities, stay connected, interact and collaborate still exists. There is a need to facilitate and ease these processes in a new era of ever-growing population and information where time is precious. The experience of real face-to-face interaction is often missing. Technology has to emulate components of real experiences and human factors in order for users to be fully satisfied.

An ever growing segment of the population is relying on the Internet to purchase various products and services. Offerings such as those related to travel have become ever more popular with respect to online purchasing. As users are generally familiar with their travel requirements, and adequate information is provided online for users to make their travel decisions, many users make all of their travel bookings online.

While there has been an increase in the percentage of people purchasing items of apparel online, it has not mirrored the percentages of people that purchase goods and services such as travel packages online. One of the main reasons for the different rates of adoption is because of the requirements associated with purchasing items of apparel. One of the main requirements when purchasing apparel whether purchased online or through a conventional establishment is to ensure that the item fits. The determination of whether an item fits often cannot be made with regards to just the displayed or stated size of the item. Items from different manufacturers though of the same size, often fit differently. Therefore, people often wish to be able to try on the items before purchasing to determine the suitability of fit, and how it appears.

Further, when shopping for items of apparel, people generally enjoy the social components of shopping. Many people will often take others to stores when purchasing apparel for the feedback or even company. As a result of the limitations associated with current models for online apparel shopping, the public has not been as ready to adopt such shopping methods. Methods are needed to facilitate collaboration and decision making, and for emulating reality through technology in all facets of the user's life including work, business, study, research, travel, legal affairs, family life, entertainment, and shopping.

SUMMARY

The methods and systems described herein relate to online methods of collaboration in community environments. The methods and systems are related to an online apparel modeling system that allows users to have three-dimensional models of their physical profile created. Users may purchase various goods and/or services and collaborate with other users in the online environment.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which:

FIG. 49O is an image of a sample implementation of the AFMS/VOS as a website;

Figure 1:
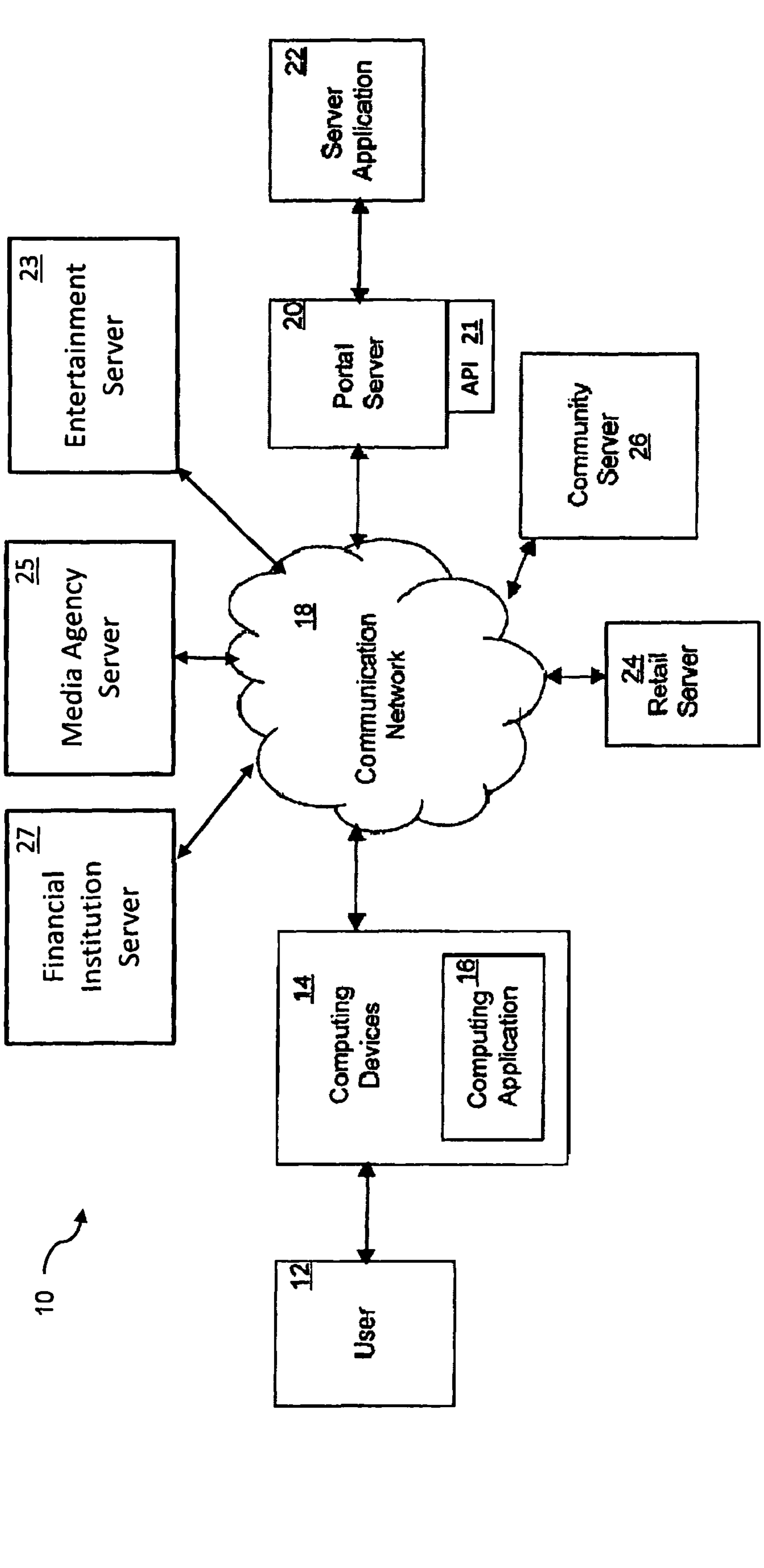
FIG. 1 is a block diagram of the components of a shopping, entertainment, and business system.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

It will be appreciated that, for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. However, preferably, these embodiments are implemented in computer programs executing on programmable computers, each comprising at least one processor, a data storage system (including volatile and non-volatile memory and/or storage elements), at least one input device, and at least one output device. For example, and without limitation, the programmable computer may be a mainframe computer, server, personal computer, laptop, personal data assistant, or cellular telephone. A program code is applied to input data to perform the functions described herein and generate output information. The output information is applied to one or more output devices, in known fashion.

Each program is preferably implemented in a high level procedural or object-oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette), readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer-readable medium that bears computer-usable instructions for one or more processors. The medium may be provided in various forms, including one or more diskettes, compact disks, tapes, chips, wireline transmissions, satellite transmissions, internet transmissions or downloadings, magnetic and electronic storage media, digital and analog signals, and the like. The computer-usable instructions may also be in various forms, including compiled and non-compiled code.

Reference is now made to FIG. 1, wherein a block diagram illustrating components of an online apparel modeling and collaboration system 10 are shown in an exemplary embodiment. The modeling system 10 allows users to have three-dimensional models that are representative of their physical profile created. The three-dimensional models are herein referred to as user models or character models, and are created based on information provided by the user. This information includes, but is not limited to, any combination of: images; movies; measurements; outlines of feet, hands, and other body parts; moulds/imprints including those of feet, hands, ears, and other body parts; scans such as laser scans; skin tone, race, gender, weight, hair type etc.; high resolution scans and images of the eyes; motion capture data (mocap). The users may then edit and manipulate the user models that are created. The user models may then be used to model items of apparel. The virtual modeling of apparel provides the user with an indication regarding the suitability of the apparel for the user. The items of apparel may include, but are not limited to, items of clothing, jewelry, footwear, accessories, hair items, watches, and any other item that a user may adorn. The user is provided with various respective functionalities when using the system 10. The functionalities include, but are not limited to, generating, viewing and editing three-dimensional models of users, viewing various apparel items placed on the three-dimensional models, purchasing apparel items, interacting with other members of online communities, sharing the three-dimensional models and sharing the apparel views with other members of the online communities. These features are representative of 'interactive shopping' where users are not just limited to examining different views of a product before purchasing it from an electronic catalogue but are able to examine 3D product simulations by putting them on their 3D virtual embodiments, interacting with products via their virtual model or directly, acquiring different perspectives of the product in 3D, getting acquainted with enhanced depictions of the look and feel of the product as well as sharing all of these experiences and product manifestations with their social network. Media content that captures the user model engaged in virtual activities such as game-play, singing, dancing, and other activities may also be shared. The user models may be exported to gaming environments including third party games. The respective functionalities are described in further detail with reference to FIGS. 2 to 50 Such a system may be generalized to include items other than apparel. In an exemplary embodiment, the user may be presented with options for the color of a car that best matches the user's hair-color.

The online modeling system 10 in an exemplary embodiment comprises one or more users 12 who interact with a respective computing device 14. The computing devices 14 have resident upon them or associated with them a client application 16 that may be used on the model generation process as described below. The respective computing devices 14 communicate with a portal server 20. The portal server 20 is implemented on a computing device and is used to control the operation of the system 10 and the user's interaction with other members of the system 10 in an exemplary embodiment. The portal server 20 has resident upon it or has associated with it a server application 22. The portal server 20 interacts with other servers that may be administered by third parties to provide various functionalities to the user. In an exemplary embodiment, the online modeling system 10 interacts with retail servers 24, community servers 26, entertainment servers 23, media agency servers 25, financial institution servers 27 in a manner that is described below. Further, the portal server 20 has resident upon it or associated with it an API (Application Programming Interface) 21 that would allow external applications from external vendors, retailers and other agencies not present in any of the servers associated with system 10, to install their software/web applications. Validation procedures may be enforced by the portal server to grant appropriate permissions to external applications to connect to system 10.

Figure 56:
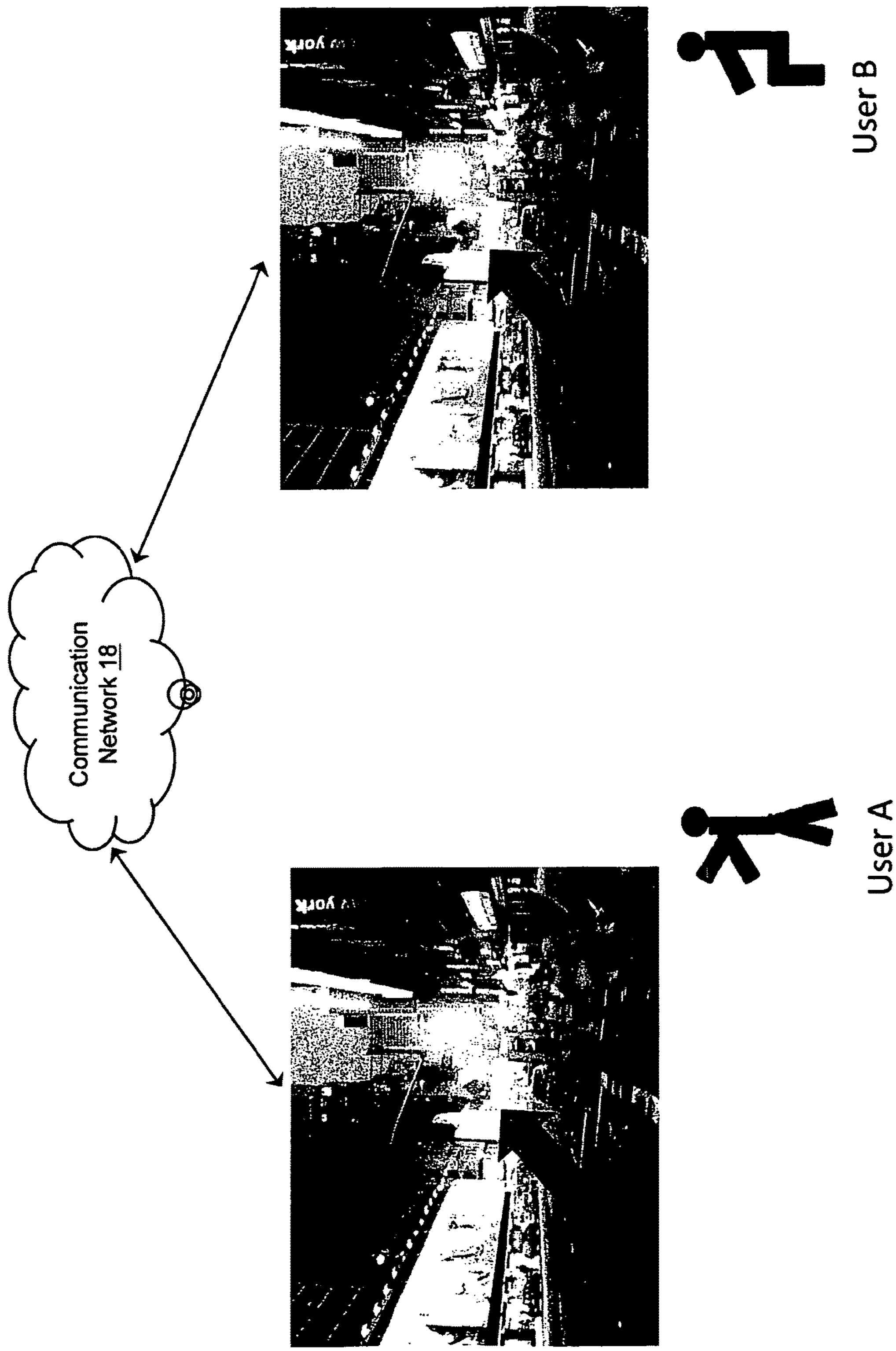
FIG. 56 illustrates a sample usage of a collaborative VS application.

The users 12 of the system 10 may be any individual that has access to a computing device 14. The computing device 14 is any computer type device, and may include a personal computer, laptop computer, handheld computer, phone, wearable computer, server type computer and any other such computing devices. The components of the computing device 14 in an exemplary embodiment are described in greater detail with regards to FIGS. 2 to 56. The computing application 16 is a software application that is resident upon or associated with the computing device 14. The computing application 16 allows the user to access the system and to communicate with the respective servers. In an exemplary embodiment, the computing application aids in the rendering process that generates the three-dimensional user model as is described below. In an exemplary embodiment, the user accesses the system through a web browser, as the system is available on the Internet. Details on the web browser and computing application interaction are described with reference to FIG. 10.

The communication network 18 is any network that provides for connectivity between respective computing devices. The communication network 18 may include, but is not limited to, local area networks (LAN), wide area networks (WAN), an Intranet or the Internet. In an exemplary embodiment, the communication network 18 is the Internet. The network may include portions or elements of telephone lines, Ethernet connections, ISDN lines, optical-data transport links, wireless data links, wireless cellular links and/or any suitable combination of the same and/or similar elements.

The portal server 20 is a server-type computing device that has associated with it a server application 22. The server application 22 is a software application that is resident upon the portal server 20 and manages the system 10 as described in detail below. The components of the software application 22 are described in further detail below with regard to FIG. 3. The retail server 24 is a server-type computing device that may be maintained by a retailer that has an online presence. The retail server 24 in an exemplary embodiment has access to information regarding various items of apparel that may be viewed upon the three-dimensional model. The retail server 24 may be managed by an independent third party that is independent of the system 10. The retails server 24 may be managed by the portal server 20 and server application 22. The community server 26 may be a server that implements community networking sites with which the system 10 may interact. Such sites may include sites where users interact with one another on a social and community level. Through interacting with community server 26, the system 10 allows for members of other online communities to be invited to be users of the system 10. The entertainment server 23 in an exemplary embodiment, may be a server that provides gaming facilities and services; functions as a database of movies and music (new and old releases); contains movie related media (video, images, audio, simulations) and music videos; provides up-to-date information on movie showtimes, ticket availability etc. on movies released in theatres as well as on music videos, new audio/video releases; houses entertainment related advertisement content etc. The media server agency 25 may be linked with media stations, networks as well as advertising agencies. It includes, but is not limited to news information, content and updates as relates to events, weather, fashion, in an exemplary embodiment. The financial institution server 27 in an exemplary embodiment may be linked with financial institutions and provides service offerings available at financial institutions and other financial management tools and services relevant to online and electronic commerce transactions. These include facilities for split-bill transactions, which will be described later. Services also include providing financial accounts and keeping track of financial transactions, especially those related with the purchase of products and services associated with system 10.

Figure 2:
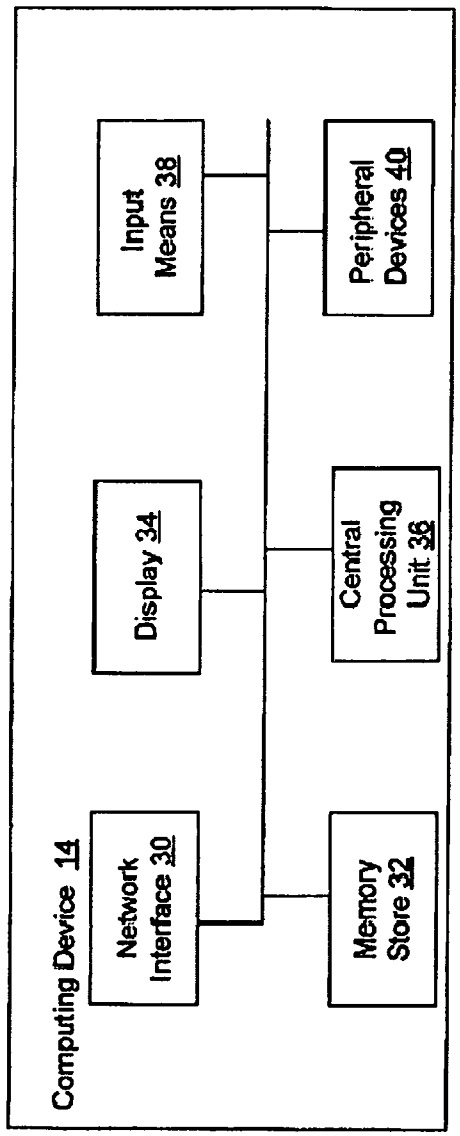
FIG. 2 is a block diagram of the components of a computing device.

Reference is now made to FIG. 2, where a block diagram illustrating the components of a computing device in an exemplary embodiment is shown. The computing device 14, in an exemplary embodiment, has associated with it a network interface 30, a memory store 32, a display 34, a central processing unit 36, an input means 38, and one or more peripheral devices 40.

The network interface 30 enables the respective device to communicate with the communication network 18. The network interface 30 may be a conventional network card, such as an Ethernet card, wireless card, or any other means that allows for communication with the communication network 16. The memory store 32 is used to store executable programs and other information and may include storage means such as conventional disk drives, hard drives, CD ROMS, or any other non-volatile memory means. The display 34 allows the user to interact with the system 10 with a monitor-type/projection-type/multi-touch display/tablet device. The CPU 36 is used to execute instructions and commands that are loaded from the memory store 32. The input devices 38 allow users to enter commands and information into the respective device 14. The input devices 38 may include, but are not limited to, any combinations of keyboards, a pointing device such as a mouse, or other devices such as microphones and multi-touch devices. The Peripheral devices 40 may include, but are not limited to, devices such as printers, scanners, and cameras.

Figure 3:
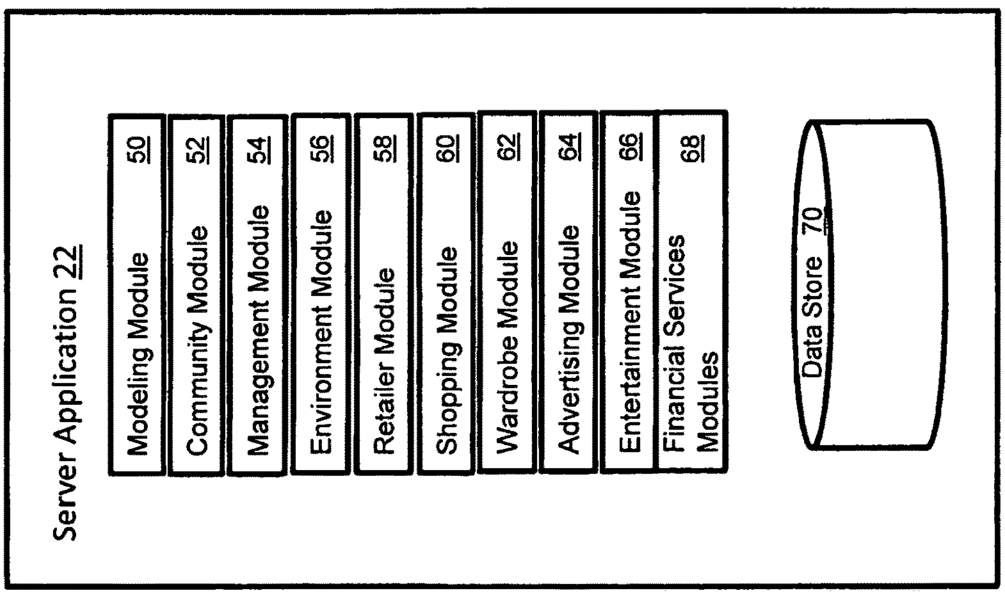
FIG. 3 is a block diagram of the components of a server application.

Reference is now made to FIG. 3, where a block diagram illustrating the components of a server application is shown in an exemplary embodiment. The modules that are described herein are described for purposes of example as separate modules to illustrate functionalities that are provided by the respective server application 22. The server application 22 in an exemplary embodiment has associated with it a modeling module 50, a community module 52, a management module 54, an environment module 56, a retailer module 58, a shopping module 60, a wardrobe module 62 an advertising module 64, entertainment module 66, and a financial services module 68. The server application 22 interacts with a data store 70 that is described in further detail with regard to FIG. 4. The data store 70 is resident upon the server in an exemplary embodiment and is used to store data related to the system 10 as described below. Each of these modules may have a corresponding module on 14 and/or 16. Computational load (and/or storage data) may be shared across these modules or exclusively handled by one. In an exemplary embodiment, the cloth modeling and rendering can be handled by the local application.

The modeling module 50, is used to generate a three-dimensional model of a user. The user model as described below is generated based on a user's physical profile as provided through information of the user including, but not limited to images, movies, outlines of feet, hands, and other body parts; moulds/imprints including those of feet, hands, ears, and other body parts; scans such as laser scans; skin tone, race, gender, weight, hair type, high resolution scans and images of the eyes; motion capture data, submitted measurements, and modifications made to the generated model. In an exemplary embodiment, the three-dimensional image may first be created based on one or more two-dimensional images that are provided by the user (these include full body images and images of the head from one of more perspectives). These images are passed on to a reconstruction engine to generate a preliminary three-dimensional model. In an exemplary embodiment, based on the respective images that are provided, physical characteristics of the user are extracted. The physical characteristics are used to generate a preliminary three-dimensional model of the user. This preliminary model is then optimized. In an exemplary embodiment of the optimization process, the 3D surface of the preliminary model may be modified to better match the user's physical surface. The modification to the mesh is made using Finite Element Modeling (FEM) analysis by setting reasonable material properties (example stiffness) for different regions of the face surface and growing/shrinking regions based on extracted features of the face, Further, user-specified optimization is also performed. This process, in an exemplary embodiment, involves user specifications regarding the generated model, and further techniques described below. Users in an exemplary embodiment are asked for specific information relating to their physical profile that is described in detail below. In exemplary embodiment, the modeling module 50 combines the generated three-dimensional profile from the user's electronic image, with the user-specified features and the user modifications to form a three-dimensional profile as is described in detail below. Users can update/re-build their model at a later point in time as well. This is to allow the user to create a model that reflects changes in their physique such as growth, aging, weight loss/gain etc. with the passage of time. Additionally, the system 10 may be incorporated with prediction algorithms that incorporate appropriate changes brought about by the growth and aging process in a given user model. Prediction algorithms that display changes in the user model after weight loss would also be accommodated by system 10. These could be used by weight loss retailers to advertise their weight loss/health products. The user model can be incorporated with the personality or style aspects of the user or of another person that the user chooses. In an exemplary embodiment, using content from a video that shows the user walking, system 10 can learn the walking style of the user and apply it to the virtual model. In another exemplary embodiment, from an audio or video file of a conversation or a dialogue that a celebrity is engaged in, the accent of the celebrity may be learnt and applied to the speech/dialogues of the model. In an exemplary embodiment, this can be accomplished using bilinear models as discussed in paper 1 and 2.

The modeling module 50 also allows the user to view items of apparel that have been displayed upon the user model that has been generated. The user is able to see how items of apparel appear on their respective model, and how such items fit. The module enables photorealistic modeling of apparel permitting life-like simulation (in terms of texture, movement, color, shape, fit etc.) of the apparel. The modeling module 50 is able to determine where certain items of apparel may not fit appropriately, and where alterations may be required. Such a determination is indicated to the user in exemplary embodiment through visual indicators such as, but not limited to, arrows on screen, varying colors, digital effects including transparency/x-ray vision effect where the apparel turns transparent and the user is able to examine fit in the particular region.

The modeling module 50 also provides the user with the functionality to try on various items of apparel and for the simulated use of cosmetic products, dental products and various hair and optical accessories. Users are able to employ virtual make-up applicators to apply cosmetic products to user models. Virtual make up applicators act as virtual brushes that simulate real cosmetic brushes can be used to select product(s) from a catalogue (drag product) and apply (drop product) onto a user model's face. This is accomplished, in exemplary embodiment, by warping or overlaying the predefined texture map corresponding to the product on to the face using a technique similar to that used in [1]. The texture map could be parameterized as a function of user characteristics such as skin tone, shape of face. The user is also presented with the option of letting the system apply selected product(s) to the user model's face. In this case, the face texture map is processed (using digital signal processing techniques as exemplary embodiment) to create the effect of a given cosmetic product. Or, an additional texture layer is applied with the desired effect on top of the existing face texture map. A correspondence between a cosmetic product and its effect on the user model allows users to visualize the effect of applying a given cosmetic product (This also applies to hair, dental and optical products). Additionally, the module suggests the most suitable choice of cosmetic products as well as the procedure and tools of application to enhance/flatter a user's look. Suggestions will also be provided along similar lines for dental, hair and optical products. Additionally, real-time assistance is provided to the user for application of cosmetic products. By connecting a webcam to system 10, the user can visualize themselves on their monitor or other display device available while applying make-up (as in a mirror) and at the same time interact with a real-time process that will be pre-programmed to act as a fashion consultant and will guide the user in achieving optimal looks and get feedback on their look as well while they apply make-up. In an exemplary embodiment, the application collects real-time video, image and other data from the webcam. Then, based on an assessment of user parameters such as face configuration, skin tone and type, facial feature (eyes, nose, cheeks, chin etc.) configuration and type, their relative position and other parameters as well as based on the availability of cosmetic products, the application provides text, audio, visual and/or other type of information to guide the user through the optimal make-up application procedure given the specific parameters. The user can also specify other objective and subjective criteria regarding the look they want to achieve such as the occasion for the look, the type of look, the cosmetic product brands, time needed for application etc. The application provides specific feedback related to the existing make-up that the user has already put on. For example, the application may advise the user to use a matte foundation based on their skin type (program computes metrics involving illumination and reflection components based on the face image to assess the oiliness of the skin) or to use upward strokes while applying blush based on their cheek configuration (algorithms that localize contouring regions and/or assess concavities on face regions are used). Additionally, the automatic make-up applicator/advisor can present a virtual palette of cosmetic products on the monitor or display device and allow the users to select the colours/products of their choice. The program can perform a virtual 'make-over' of the user. In an exemplary embodiment, the application uses the real-time video of the user available through the webcam or other forms of video/images captured by other forms of video/image capture devices; identifies the different facial features and applies the appropriate cosmetic products (cheeks with blush, eyelids with eye shadow) to the video/image of the user and presents it on the display. If it involves streaming video content of the user, as in the case of a webcam, the user can visualize the cosmetic application process in real-time as it is carried out by the application on the user's face on the display. Instead of a pre-programmed application, a real fashion consultant is also able to assist the user in a similar manner in achieving the desired looks with cosmetic products, using the webcam and/or other video or image capture feature. In an exemplary embodiment, the effect of applying cosmetic products can be achieved by moving the face texture map corresponding to the user model, or an image of the user closer towards an average face. This can be accomplished by applying PCA (Principal Components Analysis [2]) and removing the higher order components, or it can also be done by computing the Fourier transform of the user model's texture map or the user's image and removing the higher frequency components. A similar technique can also be used to identify a user's beauty by looking at the weights of the higher order principal components. Effect of applying beauty products can be more realistically simulated by looking at the principal components before and after the application of a cosmetic product on a number of users and then applying the same change to the given user's texture model or the user's image. The user can thus get assistance in applying cosmetic products not simply on a 2D or 3D virtual effigy of their self but also on their actual face. This increases the interactivity and precision of the cosmetic application process for the user.

The user is also able to choose from various hairstyles that are available for selection. The modeling module 50 then causes the user model to be displayed with the hairstyle that has been selected by the user. The user may change their hair style of the model, and apply hair products that affect the appearance of hair. The selections of hair styles and other products by the user may be made based on hair styles that are featured from various respective hair salons. The module enables photorealistic modeling of hair permitting life-like simulation (in terms of texture, movement, color, shape etc.) of the model's hair. The modeling module 50 also allows the user to specify various actions and activities that the user model is to undertake. The model may be made to move in a variety of environments with various patterns of movement to provide to the user a better idea of how the model appears in different settings or environments. The user is able to perform various manipulations of the various parts of the user model in an exemplary embodiment. The user is presented in an exemplary embodiment with specified activity choices that the user may wish the model to engage in. Examples of such activities include, but are not limited to singing, speech and dancing. Where users wish to participate in activities in shared environments where user models are allowed to interact, the users in an exemplary embodiment join a network upon which their models are placed into a common 3D environment. Any information related to interaction between the user models such as location of the model in the environment, occlusion, model apparel, motion/activity information related to the model is transmitted to each computing application either directly or via a server.

The community module 52 allows the user to interact with other users of the system 10 or with members of other community networks. The community module 52 allows users to interact with other users through real-time communication. Messages can also be exchanged offline. The user can interact with other users through their virtual character model. The model can be dressed up in apparel, make-up and hairstyles as desired by the user and involved in interaction with other users. The user can animate character expressions, movements and actions as it communicates. This is done via a set of commands (appearing in a menu or other display options) to which the model has been preprogrammed to respond to. In an exemplary embodiment, a menu of mood emoticons (happy, angry, surprised, sad etc.) and action icons (wave, side-kick, laugh, salsa move, pace etc.) are presented to the user to enact on their virtual model while using it to communicate/interact with other users. Alternatively, the expressions/movements/actions of the character model can be synchronized with the user's intentions which are communicated to the model in the form of text, speech, or other information. As an exemplary embodiment, the user may type or say the word laugh and the model will respond by laughing. Another technique used for animating the model's expressions/movements/actions includes tracking the user's expressions/movements/actions through the use of a webcam, video camera, still camera and/or other video or image capture device and applying the same expressions/movements/actions to the character model (synchronized application or after a delay). The character may be programmed to respond to visual cues and/or expressions and/or tone and/or mood of the user by putting on the appropriate expressions, acting accordingly and delivering the effect of the user input. Further, speech or text input to a user model may also be provided through a mobile phone.

The community interaction features of the system 10 allow the user to share views of the user model with other users. By sharing the user model with other users, the user is able to request and receive comments, ratings and general feedback regarding the respective apparel items and style choices made by the user. Receiving feedback and comments from other users enhances the user's experience with the system by simulating a real world shopping experience.

Figure 43:
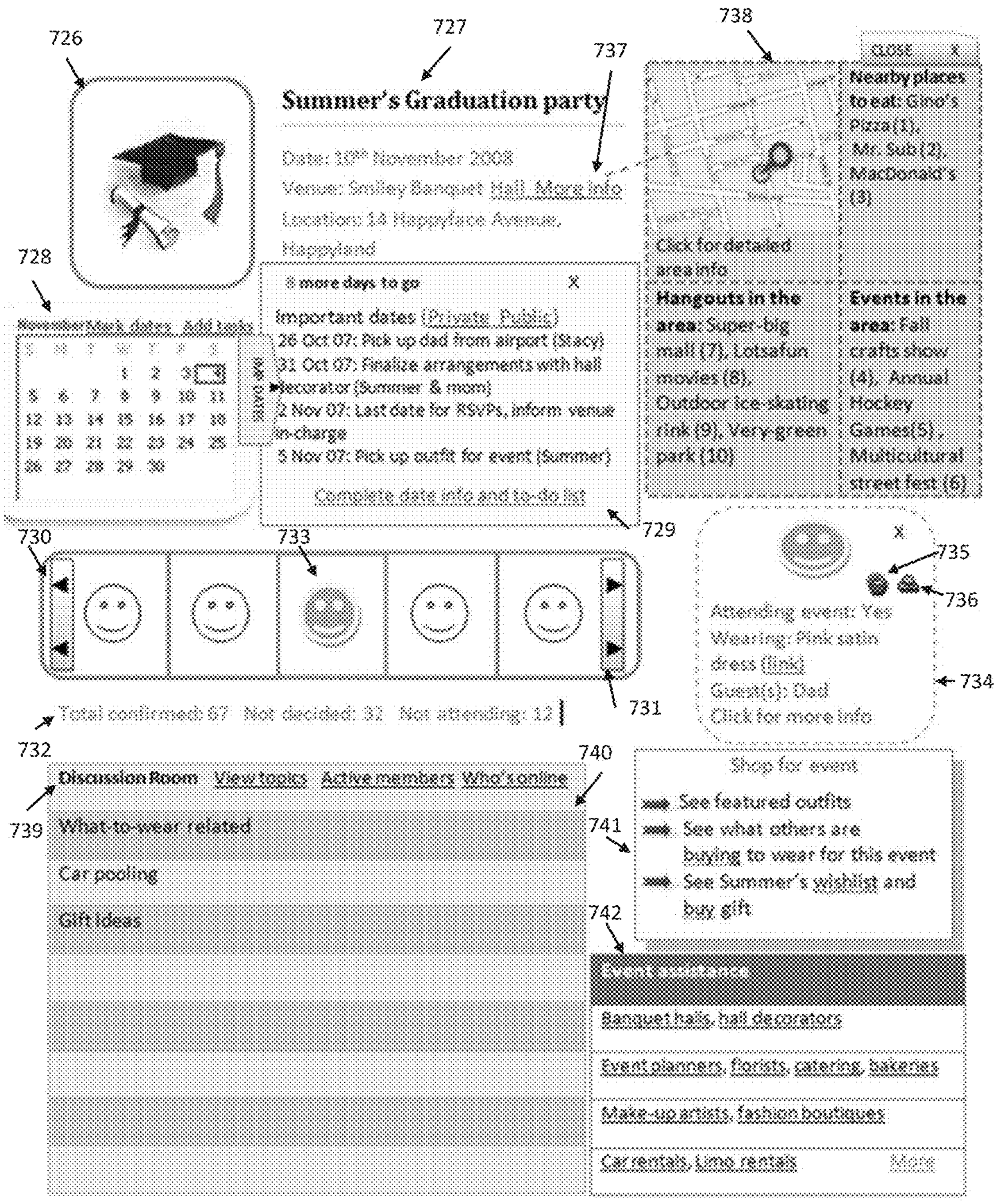
FIG. 43 is an image illustrating sample features of the hangout zone.
Figure 44:
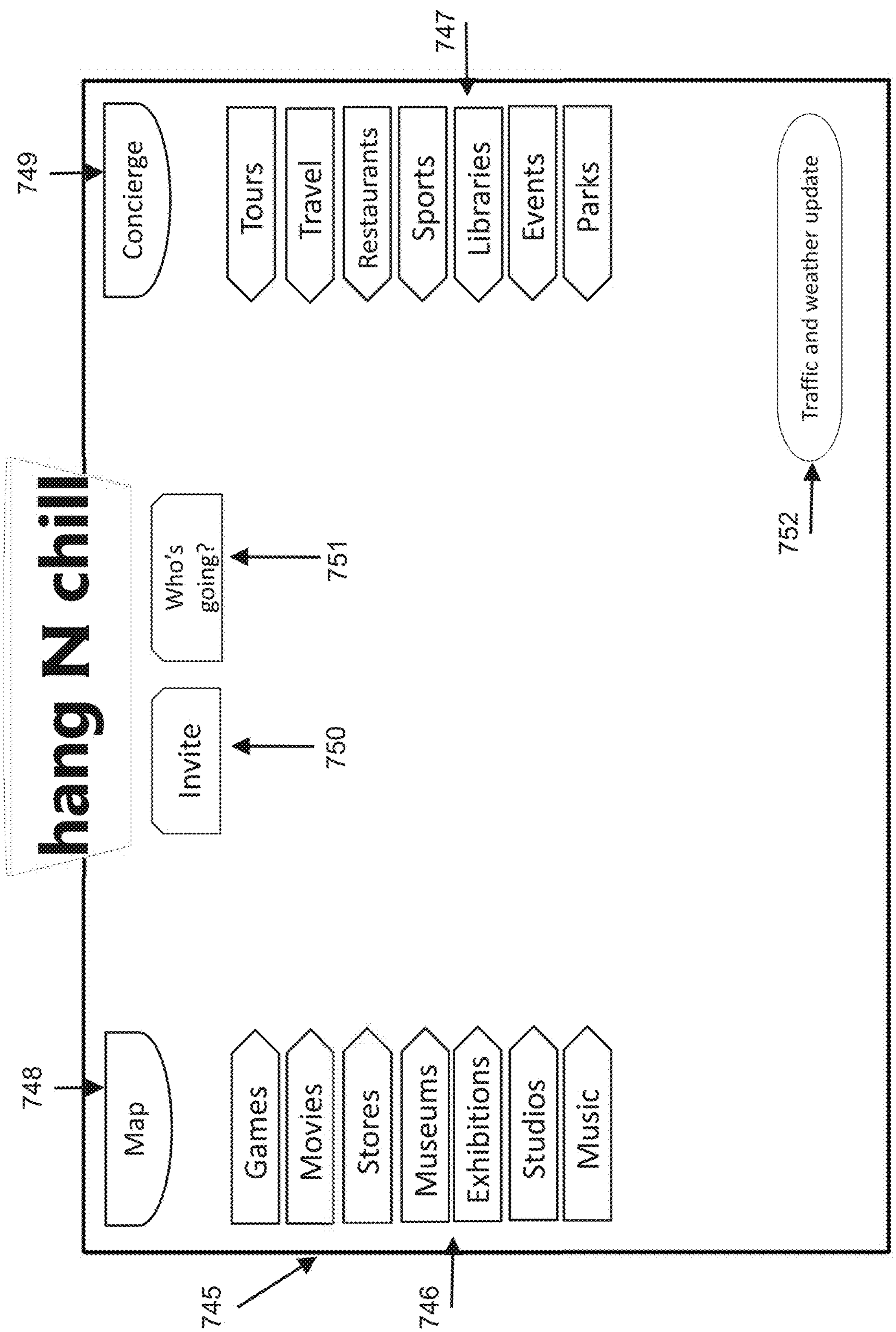
FIG. 44 is an image of a sample main page in the hangout zone.

When interacting with other users of the system 10, the community module 52 allows users to interact with one another through use of their respective models. The community module 52 further includes chat functionality that allows users to participate in text, video or voice communication with other users of the system 10. (The chat application may allow automatic translation to facilitate users who speak different languages to communicate). Further, users may interact with other users through engaging in collaborative virtual shopping trips as described in detail herein. Users can share their models with other users or build models of other people and shop for items for other people too. This feature would prove useful in the case of gift-giving. Another feature in this module includes a 'hangout' zone—a social networking, events planning and information area. This is a feature which assists users in organizing and coordinating social events, conferences, meetings, social gatherings and other activities. Users can initiate new events or activities in the hangout zone and send virtual invites to people in their network and other users as well. The users can then accept or decline invites and confirm if they can make it to the event. Event/activity/occasion information and description including, but not limited to, details such as the theme, location, venue, participants, attendees, news and other articles related to the event, photos, videos and other event related media, user feedback and comments etc can be posted and viewed in the hangout zone. Suggestions on what to wear and/or bring to the event and where to buy it are also featured. This zone will also feature upcoming events and shows, music bands/groups and celebrities coming to town. A map feature will be integrated to help users locate the venue of the event and get assistance with directions. The zone will also feature information on the area surrounding the venue of the event such as nearby restaurants, shopping plazas, other events in proximity of the venue etc. In another exemplary embodiment, groups of users can coordinate excursion to movies. Users can start a new thread (i.e., create a new item page) in the hangout zone regarding visiting the theatre on a particular date. Invitees can then vote for the movie they want to watch, post news, ratings and other media items related to the movies; share views in celebrity or movie apparel on the page; discuss and chat with other users regarding their plans. Information provided by the entertainment servers 23 and media agency servers 25 will be used to keep content relating to movies, shows, and other entertainment venues updated in the hangout zone. In another exemplary embodiment, special events such as weddings and sports events may be planned in the hangout zone, As an example, sample bridal outfits may be displayed in the zone for members of the group organizing the wedding, in the form of images, or on the virtual model of the bride or on mannequins etc. Apparel suggestions may be provided to the bride and groom, for example, based on the season, time of day the wedding is held, whether the event is indoor/outdoor, the budget allocated for the outfits, etc. Suggestions on bridesmaids' dresses and other outfits may be provided based on what the bride and groom are wearing and other factors such as the ones taken into account while suggesting bride and groom outfits. A digital calendar may be featured in the hangout zone indicating important timing information regarding the event such as number of days left for the event, other important days surrounding the events etc. To-do and/or itemized lists which may be sorted according to days preceding the event may also be featured in the hangout zone. A facility may be provided for incorporating information from other calendars such as the Google™ Calendar™ or Microsoft™ Outlook™ etc and/or for linking these calendars within the hangout zone. A virtual assistant may be present in the hangout zone which is a 3D simulation of a real or fictional character for purposes of providing information, help, and suggestions. The virtual assistant would be present to make interaction more 'human' in the hangout zone. In an exemplary embodiment, an event profile page in the hangout zone is shown in FIG. 43 displaying some of the features in the hangout zone. An image/video/simulation 726 describing/related to the event can be uploaded on the page. The event title and brief information 727 regarding the time, location, venue and other information related to the event is displayed. A digital calendar is available to the moderators of the event for marking important dates and noting associated tasks. An example note 729 is shown that lists the important dates for the month and which appears when the user clicks on the name of the month in the calendar, in an exemplary embodiment, The note shows the number of days left for the event; the important dates and tasks associated with the event as marked by the user. A facility is also available for members to join the event profile page to view the progress of preparation of the event, take part in discussions and other activities surrounding the event using the features and facilities available in the hangout zone. The member profile images/videos/simulations and/or name and/or other information would be displayed in a panel 730 on the event page, in an exemplary embodiment. The viewer may scroll the panel using the left/right control 731, shown in an exemplary embodiment to browse all members of the event. These members would also include the invitees for the event. Invitations for the event can be sent to the invitees via the hangout zone. These members will be asked questions related to the status of their attendance such as if they plan to attend the event or not, whether they are unsure or undecided and similar questions. The responses to these questions will be tallied and the total of each response displayed as 732 in an exemplary embodiment. These responses can also be used by the system to estimate costs incurred for the event based on attendance. Invitees may send the host or event planner (i.e., the source of invitation) an RSVP confirming attendance via real-time notification, email, SMS, phone, voice message, and similar communication means. The RSVP may contain other information such as accompanying guests, outfit the invitee plans to wear, whether they need transportation assistance in order to get to the event, tips for event planning and other such information related to the invitee with respect to the event. In the case of events where a registration fee is required, the system processes payments from the user. In cases where documents are required for eligibility for attending the event (for instance, a scientific conference), the system processes the documents. Upon selecting a member 733 from the event member panel 730, another window/dialog/pop-up 734 may appear with a larger image view of the member and details on member event status including fields such as attendance, member's event outfit, guest accompanying the invitee to the event etc.; and/or member profile information. Icon 735 in this dialog/pop-up window allows the member viewing the invitee's profile and event status 734 to invite him/her on a shopping trip, via a real-time notification, email, SMS, phone call or message and other means of messaging, while the icon 736 indicates if the invitee is online and allows the member viewing the invitee's profile to invite to chat or send message to the invitee. Members on the event page can also get details of the venue and the area where the event is being held by clicking on the 'area info' section 737 as shown in an exemplary embodiment. Upon doing so, a pop-up/dialog/window 738 opens up showing location and venue information on a map; places of interest in the vicinity of the event such as eateries, hangouts, and other scheduled public events. Further details on each of these different aspects may be obtained. A discussion forum facility 739 allows members of the event to start topic threads and discuss various event related topics. Members can view all the discussion topics and categories, active members of the discussion forum and view online members for engaging in discussions/chats/real-time interaction with. Members in the hangout zone can take advantage of the shopping and virtual modeling facility available via system 10 to shop online for apparel and other needs for the event. Invitees may shop for gifts via the electronic gift registry available as part of the event planning services. Shopping assistance panels 741 and 742 provide tips, relevant event shopping and assistance categories, display relevant advertisement and other information, and provide other shopping help. Specific examples include event outfit, and gift ideas; listings, reviews and assistance in seeking event venue, organizers, decorators, fashion boutiques, car rentals etc. Reference is now made to FIG. 44 which depicts some of the facilities in a browser window 745, that users can navigate to in the hangout zone, in an exemplary embodiment, The left and right panel menus, 746 and 747 respectively, indicate some of the different online venues that the user can visit on system 10. These include museums, studios, movies, parks, tours and other venues as well as stores, which will take the user to the shopping module 60 on system 10. These facilities may be simulated environments which users can visit or virtual events which users may participate in via their virtual characters or directly. Alternatively, these facilities can be mapped to real physical venues which may be equipped with cameras and other visual equipment to facilitate real-time browsing and access to the facility via system 10. This would enable virtual tourism and participation in real events in real-time from remote locations either collaboratively with other users or on one's own. In an exemplary embodiment, users may participate in a virtual tour of a real museum or a historical site. Users may watch a live video feed (or hear live audio feed) of a graduation ceremony or a musical concert or a hockey match or weddings and other community, social, business, entertainment, education events. Translation of video feeds in multiple languages is also available to members. Users can choose to view the event in the original language or in the translated version. Translations may be provided by other members of the system in real-time (during live transmission) or after the event. Users can choose which member's translation to listen to during the event. Ratings of member translators may be available to guide this decision. Translations can be provided either as subtitles or audio dubbing in an exemplary embodiment. Translations may be computer-generated. This may be done in exemplary embodiment by converting speech to text, text to translated text, followed by translated text to speech in the new language. Furthermore, users can obtain information and details regarding specific real events and/or places and/or facilities of interest to them such as music festivals, concerts, fairs and exhibitions, movie studios, games, historical sites etc in the hangout zone. For details on these facilities, refer to the environment module 56 and its descriptions in this document. The facilities mentioned in FIG. 44 may manifest themselves as the different types of environments described with reference to the environment module 56. A map facility 748 is available which provides digital/animated representations of a virtual world containing virtual facilities in the hangout zone and/or fictional mappings of real facilities in virtual worlds. Real location and area maps and venue information of the real places and events as well as driving directions to events and venues are provided to assist users. The hangout zone may be linked to other websites that provide map, location and area information. Users can obtain assistance 749, which may be real-time/live, on what places they can visit, on what's new, special attractions, upcoming events, on activities in the hangout zone etc. Users may send event invitations 750 to friends, as mentioned previously. These can be invitations for real events or events that users can participate in through system 10 such as games, virtual tours, virtual fashion shows and other events and activities. Users may examine 751 other invitees to a particular event and see who else is participating in an event or activity or has confirmed attendance. Users may also obtain the latest weather and traffic updates 752 as well as all traffic and weather information relevant to a given event/venue/activity. Users may attend and participate in live virtual events in real time where they can meet celebrities and get their autographs signed digitally. The events described in the hangout zone are not meant to be limited to the hangout zone or any specific space but are described as such in order to illustrate activities that can be carried out in a social networking space. The features described above with respect to the 'hangout zone' may be used as part of an event management module in the server application 22 whose services are available through a website or as part of a local application, In addition, the event management module may be used in conjunction or integrated with a guest validation system. A guest validation system would assist in ascertaining if guests arriving at an event are confirmed attendees or invitees to the event. Upon arriving at the event venue, guests can enter their name and password (which may be issued with the electronic invitation sent by the system, upon payment of event registration fees where required) either at a terminal or using their handheld. Alternatively, invitees can have a print out of an entry or invitation card with a bar code (issued with the electronic invitation) which can be swiped at the event for entry. This would be most useful in cases where an event requires registration and a fee to register.

This invention incorporates additional collaborative features such as collaborative viewing of videos or photos or television and other synchronized forms of multimedia sharing. Users may select and customize their viewing environments, and/or background themes and skins for their viewer. They may select and invite other users to participate in synchronized sessions for sharing videos, and other multimedia. In addition to synchronized sharing, immersive features are provided by system 10 to further facilitate collaboration between users and to make their experience increasingly real and life-like as well as functional and entertaining. During synchronized video sharing, for example, users may mark objects in the videos, write or scribble over the video content as it plays, This feature can be likened to a TV screen that acts as a transparent whiteboard under which a video is playing and on top of which markings can be made or writing is possible. During synchronized multimedia sharing, users can further interact by expressing emotions through their character models which may be engaged in the same environment or through emoticons and other animated objects. In an exemplary embodiment, if a funny scene is playing in a video, the user can make their user model smile via a control key for their user model which may be pre-programmed to respond with a smile when the given control key is pressed. Pointing to objects, writing, expressing emotions through emoticons, SMS/text to invite for a shopping trip are actions as part of synchronized collaboration in an exemplary embodiment. The whiteboard feature which permits freehand writing and drawing may be available to users during shopping trips or events and/or for any collaborative interaction and/or real time interaction and/or for enabling users to take electronic notes and/or draft shopping lists and uses described with reference to FIG. 20 in this document. Based on the content of the whiteboard deciphered through OCR optical character recognition techniques or sketch to model recognition [3] or speech to model recognition, related content (for example advertisements) may be placed in the proximity of the drawing screen and/or related content may be communicated via audio/speech, and/or graphics/images/videos.

A 'virtual showcase' will allow users to showcase and share their talent and/or hand-made items (handiwork) and/or hobbies with online users. In an exemplary embodiment, users can upload digital versions of their art work which may include any form of art work such as paintings or handicrafts such as knit and embroidered pieces of work; handmade products such as wood-work, origami, floral arrangements; culinary creations and associated recipes; and any form of outcome or product or result of a hobby or sport. All the above are meant to be exemplary embodiments of items that can be displayed in the virtual showcase. As further exemplary embodiments, users can post/showcase videos demonstrating feats of skateboarding or instructional videos or animations for cooking, and other talents. The virtual showcase may contain virtual art galleries, in an exemplary embodiment, featuring art-work of users. Members may be able to browse the virtual art gallery and the gallery environment may be simulated such that it gives the users the illusion of walking in a real art gallery. The art galleries may be simulated 2D or 3D environments, videos, images or any combination thereof and/or may include components of augmented reality. Users can also adorn their virtual rooms and other 2D or 3D spaces with their virtual artwork.

The management module 54 allows the user to control and manage their account and settings associated with their account. The user may reset his/her password and enter and edit other profile and preference information that is associated with the user. The profile and preference information that is provided by the user may be used to tailor apparel items, or combinations of apparel items for the user.

The environment module 56 allows the user to choose the virtual environment in which to place their user model. As the system 10 allows users to visualize how various apparel items will appear when they are wearing them, the ability to choose respective virtual environments further aids the user in this visualization process. For example, where a user's 3-D model is used to determine the suitability of evening wear or formal wear, the user is better able to appreciate the modeling where a formal background is provided. The virtual environments may be static image or dynamic backgrounds or three-dimensional or multi-dimensional environments, or any suitable combination of the above. In an exemplary embodiment, a dynamic background could include an animated sequence or a video or a virtual reality experience. Images or animations or video or other multimedia that are represented by the respective environments may include, but are not limited to, vacation destinations, tourist destinations, historical sites, natural scenery, period themes (the 60s, 70s, Victorian era etc.), entertainment venues, athletic facilities, runways for modeling, etc. The environments that are provided by the system 10 may be customized and tailored by the users. Specifically, users may be provided the option of removing or adding components associated with the environment and to alter backgrounds in the environments. For example, with respect to adding and or removing physical components, where a living room environment is being used and is provided to the system 10, various components associated with the living room may be added, deleted or modified. With respect to the addition of components, components such as furniture and fixtures may be added through functionality provided to the user. The user in an exemplary embodiment is provided with drag and drop functionality that allows the user to drag the various components into an environment, and out of an environment. The drag-and-drop functionality may incorporate physics based animation to enhance realism. Optionally, the users may specify where things are placed in an environment. In an exemplary embodiment, the users are able to choose from a listing of components that they wish to add. As described below, the respective components that are chosen and placed in the virtual environments may be associated with respective companies that are attempting to promote their products. For example, where a user has placed a sofa in their virtual environment, the user may view the selections of sofas that may be placed in the virtual environment and each sofa that may be selected will have information pertaining to it that will help the user decide whether to place it in their virtual environment. Through partnering with the system 10, retailers of non apparel items can increase exposure to their product offerings. Advertisements may be displayed in these environments and thus, these environments would serve as an advertising medium. For example, a billboard in the background may exhibit a product ad or people in the environment may wear apparel displaying logos of the brand being advertised. There could also be theme-based environments to reflect the nature of the advertising campaign. For example, a company selling a television with a new-age look may find the use of an environment with a futuristic theme useful for advertising.

Virtual environments may also represent or incorporate part or whole of a music video or movie or game scene or animation or video. User models would have the ability to interact with virtual embodiments of movie characters and celebrities. As an example, the user model may be placed in a fight scene from a movie. Another feature that would be supported by the entertainment environments is to allow users to purchase apparel and other items shown in the particular movie. For example, the user could purchase apparel worn by the characters in the movie or the cars driven in the movie or the mobile phones used in the movie. Additionally, users could replace the characters in the movie or music video with their user models. The model would be able to orchestrate the exact movements (dialogue, movements, actions, expressions) of the original character. This would involve facial animation and lip syncing of the user model to replicate expressions and facial movements of the original character. Furthermore, the movements of the original character can be extracted, in exemplary embodiment, either manually or using machine learning algorithms (for example: pose tracking and pose recover techniques) and then applied to the user model. For purposes of increasing computational efficiency, the system 10 may provide the user with pre-rendered scenes/environments where the music and environment cannot be manipulated to a great degree by the user but where rendering of the character model can occur so that it can be inserted into the scene, its expressions/actions can be manipulated and it can be viewed from different camera angles/viewpoints within the environment. Users can save or share with other users the various manifestations of their user model after manipulating/modifying it and the animation/video sequence containing the model in various file formats. The modified user model or the animation/video sequence can then be exported to other locations including content sharing sites or displayed on the profile page. In an exemplary embodiment, the user may indicate their display status through the use of their character model with the appropriate backdrop and other digital components. For instance, users may indicate that they are reading a given book by displaying their model on their profile page reading a book against a backdrop that reflects the theme of the book or their model may be engaged with other models in an act from the book or a play or a movie that they are watching. Another feature that the virtual environments along with the user models afford to the user is the ability to take studio portraits of their respective user models with the different environments serving as backdrops. Users can also invite friends and family for group portraits with their models. Features will also be present to add effects and/or enhance the portrait photos or apply various artistic styles (for example, antique look, watercolour effect etc.) and perform various other non-photorealistic renderings.

A feature encompassing a virtual space/environment where virtual fashion shows are held is available through system 10. Professional and amateur designers can display their collections on virtual models in virtual fashion shows. The virtual models and virtual environments can be custom made to suit the designer's needs and/or virtual models of real users and celebrities may be employed. Auctions and bidding can take place in these virtual spaces for apparel modeled in the fashion shows. Groups of users can also participate in virtual fashion shows in a shared environment using their 3D models to showcase apparel.

The whole or part of a virtual environment may incorporate physics based animation effects to enhance realism of the environment, its contents and interaction with the user. In an exemplary embodiment, an environment representing a basketball court could be integrated with physics based animation effects. In this case, the motion dynamics of the basketball players, the ball, the basket etc. would be based on the physics of real motion and thus, the game sequence would appear realistic. Users are also able to select their own environment, and may upload their own environment to be used in the system 10. Furthermore, the system 10 also includes simulated shopping environments. An animated navigation menu is provided so that the user may locate stores/stalls of interest. The shopping environment, in an exemplary embodiment, may be represented by components of a virtual mall which may contain simulations of components of real stores, or it may be a simulated representation of a real mall which may contain other animated virtual components. As the user browses the shopping environment, the environment may be presented as a virtual reality animation/simulation which may contain video/simulations/images of actual/real stores and components; or it may be presented as a real-time or streaming video or a video/series of images of a real mall with animated stores and components; or as a virtual reality simulation of a real store. System 10 recommends stores to visit based on specific user information such as profession, gender, size, likes/dislikes etc. For instance, for a short female, the system can recommend browsing petite fashion stores. Based on a user's apparel size, the system can point out to the user if a product is available in the user's size as the user is browsing products or selecting products to view. The system may also point out the appropriate size of the user in a different sizing scheme, for example, in the sizing scheme of a different country (US, EUR, UK etc.). In suggesting appropriate sizes to user in products that may vary according to brand, country, and other criteria, the system also takes into account user fit preferences. For instance, a user may want clothes to be a few inches looser than his/her actual fit size. In an exemplary embodiment, the system would add the leeway margin, as specified by the user, to the user's exact fit apparel size in order to find the desired fit for the user. As described below, a user who wishes to view and/or model apparel items may select from the various items of apparel through a shopping environment such as a store or a mall. In these respective environments, the models are allowed to browse the virtual store environment by selecting and inspecting items that are taken from the respective racks and shelves associated with the virtual environment. In the shopping environment, physics based animation can be incorporated to make the shopping environment, its contents and user interaction with the environment realistic. In an exemplary embodiment, the clothes in the shelves and racks can be made to appear realistic by simulating real texture and movement of cloth. Additionally, a live feed can be provided to users from real stores regarding the quantity of a particular item. This information can either be conveyed, for example, either numerically or an animation of a shelf/rack containing the actual number of items in inventory can be displayed or a video of the real store with the items on shelf can be displayed to the user. The live feed feature can be used by the source supplying the apparel to convey other information such as store/brand promotions, special offers, sales, featured items etc. (not restricted to real-time inventory information). Furthermore, the shopping environment can include other stores and fixtures and other items found in a real shopping mall to simulate/replicate real shopping environments as closely as possible. In an exemplary embodiment, food stores and stalls may be augmented in the virtual shopping environment. These 'virtual food stores' could represent simulations or images/videos of fictional or non-fictional stores. These virtual stores would serve as an advertising medium for food brands and products as well as superstores, restaurants, corner stores or any other place providing a food service, manufacturing or serving as the retail outlet for a food brand. There could be virtual ads, products and promotions being housed in these virtual stores. Additionally, these could be linked to actual product and store sites. Virtual characters acting as store personnel offer virtual samples of 'featured food products', just as in a real mall setting. Other items found in real shopping environments that are incorporated include fountains, in an exemplary embodiment. These virtual fountains can be incorporated with physics based animation techniques to simulate water movement as in a real fountain. Store personnel such as sales representatives and customer service representatives are represented by virtual characters that provide online assistance to the user while shopping, speak and orchestrate movements in a manner similar to real store personnel and interact with the user model. An 'augmented reality display table' is featured by system 10 where vendors can display their products to the customer and interact with the customer. For example, a jewelry store personnel may pick out a ring from the glass display for showing the user. A salesperson in a mobile phone store may pick out a given phone and demonstrate specific features. At the same time, specifications related to the object may be displayed and compared with other products. Users also have the ability to interact with the object in 2D, 3D or higher dimensions. The salesperson and customer may interact simultaneously with the object. Physics based modeling may also be supported. This display table may be mapped to a real store and the objects virtually overlaid. In some real malls, one can also find indoor game facilities such as ice-skating rinks, golf parks, basketball etc. Environments that simulate these facilities virtually will be available. Users can engage their models in these activities and participate in a game with others users. As in a real mall, the user can see other 'people' in a virtual mall. These may represent real users or fictional virtual characters. The user will have the option to set their user model as invisible or visible so that their model can be viewed by other users browsing the mall.

In an exemplary embodiment, this collaborative environment works as follows: The local application 271 provides a visualization engine. Webcam content from the customers and the sales personnel may be integrated into or used in conjunction with the engine. If 3D product models are available, they can be used interactively via the common mode or other modes of operation, as discussed with reference to FIG. 7, for example. If product models are unavailable, then webcam views may be used either directly or converted to models based on webcam images (using techniques similar to those discussed in [3] for going from sketch to model in exemplary embodiment). These models/images can then be used in the visualization engine. Interaction with the engine can take place using conventional input/output (I/O) devices such as a keyboard and a mouse, or using I/O devices discussed with reference to FIG. 54. Video capturing devices may be used to capture the view of a counter or a product display in the store, for example. This content may be transmitted both to the salesperson and the customer. Either party can then augment this content with their own input. The customer may also bring in objects into this augmented world, for example, for colour or style matching. Augmentation may be accomplished using techniques similar to those in [4]. The collaborative environment described here with reference to FIG. 36 may be thought of as a 3D version of the collaborative environment described with reference to FIG. 20. All of the tools available in the collaborative environment discussed with reference to FIG. 20 may be available in the collaborative environment of FIG. 36.

The various respective virtual environments that are used, may all have associated with them various multimedia files that may be linked to the respective environments. For example, music, or video files may be linked or embedded into the respective environments. Also, the system 10 may also allow for downloading of music (and other audio files) from a repository of music, in an exemplary embodiment, that may then be played while the user is navigating and/or interacting with their respective environment. The user will have the option of selecting music from the repository and downloading tracks or directly playing the music from a media player within the browser. Additionally, audio files can also run seamlessly in the environment. These can be set by the sponsor of an environment. For example, in a virtual music store environment, the store sponsor can play tracks of new releases or specials being advertised. In another exemplary embodiment, in a movie scene environment, the soundtrack of the movie could play within the environment. These tracks (playlist content, order of tracks, length etc.) can be customized according to the sponsor or user. The sponsor of the environment and the music or media files sponsor do not necessarily have to be the same. Additionally, the user may be given control over the type of media files that are played within or linked with an environment. Instead of a repository of audio files, the medium may also be an online radio, The radio may be mapped to real radio stations. Users have the option to share media files (name, description and other information associated with the file and/or actual content) with their social network or send links of the source of the media files. Users can also order and purchase media files that they are listening to online. In an exemplary embodiment, a 'buy now' link would be associated with the media file that would take the user to the transaction processing page to process the purchase of the media file online.

Users may create their own 3D or 2D virtual spaces by adding virtual components from catalogues. In an exemplary embodiment, a user may rent or buy virtual rooms (2D or 3D) from a catalogue and add virtual furniture, virtual artwork, virtual home electronics such as a TV, refrigerator, oven, washing machine, home entertainment system etc. and other components. The user may add rooms to create a home with outdoor extensions such as a patio and backyard to which components may also be added. Users may visit each other users' virtual spaces and environments. Users may also buy virtual food products, which may be stored in virtual refrigerators or stores. These virtual food products may be designed such that they decrease over time and eventually finish or become spoilt if unused 'virtually'. This would help kids or teenagers, for example, to understand the value of food, its lifecycle, handling and storage and other facts. Furthermore, the proceeds from the purchase of virtual food could be used to sponsor aid in developing countries. In an exemplary embodiment, purchasing a bag of virtual rice may be equivalent to donating a bag of virtual rice as food aid to developing countries. Users may furnish their rooms with objects that change or grow with time such as plants. The user may buy a virtual seed and over time, the seed would grow into a full-size virtual plant. The virtual plant may be designed such that it grows automatically or upon proper caretaking by the user such as providing virtual water, nutrients, sunlight and other necessities to the plant. This would help users to become more empathic and acquire useful skills such as gardening or caretaking. Florists and greenhouses may also find this feature useful. They may design virtual plants and flowers such that their requirements are mapped to the real plants or flowers they represent. For instance, roses may require specific nutrients, soil types, sunlight duration etc. for their proper growth. In an exemplary embodiment, virtual rose plants may be designed to grow only if provided with the necessities (virtual) that real roses require. Thus, these virtual plants would prove useful as instructional or training tools for people who would like to learn how to cultivate specific plants properly before purchasing real plants. Depending on how they raise their virtual plants, users may be given scores. Users would also be able to purchase the real plants from florists, greenhouses and other stores subscribing to system 10, whose information would be available to users. Furthermore, users may buy virtual pets. These virtual pets may be designed to grow on their own or upon proper caretaking by their owners just as in the case of virtual plants. This feature could help users to become better pet caretakers before they buy real pets. The concept of virtual pets can be taken further. Proceeds that are collected from the purchase of virtual pets may be used to support animal shelters or humane societies or animal relief or wildlife conservation efforts. A virtual pet may be mapped to an animal that has been saved as a result of the proceeds collected from the purchase of virtual pets. Users may directly sponsor an animal whose virtual representation they would own upon sponsoring the animal. Users would also receive updates about the welfare of the animal they sponsored (if they are not able to directly own the real animal such as in the case of a wild animal) and about related relief, rescue or conservation efforts associated with similar animals.

The retailer module 58 allows the system 10 to interact with the various respective retailers with which the system 10 is associated. Specifically, the retailer module 58 tracks the respective items that may be purchased through use of the system 10. The retailer module 58 interacts with the retail servers 26 of retailers with respect to product offerings that may be available through the system 10. Information from the retailer module 58 pertaining to items that can be purchased is acquired by system 10. This information may be encapsulated in a CAD (Computer Aided Design) file for example.

Figure 45:
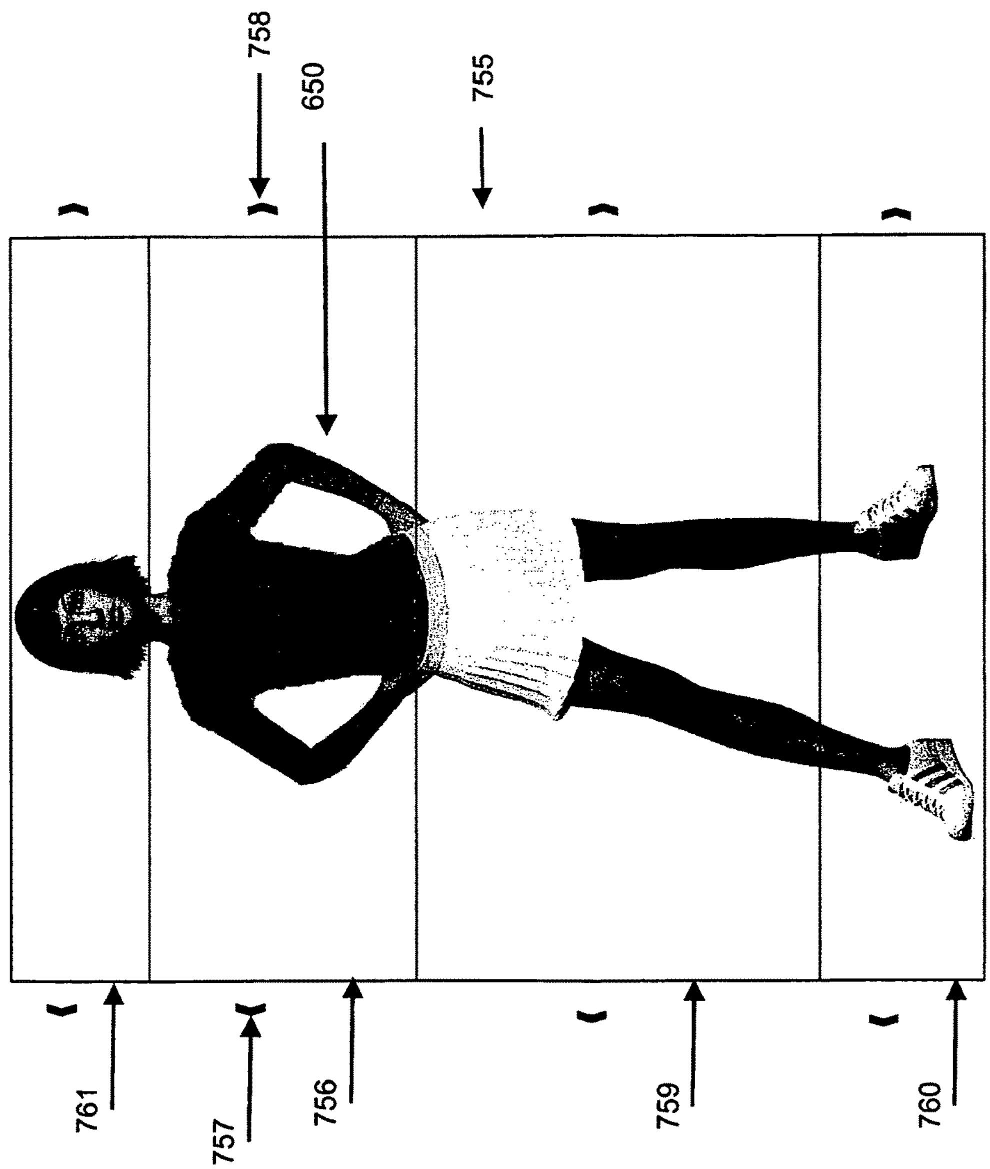
FIG. 45 is an image of a sample style browser display window.

The shopping module 60 allows for users to purchase items that may be viewed and/or modeled. Each retailer in the retailer module 58 may have a customizable store page or virtual store available in the shopping module 60. Users can administer their page or virtual/online store as discussed with reference to FIG. 42. Each store can be customized according to the retailer's needs. Retailers may add web and software components to their store available through system 10. These components include those that would allow the retailer to add featured items, special offers, top picks, holiday deals and other categories of items to their virtual store. The retailer can make available their products for sale through these stores/pages. The users of the system 10 as mentioned above have access to various online product catalogues from virtual stores and/or virtual malls. These catalogues may be mapped from virtual stores and/or virtual malls or real stores and/or malls. The user will be asked specific information relating to the shopping interests and style preferences. The shopping module 60, based on the user-specified preferences and information may also make recommendations regarding items of apparel that are based on the user's interests, preference and style that have been determined from previous purchases. This can be accomplished using a variety of machine learning algorithms such as neural networks or support vector machines. Current implementation includes the use of collaborative filtering [5]. Alternatively, Gaussian process methodologies [6] may also be used. In an exemplary embodiment, using Gaussian process classification, recommendations are made to the user based on information collected on the variables in the user's profile (example: preferences, style, interests) as well as based on the user's purchasing and browsing history. Moreover, the uncertainty that is computed in closed form using Gaussian process classification is used to express the degree of confidence in the recommendation that is made. This can be expressed using statements like 'you may like this' or 'you will definitely love this' etc. The interests of the user may be specified by the user, and alternatively may be profiled by the system 10 based on the user's demographics. The shopping module 60 also provides the user with various search functionalities. The user may perform a search to retrieve apparel items based on criteria that may include, but are not limited to, a description of the apparel including size, price, brand, season, style, occasion, discounts, and retailer. Users can search and shop for apparel based on the look they want to achieve. For example, this could include 'sporty', 'professional', 'celebrity' and other types of looks. Users may also search and shop for apparel belonging to special categories including, but not limited to, maternity wear, uniforms, laboratory apparel etc. Apparel may be presented to the user on virtual mannequins by the shopping module 60. Other forms of display include a 'revolving virtual display' or a 'conveyor belt display' etc. In an exemplary embodiment, a revolving display may assume the form of a glass-like cube or some other shape with a mannequin on each face of the cube/shape showcasing different apparel and/or jewelry. In another exemplary embodiment, a conveyor belt display may feature virtual mannequins in a window, donning different apparel and/or jewelry. The mannequins may move in the window in a conveyor belt fashion, with a sequence of mannequin displays appearing in the window periodically. The speed of the conveyor belt or the revolving display may be modified. Other displays may be used and other manifestations of the conveyor and revolving display may be used. For instance, the mannequins may be replaced by user models or by simply product images and/or other visual/virtual manifestations of the product. Reference is now made to FIG. 45 where another display scheme—the 'Style browser' 755 is shown in an exemplary embodiment, The style browser display operates directly on the user model 650 in that the apparel items in an electronic catalogue are displayed on the user model as the user browses the product catalogue. For example, in the display window 755, the user can browse tops in a catalogue in the window section 756 by using the left 757 and right 758 arrow icons. As the user browses the catalogue, the tops are modeled and displayed directly on the user model 650. Thus, the user is able to examine fit and look information while browsing the catalogue itself. In a similar fashion, the user can browse skirts and pants in the display section 759; shoes in section 760; accessories like earrings, cosmetics and hairstyles in section 760. Right-clicking on a given display section would make available to the user the categories of apparel that the user can browse in that section, in an exemplary embodiment. Displayed apparel (whether in shopping environments, stores or electronic catalogues) may be in 2D or 3D format. Users can also view detailed information regarding apparel. For example, this information includes material properties of the apparel such as composition, texture, etc; cloth care instructions; source information (country, manufacturer/retailer); images describing apparel such as micro-level images that reveal texture; etc. Other information assisting the user in making purchasing decisions may also be displayed. For example, user and customer reviews, ratings, manufacturer's/retailer's/designer's/stylist's notes etc. The display information for each apparel will also include the return policy for that item. This policy may include terms that are different in the case that an item is returned via postal mail versus if the item is taken to a physical store location for return by the customer. In an exemplary embodiment, for the latter case, the return policy may be mapped to the terms and conditions of the physical store itself. This would allow a user to purchase something online and still be able to return it at a physical store location. Alternatively, the retailer may specify a different return policy for the apparel when it is bought online as opposed to when it is bought at the physical store. The return policy may also incorporate separate terms and conditions that take into account the requirements of system 10 for returning any given item. As users are shopping, matching/coordinating items that go with the items the users are looking at or items that are in the users fitting room, shopping cart, or wardrobe, and that fit the users body and their taste, may be presented to the users. Suggestions on coordinating/matching items may also be made across users. For example, if a bride and a bridegroom go on a shopping trip, a wedding dress for the bride and a corresponding/matching tuxedo for the bridegroom that fit them respectively may be presented.

Figure 27:
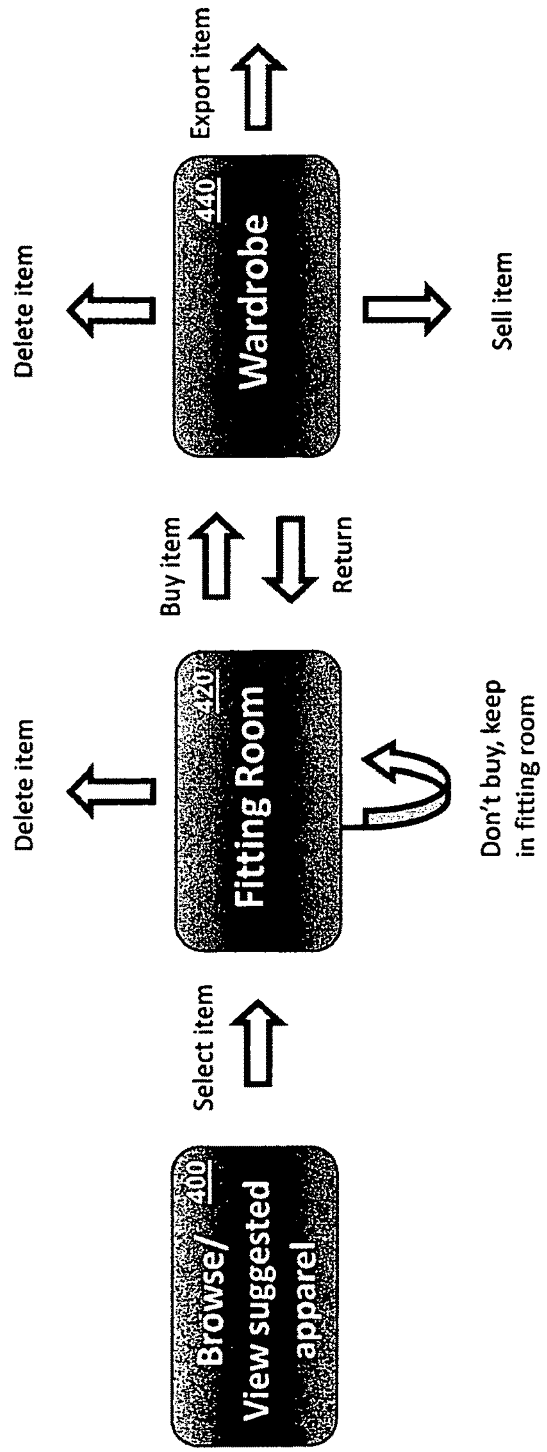
FIG. 27 is an image describing a sample instance of user interaction with the wardrobe and fitting room.

At any time while browsing or viewing products, the user may choose to try on apparel of interest on their user model to test the fit of apparel. In order to facilitate this process, a virtual fitting room is available to the user. The virtual fitting room includes items that the user has selected to try on or fit on their user model and that the user may or may not decide to purchase. In exemplary embodiment, the fitting room provides the user with a graphical, simulated representation of a fitting room environment and the apparel items selected for fitting on the user's model. The user can add an item to their fitting room by clicking on an icon next to the item they wish to virtually try on. Once an item has been added to the fitting room, that item will become available to the user in the local application for fitting on their model. An example of user interaction with the fitting room is illustrated in FIG. 27. While browsing apparel catalogues or viewing suggested apparel items by system 10, the user may choose to add an item to the fitting room for trial fit with their user model. Once the item has been added to the fitting room, the user may try on the item on their user model, and/or decide to purchase the item, in which case the apparel item can be added to the virtual wardrobe described later. Alternately, the user may decide not to purchase the item in which case the item will stay in the fitting room until the user chooses to delete it from their fitting room. Users may make the contents of their fitting room publicly accessible or restrict access to members of their social network or provide limited access to anyone they choose. This option will allow users to identify items of interest that other users have in their fitting room and browse and shop for the same or similar items on system 10. Physics based animation can be incorporated to make the fitting room, its contents and user interaction with the fitting room as realistic as possible. In exemplary embodiment, the clothes in the fitting room can be made to appear realistic by simulating real texture and movement of cloth. With regards to interaction with the digital apparel, accessories and other components, users may be able to drag and drop clothes, optical accessories, hairstyles, other apparel, accessories, and digitized components and their manifestations onto their character model. In one exemplary embodiment, they will be able to drag components placed in the fitting room or wardrobe or from an electronic catalogue onto their model. The drag-and-drop functionality may incorporate physics based animation to enhance realism. Optionally, the users may specify where things are placed on their character model. At any time while browsing or viewing products or trying apparel on their user model, the user may choose to order and purchase the real apparel online. The user may also submit fit information (visual as well as text) including information on where alterations may be needed, as provided by the modeling module 50, as well as any additional information associated with an apparel item that the user is purchasing online to a 'tailoring' service. This service would be able to make the requisite alterations for the user for a fee. A facility would also be available to the user to custom order clothes online from a designer or supplier of apparel if they (designer, supplier) choose to provide the service. In the case of purchasing gifts for other people, the user may build a model for the person for whom the gift is intended and fit apparel on to this third party model to test goodness of fit before purchasing the apparel. If the user for whom the gift is being purchased already has a user account/profile available in system 10, then their user model may be accessed by the gift-giver upon receiving permission from the user for purposes of testing goodness of fit. If a user wishes to access fit or other information or the user model of a friend, the friend would receive a notification that the specific information has been requested by the user. The friend would have the option to grant or deny access to any or all of their information or their user model. If the friend denies access, the user may still be able to purchase a gift for the friend as the system will be able to access the friend's information and inform the user if a particular apparel is available in their friend's size. The system would, thus, provide subjective information regarding the fit of an apparel with respect to another user without directly revealing any fit or other information of the user for whom the item is being purchased. If an apparel item is available in the friend's size, the user may order it upon which the system would deliver the appropriate sized apparel (based on the sizing and fit information in the friend's profile) to the friend. A confirmation request may be sent to the friend for confirming the size of the apparel before the purchase order is finalized. (This method can be used for other products such as prescription eyewear). Users have the option to display icons on their profile and/or home page that indicate gifts received from other people (items purchased on the site for respective user by other users). A 'Mix and Match' section will allow users to view items from different vendors. This could be, for instance, for purposes of coordinating different pieces of apparel (for example tops, bottoms, jewelry, bags). Users may coordinate items and visualize their appearance on the user model. This visualization would assist users in the mix and match process. Items on sale may also be presented from different vendors in the mix and match section. Items on sale/discounted items may also be presented in other areas of the site. Furthermore, there may be other sections on the site featuring special items available for purchase. In exemplary embodiment, these may include autographed apparel and other goods by celebrities. Not only is the user able to purchase real apparel from the site (described later on), but the user can also buy virtual manifestations of apparel, hairstyles, makeup etc. Users may be interested in purchasing these virtual items for use in external sites, gaming environments, for use with virtual characters in other environments etc. Users can also search for and buy items on other users' shopping lists, registries and/or wishlists. Users may also set-up gift registries accessible on their member pages for occasions such as weddings, anniversaries, birthdays etc.

The shopping module 60 also determines for each user a preferred or featured style that would be suitable for the respective user. The determination of a preferred or featured style may be based on various inputs. Inputs may include the preferences and picks of a fashion consultant of which the system 10 keeps track. The one or more fashion consultant's choices for featured styles may be updated into the system 10, and the system 10 then provides respective users with updated style choices based on the selections of the fashion consultants. Also, styles and/or apparel items may be presented to the user based on information the system 10 has collected regarding their shopping preferences, stores, brands, styles and types of apparel that are purchased, along with personal information related to their physical profile and age. In addition, the user model may be used to make apparel suggestions by the system. In an exemplary embodiment, the convex hull of the user model is used to determine apparel that would best fit/suit the user. The various featured looks that are selected by the system 10 may be presented to the user upon request of the user, and the selected featured looks may also be presented to the user upon login to the system. Also, various selected styles with a user's model may be presented to the user upon request or upon login where the user model is modeling apparel that is similar to what celebrities or other notable personalities may be wearing. Fashion consultants, stylists and designers may be available on site for providing users with fashion tips, news, recommendations and other fashion related advice. Live assistance may be provided through a chat feature, video and other means. Additionally, it may be possible for users to book appointments with fashion consultants of their choice. Animated virtual characters representing fashion consultants, stylists and designers may also be used for the purpose of providing fashion related advice, tips news and recommendations. Virtual fashion consultants may make suggestions based on the user's wardrobe and fitting room contents. It would also be possible for users interested in giving fashion advice to other users to do so on the site. In an exemplary embodiment, this may be accomplished by joining a 'fashion amateurs' network where members may provide fashion advice to other users or even display their own fashion apparel designs. Consultants may be available to provide assistance with other services such as technical, legal, financial etc.

The wardrobe module 62 provides the user with a graphical, simulated representation of the contents of their real and/or virtual wardrobe. The virtual wardrobe comprises the respective items of apparel that are associated with the user in the system 10. For example, the virtual wardrobe will store all of the items that the user has purchased. FIG. 27 describes an instance of user interaction with the virtual wardrobe 440 and fitting room 420. The user may browse apparel 400 displayed by the system, an instance of which is described with reference to FIG. 22. Once the user decides to purchase an item, it will be added to the virtual wardrobe. The user may then choose to keep the item in their wardrobe or delete it. If the user decides to return an item, that item will be transferred from the user's wardrobe to the fitting room. The virtual wardrobe may also comprise representations of apparel items that the user owns that are not associated with the system 10. For example, the user may upload respective images, animation, video and other multimedia formats or any combination thereof of various real apparel items to the system 10. Once uploaded, the users are then able to interact with their respective physical wardrobe contents through use of the system 10. Identification (ID) tags on the virtual wardrobe items may assist the user in mapping items from the real to virtual wardrobe. An ID tag can have standard or user defined fields in order to identify a given item. Standard fields, for instance, can include, but are not limited to, ID number, colour, apparel type, occasion, care instructions, price, make and manufacturer, store item was purchased from, return policy etc. User defined fields may include, for example, comments such as 'Item was gifted to me by this person on this date', and other fields. Users are able to browse the contents of their wardrobe online. This allows the user the ability to determine which apparel items they may need to purchase based on their need and/or desire. Users may make the contents of their wardrobe publicly accessible or restrict access to members of their social network or provide limited access to anyone they choose. This option will allow users to identify items of interest that other users have in their wardrobe and browse and shop for the same and/or similar items on the system 10. An icon may appear on the profile/home page of the user—'buy what this user has bought' to view recent purchases of the user and buy the same and/or similar items via system 10. The user may also decide to conduct an auction of some or all of the real items in their wardrobe. In such a case, the user will be able to mark or tag the virtual representations of these items in their virtual wardrobe and other users with access to the wardrobe can view and purchase auction items of interest to them. In exemplary embodiment, an icon may appear on the profile page of the user indicating that they are conducting an auction to notify other users. It may be possible for users to mark items in their virtual wardrobe for dry-cleaning. This information may be used to notify dry-cleaning services in the area about items for pick-up and delivery from respective users in an exemplary embodiment. Physics based animation can be incorporated to make the wardrobe, its contents and user interaction with the wardrobe as realistic as possible. In exemplary embodiment, the clothes in the wardrobe can be made to appear realistic by simulating real texture and movement of cloth.

Users may organize their virtual wardrobe contents according to various criteria. The wardrobe classification criteria may include, but are not limited to, colour, style, occasion, designer, season, size/fit, clothing type, fabric type, date of purchase etc. By indexing the apparel items that belong to the user according to various criteria, the user may then be able to determine through various search criteria what items of apparel to wear. The virtual wardrobe may also have associated with it multimedia files such as music, which provide a more enjoyable experience when perusing the contents of the virtual wardrobe. A virtual/real style consultant and/or other users may be available to advise on the contents of the wardrobe.

The advertising module 64 in an exemplary embodiment coordinates the display and use of various apparel items and non-apparel items. Advertisers associated with the system 10 wish for their particular product offering to be displayed to the user in an attempt to increase the product's exposure. The advertising module determines which offering associated with an advertiser is to be displayed to the user. Some components related to the advertising module 64 are linked to the environment module, the details of which were discussed in the section describing the environment module 56. These include, in exemplary embodiments, environments based on a theme reflecting the product being advertised; components associated with environments such as advertisement banners and logos; actual products being advertised furnishing/occupying the environments. Music advertisers can link environments with their playlists/soundtracks/radio players. Movie advertisers can supply theme based environments which may feature music/apparel/effigies and other products related to the movie. Users will be able to display character models on their profile page wearing sponsored apparel (digitized versions) that sponsors can make available to users through the advertising module 64; or users can display images or videos of themselves in their profile wearing real sponsored apparel. In a similar manner, users supporting a cause may buy real or digital apparel sponsoring the cause (for example, a political or charitable cause) and display their character model in such apparel or put up videos or images of themselves in real versions of the apparel. Advertisers belonging to the tourism industry may use specific environments that showcase tourist spots, cultural events, exhibitions, amusement parks, natural and historical sites and other places of interest to the tourist. The above examples have been mentioned as exemplary embodiments to demonstrate how advertisers can take advantage of the environment module 56 for brand/product advertising purposes.

The entertainment module 66 encompasses activities that include the user being able to interact and manipulate their model by animating it to perform different activities such as singing, dancing, etc and using it to participate in gaming and augmented reality environments and other activities. Some features associated with the entertainment module 66 have already been discussed in the context of the environment module 56. These include the ability of the user to animate the virtual model's movements, actions, expressions and dialogue; the facility to use the model in creating music videos, movies, portraits; interacting via the model with different users in chat sessions, games, shopping trips etc.; and other means by which the user may interact with the virtual model or engage it in virtual activities. Additionally, the entertainment module 66 features the user model or another virtual character on the user's profile page as an 'information avatar' to provide news updates, fashion updates, information in the form of RSS feeds, news and other feeds and other information that is of interest to the user or that the user has subscribed to. The character model may supply this information in various ways, either through speech, or by directing to the appropriate content on the page or by displaying appropriate content at the request of the user, all of which are given as exemplary embodiments. The main purpose of using the virtual model to provide information feeds and updates of interest to the user is to make the process more 'human', interactive and to provide an alternative to simple text and image information and feed content. Further to this, the 'information avatar' or 'personal assistant' can incorporate weather information and latest fashion news and trends, as an exemplary embodiment, to suggest apparel to wear to the user. Information from the media agency servers 25 and entertainment servers 23 is used to keep the content reported and used by the 'information avatar' updated. Users will be able to interact with each other using creative virtual tools. An example includes interactive virtual gifts. These gifts may embody virtual manifestations of real gifts and cards. Users may have the option to virtually wrap their presents using containers, wrapping and decoration of their choice. They may also set the time that the virtual gift automatically opens or is allowed to be opened by the gift-receiver. Exemplary embodiments of gifts include pop-up cards and gifts; gifts with text/voice/audio/video/animated messages or coupons and other surprises; gifts that grow or change over time. An example of a gift that changes over time constitutes a tree or a plant that is still a seedling or a baby plant when it is gifted and is displayed on the gift-receiver's home page for example. Over fixed time intervals, this plant/tree animation would change to reflect virtual 'growth' until the plant/tree is fully grown at a specified endpoint. The type of plant/tree may be a surprise and may be revealed when the plant/tree is fully grown at the end of the specified period. There may be a surprise message or another virtual surprise/gift that is displayed/revealed to the user when the plant/tree reaches the endpoint of the growth/change interval. Gifts that change over time may include other objects and are not necessarily restricted to the examples above.

The server application 22 also has associated with it a data store 70. The server application 22 has access to the data store 70 that is resident upon the portal server 20 or associated with the portal server 20. The data store 70 is a static storage medium that is used to record information associated with the system 10. The data store 70 is illustrated in further detail with respect to FIG. 4.

Figure 4:
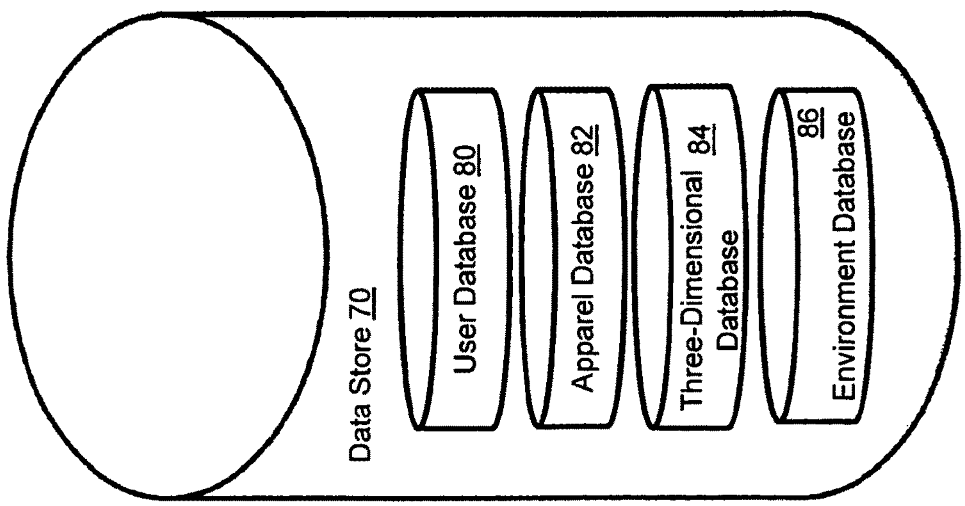
FIG. 4 is a block diagram of the components of a data store.

Reference is now made to FIG. 4 where the components of the data store 70 are shown in a block diagram in an exemplary embodiment. The components of the data store 70 shown here are shown for purposes of example, as the data store 70 may have associated with it one or more databases. The databases that are described herein as associated with the data store are described for purposes of example, as the various databases that have been described may be further partitioned into one or more databases, or may be combined with the data records associated with other databases.

The data store 70 in an exemplary embodiment comprises a user database 80, an apparel database 82, a 3-D model database 84, and an environment database 86. The user database 80 in an exemplary embodiment is used to record and store information regarding a user of the system 10. Such information includes, but is not limited to a user's access login and password that is associated with the system 10. A user's profile information is also stored in the user database 80 which includes, age, profession, personal information, and user's physical measurements that have been specified by the user, images provided by the user, a user's history, information associated with a user's use of the system. A user's history information may include, but is not limited to, the frequency of their use of the system, the time and season they make purchases, the items they have purchased, the retailers from whom the items were purchased, and information regarding the various items. Information regarding the various items may include, but is not limited to, the colour, style and description of the items. The apparel database 82 stores information regarding the various items of apparel that are available through the system 10. The 3-D model database 86 stores predetermined 3-D models and parts of various 3-D models that are representative of various body types. The 3-D models are used to specify the user model that is associated with the user. The environment database 86 stores the various environments that are provided by the system 10 and that may be uploaded by users as described below.

Figure 5:
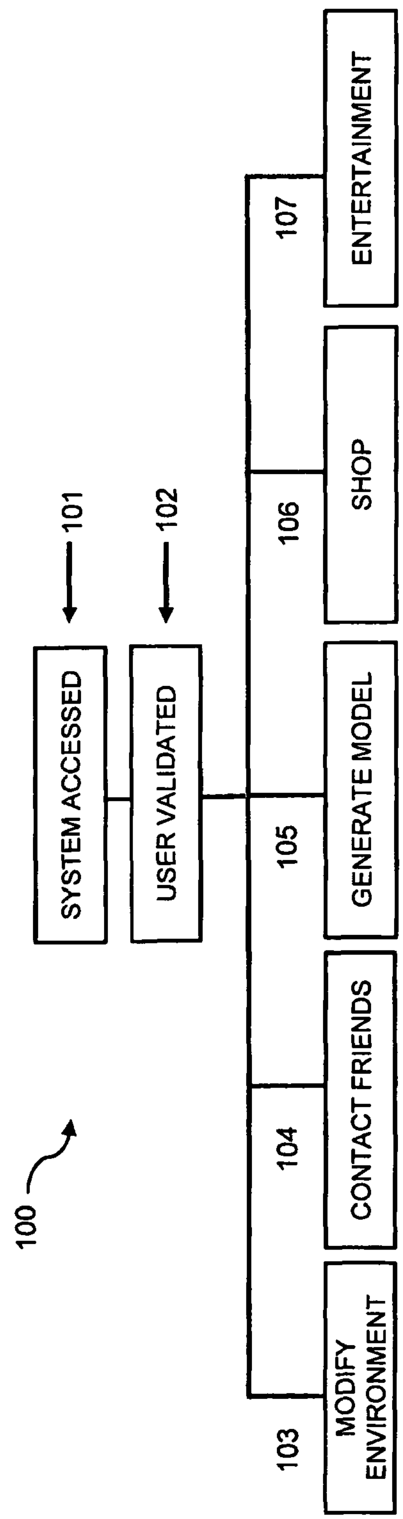
FIG. 5 is a flowchart diagram of an access method.

Reference is now made to FIG. 5, where a flowchart illustrating the steps of an access method 100 is shown in an exemplary embodiment. Access method 100 is engaged by the user when the user first logs into the system 10. The access method 100 describes the various options that are available to the user upon first accessing the system. Method 100 begins at step 101, where the user accesses the system 10 by logging into the system 10. Users can also browse the system without authentication as a guest. Guests have access to limited content. As described above in an exemplary embodiment, the system 10 is accessible through the Internet. As the system 10 is accessible through the Internet, the user accesses the system by entering the URL associated with the system 10. Each user of the system 10 has a login and password that is used to access the system 10. Upon successful validation as an authorized user, method 100 proceeds to step 102, where the user is presented with their respective homepage. The user may be shown their user model (if they have previously accessed the system) displaying featured items of apparel when they log in. The user is presented with a variety of options upon logging into the system 10. Method 100 proceeds to step 103 if the user has selected to modify their respective environments associated with the user. At step 103, the user as described in detail below has the ability to modify and alter the respective virtual environments that are associated with the user. Method 100 proceeds to step 104 when the user chooses to manage their friends. Users may add other users from within the system 10, and from external community sites as their friends, and may manage the interaction with their friends. The management of friends in the system 10 is explained in further detail below. Method 100 proceeds to step 105 when the user wishes to generate or interact with their user model. Method 100 proceeds to step 106 where the user wishes to view items that may be purchased. Method 100 proceeds to step 107 where the user may engage in different collaborative and entertainment activities as described in this document. The steps that have been described herein, have been provided for purposes of example, as various additional and alternative steps may be associated with a user's accessing of their respective home page.

Figure 6A:
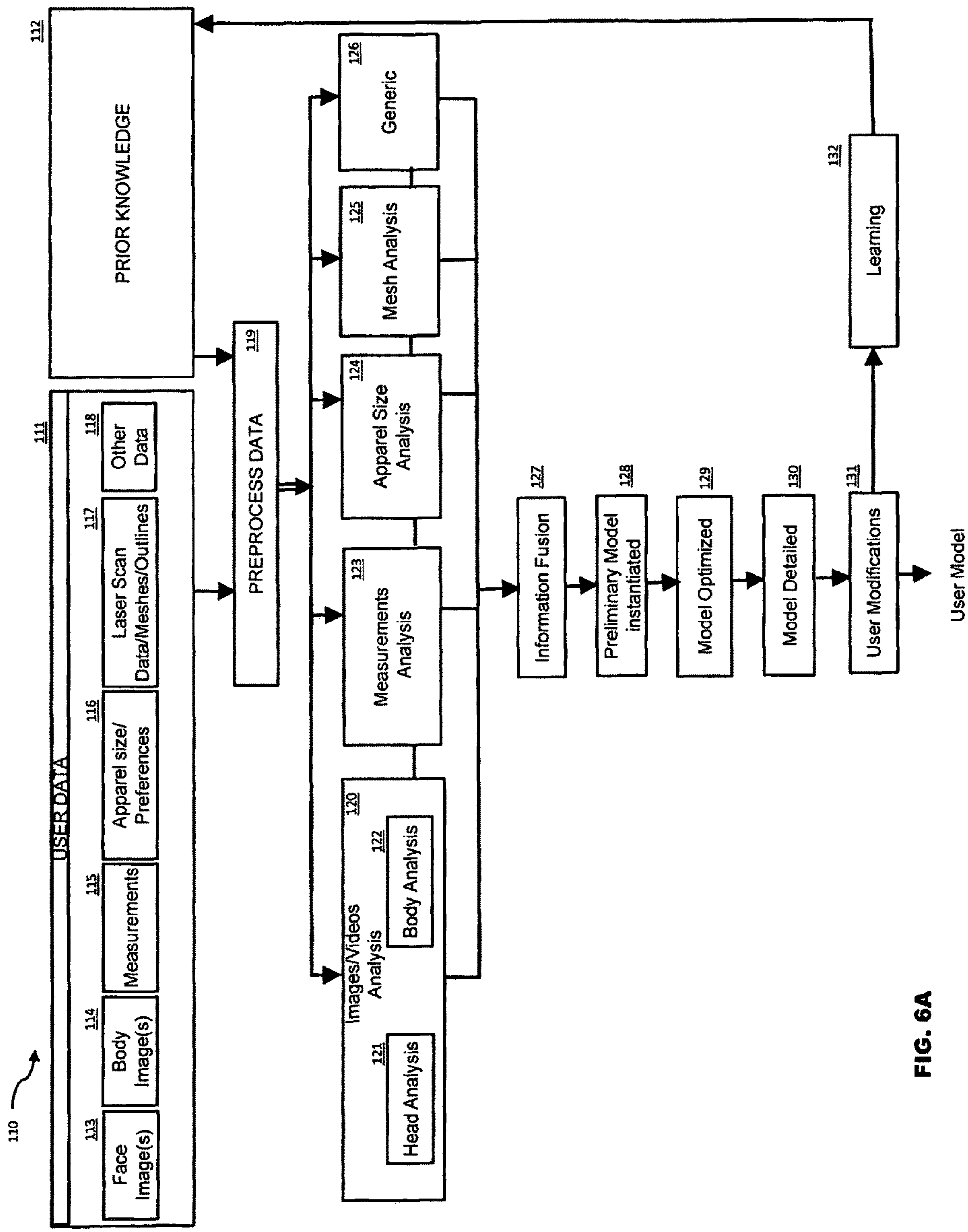
FIG. 6A-J illustrate the model generation method.
Figure 11:
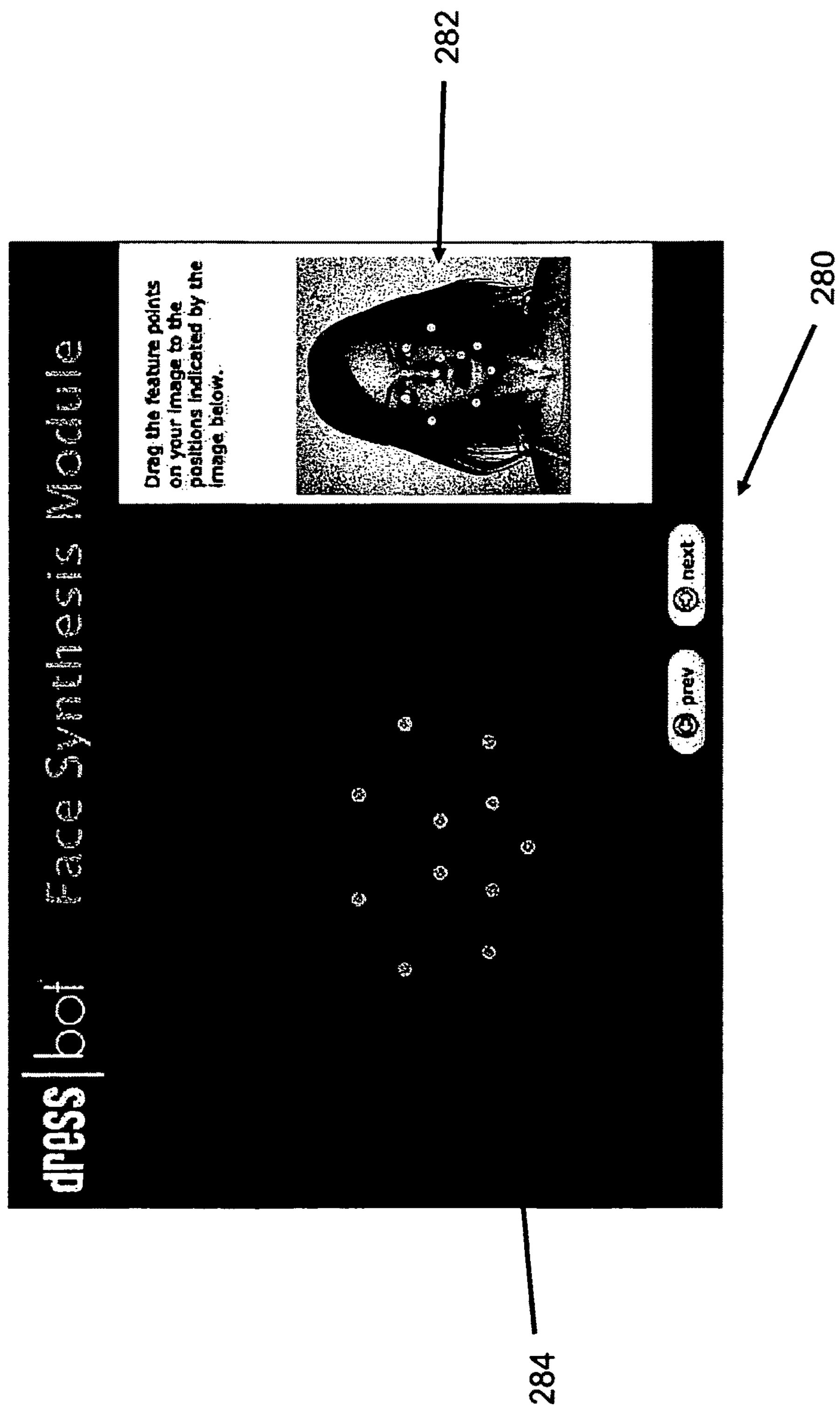
FIG. 11 is an image of a sample facial synthesis window.

Reference is now made to FIG. 6A, where the steps of a detailed model generation method 110 are shown in an exemplary embodiment. The model generation method 110 outlines the steps involved in generating the 3-D user model. Method 110 begins at step 111, at which the user provides data to the system 10. The data can be provided all at once or incrementally. The data can be provided by the user or by his/her friends. Friends may grant or deny access to data request and have control over what data is shared. The data provided may include but is not limited to image(s) and/or video(s) of the face 113 and/or body 114; measurements 115 of the body size including the head as described below; apparel size commonly worn by the user and the preferred apparel size(s) and preferences 116 for style of clothing (such as fitted, baggy, preferred placement of pants (above, below, or on waist), color, European, trendy, sophisticated etc.), brands, etc.; laser scan data (obtained, for example, from a booth at a store equipped with a laser scanner), meshes (for instance, those corresponding to impressions of the ear or foot), outlines of body parts (for instance, those of the hands and feet), mould scans, mocap data, magnetic resonance imaging (MRI), ultrasound, positron emission tomography (PET), and computed tomography (CT) data 117; and other data 118 such as correspondence between feature points on the 3D model's surface and the 2D images supplied by the user (for example the location of the feature points on the face as shown in FIG. 11), references to anatomical landmarks on the user supplied data, and user specific info such as the age or age group, gender, ethnicity, size, skin tone, weight of the user. User data may be imported from other sources such as social-networking sites or the virtual operating system described later in this document. (Such importing of data also applies to the other portals discussed in this document).

The input to the method 110 includes prior information 112 including, but not limited to, annotated 3D surface models of humans that include information such as anatomical landmarks, age, gender, ethnicity, size, etc.; anatomical information, for instance, probability densities of face and body proportions across gender, age groups, ethnic backgrounds, etc.; prior knowledge on the nature of the input data such as shape-space priors (SSPs) (described below), priors on measurements, priors on acceptable apparel sizes, priors on feature point correspondence; sequencing of steps for various action factors (described below), etc. The prior information 112 includes data stored in the data store 70. The prior information 112 is also used to determine "surprise" as described later in this document.

Based on the information provided at step 111 or data from 113-118, system 10 makes recommendations to the user on stores, brands, apparel as well as provides fit information, as described previously. As users browse apparel, the system informs the user about how well an apparel fits, if the apparel is available in a given user's size and the specific size in the apparel that best fits the user. In suggesting fit information, the system takes into account user fit preferences, for example a user's preference for loose fit clothing. The system may suggest whether apparel suits a particular user based on the user's style preferences. In exemplary embodiment, there may be a "your style" field that gives an apparel a score in terms of style preferred by the user. In another exemplary embodiment, the system may recommend a list of items to the user ordered according to user preferences. For instance, a user may prefer collar shirts over V-necks. Furthermore, the user may not like turtlenecks at all. When this user browses a store collection with different shirt styles, the system may present the shirt styles to the user in an ordered list such that the collar shirts are placed above the V-neck shirts and the turtlenecks are placed towards the bottom of the ordered list, so that the user has an easier time sorting out and choosing styles that suit their taste and preferences from the store collection.

In another exemplary embodiment, the system may combine style preferences as specified the user, and/or user style based on buying patterns of user and/or other users' ratings of apparel, and/or fashion consultant ratings and/or apparel popularity (assessed according to the number of the particular apparel item purchased for example). Any combination of the above information may be used to calculate the "style score" or "style factor" or "style quotient" of a particular item (algorithm providing the score is referred to as "style calculator). In exemplary embodiment, a user may select the information that the system should use in calculating the style factor of a particular item. The user may inquire about the style score of any particular item in order to guide their shopping decision. The system may use the scores calculated by the style calculator in order to provide apparel recommendations; style ratings of products and apparel items; user-customized catalogues and lists of products that are ordered and sorted according to an individual's preferences and/or popularity of apparel items.

Given apparel size, the system can inform a user of the body measurements/dimensions required to fit apparel of the specified size. Alternatively, given a user's body measurements, the system can inform the user of the apparel size that would fit in a given brand or make/manufacturer. Further, the system can suggest sizes to the user in related apparel. In exemplary embodiment, if a user is browsing jackets in a store and the system has information about the shirt size of the user, then based on the user's shirt size, the system can suggest the appropriate jacket sizes for the user. In an exemplary embodiment, the system can provide fit information to the user using a referencing system that involves using as reference a database containing apparel of each type and in each size (based on the standardized sizing system). Body measurements specified by a user are used by the system to estimate and suggest apparel size that best meets the user's fit needs ('fit' information incorporates user preferences as well such as preference for comfort, loose or exact fit etc.). The reference apparel size database is also used to suggest size in any of the different types of apparel such as jackets or coats or jeans or dress pants etc. In another exemplary embodiment of providing fit information using the reference apparel database, a user may be looking for dress pants, for instance, and the system may only know the user's apparel size in jeans and not the user's body measurements. In this case, in exemplary embodiment, the system compares jeans in the user's size from the reference apparel database with dress pants the user is interested in trying/buying, and by incorporating any additional user fit preferences, the system suggests dress pants that would best fit the user i.e., are compatible with the user's fit requirements. Fit information may specify an uncertainty along with fit information in order to account for, in exemplary embodiment, any differences that may arise in size/fit as a result of brand differences and/or apparel material properties and/or non-standardized apparel size and/or subjectivity in user preferences and/or inherent system uncertainty, if any exists. In exemplary embodiment, the system informs a user, who prefers exact fit in shirts, that a shirt the user is interested in purchasing, and which is a new polyester material with a different composition of materials and that stretches more as a result, fits with ±5% uncertainty. This is due to the fact that the stretch may or may not result in an exact fit and may be slightly loose or may be exact. Since the material is new and the system may not have information on its material properties and how such a material would fit, it cannot provide an absolute accurate assessment of the fit. It instead uses material information that is close to the new material in order to assess fit, and expresses the uncertainty in fit information. Fit information is communicated to the user, in exemplary embodiment, via text, speech or visually (images, video, animation for example) or any combination thereof. An API (Application Programming Interface) would be open to vendors on the retail server or portal server on system 10 so that vendors can design and make available applications to users of system 10. These applications may include, in exemplary embodiment, widgets/applications that provide fit information specific to their brands and products to users; store locater applications etc. In an exemplary embodiment, an application that lets vendors provide fit information works simply by looking up in a database or using a classifier such as Naïve Bayes [7-9] or k-nearest neighbours (KNN) [9, 10]. For example, an application may state whether a garments that a user(s) is browsing from a catalog fits the user(s). In exemplary embodiments: (1) Database. The application can look up the user's size and the manufacturer of the clothing in a database to find the size(s) corresponding to the given manufacturer that fits the user. If the item currently being viewed is available in the user's size, the item is marked as such. The database can be populated with such information a priori and the application can add to the database as more information becomes available. (2) Naïve Bayes. The a posteriori probability of an apparel size (as) fitting a user given the user's body size (us) information and the manufacturer of the apparel (m) can be computer using the Bayes rule, This can be expressed as the product of the probability of the user's size (us) given the apparel size (as) and the manufacturer (m) of the apparel, and that of the prior probability of the apparel size given the manufacturer, divided by the joint probability of the user's size apparel size given the manufacturer (i.e. $p(as|us,m)=p(us|as,m)p(as|m)/p(us,as|m)$). The prior probabilities can be learnt by building histograms from sufficiently large data and normalizing them so that the probability density sums to one. The user may be presented with items that fit the user, or the apparel sizes that fit the user may be compared with the item that the user is currently viewing and if the item that is being viewed belongs to the apparel sizes that fit the user, a check mark or a "fits me" indication may be made next to the item. (3) KNN. Information on the body size (for example, measurements of various parts of the body), apparel size for different manufacturers for both males and females, and (optionally) other factors such as age are stored in a database for a sufficiently large number of people. Each of these prices of information (i.e. body size, apparel size) is multiplied by a weight (to avoid biases). Given a new body size, the closest exemplar is found by computing the Euclidean distance between the given body size (multiplied by the associated weights for each measurement) and those in the database, The majority vote of the output value (i.e. the corresponding field of interest in the database, for example, the apparel size corresponding to the body measurements) of the k-nearest neighbours (where k is typically taken to be an odd number) is taken to be the most reasonable output. This output value is then divided by the corresponding weigh (weight can take the value 1 also). This could also be used in any other combination of inputs and outputs. For example, the input could be the apparel size for a given manufacturer and the output could be the body sizes that fit this apparel. In an exemplary embodiment, when browsing for products, given the user's body size (which may be stored in a repository) and the manufacturer whose items the user is currently looking at, the apparel sizes that fit the user may be computed and the user may be presented with the available sizes for the user. The user can also filter catalogs to show only items that fit the user or correspond to the user's preferences.

Based on a user's apparel size, the system can point out to the user if a product is available in the user's size as the user is browsing products or selecting products to view. The system may also point out the appropriate size of the user in a different sizing scheme, for example, in the sizing scheme of a different country (US, EUR, UK etc.). In suggesting appropriate sizes to user in products that may vary according to brand, country, and other criteria, the system also takes into account user fit preferences. For instance, a user may want clothes to be a few inches looser than his/her actual fit size. In an exemplary embodiment, the system would add the leeway margin, as specified by the user, to the user's exact fit apparel size in order to find the desired fit for the user.

Method 110 begins at the preprocessing step 119 at which it preprocesses the user data 111 using prior knowledge 112 to determine the appropriate combination of modules 120, 123, 124, 125, and 126 to invoke. Method 110 then invokes and passes the appropriate user data and prior knowledge to an appropriate combination of the following modules: image/video analysis module 120, measurements analysis module 123, apparel size analysis module 124, mesh analysis module 125, and a generic module 126 as described in detail below. These modules 120, 123, 124, and 125 attempt to construct the relevant regions of the user model based on the input provided. At the information fusion step 127, the data produced by the modules 120, 123, 124, 125 and 126 is fused. Method 110 then instantiates a preliminary model at step 128, optimizes it at the model optimization step 129, and details it at step 130. Method 110, then presents the user with a constructed model at step 131 for user modifications, if any. The constructed model and the user changes are passed on to a learning module 132, the output of which is used to update the prior knowledge in order to improve the model construction method 110. As method 110 proceeds, its intermediary progress is shown to the user. At any point during the model construction method 110, the user is allowed to correct the method. In an exemplary embodiment, this is done by displaying the model at the intermediately steps along with the parameters involved and allowing the user to set the values of these parameters though an intuitive interface. At the conclusion of method 110, a user model is generated. Each of the steps of method 110 is described in further detail below.

Measurements 115 provided as input to the method 110 include, in an exemplary embodiment, measurements with respect to anatomical landmarks, for example, the circumference of the head and neck, distance from trichion to tip of nose, distance from the tip of the nose to the mental protuberance, width of an eye, length of the region between the lateral clavicle region to anterior superior iliac spine, circumference of the thorax, waist, wrist circumference, thigh circumference, shin length, circumference of digits on right and left hands, thoracic muscle content, abdominal fat content, measurements of the pelvis, measurements of the feet, weight, height, default posture (involving measurements such as elevation of right and left shoulders, stance (upper and lower limbs, neck, seat, waist, etc.), humping, etc.). Apparel size/preferences 116 include, in an exemplary embodiment, clothing size such as dress size (eg. 14, 8, etc.), hat size, shoe size, collar size, length of jacket, trouser inseam, skirt length etc., including an indication of whether measurements represent an exact size or include a preferred margin or are taken over clothes. The specific measurements differ for males and females reflecting the anatomical difference between the genders and differences in clothing. For instance, in the case of females, measurements may include a more elaborate measurement of the upper thorax involving measurements such as those of the largest circumference of the thorax covering the bust, shoulder to bust length, bust to bust length etc. On the other hand, in the case of males, owing to lower curvature, fewer measurements of the chest may be required. Similarly, for the case of clothing, women may provide, for instance, the length of a skirt, while men may provide a tie size. Similarly, children and infants are measured accordingly. The availability of information on anatomical landmarks makes it possible to derive anatomically accurate models and communicate fit information to the user as described below. Strict anatomical accuracy is not guaranteed when not desired by the user or not possible, for example, under stringent computational resources. A printable tape measure is provided to the user as a download to ease the process of measuring. Image(s) and/or video(s) of the face 113 and/or body 114 provided to the system can also be imported from other sources and can also be exported to other destinations. In an exemplary embodiment, the method 110 may use images that the user has uploaded to social networking sites such as Facebook or Myspace or image sharing sites such as Flickr.

The method 110 can work with any subset of the data provided in 111, exemplary embodiments of which are described below. The method 110 is robust to incomplete data and missing information. All or part of the information requested may be provided by the user i.e. the information provided by the user is optional. In the absence of information, prior knowledge in the form of symmetry, interpolation and other fill-in methods, etc are used as described below. In the extreme case of limited user data, the method 110 instantiates, in an exemplary embodiment, a generic model which could be based on an average model or a celebrity model. Depending on factors such as the information provided by the user(s), computational power of the client platform, shader support on client machine, browser version, platform information, plugins installed, server load, bandwidth, storage, user's preferences (eg. photorealistic model or a version of nonphotorealistic rendering (NPR)) etc., the method 110 proceeds accordingly as described below. These factors are herein referred to as action factors. Depending on the action factors, a 3D model of appropriate complexity is developed. When a highly complex (a higher order approximation with a higher poly count) model is generated, a downsampled version (a lower poly count model) is also created and stored. This lower poly count model is then used for physical simulations in order to reduce the processing time while the higher poly count model is used for visualization. This allows plausible motion and an appealing visualization. Goodness of fit information for apparel is computed using the higher poly count model unless limited by the action factors.

Method 110, at the preprocessing step 119 at which it preprocesses the user input data using prior knowledge to determine which of the modules 120, 123, 124, 125 and 126 to invoke; depending on the input provided and the action factors, an appropriate combination of modules 120, 123, 124, 125 and 126 is invoked. The method 110 attempts to construct the most accurate model based on the data for the given action factors. The accuracy of a model constructed using each of the modules 120, 123, 124, 125 and 126 is available as prior knowledge 112, and is used to determine the appropriate combination of modules 120, 123, 124, 125 and 126 to invoke. In an exemplary embodiment where the client platform is computationally advanced (modern hardware, latest browser version, shader support, etc.), if only images of the face and body are provided by the user, only the image/video analysis module 120 is invoked; if only body measurements are provided, only the measurements analysis module 123 is invoked; if only apparel size information is provided, only the apparel size analysis module 124 is invoked; if only a full body laser scan is provided, only the mesh analysis module is invoked; if only apparel size information and an image of the face is provided, only the apparel size analysis module 124 and the images/videos analysis module, more specifically the head analysis module 121, are invoked; if only an image of the face is provided, only the generic module 126 and the images/videos analysis module, more specifically the head analysis module 121, are invoked; if an image of the face, body measurements and a laser scan of the foot is provided the image/videos analysis module, more specifically the head analysis module 121, the measurements analysis module and the mesh analysis modules are invoked and so on. For regions of the body, for which information is unavailable, the generic module is invoked. In the extreme case of no user information or very limited computational resources, only the generic module 126 is invoked. Other data 118 such as age and gender, if provided, and prior knowledge is available to each to the modules 120, 123, 124, 125 and 126 to assist in the model construction process. Parameters may be shared between the modules 120, 123, 124, 125 and 126. Each of the modules 120, 123, 124, 125 and 126 are described in detail next.

Reference is now made to the images/videos analysis module 120 in FIG. 6A. This module consists of a head analysis module 121 and a body analysis module 122, in an exemplary embodiment. The head analysis module 121 and the body analysis module 122 construct a 3-D model of the user's head and body, respectively, based on the image(s) and video(s) provided. The head analysis module 121 and the body analysis module 122 may work in parallel and influence each other. The head analysis module 121 and the body analysis module 122 are described in detail below.

Figure 6B:
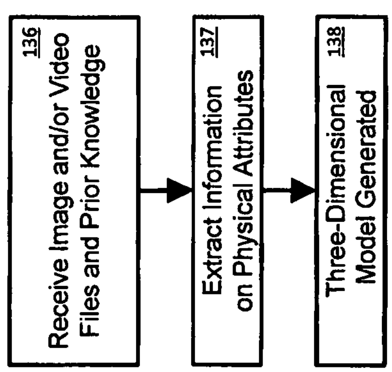

Reference is now made to FIG. 6B where the steps of the model construction process of the images/videos analysis module 120 are outlined in an exemplary embodiment. After receiving image and or video file(s), this module extracts information on the user's physical attributes at step 137 and generates a three-dimensional model at step 138. A detailed description of this process is provided below.

Figure 6C:
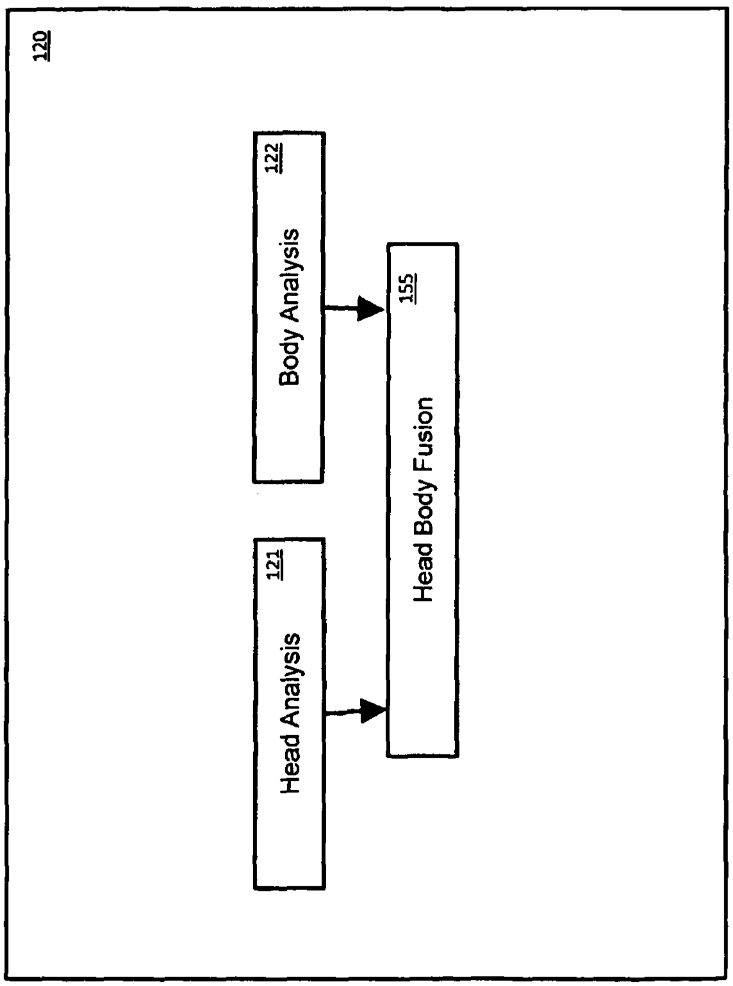

Reference is now made to FIG. 6C where it is shown, in an exemplary embodiment, that the steps of the model construction process in the image/video analysis module are handled separately for the user's face and the body. The head analysis module 121 produces a model of the user's head while the body analysis module 122 produces a model of the user's body. These models are then merged at the head-body fusion step. A detailed description of this process is provided below.

Figure 6D:
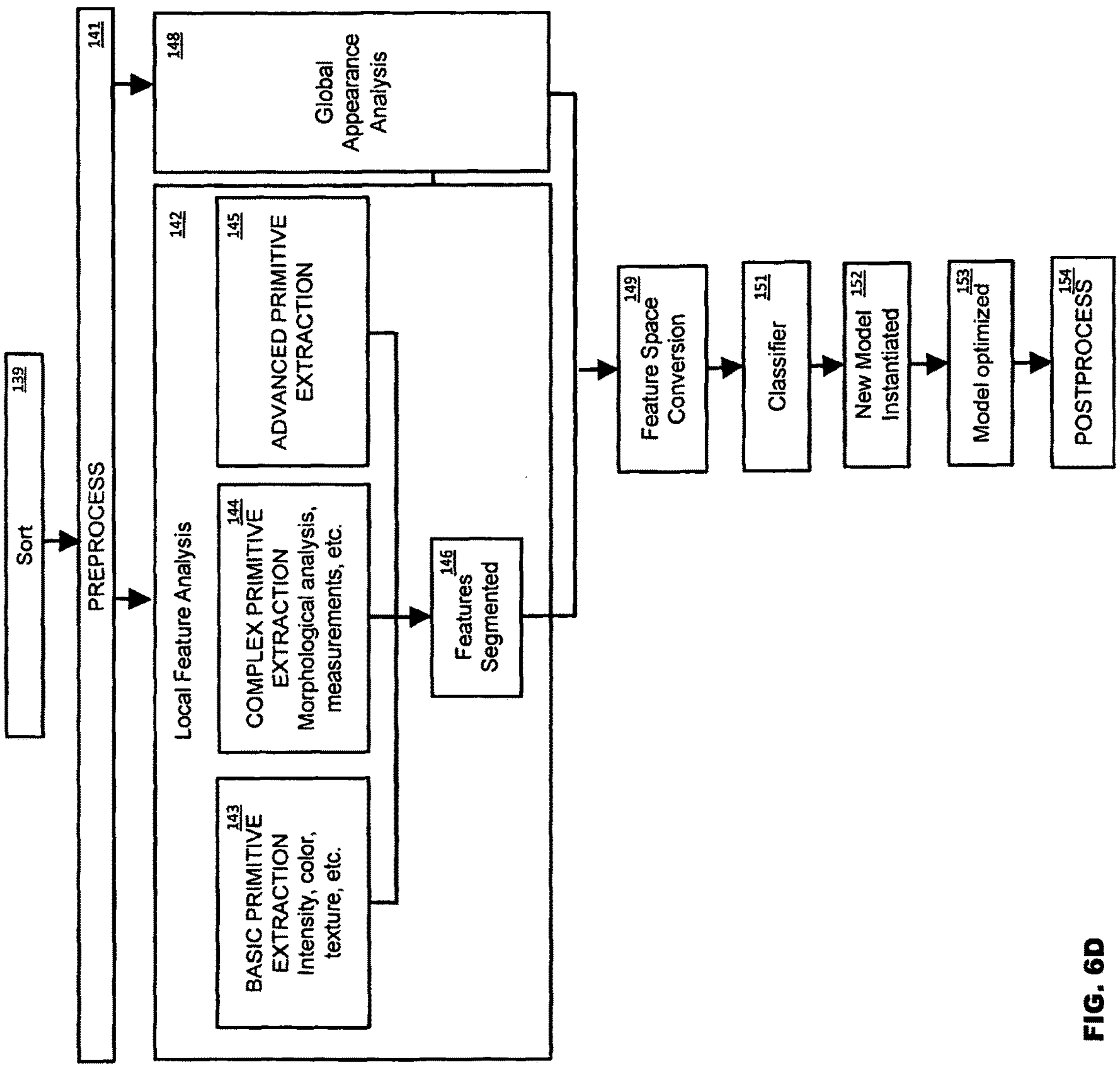

Reference is now made to FIG. 6D, wherein a detailed description of the model generation process of the images/videos analysis module 120 for steps 121 and 122 is provided in an exemplary embodiment. The steps of the model construction are first described in the context of the head analysis module 121. The body analysis module 122 proceeds in a similar fashion. Once invoked by method 110, the module 120 after receiving image(s) and/or videos and prior knowledge, first sorts the data into images and videos at step 139, based on the file extension, file header, or user tag in an exemplary embodiment. If only image(s) are present, the method proceeds to the preprocessing step 141. If only video(s) are present, the method first extracts images from the video that approximately represent a front view of the face and/or a side view of the face, if available and proceeds to the processing step 141. This is done in an exemplary embodiment using a technique similar to that used in [11]. In another exemplary embodiment, a 3D model of the face is constructed using a technique similar to that in [12]. If a combination of videos and images are present and the resolution of the image(s) is higher than that of the video, the method proceeds to the preprocessing step 141 using the higher resolution images. If a low resolution video is present, for example a video captured using a cell phone, high resolution images are first generated and then the method proceeds to the processing step 141. This can be done, in an exemplary embodiment, using a technique similar to that used in [13]. Stereo images and/or videos can also be processed. In an exemplary embodiment, this can be done using a technique similar to [14].

Reference is now made to the preprocess step 141 in FIG. 6D of the image/video analysis module 120, wherein the image(s) are preprocessed. This involves, in an exemplary embodiment, resizing, scaling, de-noising, etc., if necessary to bring the images to a canonical form. An approximate region containing the face region in the images is identified at this step. This is done, in an exemplary embodiment, using a rotationally invariant neural network. In another exemplary embodiment, this can be done using support vector machines (SVMs) in a manner similar to that described in [15]. The location(s) of the face(s) in the image(s) and associated parameters (eg. approximate facial pose, scale, etc.), and a probability density over the image space identifying the foreground (face regions) and the background are then passed to the next step. In an exemplary embodiment, this density is defined as a Gaussian about the location of the face. Facial pose is defined as the 3D orientation of a person's face in 3D space. It can be parameterized, in an exemplary embodiment, by the orientation of the line joining the eyes and the two angles between the facial triangle (formed by the eyes and nose) and the image plane. The scale of the image is computed, in an exemplary embodiment, using (i) the measurement of a reference region as marked by the user, if available, or (ii) the size of a common object (eg. a highlighter) in the image at approximately the same depth as the person in the image, if available, or (ii) the measured size of a known object (eg. a checkered pattern) held by the user in the image. If multiple faces are detected in a single image, the user may be asked which face the user would like a model created for or a model may be created for each face in the image allowing the user to decide which ones to store and which ones to delete. The method 110 then proceeds to step 148, where the global appearance is analyzed, and step 142, where the local features of the head are analyzed. The global appearance analysis step 148 involves, in an exemplary embodiment, projecting the foreground on a manifold constructed, for example, using principal component analysis (PCA), probabilistic principal component analysis (PPCA), 2D PCA, Gaussian Process Latent Variable Models GPLVM, or independent component analysis (ICA). This manifold may be parameterized by global factors such as age, gender, pose, illumination, ethnicity, mood, weight, expression, etc. The coefficients corresponding to the projection are used to produce a likelihood of observing the images given a face model. In an exemplary embodiment, this is given by a Gaussian distribution centered at the coefficients corresponding to the projection. The estimated parameters from the previous step are updated using Bayes rule and the likelihood determined at this step. The posterior global parameters thus computed serve as priors at step 142. Depending on the action factors, the method 110 segments the face into various anatomical regions (steps 143-146), projects these regions onto local manifolds (at steps 149 and 150) to generate local 3D surfaces, fuses these local 3D surfaces and post processes the resulting head surface (steps 151 and 152), optimizes the model 153 and adds detail to the model 154. These steps are described in detail below.

The method 110 at step 142 identifies various anatomical regions of the face in the image and uses this information to construct a 3D surface of the head. This is done, in an exemplary embodiment, using shape space priors (SSPs). SSPs are defined here as a probability distribution on the shape of the regions of an object (in this context a face), the relative positions of the different regions of the object, the texture of each of these regions, etc. SSPs define a prior on where to expect the different regions of the object. SSPs are constructed here based on anatomical data. In an exemplary embodiment, an SSP is constructed that defines the relative locations, orientations, and shapes of the eyes, nose, mouth, ears, chin and hair in the images. Using priors from step 148 and SSPs on the face, the method 110 at step 143 extracts basic primitives from the images such as intensity, color, texture, etc. The method 110 at step 2326, to aid in segmentation of facial features, extracts more complex primitives such as the outlines of various parts of the face and proportions of various parts of the face using morphological filters, active contours, level sets, Active Shape Models (ASMs) (for example, [16]), or a Snakes approach [17], in an exemplary embodiment. As an example, the active contours algorithm deforms a contour to lock onto objects or boundaries of interest within an image using energy minimization as the principle of operation. The contour points iteratively approach the object boundary in order to reach a minima in energy levels. There are two energy components to the overall energy equation of an active surface. The 'internal' energy component is dependent on the shape of the contour. This component represents the facets acting on the contour surface and constraining it to be smooth. The 'external' energy component is dependent on the image properties such as the gradient, properties that draw the contour surface to the target boundary/object. At step 146, the outputs of steps 143 and 144 which define likelihood functions are used together with SSPs, in an exemplary embodiment using Bayes rule, to segment the regions of the head, helmet, eyes, eyebrows, nose, mouth, etc. in the image(s). A helmet is defined here as the outer 3D surface of the head including the chin, and cheeks but excluding the eyes, nose, mouth and hair. The result is a set of hypotheses that provide a segmentation of various parts of the head along with a confidence measure for each segmentation. (Segmentation refers to the sectioning out of specific objects from other objects within an image or video frame. In an exemplary embodiment, an outline that conforms to the object perimeter is generated to localize the object of interest and segregate it from other objects in the same frame). The confidence measure, in an exemplary embodiment, is defined as the maximum value of the probability density function, at the segmented part's location. If the confidence measure is not above a certain threshold (in certain challenging cases eg. partial occlusion, bad lighting, etc.), other methods are invoked at the advanced primitive extraction step 145. (For example methods based on depth from focus, structure from motion, structure from shading, specularity, silhouette, etc.; techniques similar to [18], [19], [20], [21] and [22]). In an exemplary embodiment, this is done by selecting a method in a probabilistic fashion by sampling for a method from a proposal density (such as the one shown in FIG. 6I). For example, if the face of the user is in a shadow region, a proposal density is selected that gives the probability of successfully segmenting the parts of a face under such lighting conditions for each method available. From this density a method is sampled and used to segment the facial features and provide a confidence measure of the resulting segmentation. If the updated confidence is still below the acceptable threshold, the probability density is sampled for another method and the process is repeated until either the confidence measure is over the threshold or the maximum number of iterations is reached at which point the method asks for user assistance in identifying the facial features.

Figure 6E:
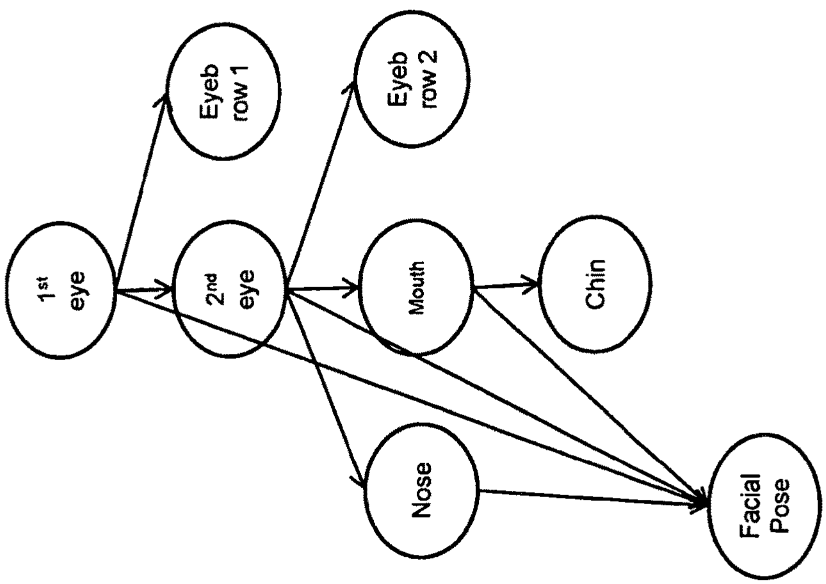
Figure 6F:
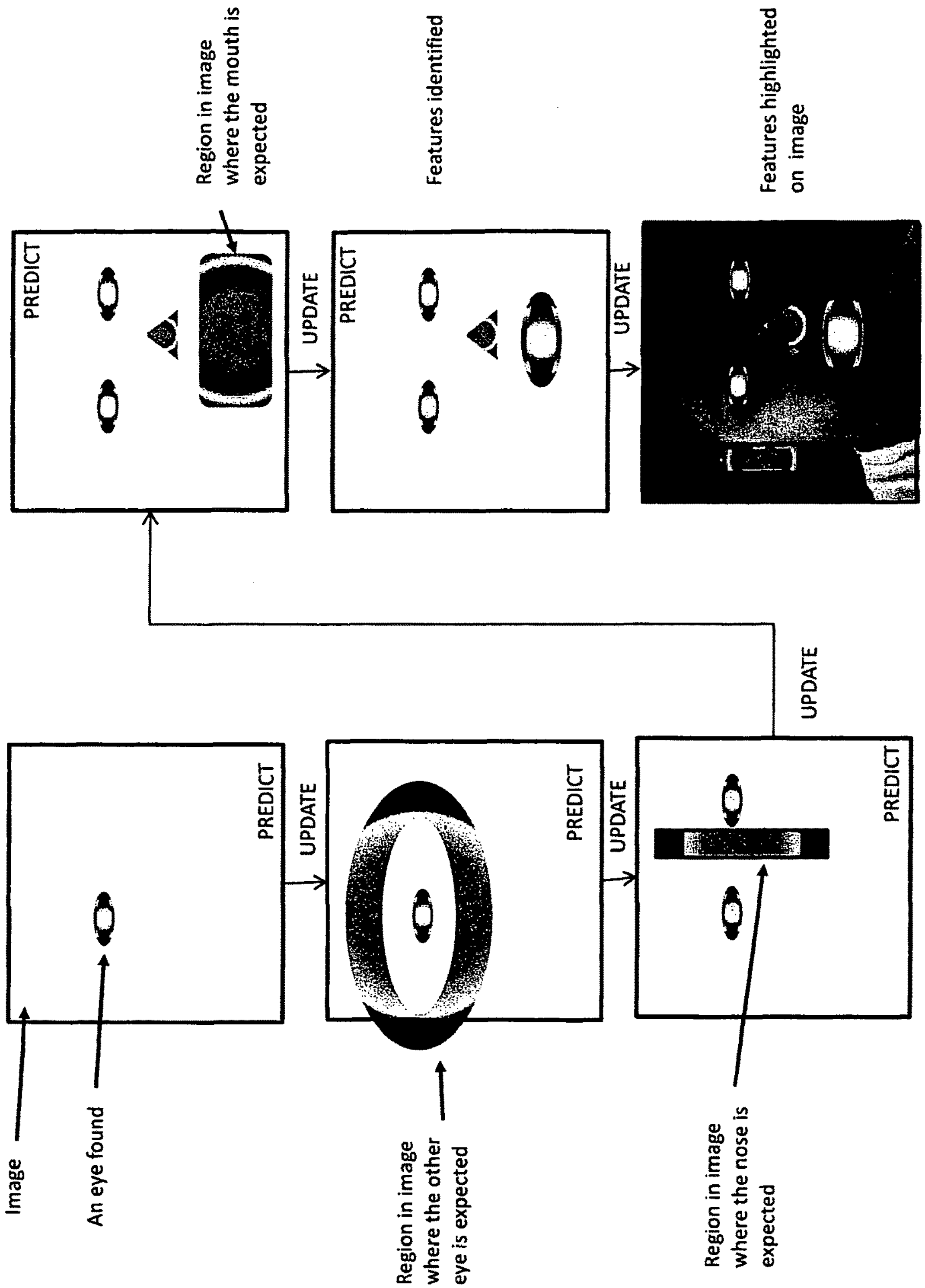

As each of the features or parts of the face is successfully segmented, a graphical model is built that predicts the location of the other remaining features or parts of the face. This is done using SSPs to build a graphical model (for eg. a Bayes Net). Reference is made to FIG. 6E, where a graphical model is shown in an exemplary embodiment, and to FIG. 6F, where the corresponding predicted densities are shown in image coordinates. The connections between the nodes can be built in parallel. As the method progresses, the prior on the location from the previous time step is used together with the observation from the image (result of applying a segmentation method mentioned above), to update the probability of the part that is being segmented and the parts that have been segmented, and to predict the locations of the remaining parts using sequential Bayesian estimation. This is done simultaneously for more than one part. For example, if the location of the second eye is observed and updated, it can be used to predict the location of the nose, mouth and the eyebrow over the second eye as shown in FIG. 6E. A simplified walkthrough of the sequential Bayesian estimation for segmenting the regions of the face is shown in FIG. 6F.

Simultaneously with steps 143-145, the pose of the face is determined. In an exemplary embodiment, on identification of specific facial features such as the eyes and mouth, an isosceles triangle connecting these features is identified. The angle of facial orientation is then determined by computing the angle between this isosceles triangle and the image plane. The pose thus computed also serves as a parameter at the classification step 151. The segmentation methods used are designed to segment the parts of the head at smooth boundaries. Next, parameters corresponding to these parts such as pose, lighting, gender, age, race, height, weight, mood, face proportions, texture etc. are computed. In an exemplary embodiment, this is done as follows: once a majority of the parts of the head are identified, they are projected onto a corresponding manifold in feature space (eg. edge space). In an exemplary embodiment, a manifold exists for each part of the face. These manifolds are built by projecting the 3D surface corresponding to a part of the face onto an image plane (perspective projection) for a large number of parts (corresponding to different poses, lighting conditions, gender, age, race, height, weight, mood, face proportions, etc.), applying a feature filter (eg. a Canny edge detector) at step 149 to convert to a feature space (eg. edge space, color space, texture space, etc.), and then applying a dimensionality reduction technique such as principal component analysis (PCA), probabilistic principal component analysis (PPCA), 2D PCA, Gaussian Process Latent Variable Models GPLVM, or independent component analysis (ICA). Since the manifolds are parameterized by pose, lighting, gender, age, race, height, weight, mood, face proportions, texture etc., projecting a given segmented part of the head onto the manifold allows recovery of these parameters (for example [23]). These parameters are then passed onto a classifier (at step 151), in an exemplary embodiment, a Naïve Bayes classifier, a support vector machine (SVM), or a Gaussian Process classifier, to output the most plausible 3D surface given the parameters. In an exemplary embodiment, if a particular parameter is already supplied as part of 118, for eg. the gender of the user, then it is used directly with the classifier and the corresponding computation is skipped (eg. estimation of gender). Teeth reconstruction is also handled similarly. The teeth that are constructed are representative of those in the image provided including the color and orientation of teeth. This is needed later for animation and other purposes such as to show virtually results of dental corrections, whitening products, braces, invisalines, etc. Hair are also handled similarly. In this case, the manifold is additionally parameterized by the 3D curvature, length, specularity, color, 3D arrangement, etc. In an exemplary embodiment, a helical model is used as the underlying representation for a hair strand. In an exemplary embodiment hair can be modeled from image(s) using techniques similar to [24-26]. If, however, the action factors do not allow a representation of the teeth, ears and hair exactly as in the image, less complex precomputed models are used. Once 3D surface exemplars for various parts of the head (for example, a helmet defined below, eyes, nose, mouth, etc.) are identified as outputs of the classifier, at step 152 a new model is instantiated by instantiating a copy of the identified exemplar surfaces. Since the instantiated surfaces are parametric by construction, these parametric models are modified slightly (within allowed limits), if necessary, to represent parameters as extracted from the image(s) wherever possible at the optimization step 153. The exemplars that are used with the classifier are rigged models and thus enable easy modifications. In an exemplary embodiment, the size of the skeletal structures and the weight of the nodes are modified to match the extracted parameters. The rigged models also allow user modifications (as described with reference to FIG. 29B) and facilitate animations. At the postprocessing step 154, the 3D surfaces generated at step 153 are merged. The boundaries of the 3D surfaces corresponding to the parts of the face are merged and smoothed using techniques similar to those used at the head-body fusion step 155 (FIG. 6C). Symmetry is used to complete occluded or hidden parts. For example, if the user's hair are partially occluding one side of the face, symmetry is used to complete the missing part. If not enough information is available, the most likely surface and texture are substituted. For example, if the user's teeth not visible owing to the mouth being closed, the most likely set of teeth, given the parameters corresponding to the user. In an exemplary embodiment, the most likely surface and texture are computed using a classifier such as Naïve Bayes, while the placement is computed using SSPs and Bayesian inference. As an alternate embodiment, 3D surfaces of the entire head for different combinations of constituent part parameters are maintained and an appropriate model is instantiated at step 152 based on the output of the classification step 151. At the conclusion of the postprocessing step 154, a preliminary 3D model of the user's head is available which is passed onto the head-body fusion step 155. As mentioned earlier, the body analysis module 122 proceeds similar to the head analysis module 121, where instead of extracting parameters of parts of the face, parameters of the various body parts (excluding the head) are extracted from the image(s) and/or videos. In an exemplary embodiment, the local feature analysis step 142 for the body analysis module 122 involves individually analyzing the upper limbs, the lower limbs, the thorax, the abdomen, and the pelvis. In an exemplary embodiment, the location of the body in the image and its pose is identified at the preprocessing step 141 using a technique similar to that used in [27]. At the conclusion, of the postprocessing step 154 of the body analysis module 122, a preliminary 3D model of the user's body is generated which is passed onto the head-body fusion step 155.

Figure 6G:
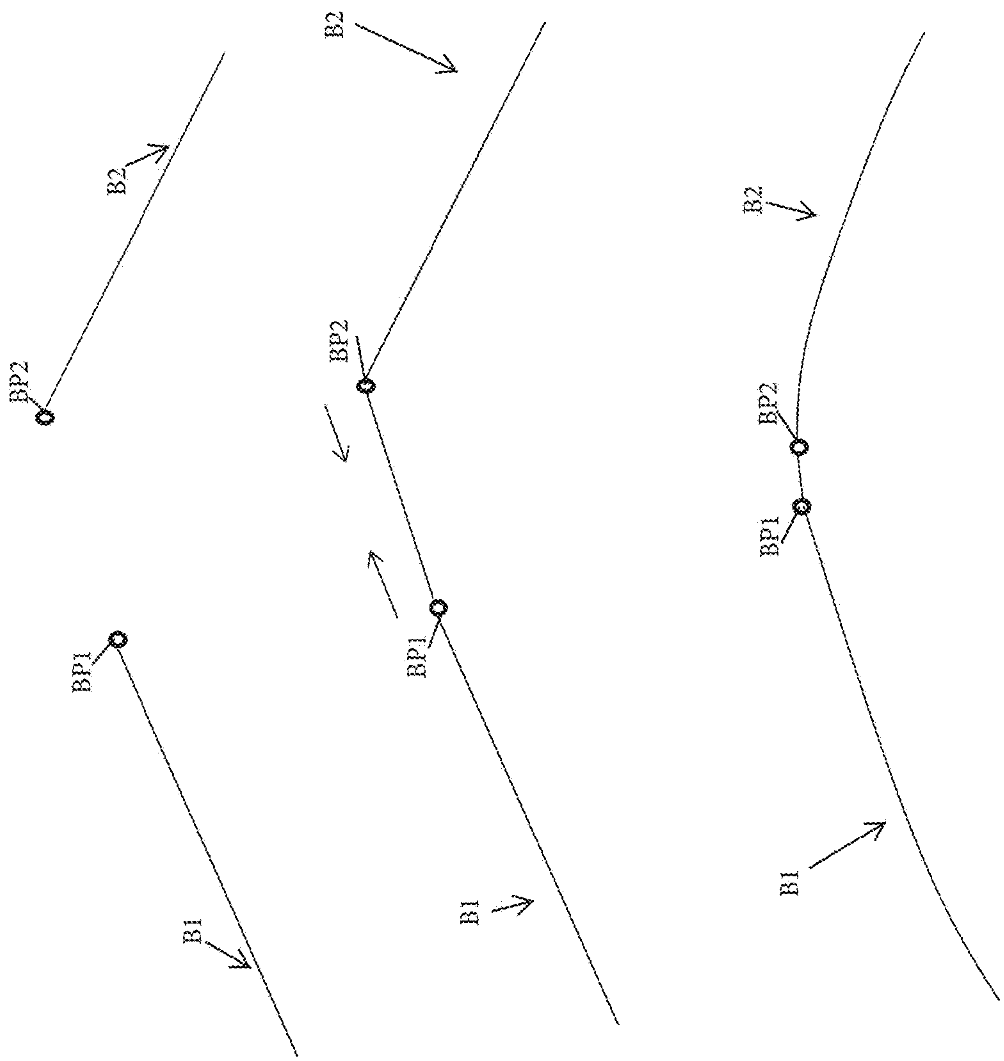

At the head-body fusion step 155, the head model estimate and the body model estimate are merged using smoothness assumptions at the boundaries, if necessary. In an exemplary embodiment this is accomplished by treating the regions at the boundaries as B-splines and introducing a new set of B-splines (B1, B2) to interconnect the two regions to be merged (analogous to using sutures) and shrinking the introduced links until the boundary points (B1, B2) are sufficiently close. A 1-D example is shown in FIG. 6G. Alternatively, the boundaries at the neck region may be approximated as being pseudo-circular and the radii of the body model's neck region and the head model's neck region can be matched. This may involve introducing a small neck region with interpolated radius values. Other methods such as the one proposed in [28] could also be used. The choice of the method used for fusion depends, in an exemplary embodiment, on the action factors. For instance, if limited data is provided by the user leading to a relatively coarse approximation to the user, the pseudo-circular approximation method mentioned above is used. As another example, a particular version of an NPR model desired by the user may not require sophisticated model for which the pseudo-circular approximation method mentioned above is used. The output of the head-body fusion step 155 is passed onto the information fusion step 127.

Reference is now made to the measurements analysis module 123 that processes the measurements provided by the user in order to construct a user model or part thereof. These measurements include the various head and body measurements 115 provided by the user. The measurements 115 provided are used to estimate any missing measurements based on anatomical and anthropometric data, and data on plastic surgery available as part of the prior knowledge 112. As an example of the construction of a head model, given the width, x, of one of the user's eyes, the proportions of the remaining parts of the head are generated based on anthropometric data as follows: the diameter of the head, along the eyes and the ears is taken to be 5×, the distance from the trichion to the menton is taken to be 6×. If the user's ethnicity is known, then the shape is appropriately adjusted based on anthropometric data. For example, the shape of an average Asian head as seen from above is circular while that of an average Caucasian is elliptical. This information is then passed to a classifier to output the most plausible 3D surface of the head given the parameters. Measurements of the body are used to instantiate a model corresponding to these measurements from a generative model. A generative model is available as part of the prior knowledge 112 and is constructed, in an exemplary embodiment, using anthropometric data. In an exemplary embodiment, this is done using techniques similar to those used in [29, 30]. If a very limited number of measurements are available in addition to images, they are passed onto the classifier at step 151 and the extraction of the corresponding measurement from the image(s) or video(s) is skipped, in an exemplary embodiment. The output of the measurements analysis module is passed onto the information fusion step 127.

Reference is now made to the apparel size analysis module 124 in FIG. 6A that processes the apparel size/preferences 116 provided by the user in order to construct a user model or part thereof. Prior knowledge 112 includes an association of an average 3D model with size data for shirts, dresses, trousers, skirts, etc. For example, there is an average 3D model of the upper body of a male associated with a men's shirt collar size of 42 and similarly a model of the lower body for a trouser waist size of 32 and a length of 32, or a hat size of 40 cm, or a shoe size of 11. This can be done, in an exemplary embodiment, by computing the average of the upper body 3D surface of several models (obtained from rage scans after filtering noise and rigging) of men who have identified a collar size of 42 as their preferred shirt size. In another exemplary embodiment, the generative models learnt from anthropometric data, for example as in [29] may have size parameters mapped to apparel size, thereby giving a generative model that is parameterized by apparel size. These models are also rigged, in an exemplary embodiment using a technique similar to that used in [31], to allow animation. Thus, in an exemplary embodiment, a user model can be created from apparel size data by (i) instantiating the corresponding average 3D model for the various body parts for which an apparel size is specified, or instantiating the part of the body corresponding to the apparel using a generative model parameterized by apparel size, and (ii) merging the 3D surfaces for the various body parts using merging techniques similar to those used at step 155 using most probable generic models for body parts (available from the generic module 126) for which apparel size is not provided. The output of the apparel size analysis module is passed onto the information fusion step 127.

Figure 6H:
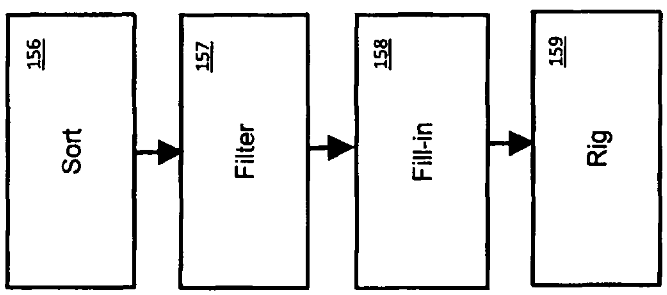
Figure 6I:
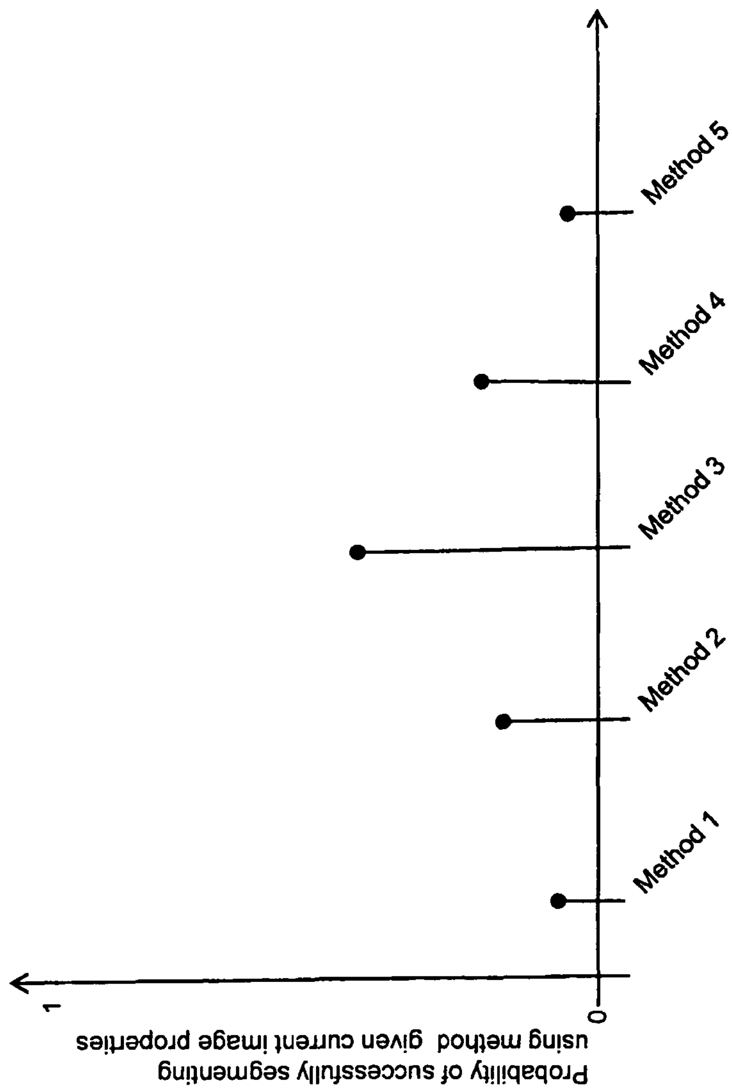

Reference is now made to the mesh analysis module 125 in FIG. 6A that processes the laser scan data/meshes/outlines 117 provided by the user in order to construct a user model or part thereof. The steps of the mesh analysis module are shown in FIG. 6H in an exemplary embodiment. After receiving user data 111 and prior knowledge 112, once invoked, this module first sorts 156 the data [such as laser scan data, meshes (for instance, those corresponding to impressions of the ear or foot), outlines of body parts (for instance, those of the hands and feet), mocap (motion capture) data, magnetic resonance imaging (MRI), ultrasound, positron emission tomography (PET), and computed tomography (CT) data] to determine the most accurate choice of data to use for model construction. This is done using knowledge of the accuracy of a model constructed using each piece of the pieces of data above, available as part of prior knowledge 112, and the quality of the data provided such as the poly count of a mesh. The user is also allowed to force the use of a preferred data, for example mocap data as opposed to a laser scan, for model construction by specifying the reliability of the data manually. For meshes, the module 125 then proceeds as follows: The module 125 filters the data at step 157 to remove any noise and to correct any holes in the data. This is done, in an exemplary embodiment, using template-based parameterization and hole-filing techniques similar to those used in [29]. At this step, unnecessary information such as meshes corresponding to background points is also removed. This can be done, in an exemplary embodiment, by asking the user to mark such regions through an intuitive user interface. This is followed by the fill-in step 158 at which symmetry is used to complete missing regions such as an arm, if any, using symmetry. If mesh or volume data is not available for the missing regions, the corresponding regions are generated by the generic module 126 and fused at the information fusion step 127. The model is then rigged at the rigging step 159. Rigging provides a control skeleton for animations and also for easily modifying the body parts of the user's model. The mesh output from step 158 is used with a generic human skeleton and an identification of the orientation of the mesh to automatically rig the mesh. Generic male and female versions one for age group 0-8, 8-12, 13-20, 21-30, 31-60, 60+ in an exemplary embodiment are available as part of the prior knowledge 112. The orientation of the mesh (i.e which side is up) is obtained from the mesh file's header. If unavailable in the header, the orientation of the header is obtained by asking the user through an intuitive user interface. Rigging is done automatically, in an exemplary embodiment, using a technique similar to that used in [31]. It can also be done using techniques similar to those used in [32, 33].

For laser scan data, a mesh is first constructed, in an exemplary embodiment, using a technique similar to that used in [34]. This mesh is then passed on to the fill-in step 158 and the rigging step 159 described above. For mocap data, a model is generated using shape completion techniques such as that used in [35], in an exemplary embodiment. The model thus generated is rigged automatically, in an exemplary embodiment, using a technique similar to that used in [31]. For outlines, this module extracts constraints from the outlines and morphs the mesh to satisfy the constraints. In an exemplary embodiment, this is done as follows: (i) Feature points on the outline corresponding to labeled feature points on the mesh (for example, points over the ends of eyebrows, over the ears, and the occipital lobe) are identified by the user through a guided interface such as the one shown in FIG. 11. This can also be automated using perceptual grouping and anatomical knowledge. For example, consider a scenario where a user prints out a sheet that has a reference marker from the website and draws an outline of his/her foot, or takes an image of his/her foot with a penny next to the foot. Given such an image, the image is first scaled to match the units of the coordinate system of the 3D mesh using scale information from the reference markers in the image. If a reference marker is not present, the image is search for commonly known objects such as a highlighter or a penny using template matching and the known size of such objects is used to set the scale of the foot outline. Or, the user may be asked to identify at least one measurement on the foot. The orientation of the foot is then identified. This is done by applying a Canny edge detector to get the edge locations and the orientations, connecting or grouping edgels (a pixel at which an edge has been identified) that have an orientation within a certain threshold, and finding the longest pair of connected edges. This gives the orientation of the foot. Both ends of the foots are searched to identify the region of higher frequency content (using a Fourier Transform or simply projecting the region at each end onto a slice along the foot and looking at the resulting histogram) corresponding to the toes. The big toe is then identified by comparing the widths of the edges defining the toes and picking the one corresponding to the greatest width. Similarly, the little toe and the region corresponding to the heel are identified and reference points on these regions corresponding to those on the 3D meshes are marked which now define a set of constraints. (ii) The corresponding reference points are then displaced towards the identified reference points from the image using Finite Element Analysis (FEM) techniques such as those used in [36], [37], or as in [38]. The extracted constraints are also passed onto the other modules 120, 123, 124 and 126 and a similar method is applied to ensure that the generated model conforms to the constraints. Such morphing of the mesh to conform to constraints is particularly used, if action factors allow, for parts of the body that cannot be easily approximated by a cylinder such as the head. Such morphing of the mesh based on constraints provided by the user such as an outline or an image of their foot or fingers are useful for computing goodness of fit information for apparel such as shoes and rings. (For the case of rings, it is also possible to simply measure the circumference of the ring and let the measurement analysis module construct the appropriate model). For rings, two roughly orthogonal images of the fingers with a reference material in the background or an outline of the fingers on a printable sheet containing a reference marker could be used and analyzed as above. Or, a users hand can be placed in front of a webcam with a ref on paper in the background or a computer screen in the background containing a reference marker. The advantage of such an image based constraint extraction is that it allows multiple fingers to be captured at once. This is particularly useful when buying, say mittens or gloves or a ring, for a friend as a surprise gift. The user simply needs to take an image(s) of the appropriate region of his/her friend's body, mark the size of some known object in the image, for example, the width of the user's face. The more information is provided, the more accurate the user's model becomes. For example, for some people, the ring size for the right index finger is different from that of the left hand; images of both hands ensure a more accurate goodness-of-fit. Imprints and moulds such as those of the foot and ears can be converted to meshes can be done either by laser scanning. It can also be done taking multiple images of the imprints and moulds and constructing the mesh using structure from focus, structure from motion, structure from shading, specularity, etc.; techniques similar to those used in [18] and [22]. Medical images and volumes such as MRI and CT volumes can also be used, if available, to create the user model or part thereof. This can be done using techniques similar to those used in [39, 40].

Figure 6J:
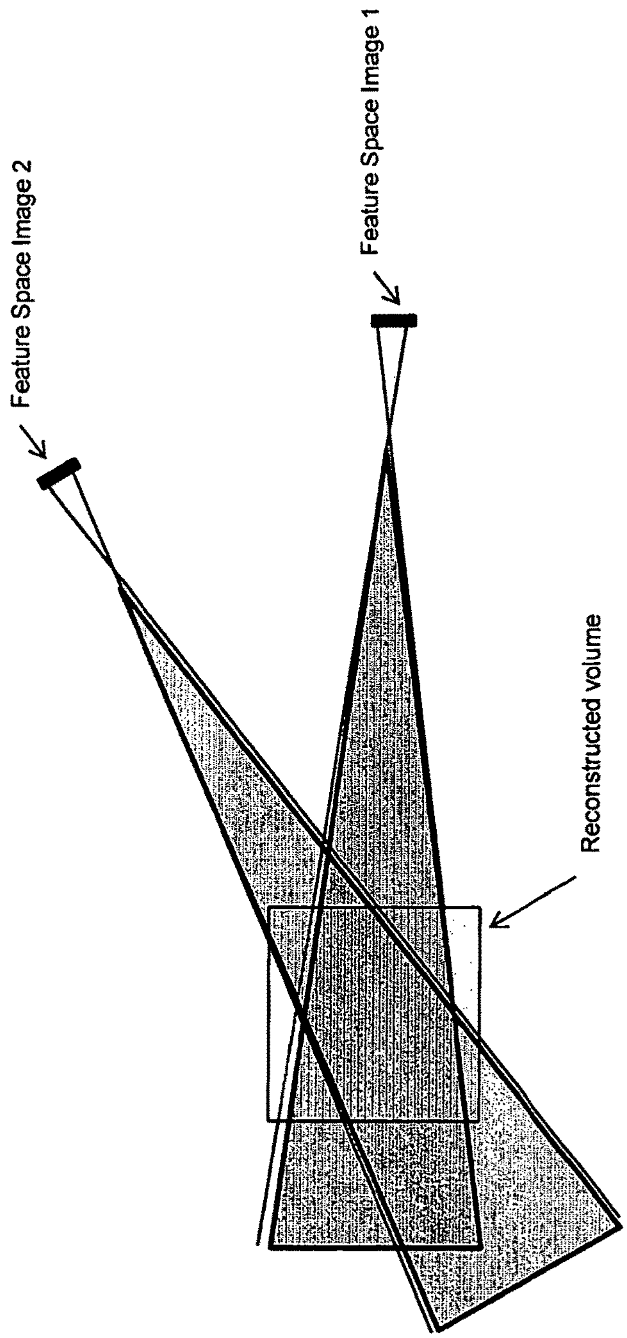

For images from multiple views of a user with known image acquisition geometry, a volume is first created as follows and processed as described above for the case of laser scan data. (i) Each image is preprocessed and a transform is applied producing a feature space image. For example, a silhouette transform is applied which produces an image with a silhouette of the object(s) of interest. This can be done in an exemplary embodiment using a technique similar to that used in [41]. (ii) The silhouette is then backprojected. This can be done, in an exemplary embodiment, by summing the contributions from each of the silhouettes taking into account the geometry provided as shown in FIG. 6J. Using the geometry of the image capture (this is usually a perspective projection or can be approximated with an orthographic projection), rays are traced from pixels on the feature space transformed images to voxels (3D pixels) of a volume (a 3D image). To each of the voxels along the path of a ray, the value of the pixel in the feature space transformed image is added. This added value may be corrected for a $1/r^2$ effect (inverse square law of light and electromagnetic radiation). Once a mesh is created, knowledge of the silhouette is used to extract the texture of the object of interest and using image acquisition geometry, the model is textured as described at the primary model instantiation step 128. It can also be done in the frequency domain using a technique similar to that described in [42]. Instead of using the silhouette above, any other feature space transform can be used. For images from multiple views of an object(s) with unknown or limited geometry information, the images are processed as described above with geometry information extracted from the images as follows: (i) Detect salient features. This is done in an exemplary embodiment by using statics on regions that are interesting to humans extracted by tracking eye movements. In another exemplary embodiment, it can be done using prior knowledge of the parts of the object of interest. For example, the eyes, nose and mouth can be identified similar to techniques used at step 121 (ii) Form triangles by connecting the salient features. For example, the eyes, nose, and mouth of a person in an image may be connected to form a triangle. (iii) Determine image to image transformations of the corresponding triangles. This can be done in an exemplary embodiment using a technique similar to that used in [43]. These transformations define the image acquisition geometry which is then processed along with the images to construct a model as described above. In Instead of using triangles other structures or network of structures may be used above. The method described above allows construction of a model from arbitrary views of an object or person taken using an ordinary camera. Planes in the image can also be identified by detecting lines diminishing towards a vanishing point. This can be used to construct a model of the environment, if desired. It can also be used to aid in background subtraction. A technique similar to the one presented in [44] can also be used for the environment. The output of the mesh analysis module is passed onto the information fusion step 127.

Reference is now made to the generic module 126 in FIG. 6A to construct a user model or part thereof. This module processes other data 118, if available, together with prior knowledge 112 in order to produce a generic model or part thereof. This module is invoked when there is insufficient information for constructing a user model or part thereof via the other modules 120, 123, 124, and 125, or if the action factors do not allow the generation of a more accurate model that is conformal to the user through modules 120, 123, 124, and 125. When invoked, the information in other data 118 or that provided by the modules 120, 123, 124, and 125 is passed onto a classifier similar to that used at step 151. In an exemplary embodiment, a Naïve Bayes classifier, a support vector machine (SVM), or a Gaussian Process classifier is used, to output the most plausible 3D surface given the information. If only a part of the model (such as a limb) is required by the other modules 120, 123, 124, and 125, then only the required part is generated using the classifier. If the whole model is required, then the entire user model is generated using the classifier. In an exemplary embodiment, the classifier outputs an exemplar that is a rigged model. The rigged exemplar is then modified, if necessary, to better match the user. For example, if other data 118 specifies an age of five years and a height of five feet, and the closest exemplar is a user model corresponding to a five year old that is four and half feet tall, the height of this exemplar is changed from four and half to five feet by setting the parameters of the rigged user model accordingly. The classifier is built using labeled training data. In an exemplary embodiment, this is done using rigged 3D surfaces or meshes that have associated with them labels identifying the age, gender, weight, height, ethnicity, color, apparel size etc. of the corresponding 3D surface or mesh. The labeling can be done manually as it only needs to be done once when building the classifier. The classifier is stored and available as part of prior knowledge 112. As more and more data becomes available, the classifier is updated at the learning step 132. In essence, the method 110 is constantly learning and improving its model construction process.

The processed information from the modules 120, 123, 124, 125, and 126, if available, is then fused at the information fusion step 127. At this step, merging of the outputs of components of 120, 123, 124, 125, and 126 takes place. There is an accuracy associated with the output of the modules 120, 123, 124, 125, and 126 available as part of prior knowledge 112. Based on this accuracy components of various parts of the user's model are merged. For example, the full body output of the generic module 126 may be merged with a high resolution model of the user's foot available as an output of the mesh analysis module 125. This can be done, in an exemplary embodiment, using techniques similar to those used at the head-body fusion step 155. Parts of the skeleton are also joined at the joint locations. For example, for the above example, the full body skeleton is joined with the foot skeleton at the ankle joint. For regions of the body for which data is unavailable, the output of the generic module is used. For regions of the body for which multiple models of similar accuracy exist, the corresponding models are merged in a probabilistic framework. For example, the expected value of this 3D model's surface is computed over all pieces of data available as outputs of 120, 123, 124, 125, and 126 to produce an estimate of the 3D model of the user's head. In an exemplary embodiment, this is done using Bayesian model averaging, committees, boosting and other techniques for combining models may be used.

At step 128, a preliminary 3D model is instantiated using the output of the information fusions step. The model is named and all the appropriate data structures are updated. The model is also textured at this step. This is done by setting up a constrained boundary value problem (BVP) with constrains defined by the feature point correspondence and using texture from the image(s) provided by the user. In an exemplary embodiment, this is done using a technique similar to that presented in [45] for the face. The feature point correspondence between points on the 3D model and those in the images is obtained using the segmentation results from step 146. Alternatively, this correspondence data may be obtained through a user interface. An exemplary embodiment of such a user interface is discussed in reference to FIG. 11. A texture map for the face is obtained by unwrapping a texture map from the input video sequence or input images using a technique similar to the texture mapping technique described in [46]. Before unwrapping the texture, the images may be processed to complete missing or occluded regions (such as occlusion by hair, glasses, etc.) using shape space priors and symmetry. Skin tone is also identified at this step. In an exemplary embodiment, regions representing skin can be identified by converting the image to a representation in the HSV (Hue, Saturation, Value) color space or RGB (Red, Green, Blue) color space. Skin pixels have characteristic HSV and RGB values. By setting the appropriate thresholds for the HSV or RGB parameters, the skin regions may be identified. The skin reflectance model may incorporate diffuse and specular components to better identify the skin. The variation of the pixel values (and higher order statistics) for example in RGB space can be used to estimate the skin texture. This texture is then used to fill in skin surfaces with unspecified texture values, for example, ears that are hidden behind hair. In an exemplary embodiment, skin texture is extracted from the face and used wherever necessary on the head and the body since the face of a user is usually visible in the image or video. Similarly, texture is computed and mapped for teeth, hair, and the iris and pupil of the eyes. If image or video data is unavailable, a generic texture is used. The choice of a generic texture is based on other information provided by the user as part of other data 118 (eg. age, race, gender, etc.), if available.

The model is then optimized at step 129. Optimization involves improving the model to better match the user. Optimization procedures similar to those employed at step 125 and 153 are used at a global scale, if necessary or possible, again depending on user data and the action factors. Consistency checks are also made to ensure that scale and orientation of the different regions of the model are plausible and appropriate corrections are made if necessary. Textures on the model are also optimized at this step if the action factors allow. This involves optimizations such as reilluminating the model so that the illumination is globally consistent and so that the model can be placed in new illumination contexts. This is done in an exemplary embodiment using techniques similar to those used in [19, 20, 47]. Forward and backward projection (from the 3D model to the 2D image and vice-versa) may be applied in a stochastic fashion to ensure consistency with the 2D input image, if provided, and to make finer modifications to the model, if necessary depending on action factors. The comparison of the projected 3D model and the 2D image may be done in one or more feature space(s), for example in edge space. All of the actions performed are taken depending on the action factors as described earlier.

The method 110 then proceeds to step 130 at which the model is detailed. The photorealism of the model is enhanced and any special effects that are required for NPR are added based on the action factors. The photorealism is enhanced, for example, by using bump maps for, say, wrinkles and incorporating subsurface scattering for skin. Facial hair, facial accessories and finer detail are also added to the model.

Method 110 then proceeds to the user modification step 131 at which the user is allowed to make changes to the model if desired. These changes include, in an exemplary embodiment, changes to the skin tone, proportions of various body parts, textures (for example, the user may add scars, birthmarks, henna, etc.), etc. An easy to use user interface allows the user to make such changes as described later in this document. Users are also allowed to set default preferences for their model at this point. For instance, they may choose to have a photorealistic model or a nonphotorealistic (NPR) model as their default model (NPR models may be multi-dimensional—1-D, 2-D, 2.5D, 3-D, 4-D or higher). Users can also create several versions of their NPR model based on their specific taste. Such NPR models can be constructed by simply applying a new texture or using algorithms such as those described in [48-50]. At any point during model construction, the method may ask the user for assistance. The user is allowed to make changes to the model at any time. As the user ages, loses or gains weight, or goes through maternity, the model can be updated accordingly. As newer versions of the software are released, newer, more accurate versions of the model may be created using the information already supplied by the user or prompting the user to provide more (optional) information. All the models created by the user are stored and the user is allowed to use any or all of them at any time. The models created by the user are stored in the user database 80 and are also cached on the client side 14 and 16 for performance purposes.

The model generated before user modifications as well as the user modifications and user data 111 are passed onto the learning step 132, the output of which is used to update the prior knowledge 112 in order to improve the model construction method 110 over time. This can be done using reinforcement learning and supervised learning techniques such as Gaussian process regression. In an exemplary embodiment, the manifolds and the classifier used in the model construction process are updated. In an exemplary embodiment, if a model that is created is significantly further away in distance from the existing exemplars of the classifier and has been found frequently, it is added as a new exemplar. At the conclusion of the user modifications step 131, a user model is created.

If the user provides more data 111, the method accesses the quality of the data, for example, the resolution of the images, the poly count of the meshes, etc. in order to determine if the newer data can improve the model. If it is determined that the new data can improve the module, the method 110 processes the data to improve the quality of the user model and a new version of the model is created and stored. The measurements of various body parts can be updated at any time as the user ages, gains/loses weight, goes through maternity etc.

The method 110 described above can be used for building models of other objects. For example, 3D objects for use in the virtual world. In an exemplary embodiment, the user can identify the class of the object (such as a pen, a laptop, etc.) for which a model is being created. The class of the object for which a model is being created is useful for selecting the appropriate priors for model construction for the given object from the prior knowledge 112. In an alternative embodiment, the class of the object being considered can be automatically determined as discussed with reference to FIG. 49Q.

In an exemplary embodiment, a generative model for motion is used. For example, for the case of walking, users are allowed to tune various parameters corresponding to a walking style such as a masculine/feminine walking style, a heavy/light person walking style, a happy/sad walking style etc. Such generative models are learnt, in an exemplary embodiment, using Gaussian process models with style and content separation using a technique similar to that used in [51].

When the action factors are very limiting, for example, on limited platforms such as a cell phone or a limited web browser, several approximations may be used to display a 3D model. In an exemplary embodiment, on rotating a user model, the user is presented with a 3D model of the user from a quantized set of views i.e. if a user rotates his/her viewpoint, the viewpoint nearest to this user selected viewpoint from a set of allowed viewpoints is chosen and displayed to the user. In this way, an entire 3D scene can be represented using as only as many viewpoints as the system permits, thereby allowing a more compact and responsive user experience. In an exemplary embodiment, if a generic user model is used, precomputed views of the model corresponding to different viewpoints are used. In an exemplary embodiment, the apparel on a generic user model of a given size and the corresponding fit info is precomputed for various parameters (for example, for different apparel sizes) and the appropriate view is displayed to the user. In an exemplary embodiment, the view may be an image or an animation such as one showing the user walking in a dress. As an exemplary embodiment of how a 3D environment can be displayed when the action factors are limiting, static backgrounds may be used instead of dynamic one. Moreover, instead of displaying a fully 3D environment, a quantized version of the environment may be displayed i.e. as with the case of the user model, when the user chooses to navigate to a certain viewpoint, the closest available viewpoint from a set of allowed viewpoints for the environment is chosen and displayed to the user.

Users can also choose to create a strictly 2D user model and try out apparel in 2D. This is one of the several options available for NPR models. In an exemplary embodiment, this is done by invoking the generic module 126 with a 2D option for the classifier i.e. the output of the classifier is a 2D rigged mesh. The 2D classifier is built using the same technique as described for the 3D models but using 2D rigged models instead. Users can also draw a model of themselves. This can then be either manually rigged through a user-interface or automatically using a 2D form of the technique used in [31], in an exemplary embodiment. Users also have the option of creating their own 3D models, and using them for trying out apparel and for various entertainment purposes such as playing games and creating music videos containing their user model.

All data provided by the users and models constructed are saved in a repository. In an exemplary embodiment, an application programming interface (API) may be available for developers to build applications using this data. In an exemplary embodiment, an application could use this data to determine items that fit a user as a user browses a catalog, as described later. In another exemplary embodiment, a mobile device or cell phone application could allow users to scan a bar code or an RFID (radio frequency identification) tag on an apparel in a real store and see if the apparel fits the user. (Such scanning of bar codes or RFIDs and looking up of repositories can have other applications such as scanning a food item to check if it is consumable by the user i.e. its ingredients satisfy the dietary restrictions of a user).

Figure 20:
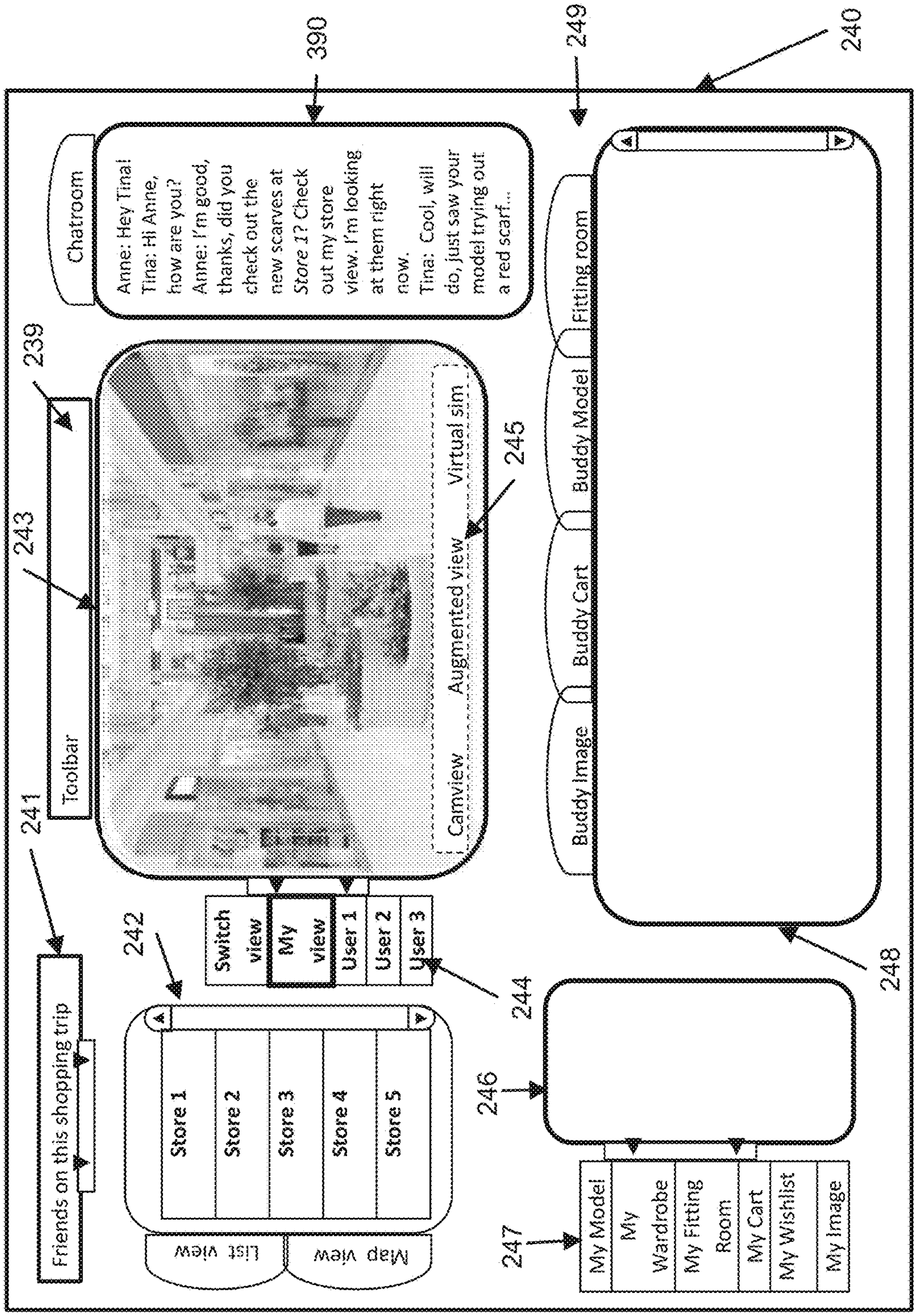
FIG. 20 is an image of a sample collaborative environment.

Reference is now made to FIGS. 7A-D which illustrate protocols for collaborative interaction in exemplary embodiments. These protocols can be used for a number of applications. These protocols are described next for the modes of operation of a Shopping Trip™. Other applications based on these protocols are described later in this document. A user may initiate a shopping trip at any time. There are four modes of operation of a shopping trip: regular, asynchronous, synchronous and common. In the regular mode, a user can shop for products in the standard way—browse catalogues, select items for review and purchase desired items. Whereas the regular mode of shopping involves a single user, the asynchronous, synchronous and common modes are different options for collaborative shopping available to users. In the asynchronous mode, the user can collaborate with other shoppers in an asynchronous fashion. The asynchronous mode does not require that other shoppers the user wishes to collaboratively shop with, be online. The user can share images, videos, reviews and other links (of products and stores for instance) they wish to show other users (by dragging and dropping content into a share folder in an exemplary embodiment). They can send them offline messages, and itemized lists of products sorted according to ratings, price or some other criteria. Any share or communication or other electronic collaborative operation can be performed without requiring other collaborators to be online, in the asynchronous mode at the time of browsing. The synchronous and common modes require all collaborating members to be online and permit synchronized share, communication and other electronic collaborative operations. In these modes, the users can chat and exchange messages synchronously in real-time. In the synchronous mode, 'synchronized content sharing' occurs. Reference is made to FIG. 20 to describe this operation in an exemplary embodiment. Users involved in synchronized collaboration can browse products and stores on their own. 'Synchronized content sharing' permits the user to display the products/store view and other content being explored by other users who are part of the shopping trip by selecting the specific user whose browsing content is desired, from a list 244 as shown in FIG. 20. For example, consider a shopping trip session involving two users—user 1 and user 2, browsing from their respective computing devices and browsers. Suppose user 1 and user 2 are browsing products by selecting "My view" from 244. Suppose user 1 now selects user 2 from the view list 244. As the selected user (user 2) browses through products/stores, the same content is displayed on user 1's display screen thereby synchronizing the content on the display screens of users 1 and 2. User 1 may switch back to her view whenever she wants and continue browsing on her own. Similarly, user 2 can view the content of user 1 by selecting user 1 from the switch view list. In the common mode, users involved in the collaborative shopping trip are simultaneously engaged in browsing products or stores on their display screens. This mode can assume two forms. In the first form, a user is appointed as the 'head' from among the members of the same shopping trip. This head navigates/browses products and stores on their display screen and the same view is broadcast and displayed on the screens of all users of the same shopping trip. In the second form, all users can navigate/browse through product, store or other catalogues and virtual environments and the information/content is delivered in the sequence that it is requested (to resolve user conflicts) and the same content is displayed on all user screens simultaneously using the protocol that is described below. In the common mode, all the users are engaged in a shopping trip in a common environment. This environment may be browsed independently by different members of the shopping trip leading to different views of the same environment. The system in FIG. 20 involving synchronous collaboration between users may be integrated with a 'One Switch View' (OSV) button that allows users to switch between user views just by pressing one button/switch, which may be a hardware button or a software icon/button. The user whose view is displayed on pressing the switch is the one on the list following the user whose view is currently being displayed, in exemplary embodiment. This OSV button may be integrated with any of the collaborative environments discussed in this document.

Figure 7A:
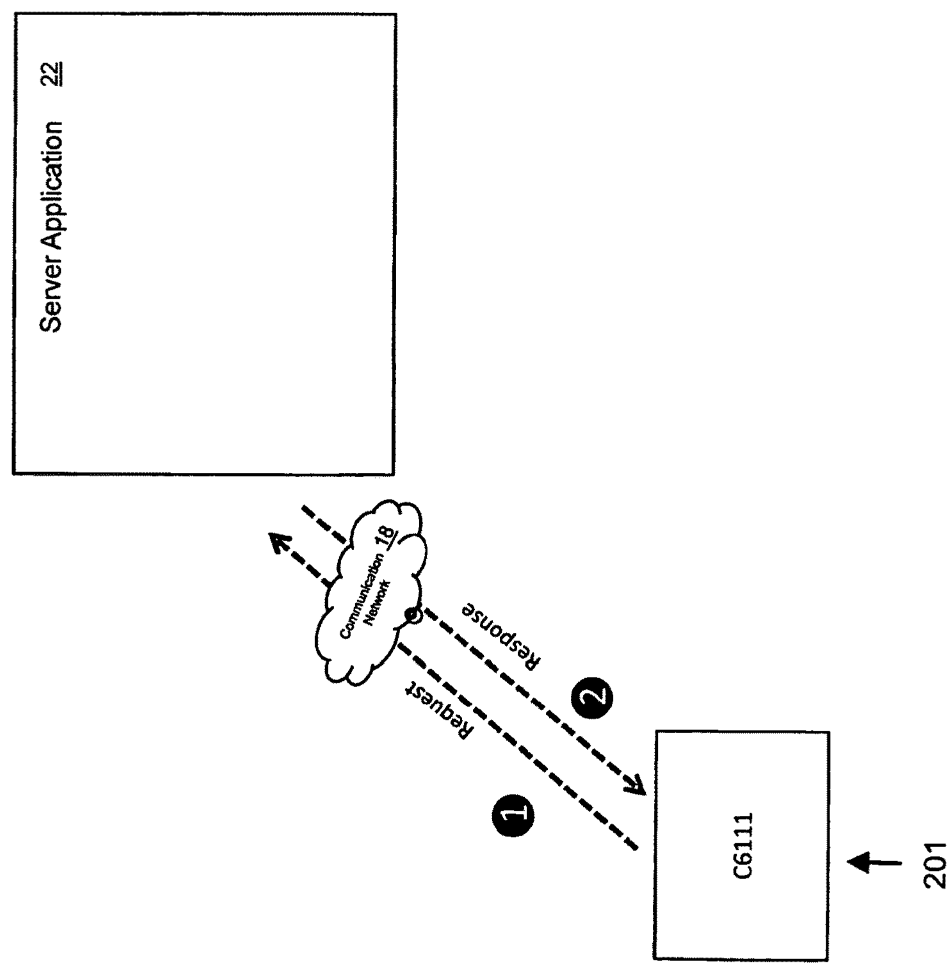
FIG. 7A-D illustrate the modes of operation in a collaborative environment.
Figure 7B:
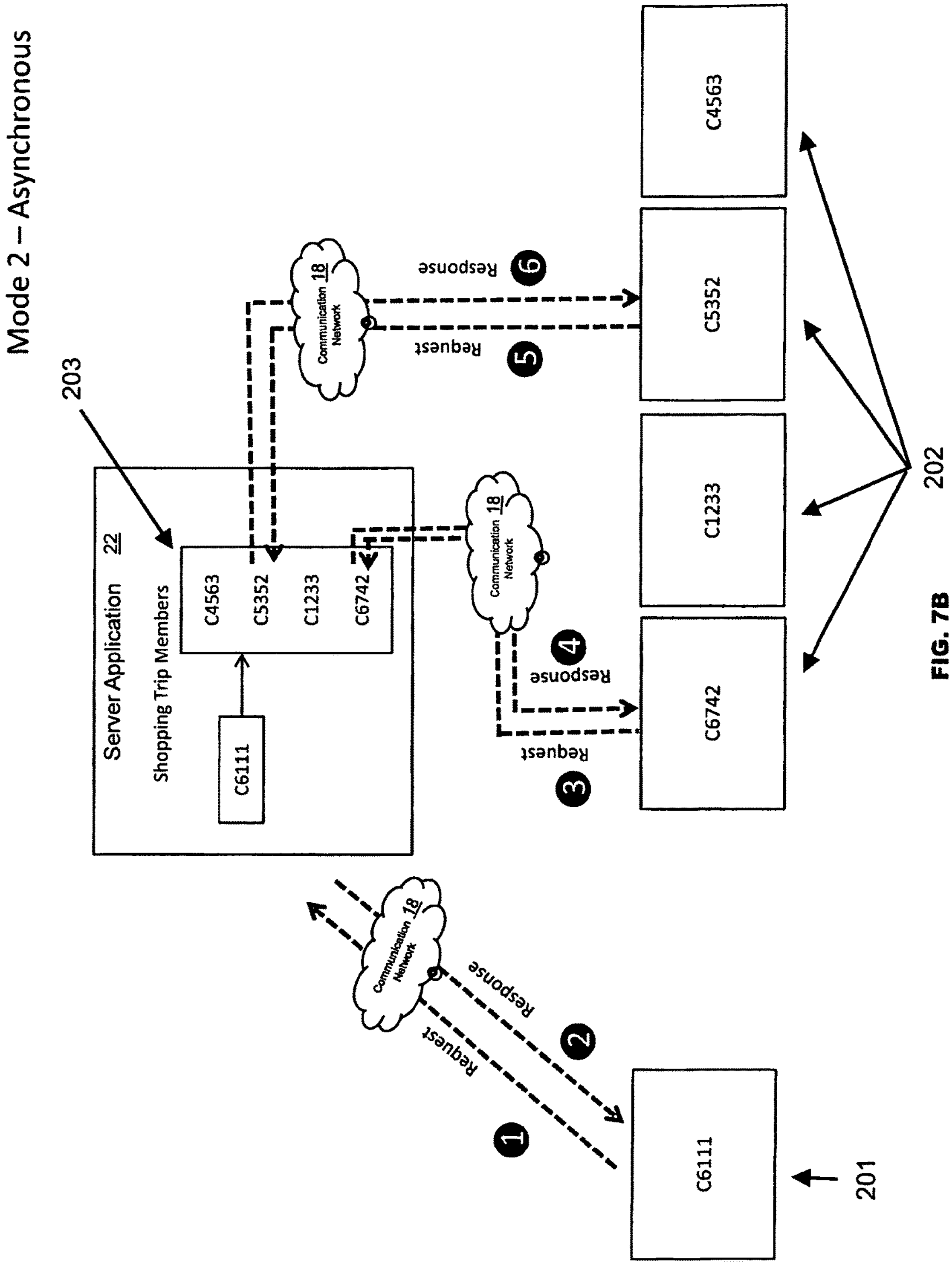
Figure 7C:
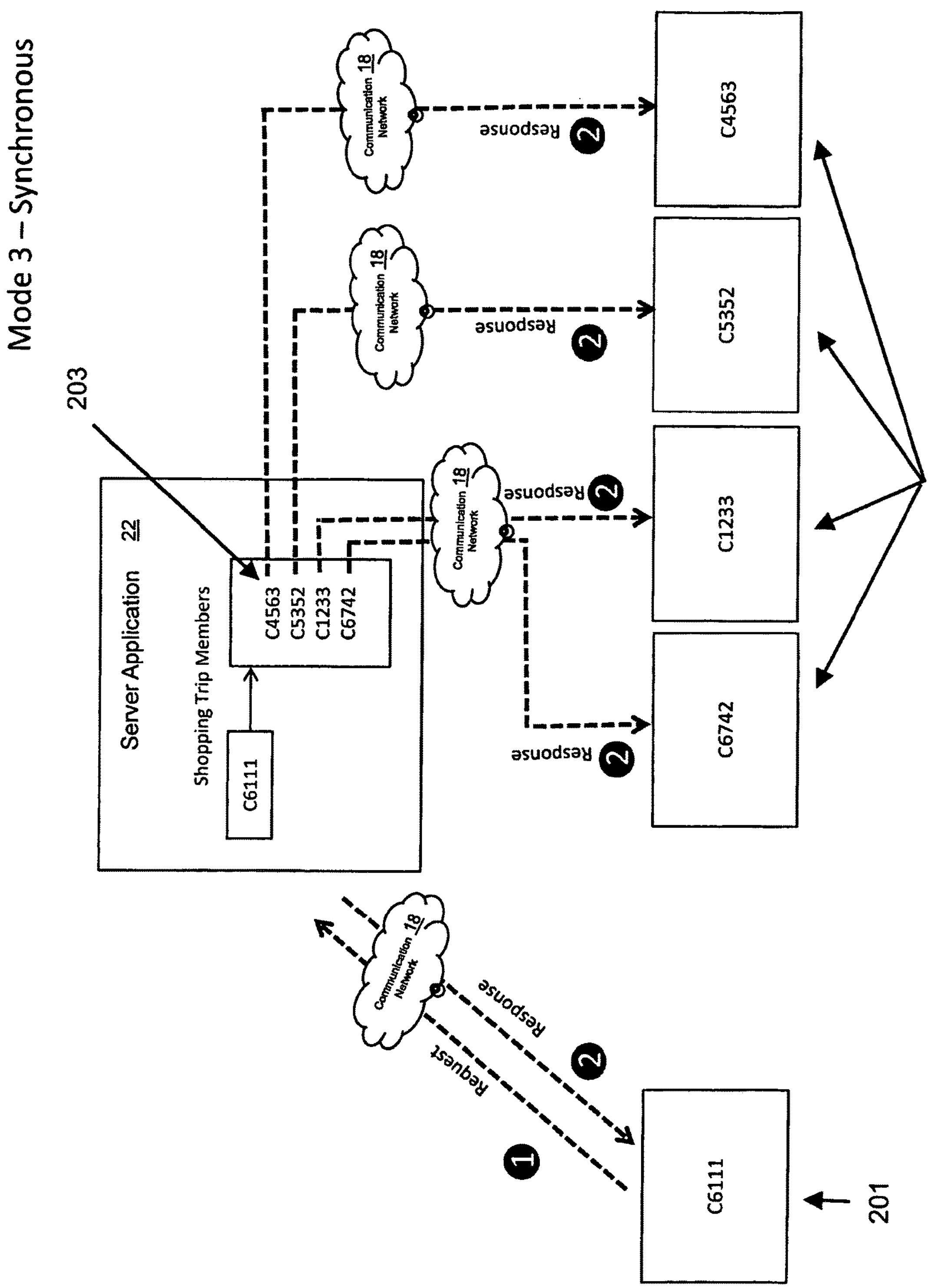
Figure 7D:
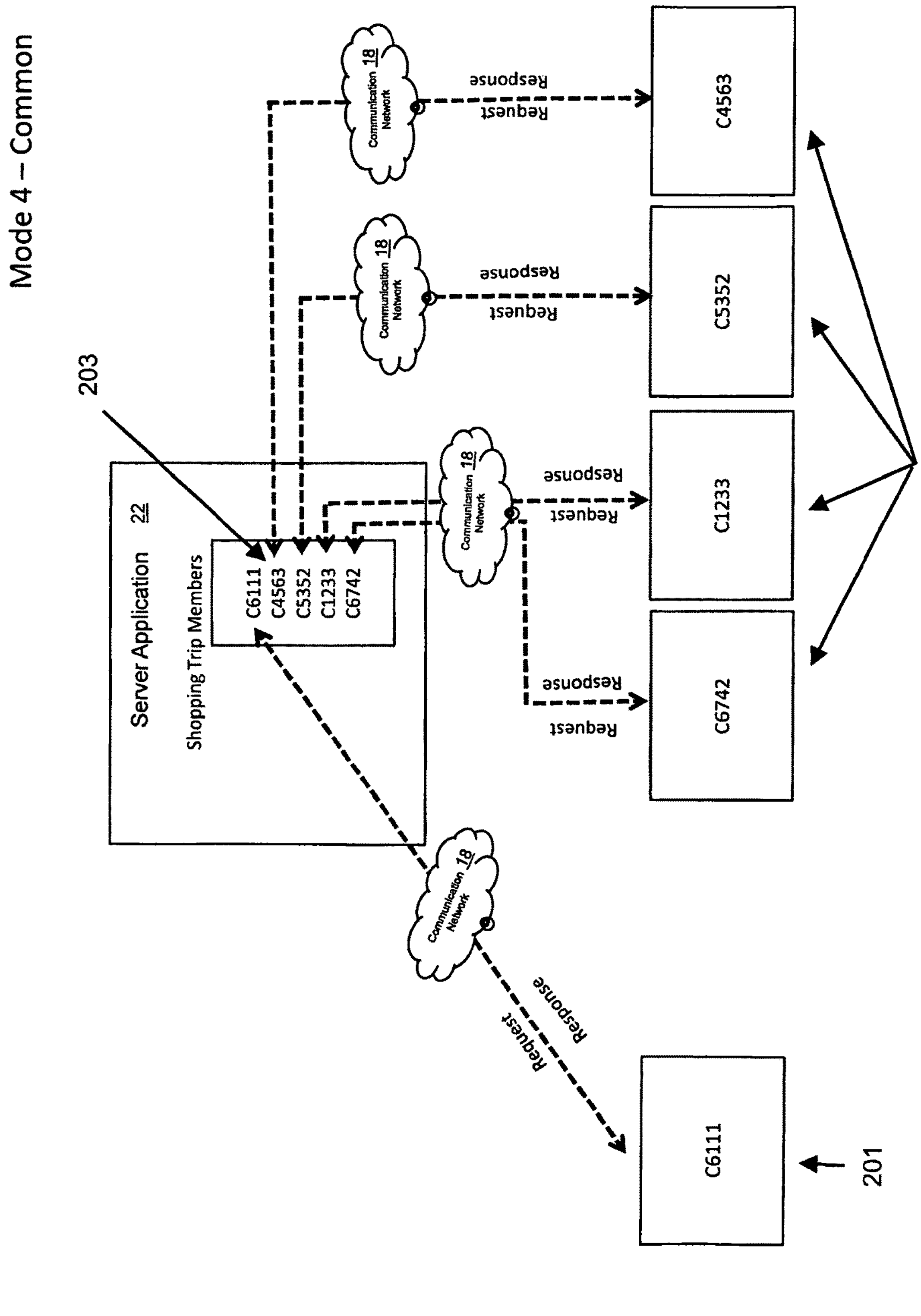

The techniques for accomplishing each of the four modes of operation are described next in an exemplary embodiment. Reference is now made to FIG. 7A where the regular mode of operation of a shopping trip is shown. An instance of a client 201 in the regular mode of operation makes a request to the server application 22 to view a product or a store or other data. In exemplary embodiment, the request can be made using HTTP request, RMI (remote method invocation), RPC (remote procedure call). The client instance then receives a response from the server. Reference is now made to FIG. 7B where an asynchronous mode of operation is shown in an exemplary embodiment. In this case, the user instance 201 makes a request to the server. A list 203 of shopping trip members and their information is maintained on the server for any given user. The list 203 is a list of users that have been selected by the client C6111 to participate in the shopping trip. In response to the client's request, the server then sends a response to the client 201 with the requested content. If the item is tagged for sharing, the server adds it to a list of shared items for that user. Other users on the shopping trip may request to view the shared items upon which the server sends the requisite response to this request. For instance, a user may view a product while browsing and may tag it as shared or add it to a share bin/folder. For instance, a user (C6111) may view a product and add it to a share bin. Other users (C6742, C5353) may then view the items in that bin. The shopping trip members list 203 may also be stored locally on the client's side in an alternative exemplary embodiment. Reference is now made to FIG. 7C where the synchronous mode of shopping is shown in exemplary embodiment. When a client instance 201 makes a request to the server to view a product, for example, an appropriate response is sent not only to the client requesting the information but also to all members on the shopping trip list who have selected that client's browsing contents (refer FIG. 20). In another exemplary embodiment, the synchronous mode works as follows: (1) A user, say USER1, visits a product page. (2) The product is registered in a database as USER1's last viewed page. (3) If another user, say USER2, has selected the option to show USER1's view, their view is updated with USER1's last viewed product. (4) When USER2 selects USER1's view, the view is updated every 3 seconds. (If there is no activity on part of USER2 for a given period of time, USER2's client application may pause polling the database to save bandwidth and other computational resources. Upon reactivation by USER2, view updating may resume). Thus, updating of the views may be server driven or client driven. Users can specify user access privileges to content that belongs to them. For example, they can set access privileges to various apparel items in their wardrobe allowing other users to access certain items and denying access to certain others. An icon notifies the user if the current view is being broadcast. The history of a trip is also available to the users. In an exemplary embodiment, this is done by showing the user the items that were registered in the database in step (2) above. This history can also be downloaded and saved by the users and can be viewed later. Reference is now made to FIG. 7D where the common mode of a shopping trip is shown in exemplary embodiment. In this figure, it is shown that several clients can simultaneously make a request and simultaneously receive a response. At any given time, any of the clients can send a request to the server to view an item, to explore an item (as discussed in reference to FIG. 36), etc. in exemplary embodiment. The following is a description of the communication protocol for the common mode of operation of a shopping trip. When a client sends a request to the server, it also monitors a channel on the server (could be a bit or a byte or any other data segment on the server in exemplary embodiment) to see if there any simultaneous requests made by other users. If no simultaneous requests are detected, the client completes the request and the server responds to all clients in the shopping trip with the appropriate information requested. For instance, if a catalogue item is viewed by one of the users, all other clients see that item. As another example, if a client turns over a 3D item, then all other clients see the item turned over from their respective views. If however, a simultaneous request is detected at the channel, then the client aborts its request and waits for a random amount of time before sending the request again. The random wait time increases with the number of unsuccessful attempts. If the response duration is lengthy, then requests are suspended until the response is completed by the server, in exemplary embodiment. Alternatively, a conflict management scheme may be implemented wherein the client also monitors the server's response for a possible conflict and sends the request when there are no conflicts. In yet another exemplary embodiment, the server may respond to requests if there are no conflicts and may simply pause if there is a conflict. These protocols also apply to peer-to-peer environments with the source of the data being the server and the requesting party being the client.

While viewing products, the content from audio and video channels of users on the shopping trip, and also the output of common (collaborative) applications (such as a whiteboard-like overlay that users can use to mark items on the web page or in the environment, or write and draw on) can also be shared simultaneously. In an exemplary embodiment, for the asynchronous mode, the user may tag an item for sharing and add it to a bin along with a video, audio and/or text message. When other users request to see items in this bin, they are shown the product along with the audio, video or text message. In exemplary embodiment, for the synchronous mode, the audio channels for all the users are added up and the video channel for whichever user's view is selected (FIG. 20) is shown. For the common mode of operation, in an exemplary embodiment, the audio channels from the users on the shopping trip are added up and presented to all the users while the video stream may correspond to the user who has just completed sending a request successfully through the common mode communication protocol described above. Sessions may be saved as described before. The views and the timeline during any session can be annotated. These pieces of information are cross-referenced to enable the user to browse by any of the pieces of information and view the corresponding information.

For each of the above modes, the clients may also interact in a peer to peer fashion as opposed to going through a server. In an exemplary embodiment, in the synchronized mode, if the user makes a request for a webpage to the server, then that information can be passed on to the other clients on the shopping trip via a peer to peer protocol. A user may also be engaged in multiple shopping trips (in multiple shopping trip modes) with different sets of users. Additionally, sub-groups within a shopping may interact separately from the rest of the group and/or disjoin the rest of the members of the shopping trip and then later resume activities with the group.

While operating in any of these modes, the user has the option to turn on an 'automatic' mode feature whereby the system engages the user in a guided shopping experience. In an exemplary embodiment, the user may select items or categories of items that the user is interested in and specify product criteria, preferences and other parameters. The user may also specify stores that the user is interested in browsing. Once this is done, the system walks the user through relevant products and stores automatically for a simulated guided shopping experience. The automated mode may be guided by a virtual character or a simulated effigy or a real person. The user can indicate at any time if she wishes to switch to the manual mode of shopping. The modes of operation presented here for shopping can be applied to other collaborative applications. For instance, going on a field trip, or virtual treasure hunt, or sharing applications as discussed with reference to FIG. 49 O.

Reference is now made to figures that describe the system 10 in greater detail, through sample images that are taken from the system 10. The sample images describe the operation of the system 10 with examples that are provided through sample screen shots of the use of the system 10.

Figure 8:
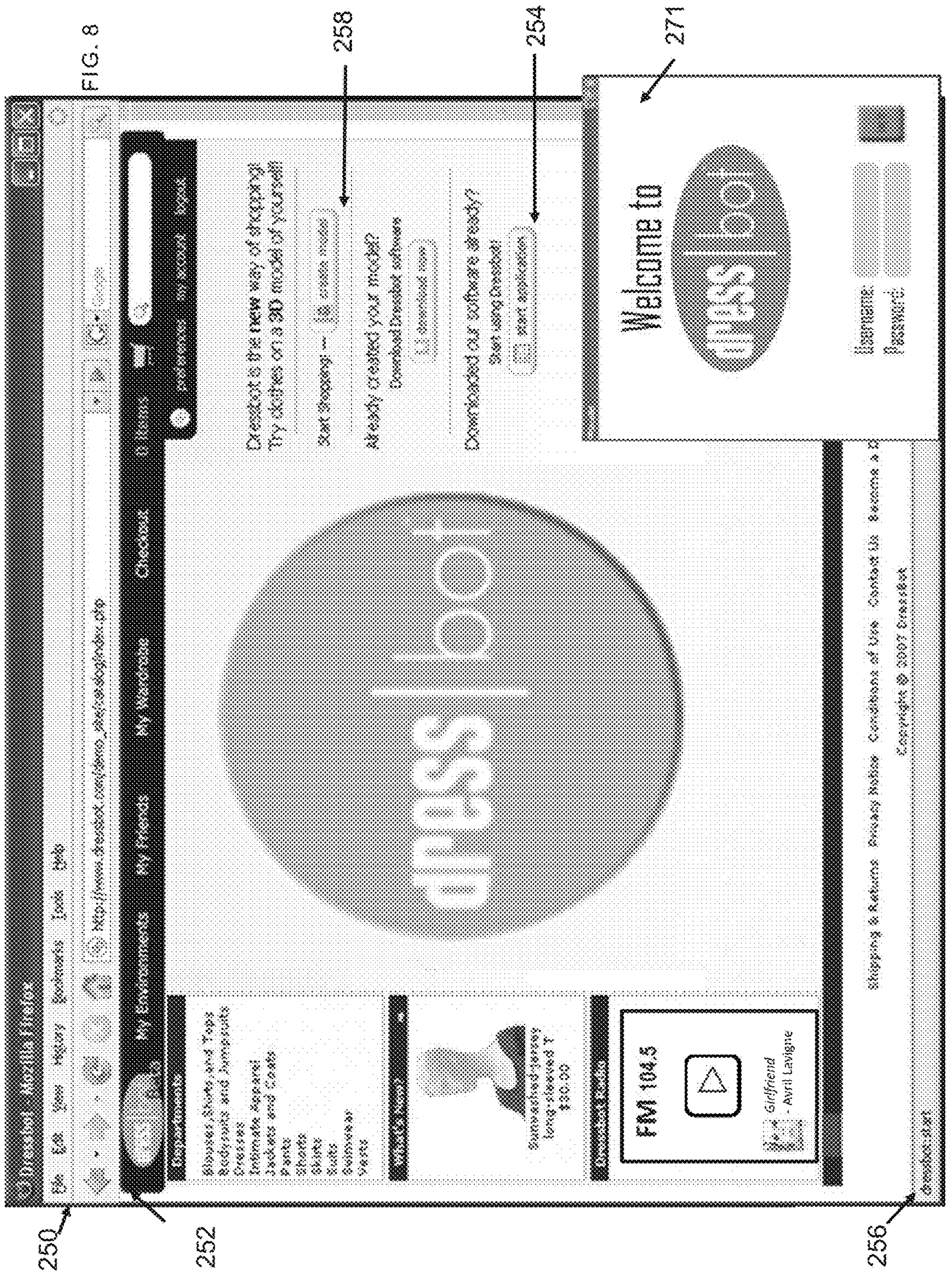
FIG. 8 is an image of a sample main page screen for shopping.
Figure 31:
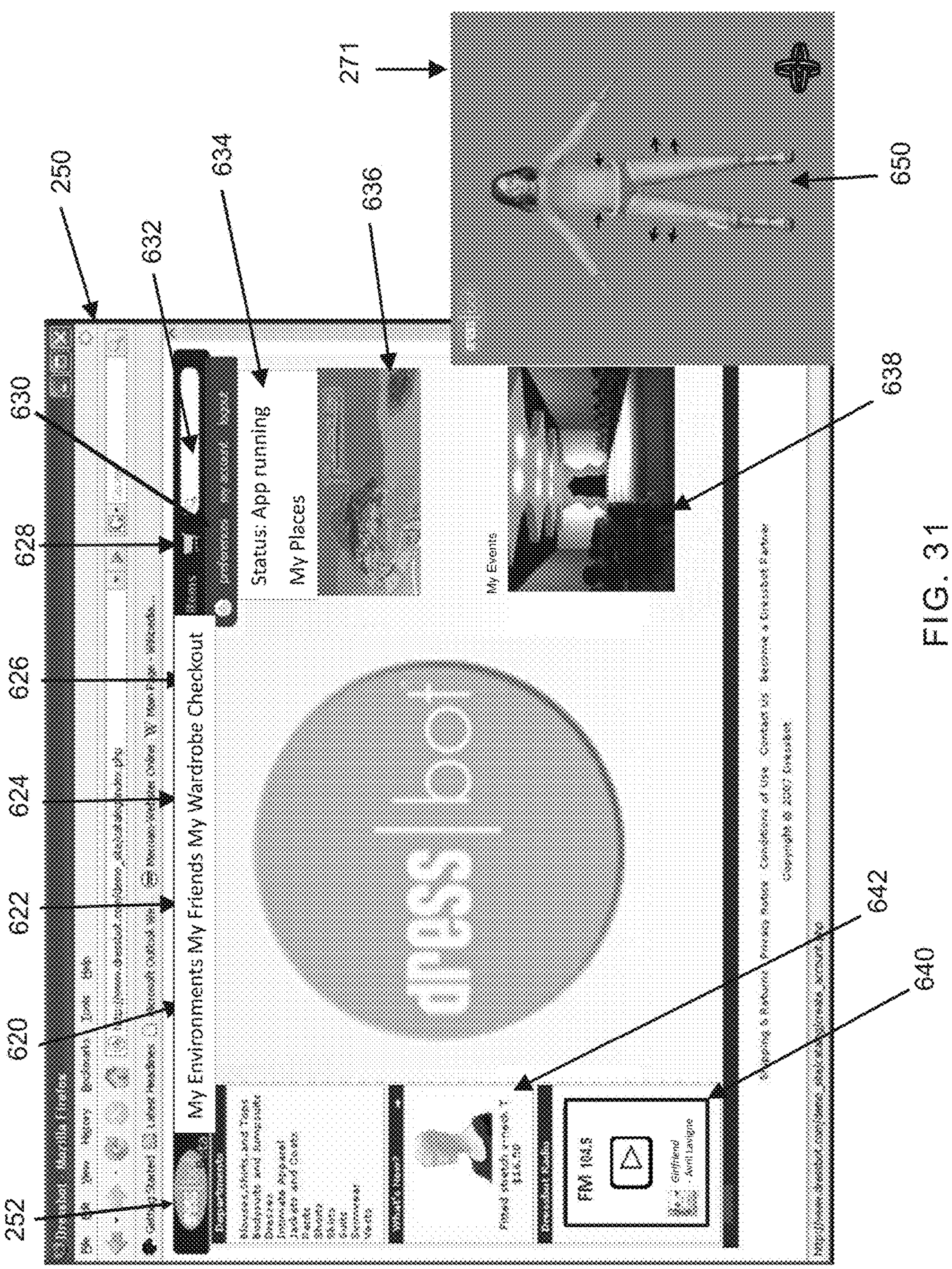
FIG. 31 is an image of a sample browser main page screen and a sample local application screen, showing sample features.

Reference is now made to FIG. 8 and FIG. 31, where a sample main page screen 250 is shown, in an exemplary embodiment. The sample main screen 250 is used for purposes of example. The main screen 250, in an exemplary embodiment presents the user with various options. The options in an exemplary embodiment include the menu options 252. The options menu 252 allows a user to select from the various options associated with the system 10 that are available to them. In an exemplary embodiment, the options menu allows a user to select tabs where they can specify further options related to their respective environment 620, friends 622 and wardrobe 624 as has been described in FIG. 5. Users can search the site for appropriate content and for shopping items using the search bar 632; they can browse for items and add them to their shopping trolley 628 which dynamically updates as items are added and removed from it; and complete purchase transactions on the checkout page 626. The options that have been provided here, have been provided for purposes of example, and other options may be provided to the user upon the main page screen 250. Furthermore, users can choose and set the theme, layout, look and feel, colours, and other design and functional elements of the main and other pages associated with their account on system 10, in the preferences section 630. In an exemplary embodiment, users can choose the colour scheme associated with the menu options 252 and the background of the main and other pages. The local application described further below is launched on clicking the button 254. The status bar 256 displays the command dressbot: start which appears as the local application is started. Button 258 starts the model creation process. When the local application 271 is running on the local machine, a notification 634 is displayed inside the browser window 250. Along with apparel shopping and modeling, users can engage, with their virtual model and with other users, in collaborative activities which include, in exemplary an embodiment, participating in virtual tours and visiting virtual destinations 636; taking part in virtual events 638 such as fashion shows, conferences and meetings etc, all or some of which may support elements of augmented reality. A media player or radio may be available/linked available in the browser in an exemplary embodiment 640, Featured apparel items 642 and other current offers or news or events may also appear on the main page 250 in an exemplary embodiment.

Figure 9:
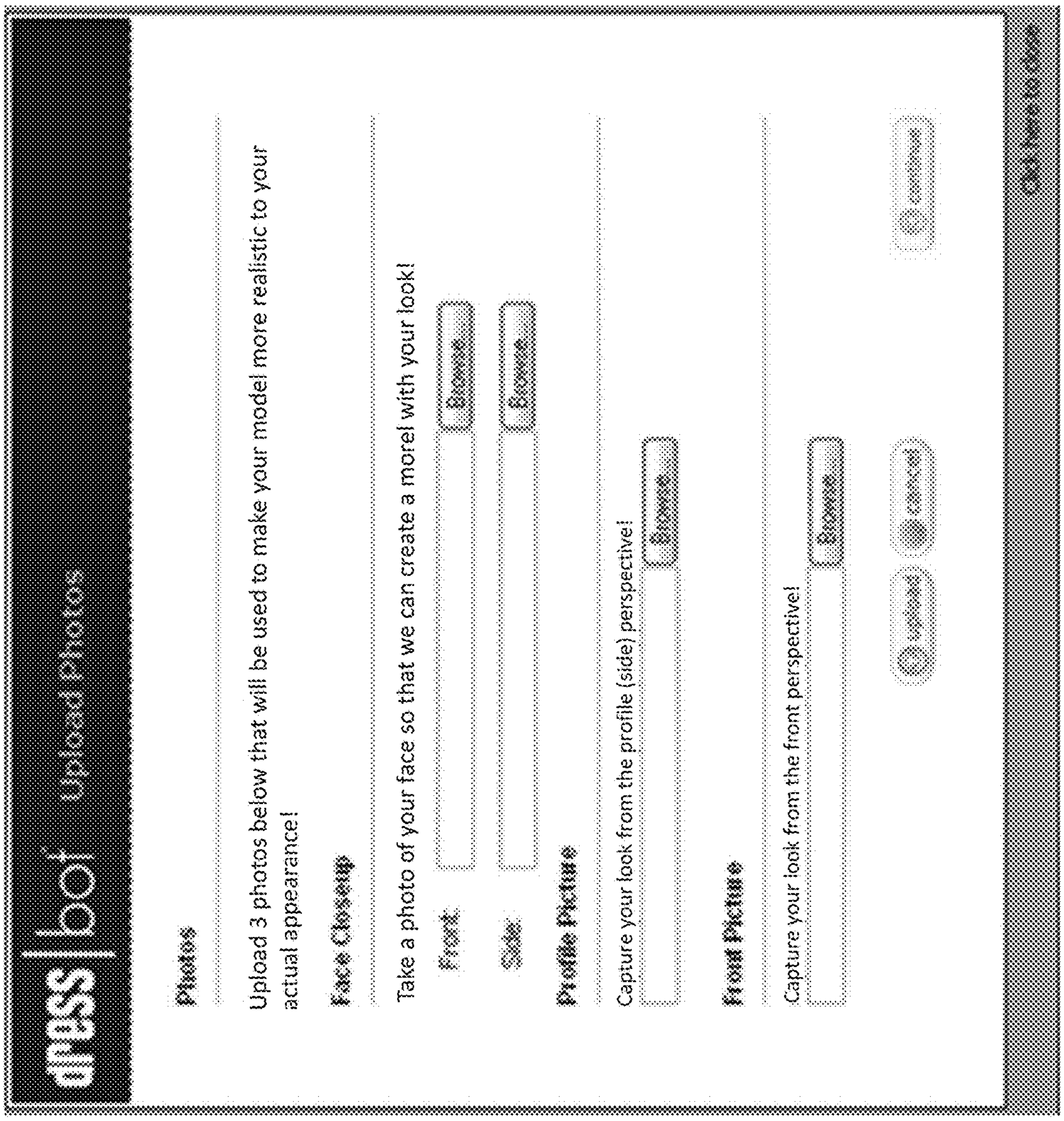
FIG. 9 is an image of a sample upload window for data for model generation.

Reference is now made to FIGS. 9 to 13, to better illustrate the process by which a 3D user model is created. As described above, the 3-D user model is created by first receiving user input, where the user supplies respective images of themselves as requested by the system 10. Reference is now made to FIG. 9, where a sample image upload window is shown in an exemplary embodiment. The image upload window is accessible to the user through accessing the system 10. As described above, in an exemplary embodiment, the system 10 is accessed through the Internet. The sample upload window 260 is used to upload images of the user that are then used by the system 10 to generate the user model. As shown in FIG. 9, the user is requested to upload various images of themselves. The user in an exemplary embodiment uploads images of the facial profile, side perspective and a front perspective. In an exemplary embodiment, the user is able to upload the images from their respective computing device or other storage media that may be accessed from their respective device.

Figure 10:
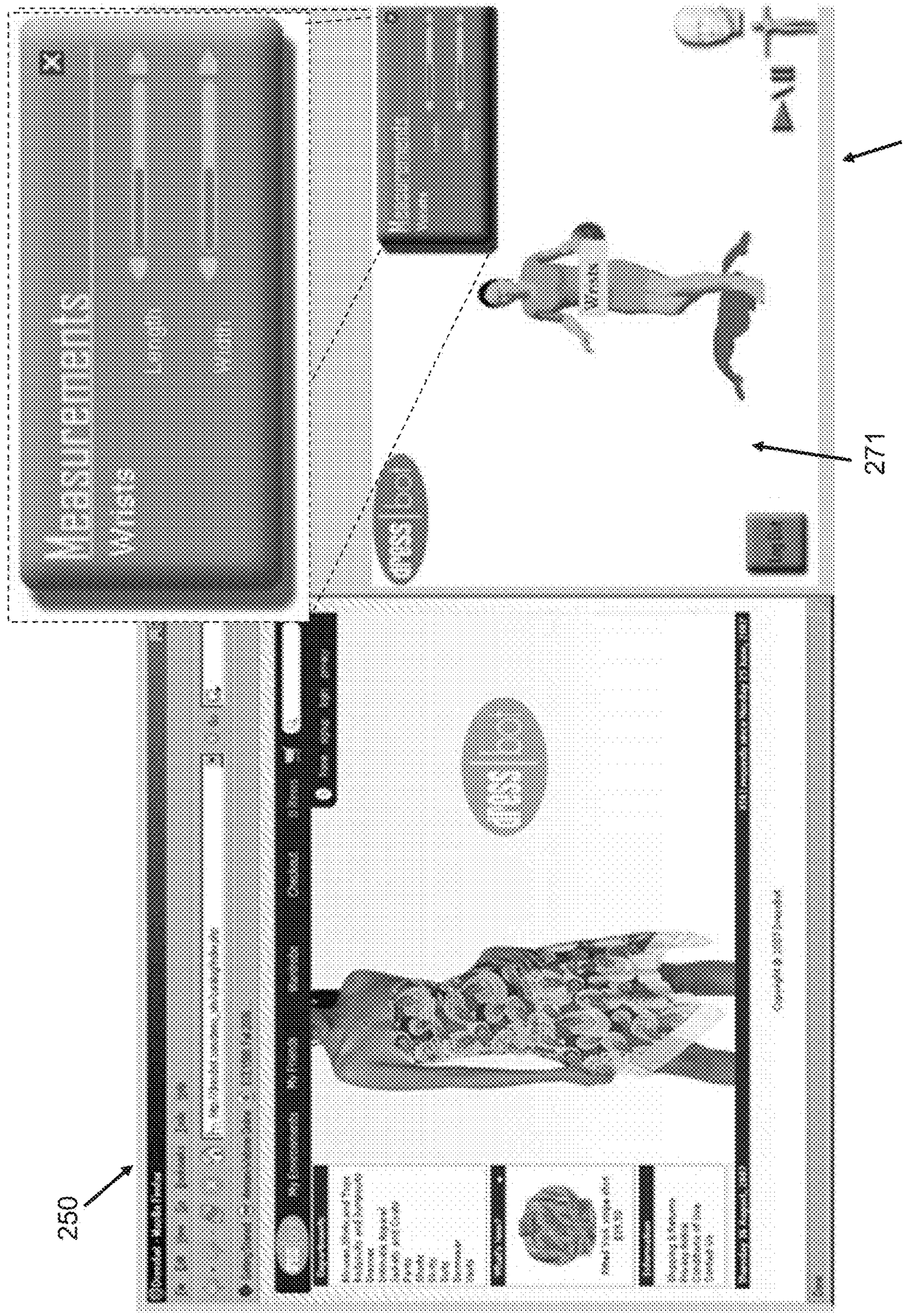
FIG. 10 is a image of a sample local application window and a sample browser window.

Reference is now made to FIG. 10, where a sample image of a client application window 270 is shown. In an exemplary embodiment, the client application 16 resident, or associated with the computing device causes a client application window 270 to be displayed to the user when the user model is being created. The client application can request and submit data back to the server. The protocol for communication between the application 16 and server 20 is the HTTP protocol in an exemplary embodiment. The application 16, in an exemplary embodiment initiates authenticated post requests to a PHP script that resides on the portal server and that script relays the requested information back to the application 16 from the server 20. People are comfortable with shopping on the internet using a browser and with monetary transactions through a browser. In order to provide the user with a rich experience, a rich 2D and/or 3D environment is desired. Such an environment can be a computational burden on the portal server. To reduce the computational load on the portal server, the computationally intensive rendering aspects have been pushed to the client side as an example. In an exemplary embodiment, this computational efficiency can be achieved through the use of a local stand-alone application or a browser plug-in, or run within a browser, or a local application that interacts with the browser and portal server 20. The current implementation, in an exemplary embodiment, involves a local application 271 that interacts with the browser and the portal server and is a component of the client application 270. In a typical setting, the local application and the browser interact with each other and also with the portal server 20, which in turn interacts with other components of the internet. Each of the modules of the portal server 20 may have a corresponding module on the client application. This may be a part of the browser or local application 271, the browser or a combination of the two. The browser and the local application interact in an exemplary embodiment, via protocols like HTTP and this communication may take place via the portal server 20 or directly. The purpose of the local application 271 is to enable computationally intensive tasks to be carried out locally such as computations required for 3D renderings of the apparel, the user's model and the environments. This gives the appearance of running 3D graphics in a browser. This permits online transactions within the browser (buying apparel) and at the same time gives the user a rich experience by using the power of the local machine and not overburdening the server. For those users who are not comfortable with downloading the local application 271, a 2D, 2.5D or less sophisticated 3D rendering of the graphics is displayed within the browser. Details of the browser-local application interaction are described next. In an exemplary embodiment, on a Windows® platform, registering the protocol associates a keyword with the local application 271 on the user's system in the registry. Thus, when the start application button 254 is pressed, the local application 271 is launched. When a user clicks on the 'try on' button from the fitting room or wardrobe, a notification is sent to the local application indicating that the user wants to try an apparel item. A callback function is implemented within the local application that listens for such notifications. When a notification is received, the appropriate callback function is invoked. This callback function then queries the portal server or browser for the appropriate parameters and renders the scene. For example, clicking on an apparel item in the fitting room prompts the browser to send the command "dressbot:tryon=5" to the local application which then places the item with ID=5 on the user model. The gathering of information from the server is done using HTTP. Such a framework leverages the advantages of both familiar experience of a browser and the computational power of a local application. The above procedure and details have been described as an exemplary embodiment and may be implemented with other techniques. In an alternative embodiment, local application features may be implemented as part of a web browser.

By accessing the user model creation functionalities on the user's local computing device, the speed at which the model is generated and then modified (through the user's commands) is increased. The application window 270 displays to the user the current state of the model, and allows the user to perform various modifications to the user model, as detailed below.

As described above, the user is able to modify the respective measurements that are associated with a preliminary user model that has been generated. The measurements specified by the user may be specific measurements that more closely resemble the user's physical profile. However, the measurements that are specified may also be prospective measurements, where the user may wish to specify other measurements. For example, the user may specify measurements that are larger than their current measurements, if for example, they wish to model maternity clothes. Also, the user may specify measurements that are smaller than their current measurements, thereby providing prospective looks with regards to what a user may look like if they were to lose weight.

Figure 12A:
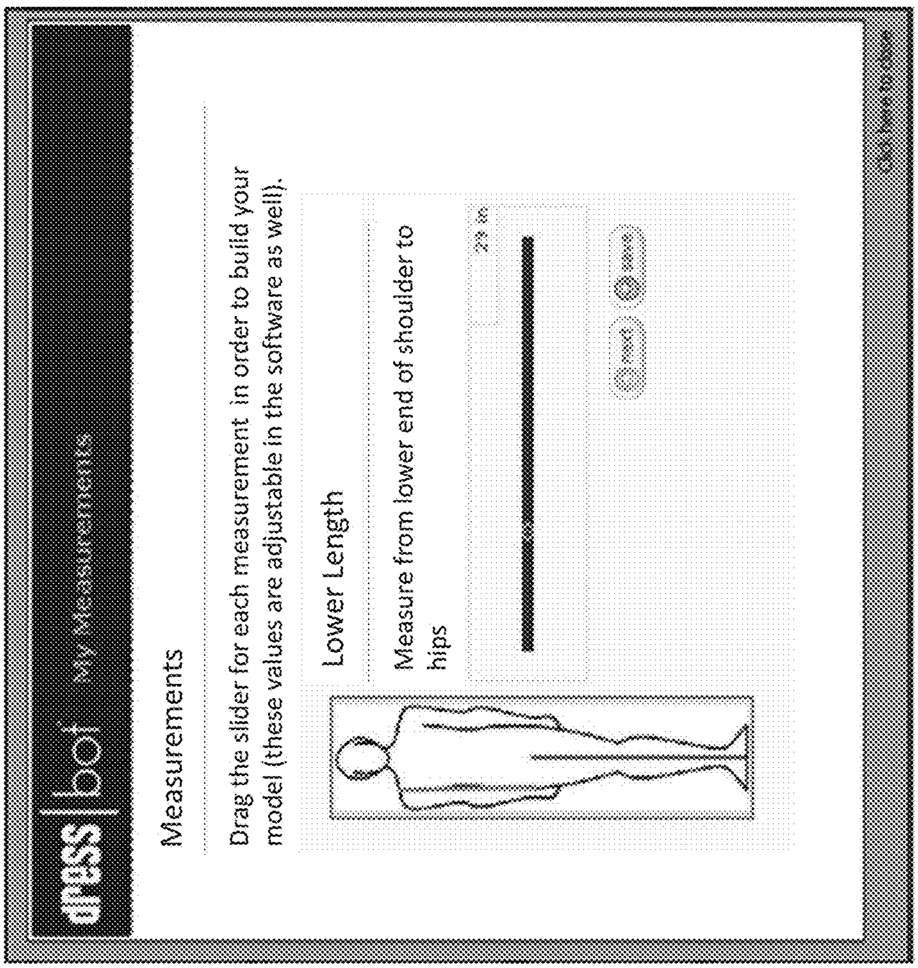
FIG. 12A is an image of a sample measurement window.

The head and face region of the user's model is simulated by the modeling module 50 utilizing images of the user's face taken from different angles. The face generation process may be completely automated so that the modeling module 50 synthesizes the model's face by extracting the appropriate content from the user's images without any additional input from the user or it may be semi-automated requiring additional user input for the model face generation process. Reference is now made to FIG. 11, where a sample facial synthesis display window 280 is shown illustrating a semi-automated facial synthesis procedure. The reference image 282 shows the user where to apply markers on the face i.e., points on the face to highlight. The sample image 284, in an exemplary embodiment shows points highlighting regions of the user's face corresponding to the markers in the reference image 282. The modeling module 50 may require additional inputs from the user to further assist the face generation process. This input may include information on facial configuration such as the shape or type of face and/or facial features; subjective and/or objective input on facial feature dimensions and relative positions and other information. The type of input acquired by the modeling module 50 may be in the form of text, speech or visual input. Additionally, the modeling module 50 may provide options to the user in order to specify various areas/points upon the respective area of the model that they wish to make further modifications/refinements/improvements to. It may then be possible to tweak or adjust certain facial features using adjustment controls as in the case of the slider control feature for tweaking body measurements described later in exemplary embodiment. To be able to better illustrate the how the user may make modifications to the user model in an exemplary embodiment, reference is made now to FIGS. 12 to 13. Reference is now made to FIG. 12A, where a sample measurement window 290 is shown, in an exemplary embodiment. The measurement window 290 allows the user to specify empirical data that is used to generate or modify the user model. The user is able to specify the measurements through aid of a graphical representation that displays to the user the area or region for which a measurement is being requested. In addition, videos and/or audio may be used to assist the user in making measurements. When a user does not specify the measurements that are to be used, default values are used based on data that is computed from the respective images that the user has provided. Measurements associated with a user's waist have been shown here for purposes of example as the user may specify measurements associated with other areas of their body as described above. The user may specify various modifications of the user model that are not limited to body size measurements. Such modifications may include, but are not limited to, apparel size, body size, muscle/fat content, facial hair, hair style, hair colours, curliness of hair, eye shape, eye color, eyebrow shape, eyebrow color, facial textures including wrinkles and skin tone.

Figure 12B:
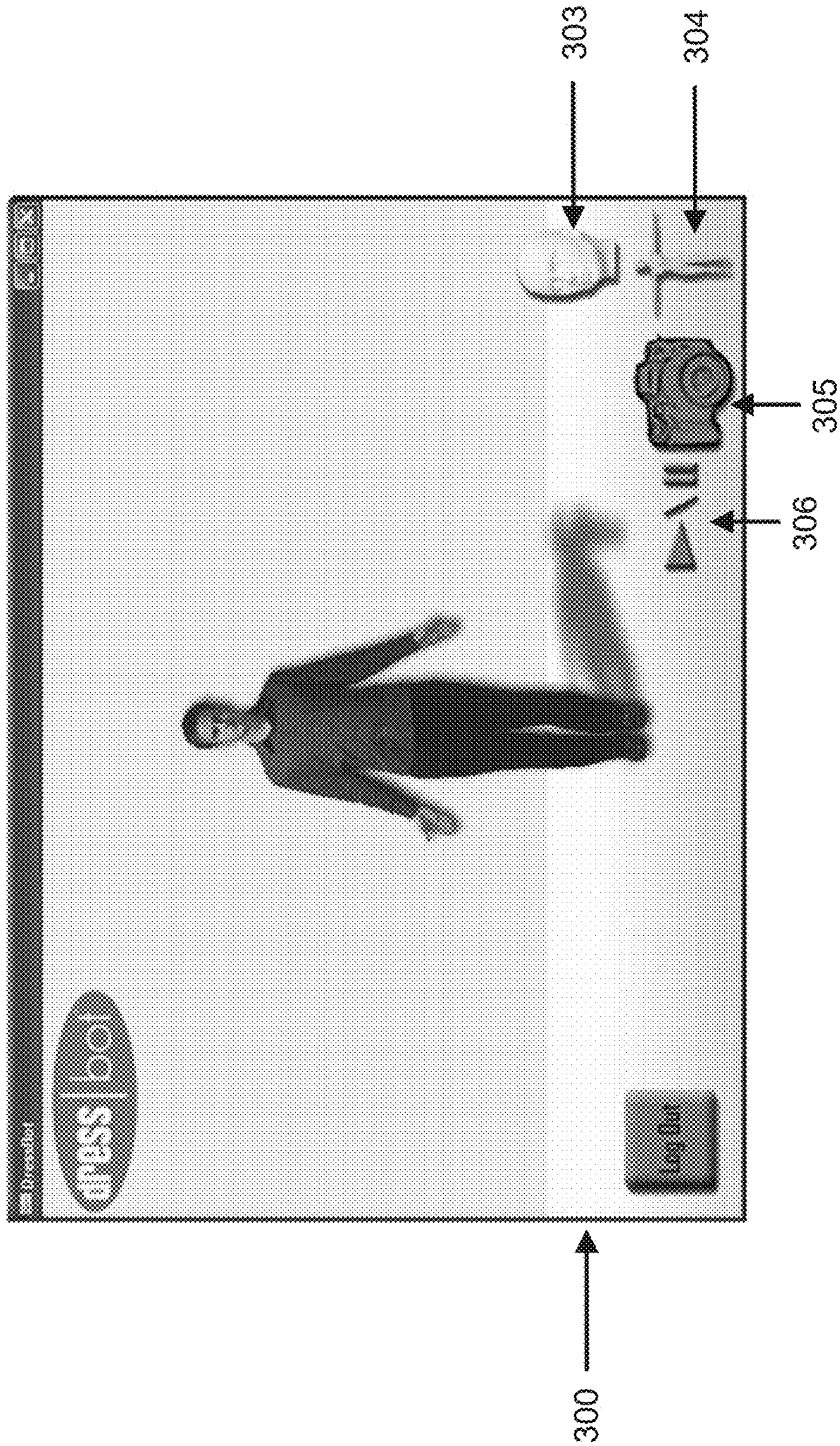
FIG. 12B is an image of a sample constructed photorealistic model.
Figure 12C:
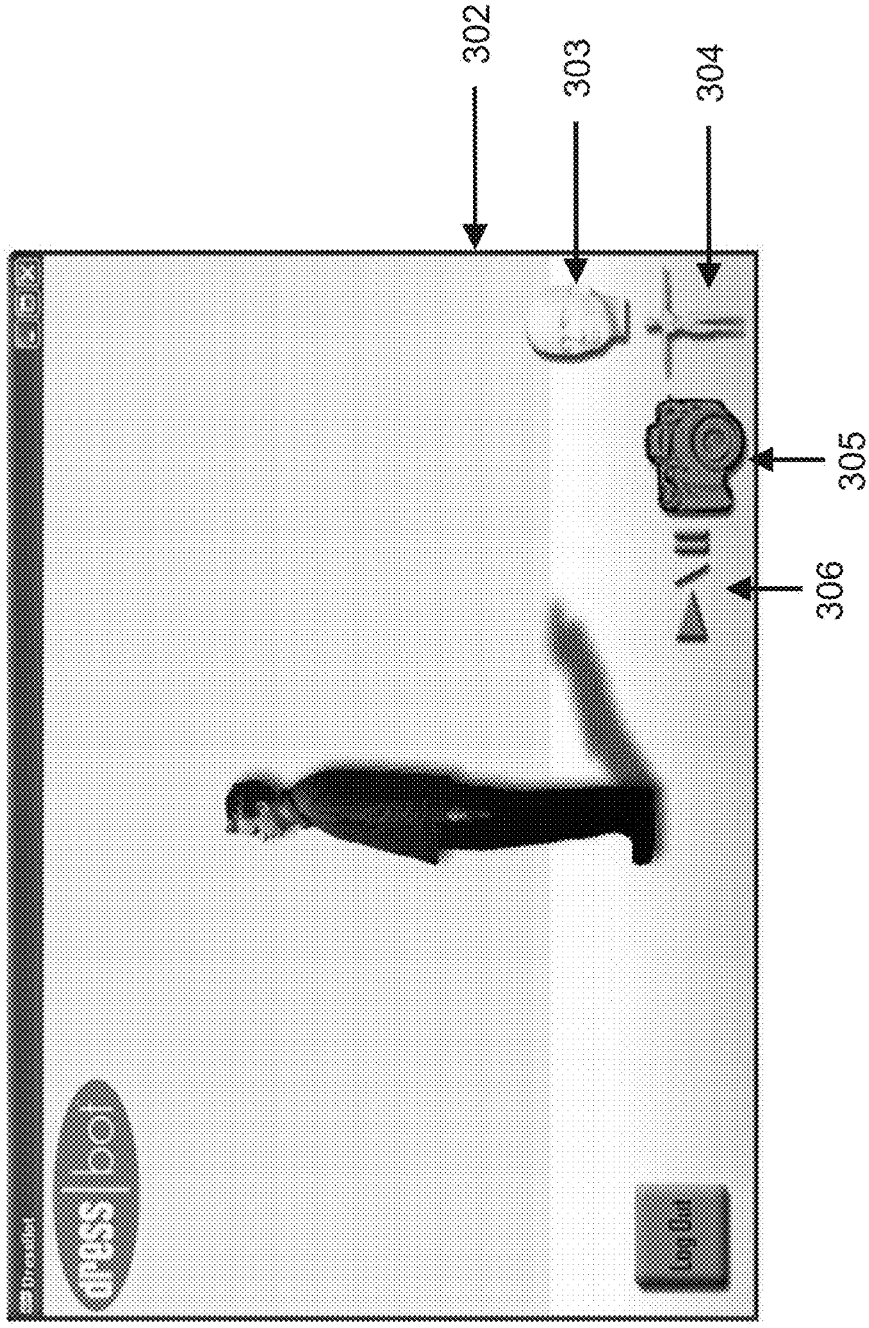
FIG. 12C is another image of a sample constructed photorealistic model.

Reference is now made to FIGS. 12B and 12C, where a sample image of a constructed model image 300 and 302 are shown, respectively. The model image window allows the user to inspect the created user model, by analyzing various views of the created model. Various features are provided to the user to allow the user to interact with the created model, and to be able to better view various profiles associated with the model. Features 303, 304, 305 and 306 are depicted as examples. Pressing button 306 presents the user with options to animate the user model or the environment. In an exemplary embodiment, the user may be presented with animation options on the same page or directed to a different page. The user may be presented with specific preset expressions/actions in a menu, for example, to apply on their user model. In an alternate exemplary embodiment, the user may animate their model through text/speech commands or commands expressed via other means. The user may also choose to synchronize their model to their own expressions/actions which are captured via a video capture device such as a webcam for example. The user is also provided with environments to embed the character in as it is animated. Icon 306 allows the user to capture images of the model, or to record video sequences of model animation, which may then be shared by the user with other users. The facial icon 303 when engaged causes the face of the generated model to be zoomed in on. The body icon 304 when engaged causes the entire user model to be displayed on the screen.

Figure 13A:
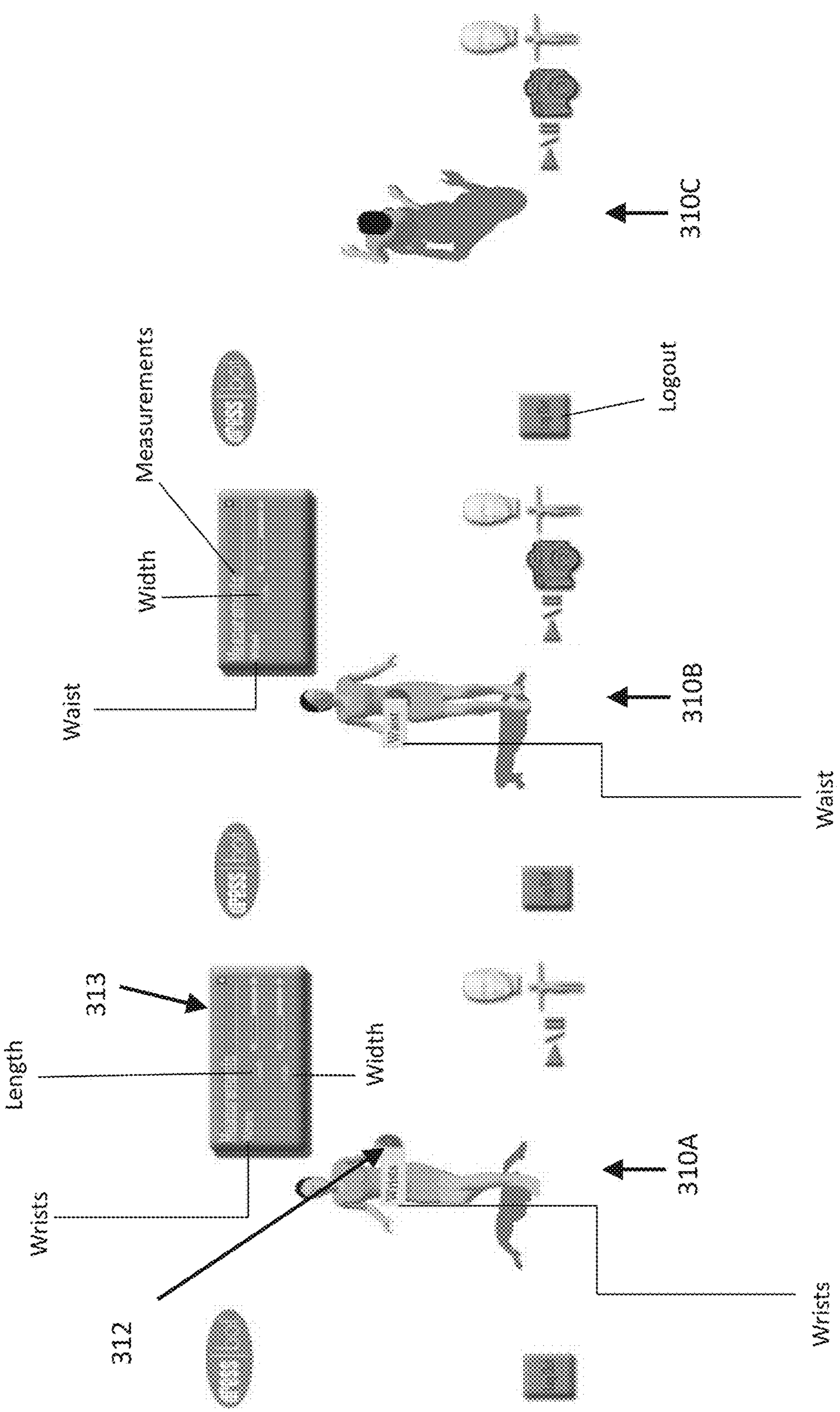
FIG. 13A is an image of a set of non photorealistic renderings of the user model shown from different viewpoints.
Figure 13B:
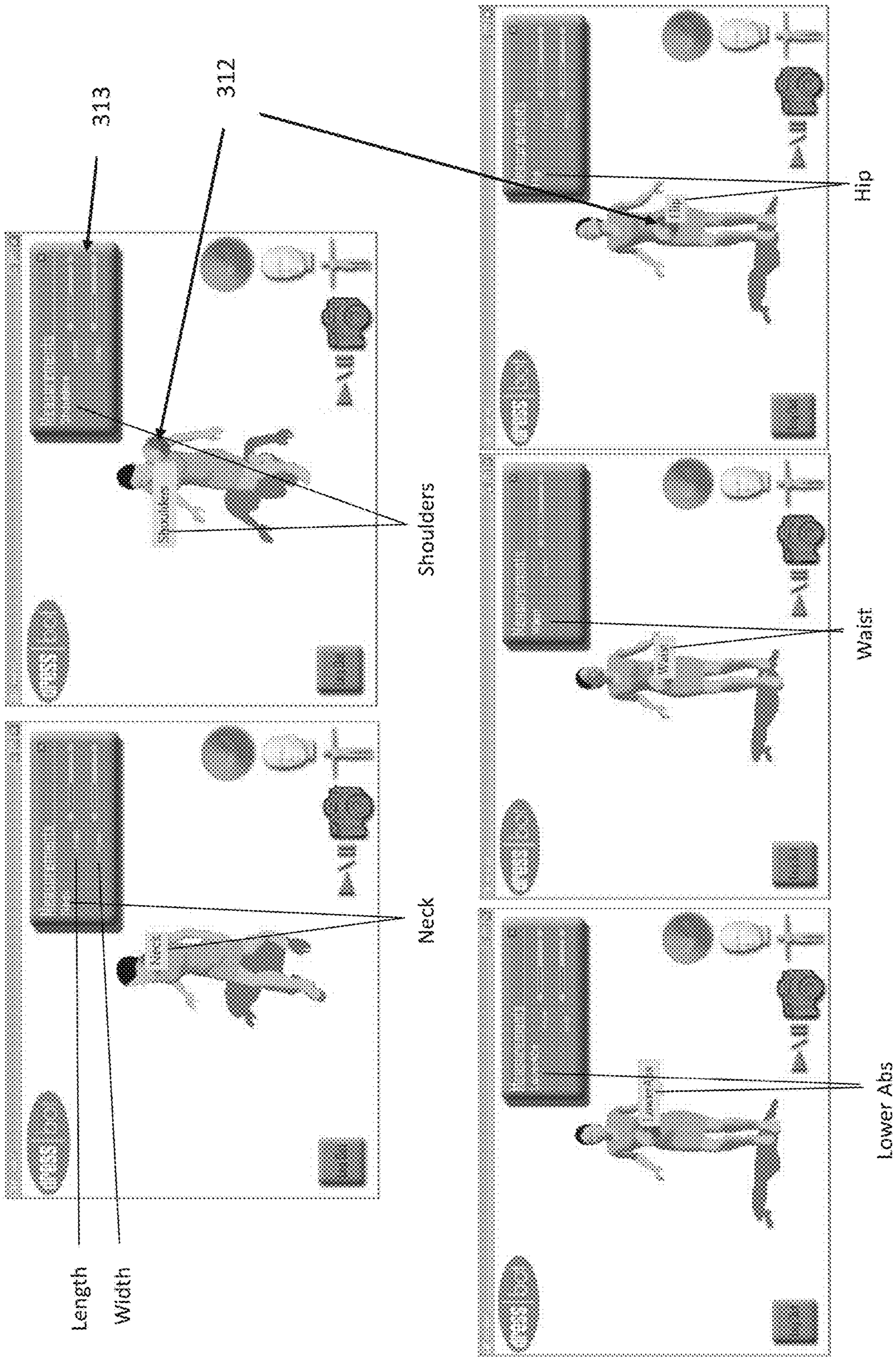
FIG. 13B is an image showing a sample mechanism that allows users to make body modifications directly on the user model using hotspot regions.

Reference is now made to FIG. 13A, where a set of sample non photorealistic renderings are shown. Specifically, exemplary embodiments of non photorealistic renderings 310A, 310B, and 310C are shown. The non photorealistic renderings display a series of images, illustrating various views that may be seen of a user model. The respective non-photorealistic renderings illustrate the various rotations of the user model that the user may view and interact with. Further, non photorealistic renderings 310A and 310B illustrate how the user may modify the wrist dimensions of the model. In an exemplary embodiment, the user may select areas on the user model where they wish to modify a respective dimension. For example, by engaging the user's model at pre-selected areas or 'hotspot' regions, a window will be displayed to the user where they may specify alternative dimensions. FIG. 13A shows the wrist being localized via a highlighted coloured (hotspot) region 312 as an example. The dialog box 313 containing slider controls can be used by the user to adjust measurements of the selected body part and is shown as an exemplary embodiment. FIG. 13B shows more sample images of how users can make body modifications directly on the user model using hotspot regions 312.

Figure 13C:
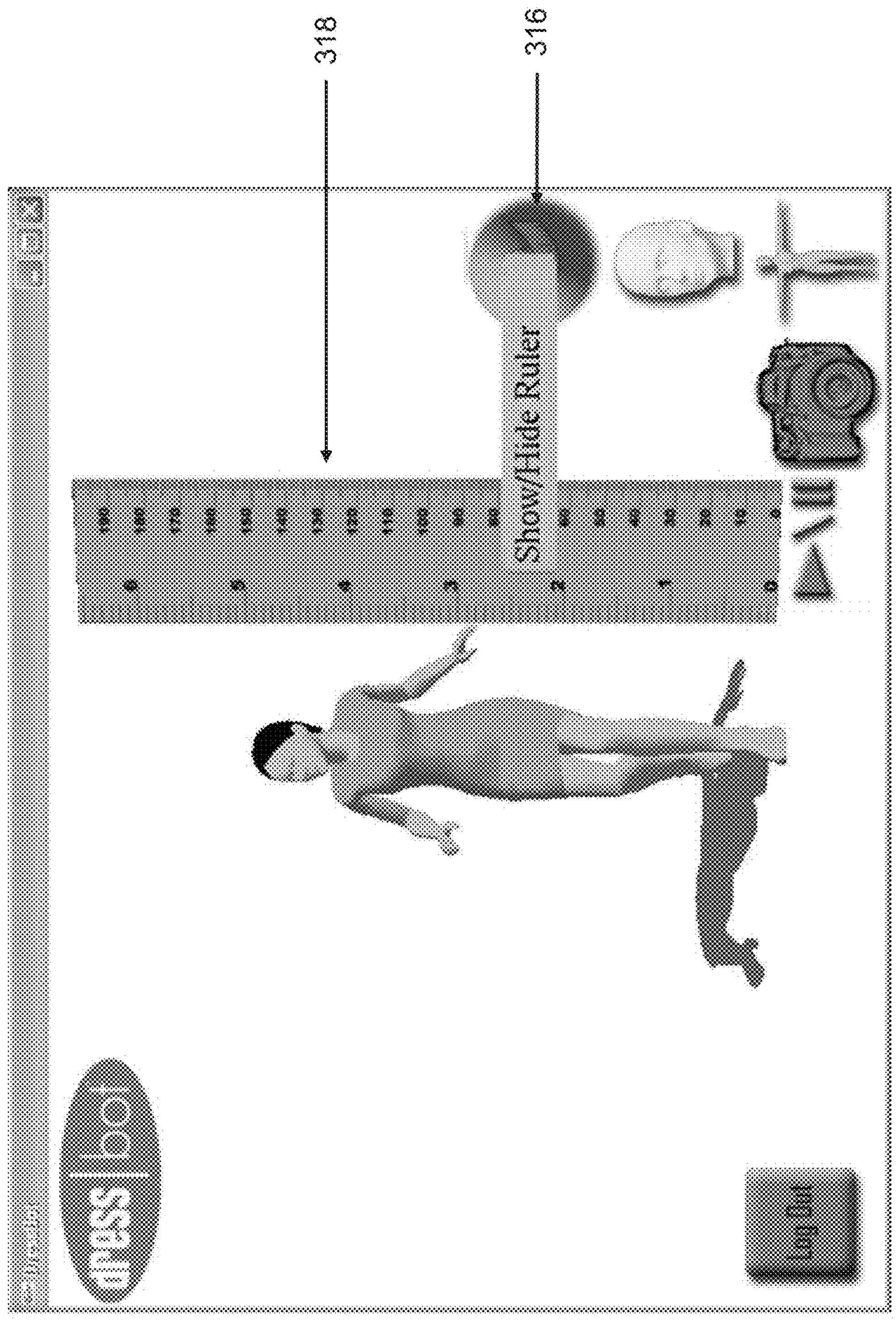
FIG. 13C is an image showing a sample ruler for taking measurements of the user model.

Reference is now made to FIG. 13C which shows a sample ruler for taking measurements of the user model which may be displayed by clinking on a ruler display icon 316. This ruler allows the user to take physical measurements of the user model and to quickly check measurements visually. The ruler may also prove useful to the user in cases where they wish to check how a given apparel or product affects original measurements. In an exemplary embodiment, the user may try on different pairs of shoes on the user model and check how much the height changes in each case.

Figure 14:
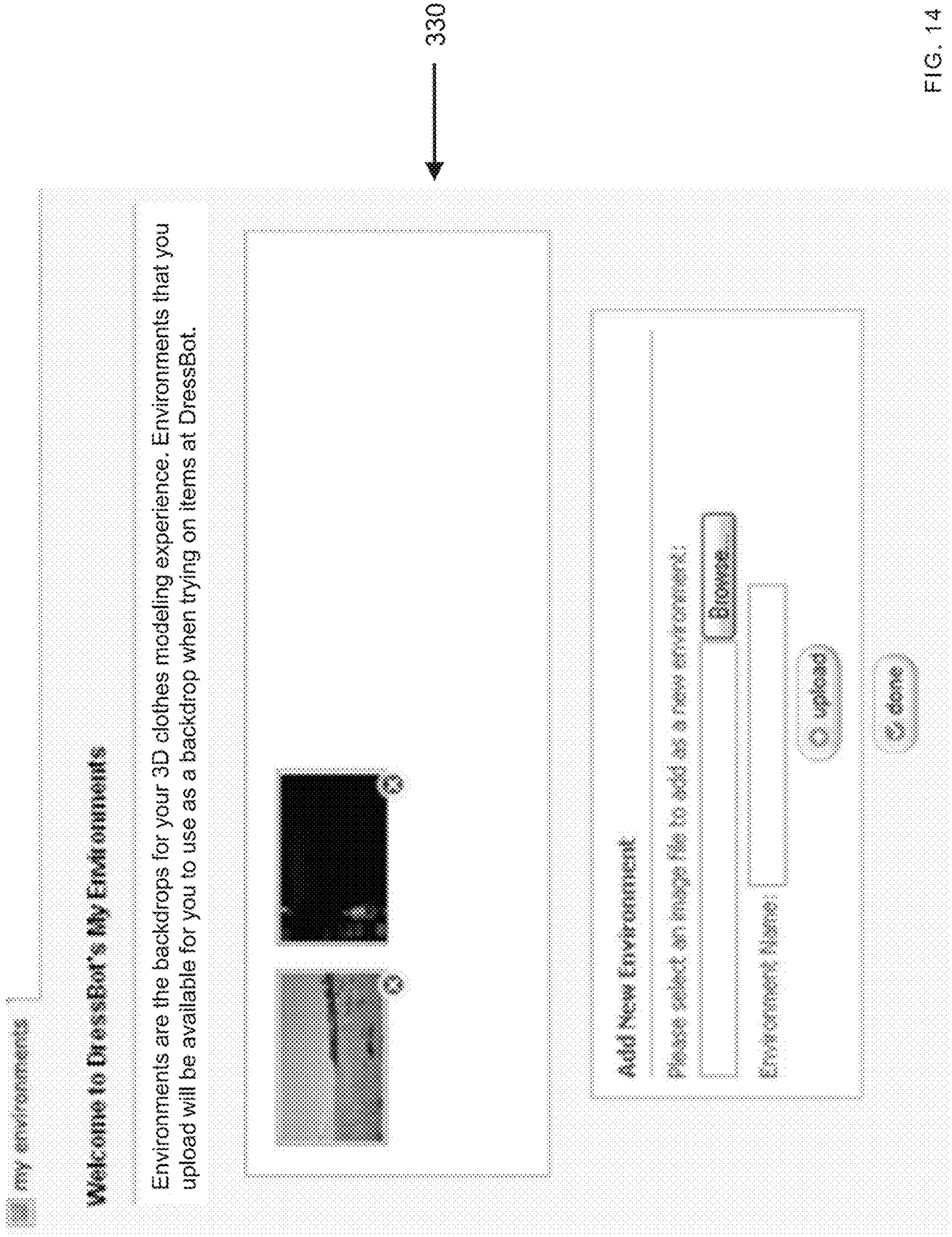
FIG. 14 is an image of a sample environment manager.

Reference is now made to FIG. 14, where a sample environment manager window 330 is shown in an exemplary embodiment. The environment module as described above, allows a user to choose respective environment backgrounds. The system 10 has default backgrounds that the user may select from. Also, the user is provided with functionality that allows them to add a new environment. By uploading an image and providing it with a name, the user is able to add an environment from the list that they may select from. Various types of environments may be added, including static environments, panoramic environments, multidimensional environments and 3-D environments. A 3D environment can be constructed from image(s) using techniques similar to those presented in [44].

Figure 15A:
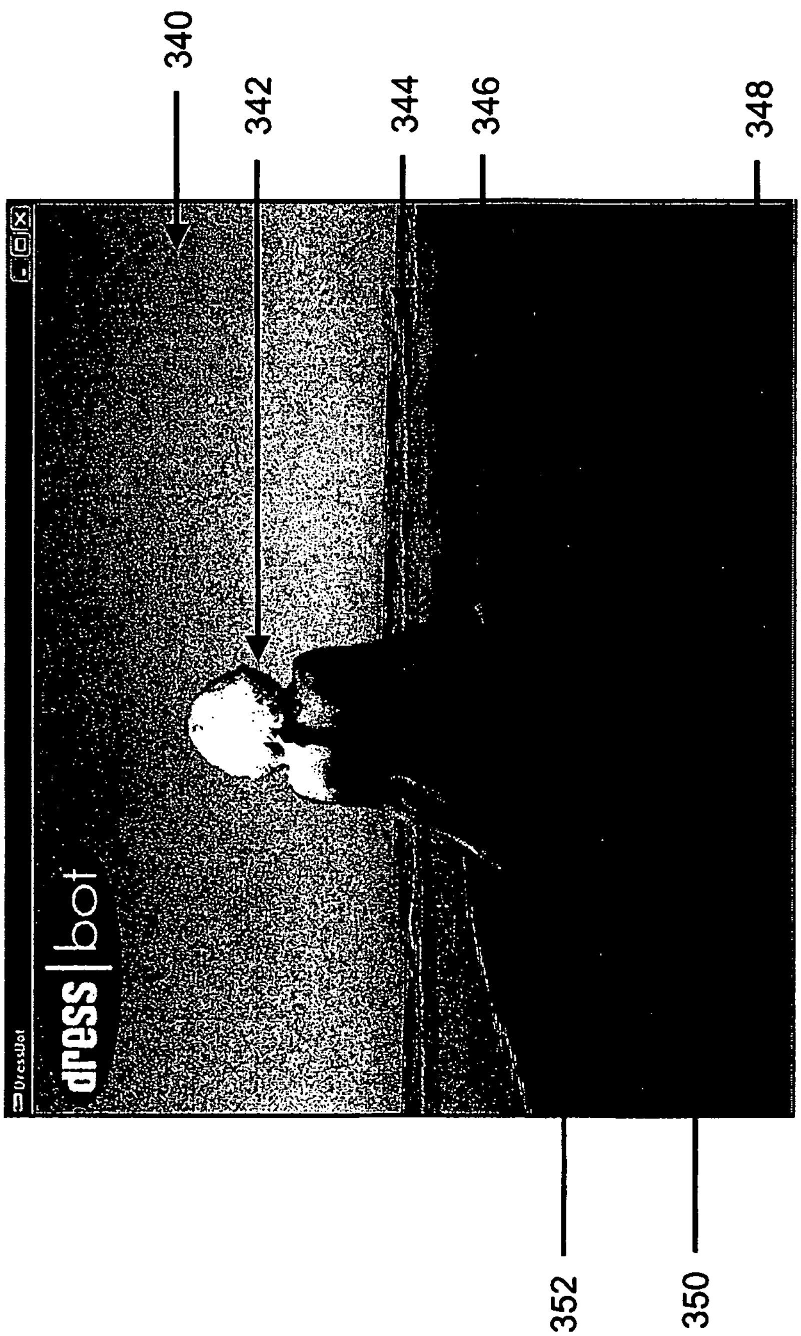
FIG. 15A is an image of a sample user model environment.
Figure 15B:
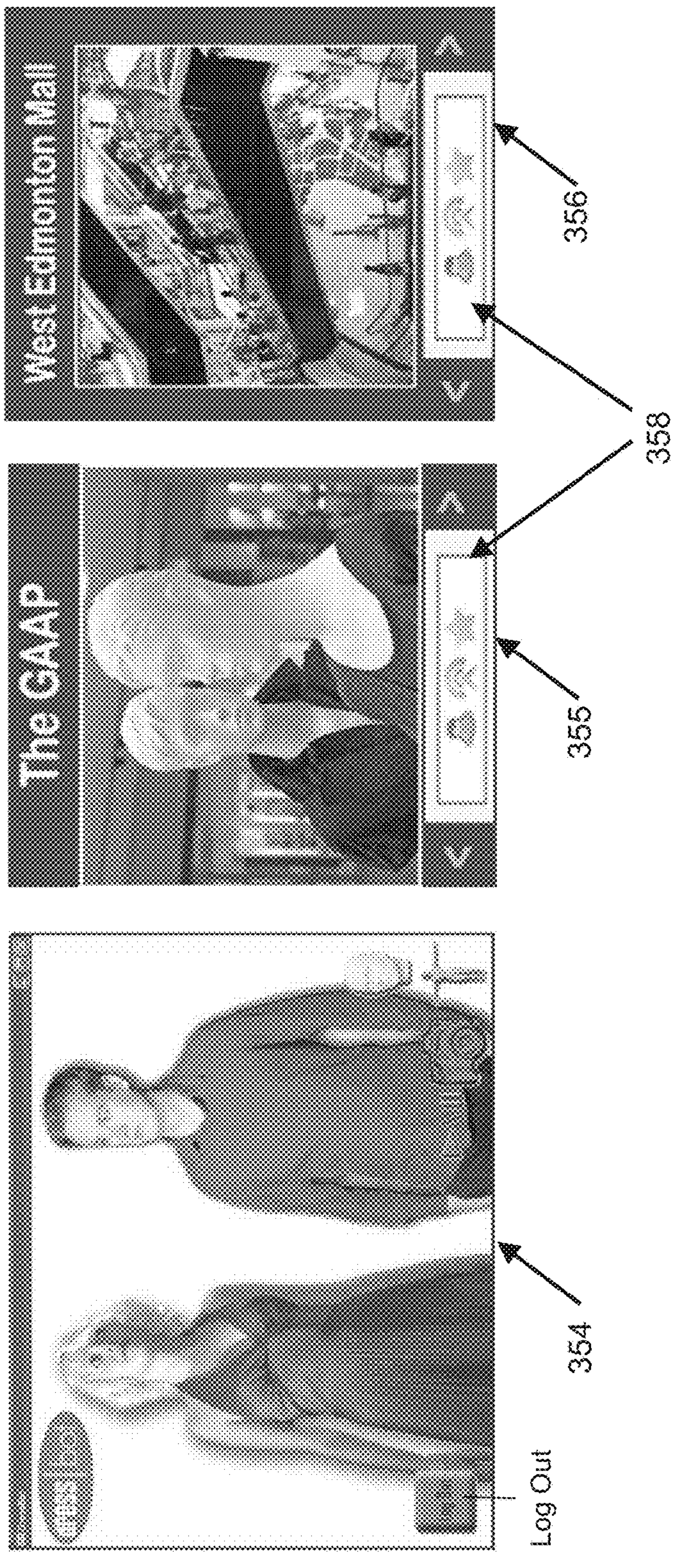
FIG. 15B is an image illustrating sample features of collaborative shopping.

Reference is now made to FIG. 15A, where a sample user model environment image 340 is shown containing a photorealistic user model. The image 340 is shown for purposes of example, and as explained, various background environments may be used. Further, the user model that is shown in FIG. 15A, has been customized in a variety of areas. Along with the apparel that the user has selected for their respective user model, the user is able to perform different customizations of the model and environment. Examples of which are shown here for purposes of example. With reference to labels 342, the user has customized the hair of the user. The customization of a user model's hair may include, the style, hair and colour. With reference to label 344, the environment may be customized, including the waves that are shown in the respective beach environment that is illustrated herein. With reference to label 346, one example of the types of accessories that the user can adorn their respective model with are shown. In this example image, a bracelet has been placed upon the user model's wrist. As a further example of the various accessories that may adorn the model, reference is made to label 348, wherein shoes are shown upon the respective user model. Reference is now made to FIG. 15B where some aspects of collaborative shopping are illustrated. User model views may be shared between users. Users may also interact via their model in a shared environment. In an exemplary embodiment, window 354 shows two user models in a shared window between users. Product catalogue views 355 may also be shared between users. For example, views of mannequins displaying apparel in product display window 355 may be shared with other users using the share menu 358. In another exemplary embodiment of a collaborative shopping feature, views of shopping malls 356 may be shared with other users as the user is browsing a virtual mall or store.

Figure 32:
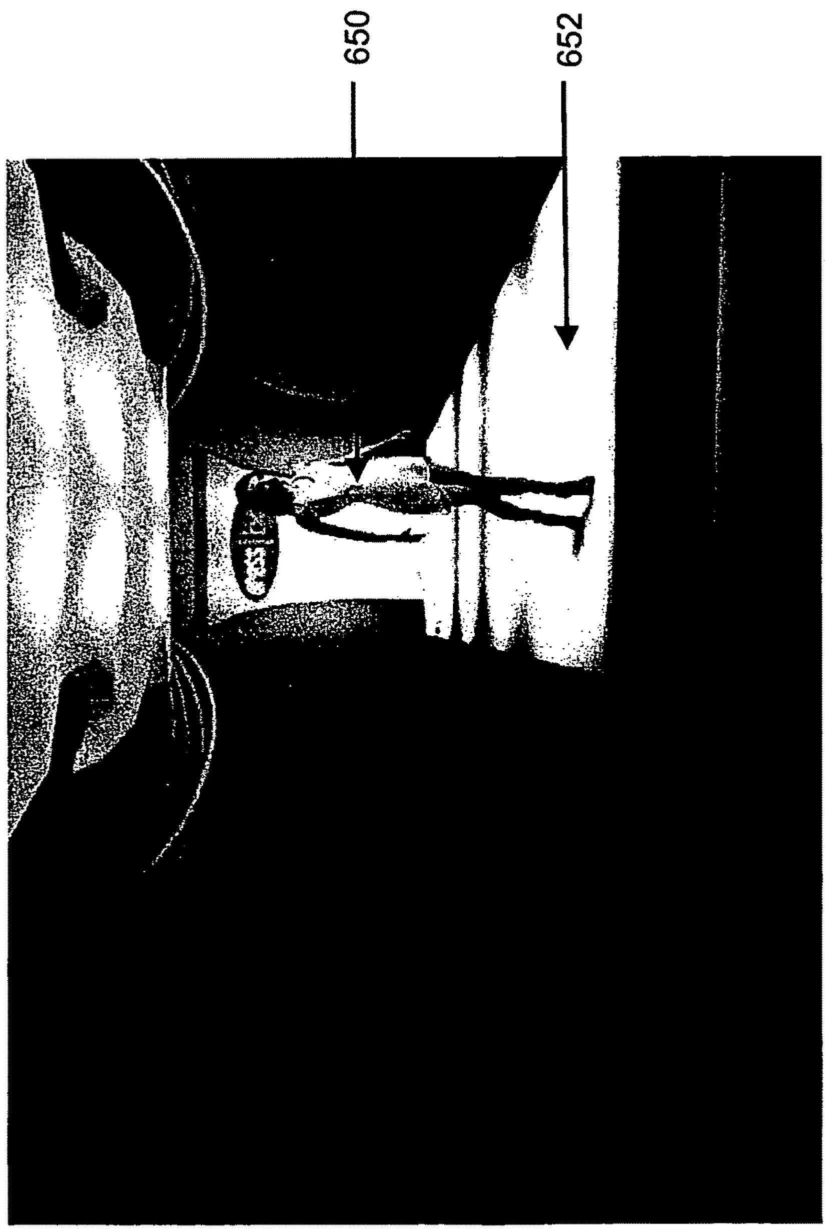
FIG. 32 is an image of a sample user model environment.
Figure 33:
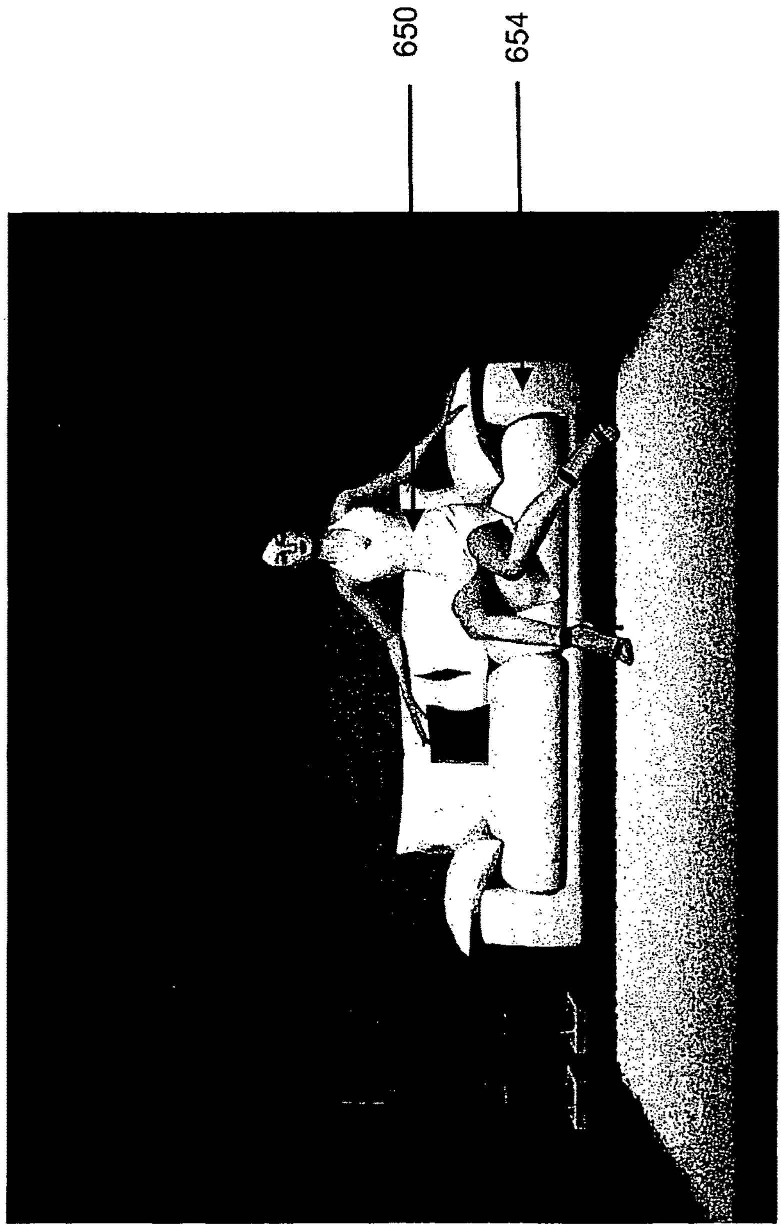
FIG. 33 is an image of a sample user model environment with sample virtual components.

Reference is now made to FIG. 32 and FIG. 33, where more sample environments and the types of activities the user can engage in with their virtual models are shown in exemplary embodiment. FIG. 32 depicts an environment where a fashion show is taking place and where one or more users can participate with their virtual models 650. The environment settings, theme and its components 652 can be changed and customized by the user. This is a feature that designers, professional or amateur, and other representatives of the fashion industry can take advantage of to showcase their products and lines. They may also be able to rent/lease/buy rights to use the virtual model of users whom they would like to model their products. Users may also be able to purchase/obtain tickets and attend live virtual fashion shows with digital models featuring digital apparel whose real and digital versions could be bought by users. FIG. 33 shows a living room scene which can be furnished by the user with furniture 654 and other components from an electronic catalogue in an exemplary embodiment. Users may use their model 650 to pose or perform other activities to examine the look and feel of the room, the setting and furnishing, which they may replicate in their own real rooms. This feature is further representative of 'interactive' catalogues where users are not just limited to examining different views of a product before purchasing it from an electronic catalogue but are able to examine it in a setting of their choice, interact with it via their virtual model or directly, acquire different perspectives of the product in 3D, and get acquainted with enhanced depictions of the look and feel of the product. Environments will also be available to users that change with time or other properties. For instance, an environment that represents the time of day may change accordingly and show a daytime scene (with the sun possibly and other daytime environment components) during daylight hours which changes to represent the way the light changes and dims during the evening time which subsequently changes into a night scene with the appropriate lighting, other environmental conditions and components in an exemplary embodiment. Environments that reflect the weather would also be available. Retailers would have the opportunity to make available their apparel digitally with the appropriate environments. For instance, galoshes, raincoats, umbrellas and water-resistant watches and jewelry may be featured in a rainy scene. Users may also customize/program scenes to change after a certain period of time, in an exemplary embodiment. For instance, they can program a given scene or scene components to change after a fixed period of time. User models may also be programmed to reflect changes over time such as ageing, weight loss/gain etc.

Figure 34:
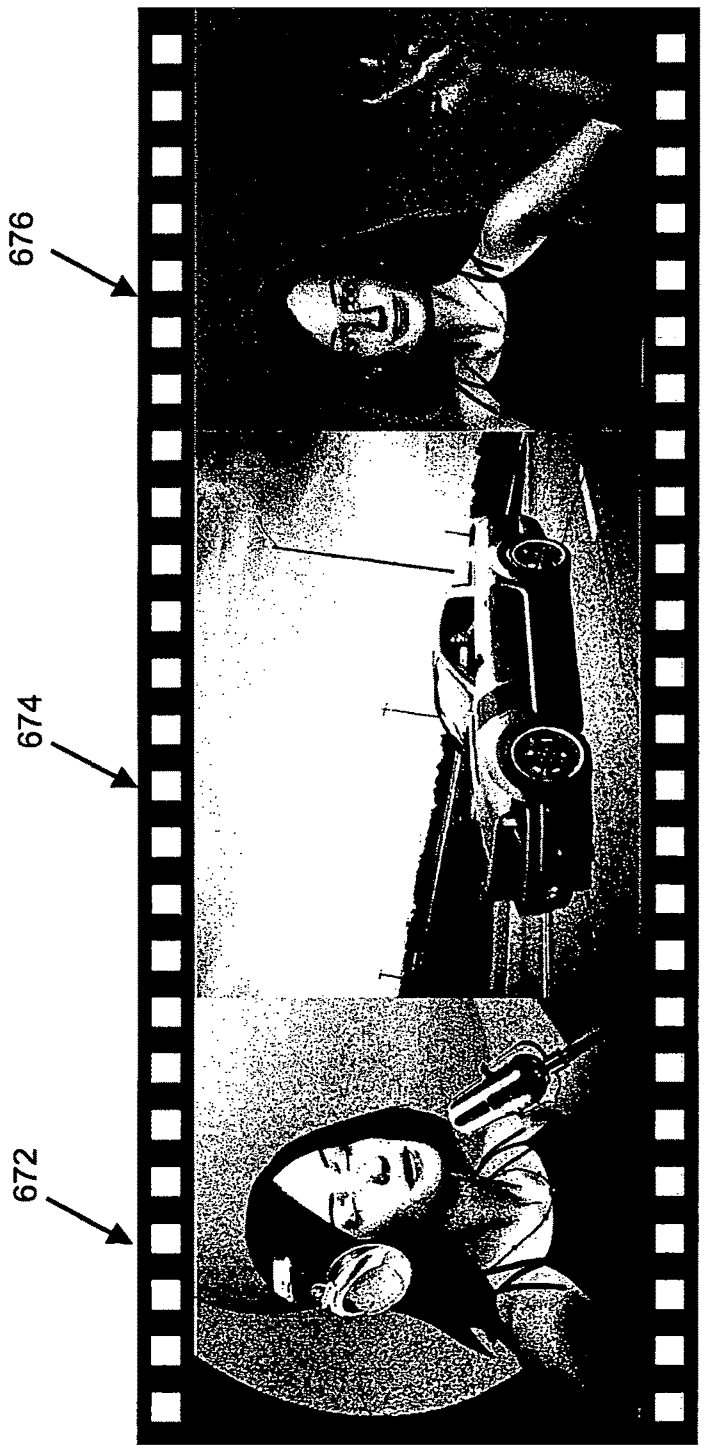
FIG. 34 is an image where a sample user model music video is shown.

Reference is now made to FIG. 34, where a sample virtual model is shown in a customized music video that the user has generated. This figure is shown in exemplary embodiment and it illustrates the different activities the user can engage their virtual model in; the different environments they can choose to put their model in as well as the expression/action animation control they have over their virtual character model. Display window 672 shows the virtual model singing in a recording studio; display window 674 shows the model driving in a sports car while display window 676 shows the model waving and smiling. The user can choose to combine the different scenes/animations/frames to form a music video as depicted in FIG. 34. Another feature is a voice/text/image/video to song/music video conversion. Users can upload audio/video/text to the system and the system generates a song or a music video of the genre that the user selects. As an example, a user can enter text and specify a song style such as 'country' or 'rock' and other styles. Based on this, the system generates a voice that sings the written text in the specified style. The voice may also be selected (based on samples provided by the system) by the user or picked by the computer. (Given some content, the system can find related words to make rhymes while adhering to the provided content. In an exemplary embodiment, this can done by analyzing phonemes and looking up in a thesaurus to find rhyming words where necessary). For purposes of increasing computational efficiency, the system 10 may provide the user with pre-rendered scenes/environments where the music and environment cannot be manipulated to a great degree by the user but where rendering of the character model can occur so that it can be inserted into the scene, its expressions/actions can be manipulated and it can be viewed from different camera angles/viewpoints within the environment. Users can save and/or share with other users the various manifestations of their user model after manipulating/modifying it and the animation/video sequence containing the model in various file formats. The modified user model or the animation/video sequence can then be exported to other locations including content sharing sites or displayed on the profile or other pages. In an exemplary embodiment, users may want to share their vacation experiences with other users. In such a case, users can show their character model engaged in different activities (that they were involved in during their vacation), against different backdrops representing the places they visited. This could also serve as an advertising avenue for the tourism industry. The model may be animated to reflect the status of the user and then displayed on the profile page to indicate other members of the status of the user. For instance, the character model may reflect the mood of the user—happy, excited, curious, surprised etc. The model may be shown running (image/simulation/video) in a jogging suit to indicate that the user is out running or exercising, in one exemplary embodiment. The brand of the digital apparel may appear on the apparel in which case featuring the model on the profile page with the apparel on would serve as brand advertisement for that apparel.

Along with the specification of accessories, the users as explained below, are able to modify textures associated with the user model. With reference to label 350, an example of the texture modification of a user model is illustrated. Skin color can be changed by changing HSV or RGB and skin texture parameters as discussed with reference to step 128 in FIG. 6A. Skin embellishments such as henna or natural skin pigmentation such as birthmarks etc. can be added by using an image of the respective object and warping it onto the user model where placed by the user. Color palettes (a colour wheel for example) may be provided with different variations of skin tones for users to pick a skin tone. Similar palettes may exist for makeup application.

As described above, the community module allows the respective user to interact with other users of the system 10. Along with other users of the system 10, users are also able to invite other members to be users of the system 10.

The system 10 allows for multiple methods of interaction between the respective users of the system. The various methods of interaction are described herein. One such method of interaction is the concept of a collaborative shopping trip that is described in further detail herein. By having multiple users participate in a shopping trip, where users of the system 10 may interact with one another with respect to items of apparel or other products, each other's models, messages, and pictures or images. By creating and participating in a shopping trip as described herein, the real-world concept of inviting friends, shopping, and receiving their respective feedback on purchased items is emulated through the system 10.

Figure 16:
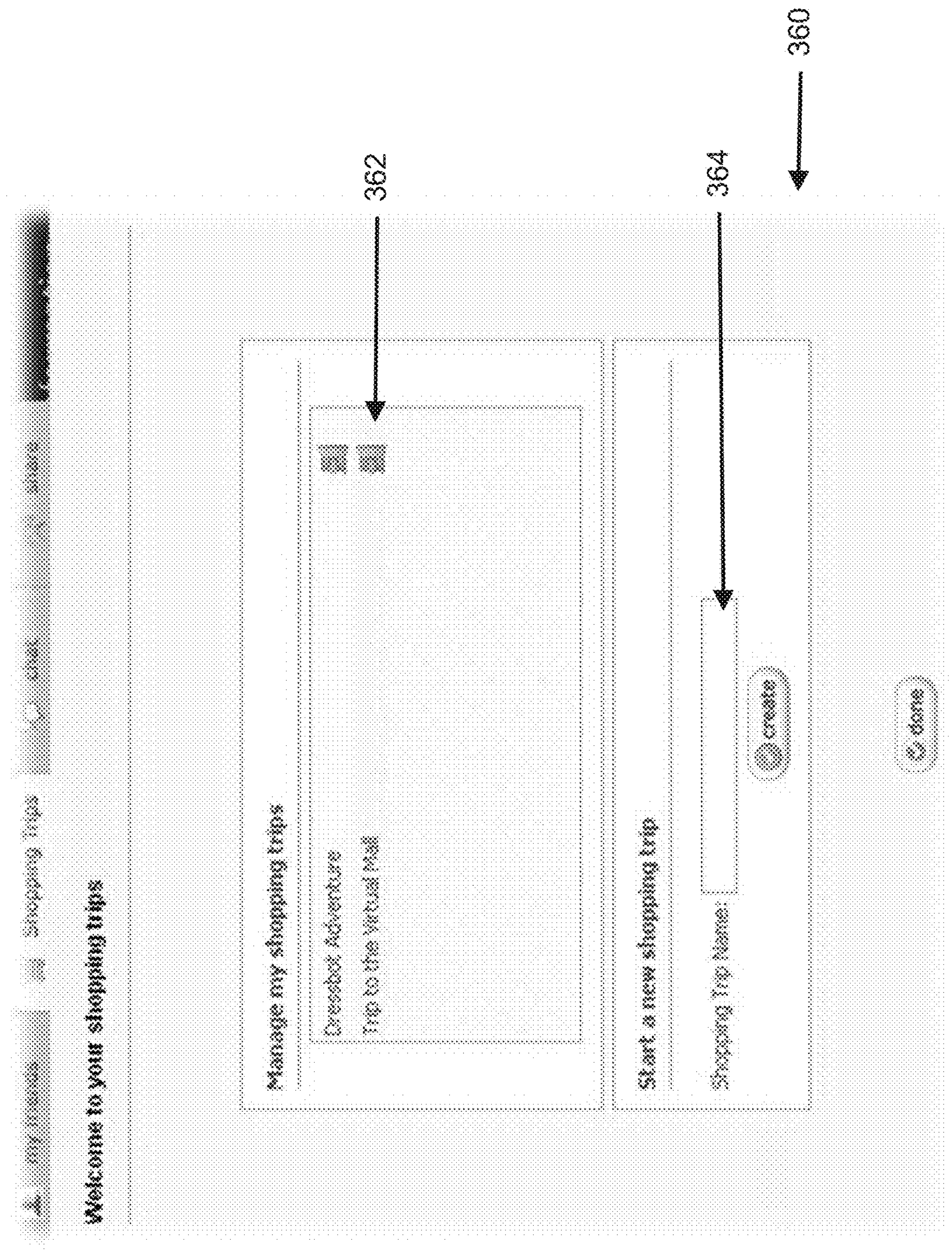
FIG. 16 is a sample image of a component of a Shopping Trip management panel.

Reference is now made to FIG. 16, where a sample image of a shopping trip management panel 360 is shown in an exemplary embodiment. The shopping trip management panel 360 allows users to manage existing shopping trips that they have created, or to create new shopping trips. Once the user has created a new shopping trip, the user may then invite other users to become members of their shopping trip as described with reference to FIG. 40. The user may send invites for shopping trips and other synchronized collaboration via the messaging service provided through system 10 and through other online or offline modes of messaging including email, SMS or text, chat and other means. Notifications can also be sent to users on social networking sites inviting them for collaborative activities. Users can also access past sessions that they were on through the panel 360.

Figure 17:
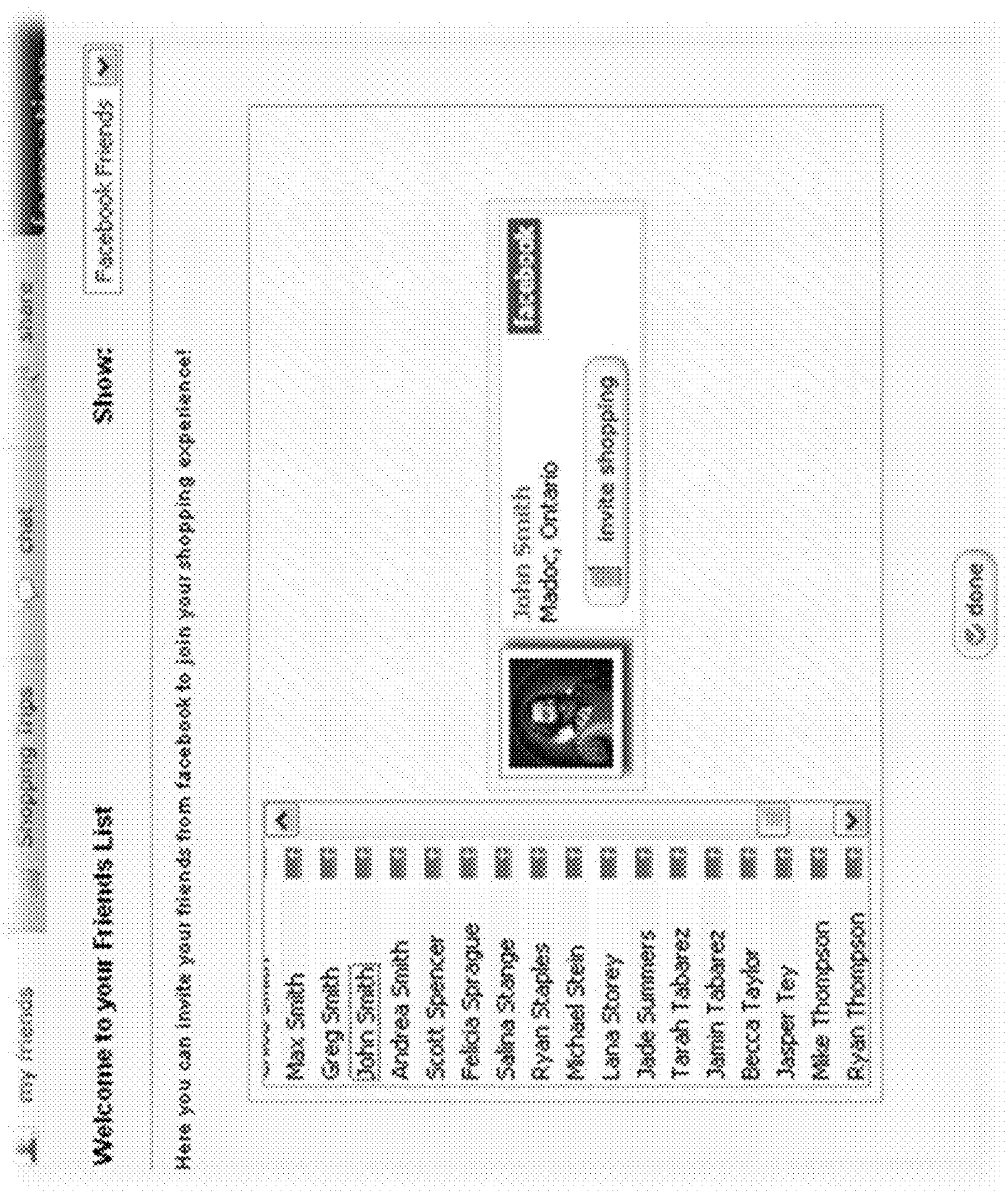
FIG. 17 is an image of a sample friends manager window.
Figure 39A:
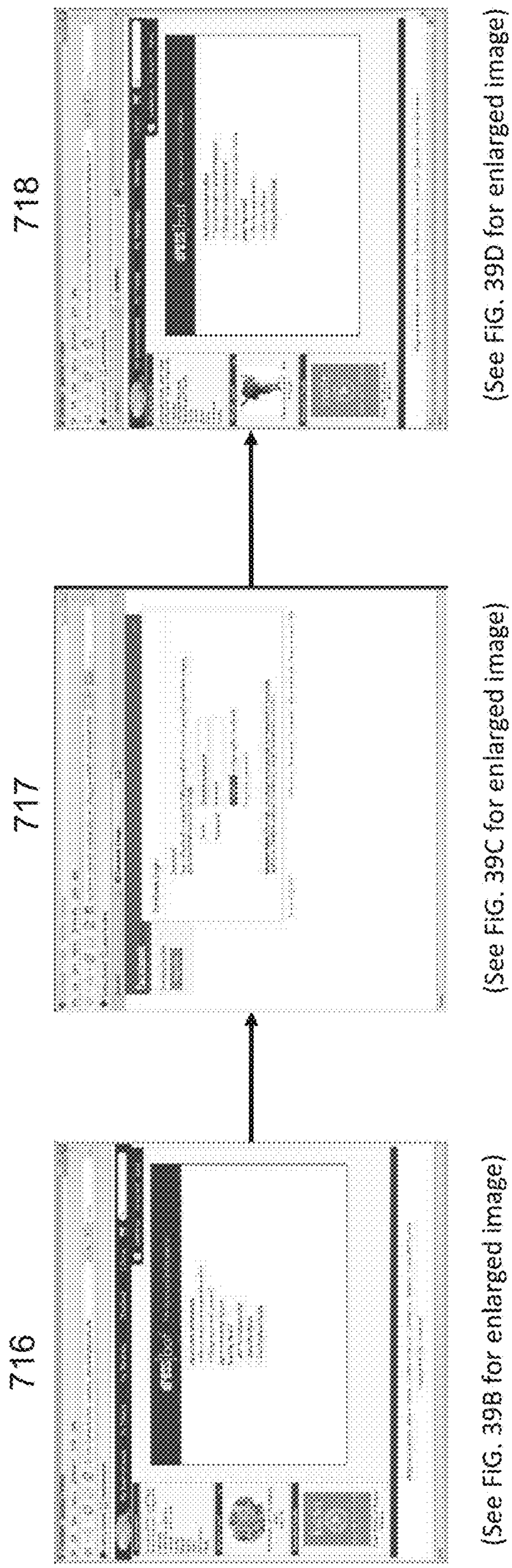
FIG. 39A is in image of a sample procedure for a user to gain access to friends on system 10 from the user's account on a social networking site such as Facebook.
Figure 39B:
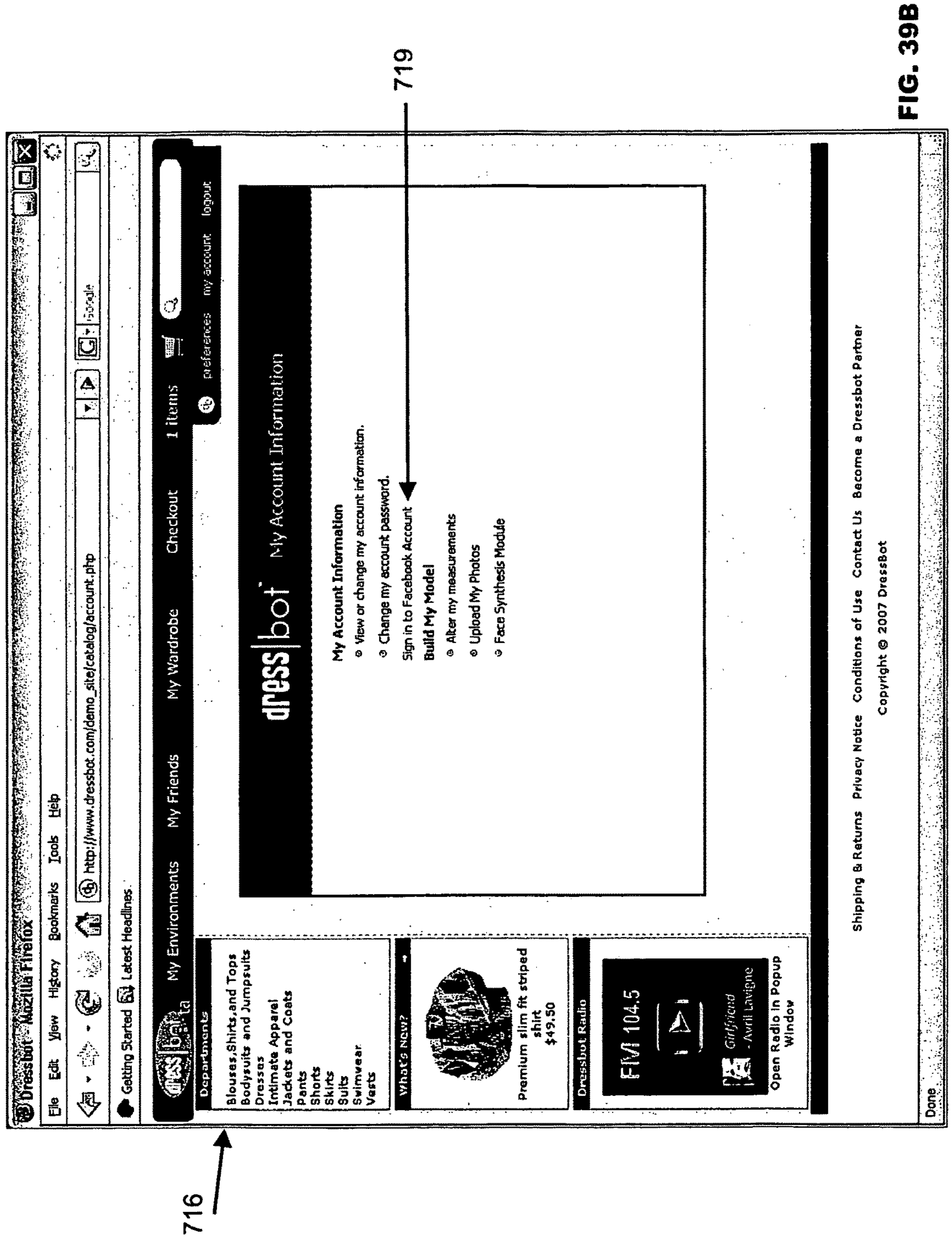
FIG. 39B is an image of a sample user account page on system 10 before a user has logged into Facebook.
Figure 39C:
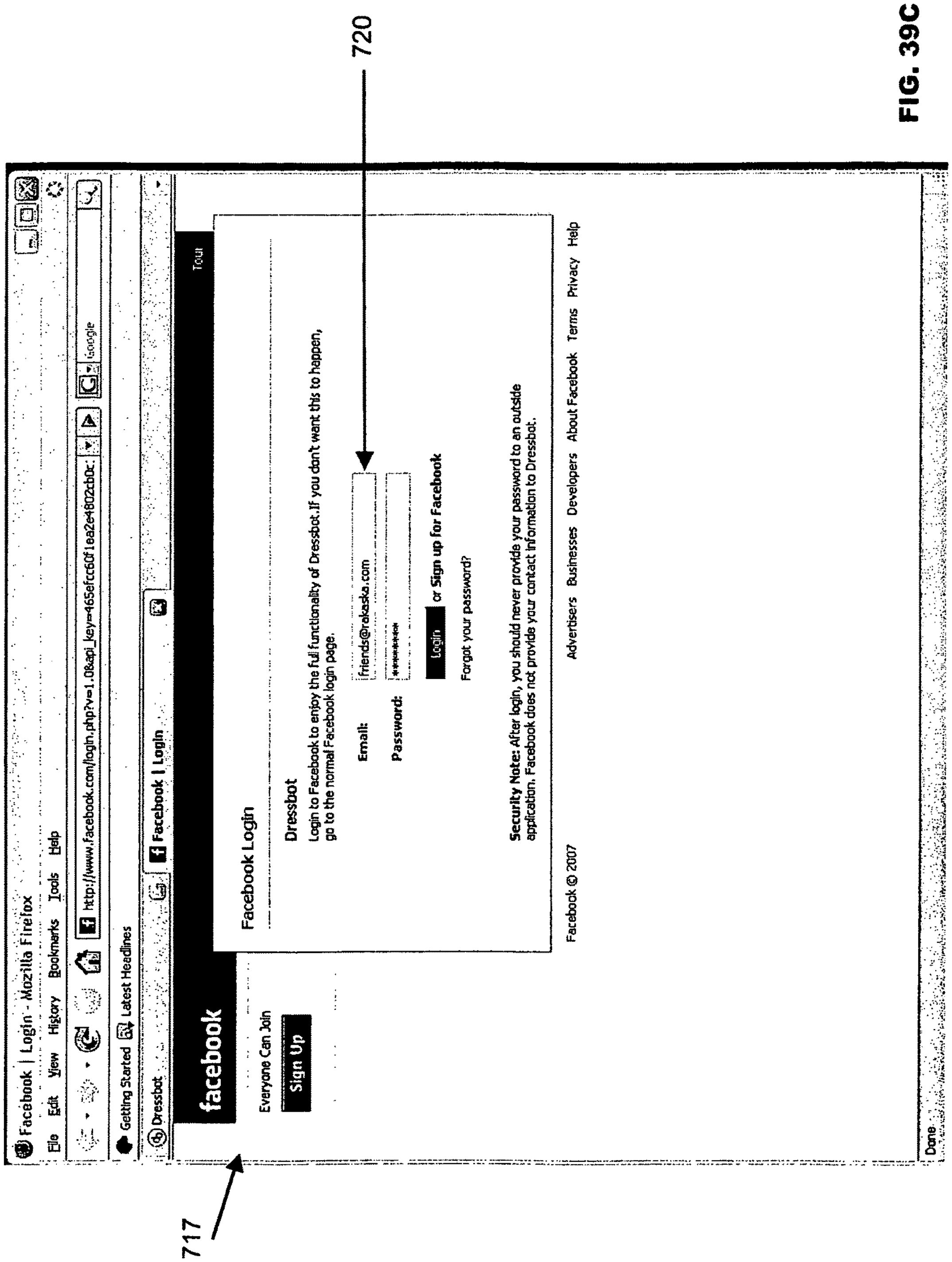
FIG. 39C is an image of a sample page for accessing a social networking site (Facebook) through system 10.
Figure 39D:
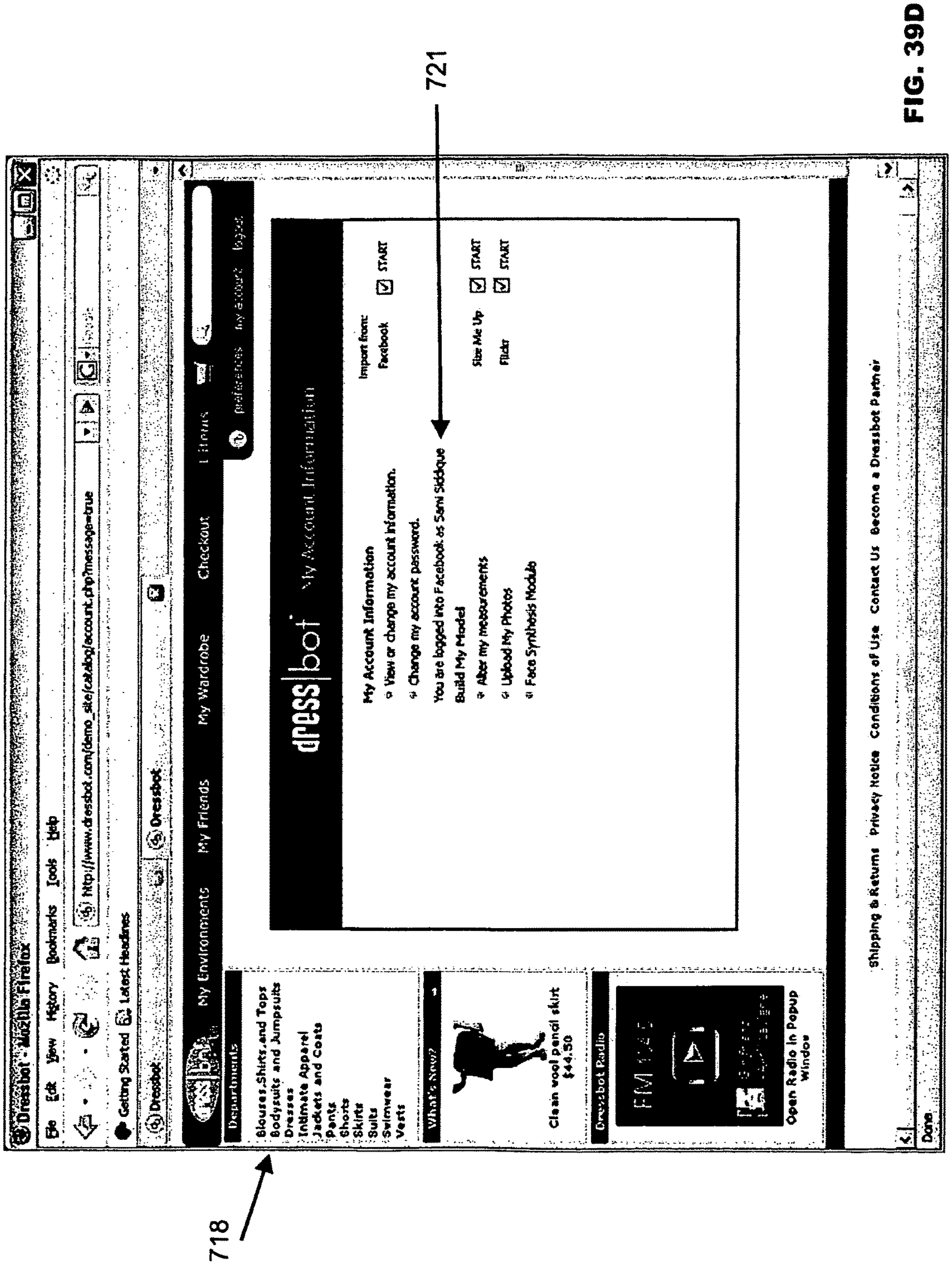
FIG. 39D is an image of a sample user account page on system 10 after a user has logged into Facebook.

Reference is now made to FIG. 17, where a sample friends manager window 370 is shown in an exemplary embodiment. The friends manager window 370 allows users to invite other users to join them in their shopping trips. As illustrated with reference to FIGS. 17 and 18, the system 10 allows for friends that are associated with the system 10, and those that may be associated with one or more other community networking sites to be invited. Community networking sites include sites such as Facebook, or My Space and others that allow their API to be used by external applications In an exemplary embodiment, a user's list of friends from social networking sites may be displayed within the system 10. In an exemplary embodiment, a procedure for accessing friends on a user's Facebook account is presented in FIGS. 39 to 42. FIG. 39A presents the sequence of events leading to the availability of one's Facebook friends on their account in system 10. FIGS. 39B to 39D display magnified views of each of the windows shown in FIG. 39A. Upon logging into system 10, the user can view his account information 716 as shown in FIGS. 39A and 39B. A provision 719 exists on the account page 716 for signing into Facebook, an external social networking site, which will facilitate access to Facebook account resources (other social networking sites may be present and accessed through system 10). As illustrated in FIGS. 39A-B, this will take the user to their login page 717 on Facebook, upon which the user may log in to his Facebook account 720. This will take the user back to their account 718 on system 10, this time with access to the user's Facebook friends 721 and other information available through their account on system 10 as shown in FIGS. 39C and 39D. When the user decides to logoff from their account on system 10, the user is asked if he/she wishes to logoff from Facebook as well. Users are also able to import data from external sites. For example, contact information or images may be imported from social networking sites such as Facebook, Personal data such as measurements of the user's body may be imported from a repository containing information on the user's measurements 115 described with reference to FIG. 6A. Pictures may be uploaded to the users account on system 10 from a photo sharing site.

Users are able to invite friends from the community network sites to interact with. Upon requesting that a friend from a community networking site join in a shopping expedition, the friend when accessing their account in the community network site, receives a notification that a request has been made. The user may choose to accept or reject the request.

Figure 18:
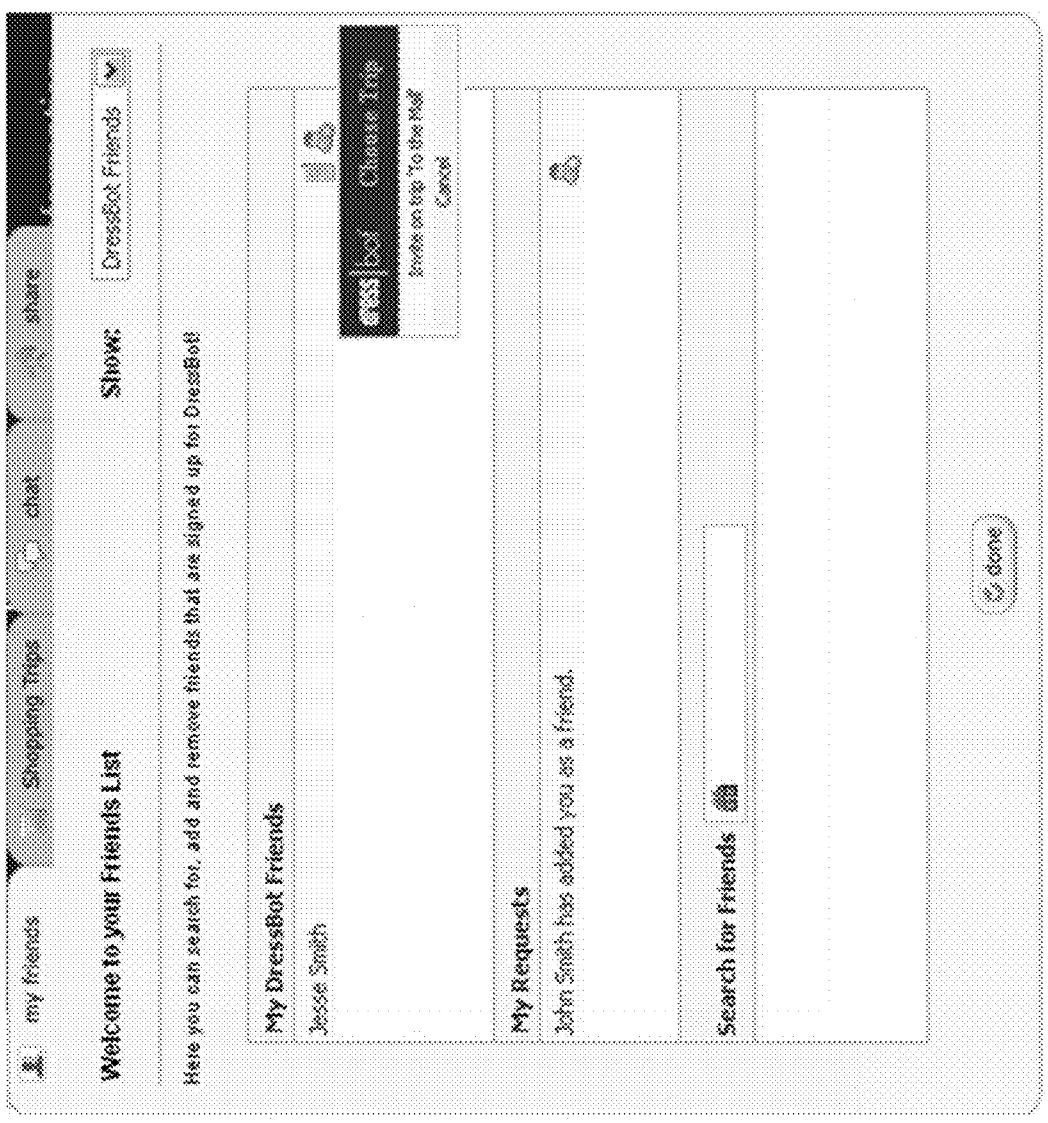
FIG. 18 is an image of a sample friendship management window.
Figure 19:
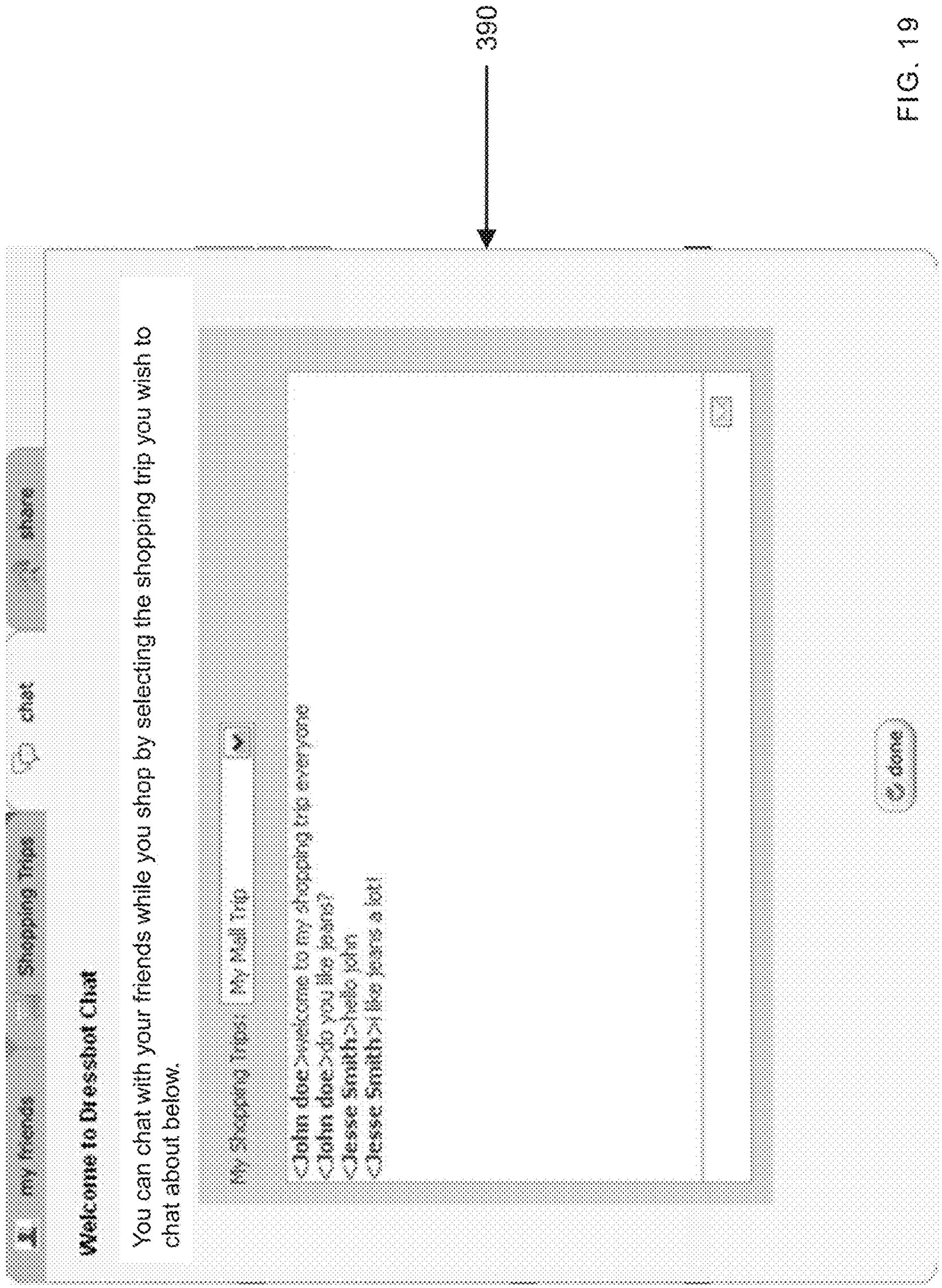
FIG. 19 is an image of a sample chat window.

Reference is now made to FIG. 18, where a sample system friendship management window 380 is shown in an exemplary embodiment. The system friendship manager is used to manage a user's relationship with other users of the system 10. The manager window 380 lists a user's friends, along with friend requests that are still pending. Search functionality is also provided for, where a user may search for other users by entering their names Reference is now made to FIG. 19, where a sample chat window 390 is shown in an exemplary embodiment. The chat window in an exemplary embodiment may be created for every shopping trip that is associated with the user. Through the chat window 390, users are able to engage in an interactive chat session with one or more other users. The shopping trip feature allows two or more users to collaborate while shopping online. This may entail limited or full sharing of account resources for the duration of the shopping trip. In an exemplary embodiment, users can view the contents of each other's shopping carts, shopping lists, wishlists, fitting rooms, user models, and share audio play lists and other resources. They can set and view shared ratings, feedback, comments and other user-specified information regarding a product. They can mark items with user tags that can be shared between members of the shopping trip. Additionally, users can shop in collaborative environments wherein, in an exemplary embodiment, users can agree on a selected virtual mall environment and browse virtual stores and items concurrently. Reference is now made to FIG. 20 where a collaboration interface for a shopping trip 240 is shown in exemplary embodiment. Members of the shopping trip are shown by clicking on button 241. Here a list of stores that the users can browse is presented in panel 242. This panel may show all the stores subscribing to system 10. Alternately, the members of the shopping trip may add stores of interest to them or remove stores from the panel. The store names may be presented as a list or on a map of a virtual or real mall in an exemplary embodiment. In this example, the stores appear in a list 242. Users can select the shopping environment 243 for a shopping trip session. The shopping environments may be animated and/or video/image representations of fictional malls or real malls, or other manifestations as described previously with reference to the environment module 56, the shopping module 60, and the entertainment module 66. The shopping environments may incorporate a mode with augmented reality features, which were described previously with reference to the shopping module 60. Users can engage in an interactive session within a store environment in 243, as in FIG. 46, when operating via this mode. Users can also view product catalogues and individual products in 243. Users can also view stores in 243 that are available on the retail server 24. Users can acquire different product views, and examine products in 3D in 243. Additionally, a mode with physics based effects may be incorporated to simulate product look and feel as well as simulate realistic interaction with the product virtually via display 243. In an exemplary embodiment, information of a specific mall may be provided in the form of audio and visual (video/image sequences and/or text) feeds via 243 when a user selects a particular mall. This way, users would be able to shop remotely in malls or stores located in other countries such as Paris, Milan, New York and other cities and shopping hubs. Individual stores in the mall may also transmit live feeds via webcams, in exemplary embodiment, (and/or other image, video capture devices) which users can view in 243. This feed content may incorporate information on the latest stock, new arrivals, promotions, sales, window displays, shelf contents, inventory, salespeople, store arrangements, live reviews and other information relevant to the store. Miscellaneous information such as job openings in the store may also be included. Feed information would be uploaded via a web page onto the portal server 20. This information would be broadcast in 243 to clients requesting the feeds. Tools may be available to vendors to edit feed information. For instance, video feed information may be edited, image information may be enhanced through photorealistic effects etc. Feed information would provide a mode of advertising to stores. The facility to publish feed content may be available through an independent plug-in or software application to stores. The feed information does not necessarily have to be generated from physical store locations. This information may be provided by the brand or store head office. In the case that a customer browses a mall, an association file would assist in linking stores and/or brands to malls in which they have physical presence. Feed content may be hyperlinked. In exemplary embodiment, as customers browse store feeds, they may click on a product item to browse its details such as those described with reference to 22. Other details may be included such as inventory details of a particular item; product ratings (maybe assigned by customers or style consultants); style information; links to other products that can be worn with it and/or other similar styles in the store. The hyperlinks may be represented by icon such as animated tags. Other hyperlinks that may be present in the store feeds include links to electronic fashion magazines or videos containing information or demos or reviews about specific store products, styles, brands, etc.

On a shopping trip that involves more than one user, shopping trip members may choose to shop collaboratively. There are several ways to engage in a collaborative shopping trip, as described previously in this document. A user may browse the chosen environment and/or products, and at any given time, the video, animation or image sequence information that is displayed on the user's screen while the user is browsing the environment and products is considered the specific user's 'view'. Users can choose to display the views of all members, which will appear on a split-window screen in an exemplary embodiment. Alternatively, they can choose to display a specific member's view on their screen or return to their own view. Members on a shopping trip can switch between views 244 of individual members browsing the common environment or product 243. Furthermore, users can choose to browse different digital manifestations 245 of the environment and/or product such as streaming video, image sequences, virtual simulation, augmented reality, other media content or any combination thereof. In the asynchronous mode, users can drag-and-drop and/or add items and products that they wish to share with other users from display screen 243 to a sharing folder, the contents of which can be viewed by the members of the shopping trip at any time. Users may view and examine their own account resources such as their virtual/digital model, wardrobe and fitting room contents, shopping cart, wishlist, image and other features during the shopping trip. In an exemplary embodiment, the user may view his resources in the window 246, by selecting from the menu 247. Currently, the user model is displayed in 246. Users can share their account resources such as their profile images, shopping cart contents, character model and fitting room content with other members of the shopping trip. Shared information by other users is viewable in display window 248. By selecting from the tabbed menu 249, shown here in an exemplary embodiment, a user can view the particular resource of the members of the shopping trip in 248. Users can add their virtual models to the environment which can be viewed by the members on the shopping trip who have the required access and permissions. Users on a shopping trip will be able to communicate with each other via multiple-way conferencing, chat (which may include text and/or speech communication; 3D visualization and/or augmented reality viewing and interaction). FIG. 20 shows a chat window 390 in another exemplary embodiment, within the shopping trip scenario. FIG. 20 could also be used in other scenarios as well such as choosing a restaurant to visit for dining. A user and their friends can collaboratively view information on restaurants in 243. Visual 3D menus may be available for viewing restaurant meal choices, for receiving feed information on specials, promotions, reviews and other relevant restaurant information. Users would also be able to collaboratively order a meal for take-out and review restaurant menus and other information online in order to decide where they would like to go for dining.

Figure 40:
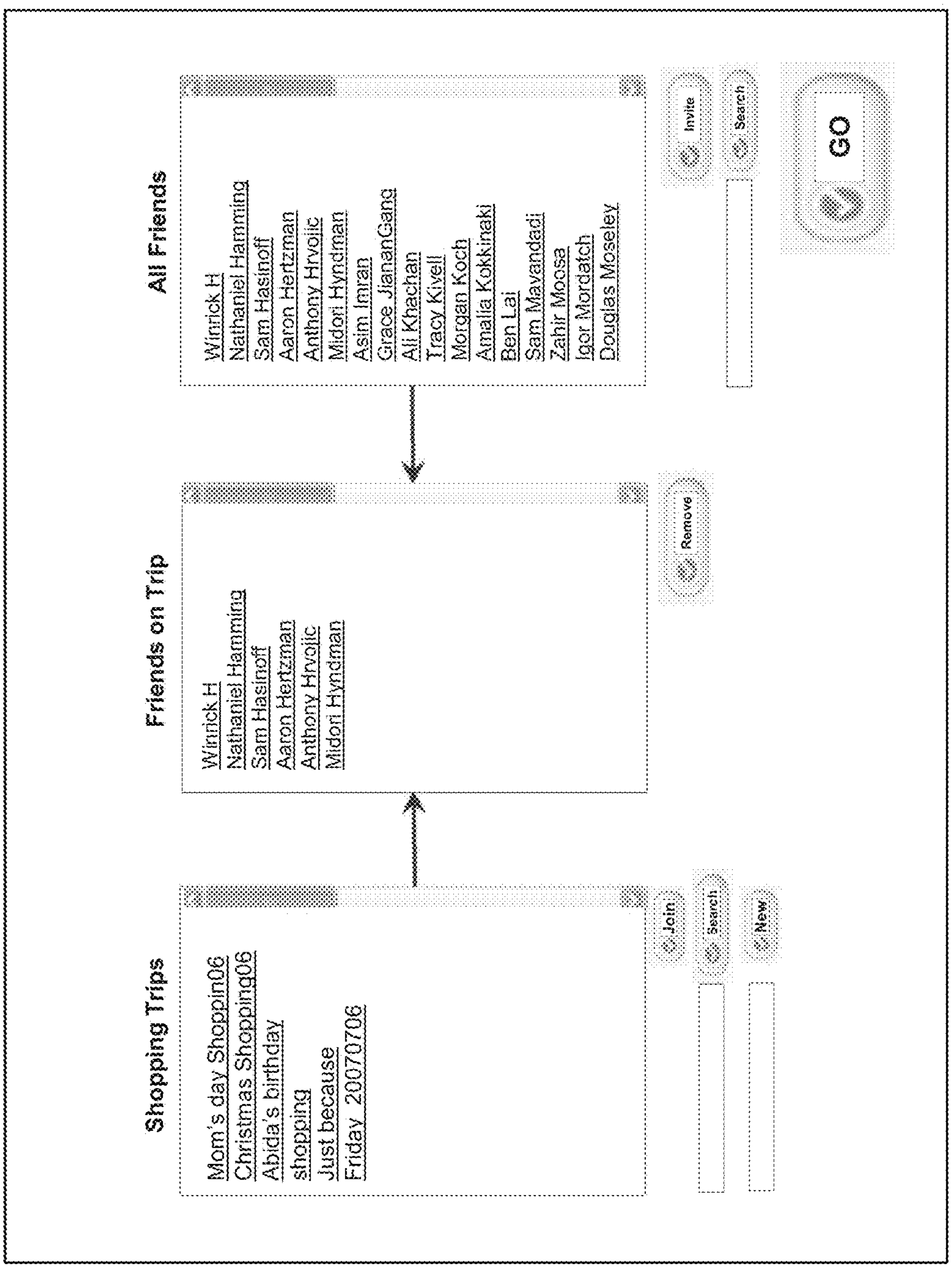
FIG. 40 is a sample image of a Shopping Trip management panel.

Reference is now made to FIG. 40 where an exemplary embodiment of the process joining a shopping trip through a user interface is shown. In an exemplary embodiment, this process proceeds as follows: When a user clicks on a "Go Shopping" button, he/she is presented with a screen with three columns—left, middle, right. The column on the left lists all existing shopping trips that the user's friends are currently engaged in. The user can choose to join any of these shopping trips by clicking on a "join" button. The user also has the option of searching for a shopping trip of interest. When a key word is searched for the related shopping trips are presented in the left column. The keyword could be the name of a shopping trip or an item of interest that is being shopped for, or an occasion, as examples. When the user clicks on the name of a shopping trip in the left column, the members of that shopping trip are shown in the middle column. The user can also invite other friends by clicking on the name of a friend from the right column and then clicking on the "invite" button. (The right column includes a list of all the user's friends. These friends include friends on from our shopping site, social networking sites such as Facebook, or friends from the virtual operating system/immersive system described in this document. The user can also search for a name of friend to add to the shopping trip. If the friend is found, the name appears in the right column and the user can invite the friend by clicking on the invite button). The friend then receives an invitation via a notification on a social networking site, a phone call, an SMS, an email or other means as described before. The friend's name appears in the middle column in red until the friend accepts the invitation. If the user's friend accepts the invitation, that friend's name appears in the middle column in blue. An orange color indicates that the friend will be joining later. Other cues may also be used to display the status of the friend. The user can also initiate a new shopping trip by specifying a name and clicking on the "new" button. The user also has the option of removing friends from a shopping trip that the user has initiated by clicking on the remove button under the middle column. The user can start the shopping trip or resume a shopping trip by clicking on the "GO" button. The next screen presented on clicking "GO" is a screen listing cities, malls, and stores. The users can pick any city, mall, or store to go to and shop via any of the modes of interaction of a shopping trip described earlier with reference to FIG. 7. At any given time, the user can be engaged in multiple shopping trips and can switch between any of the trips or add/remove friends by coming back to this interface. The name of the shopping trip that the user is currently viewing in appears on top as the user shops. Such an interface is also used for going to events such as those described with respect to the "hand and chill" feature (For example, as described with reference to FIG. 44). In an exemplary embodiment, the main shopping page includes two buttons—"Browse" and "Shopping Trip". Clicking on "Browse" lets the user shop in the regular mode of shopping. Clicking on "Shopping Trip" loads the screen shown in FIG. 40.

Figure 41A:
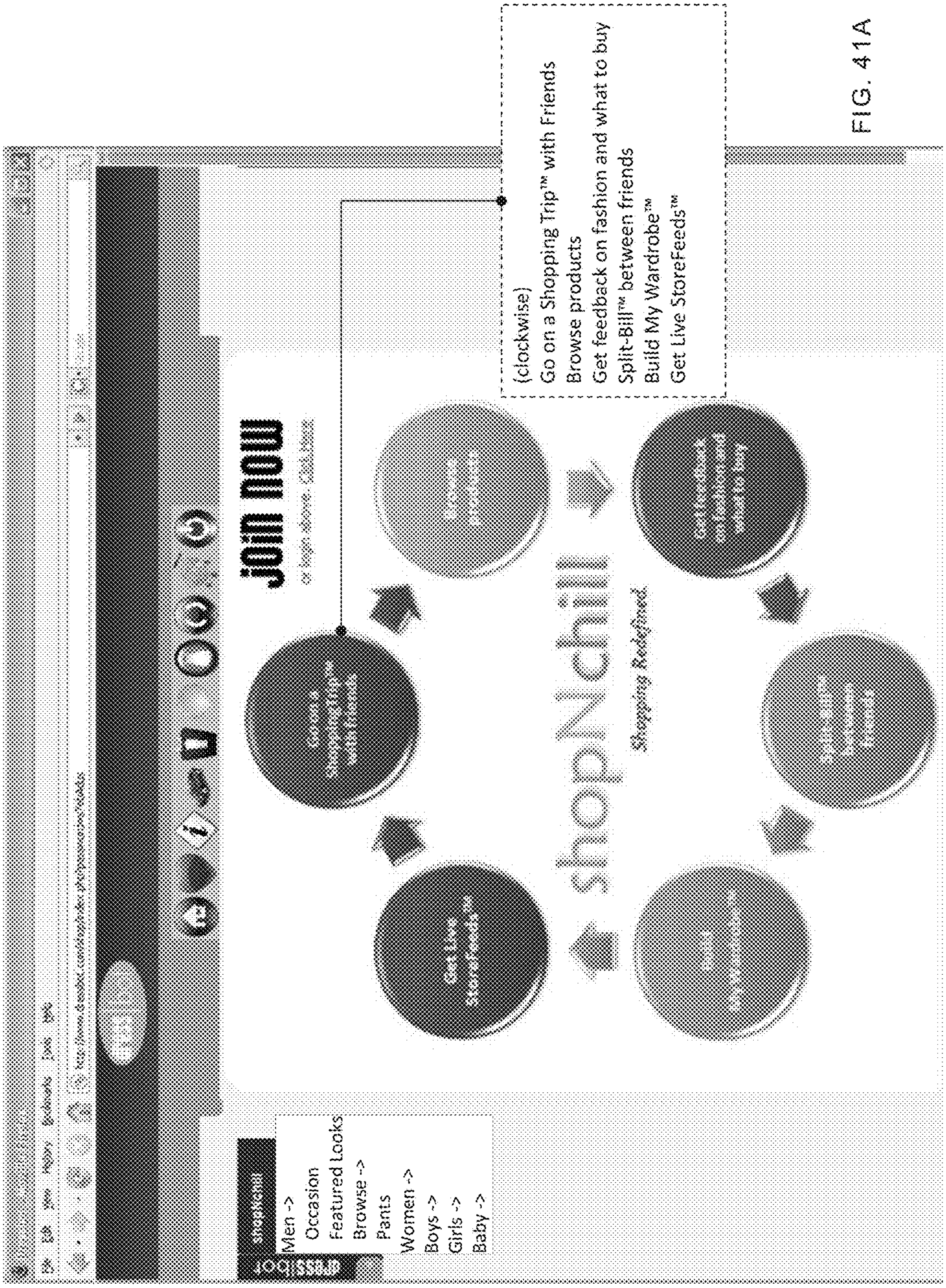
FIG. 41A-F are snapshots of a sample realization of the system discussed with reference to FIG. 20.
Figure 41B:
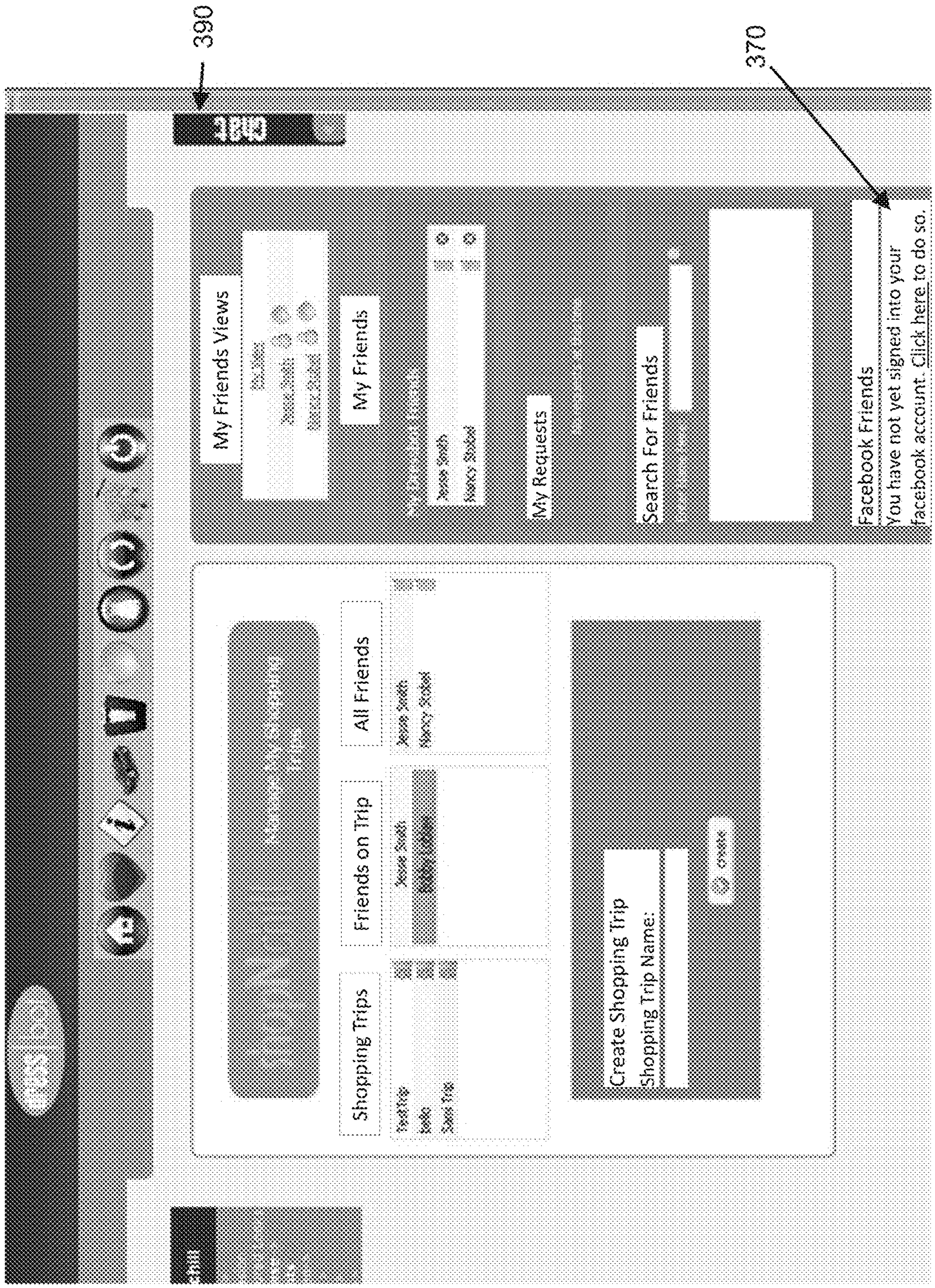
Figure 41C:
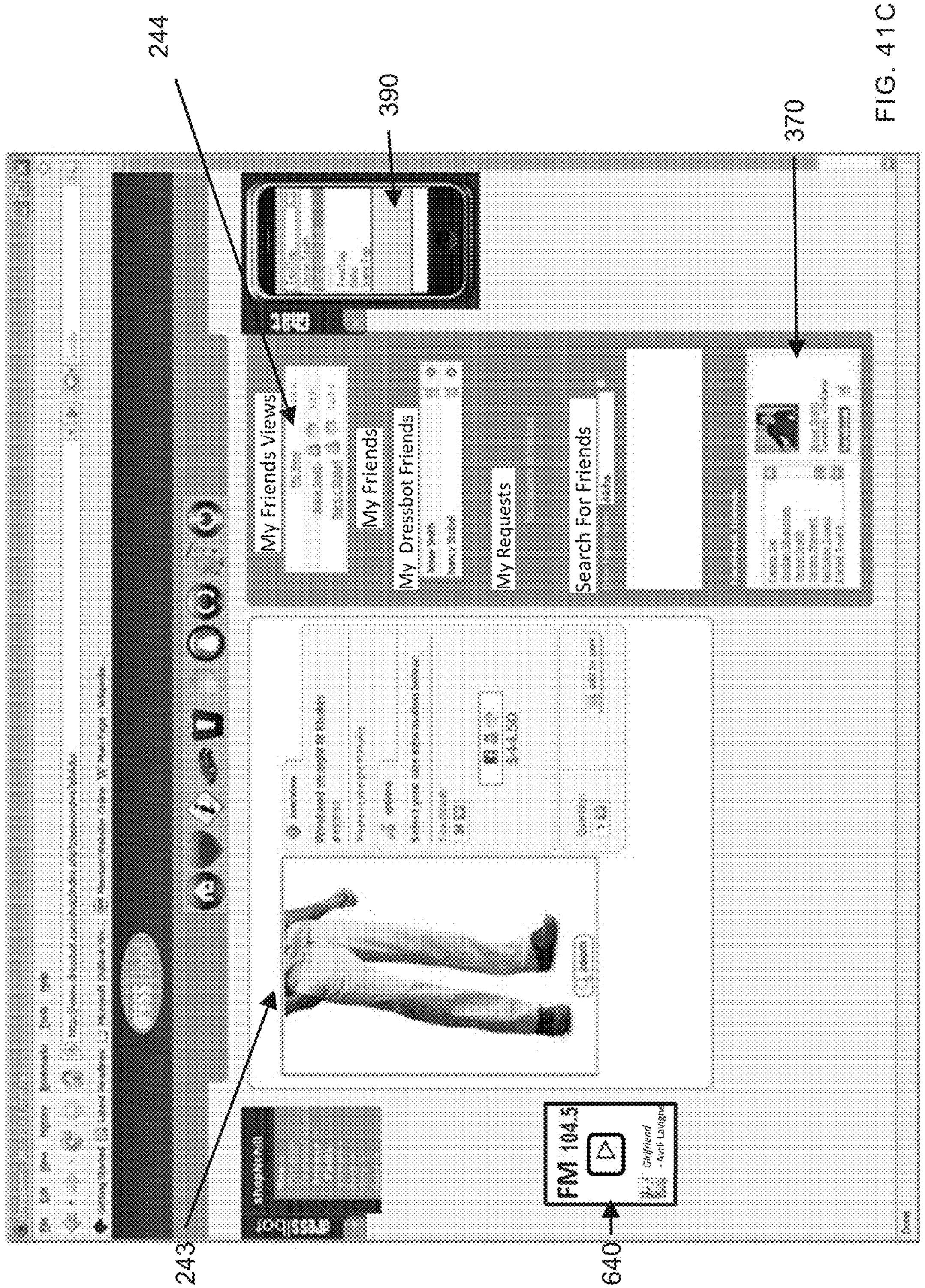
Figure 41D:
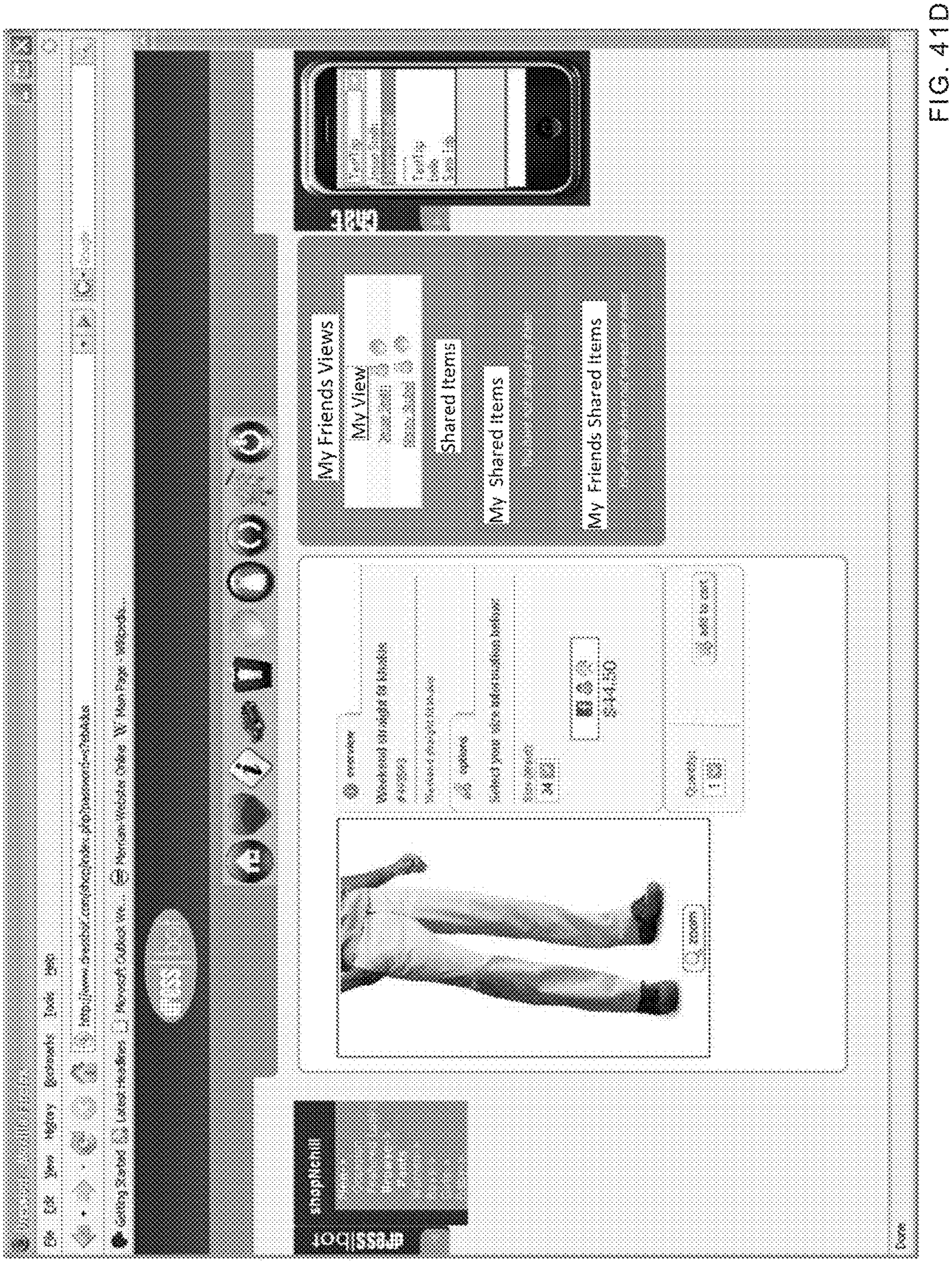
Figure 41E:
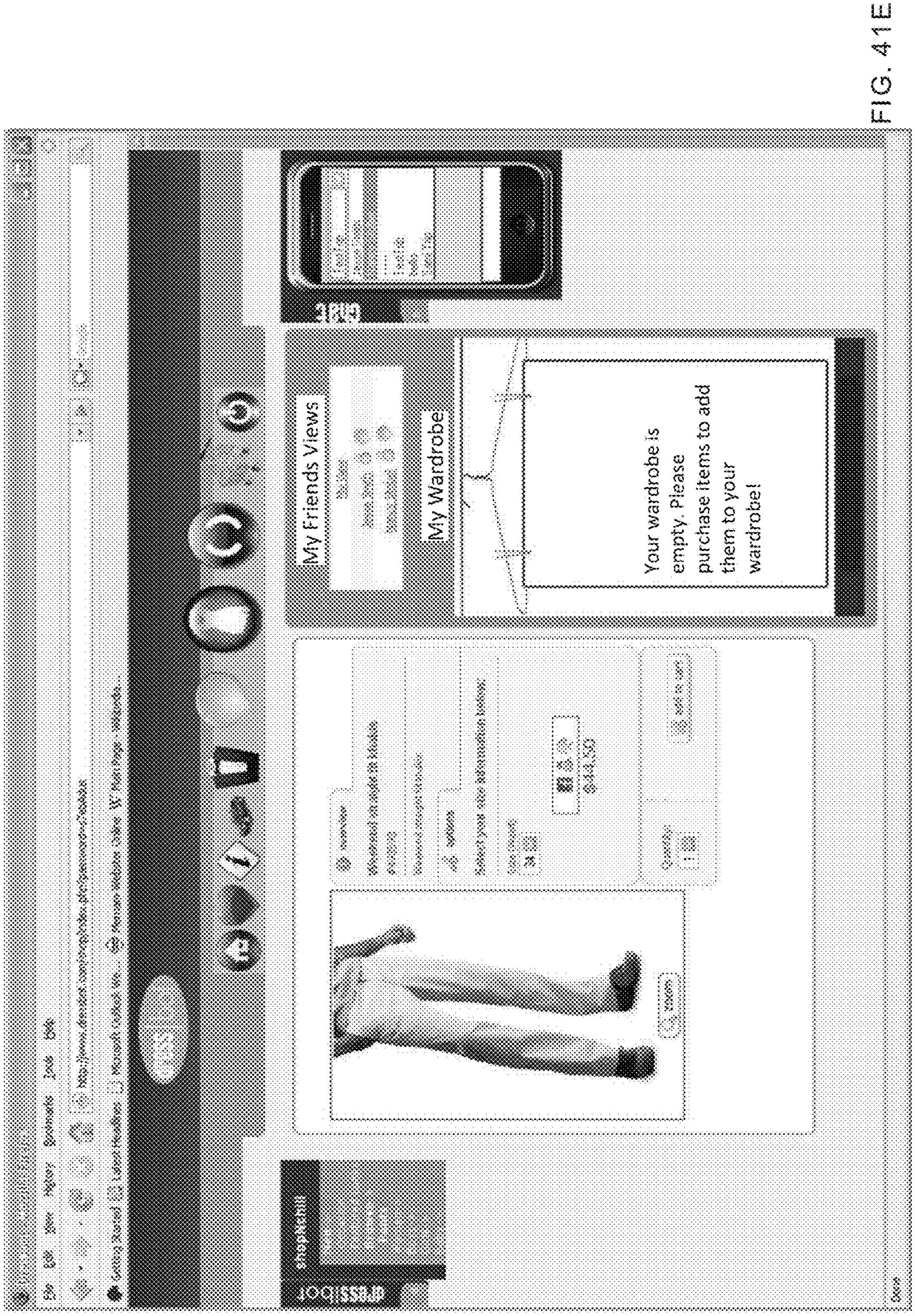
Figure 41F:
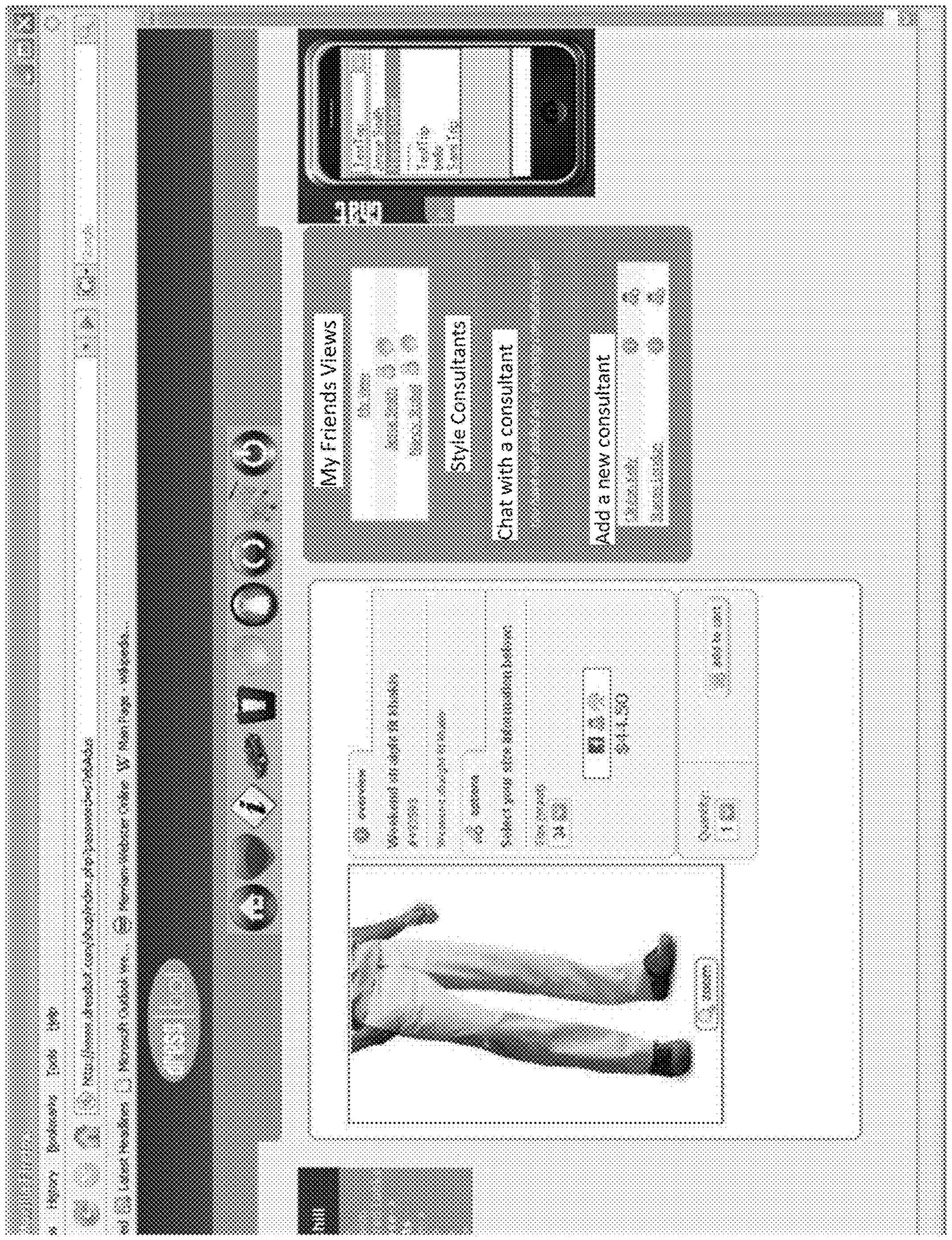

Reference is now made to FIG. 41A-F where snapshots of a realization of the system discussed with reference to FIG. 20 are shown in an exemplary embodiment. Upon visiting the site (in a browser in this case), the user is presented with the option of logging in or browsing in regular mode (as shown in FIG. 41A). After logging in, the user can click on the "Shopping Trip" icon from the top menu. As shown in FIG. 41B, this brings up the shopping trip screen discussed with reference to FIG. 40. Shown in the middle column are the friends that are on the selected shopping trip. Friends that have not yet accepted the invitation to join the shopping trip are highlighted in red. Trip requests show up in the panel on the right and/or as a Facebook notification and/or as an SMS, etc. depending on preferences specified by the user. A sliding chat window 390 can be used at any time. In an exemplary embodiment, shown in FIG. 41C is one instance of the synchronous mode of operation of a shopping trip in use. In an exemplary embodiment, after starting a shopping trip, users are presented with a list of stores that they can go to. On selecting a store to visit, the user is presented with a menu (menu on the left in FIG. 41C) for browsing through products. This menu may be customized for each store, for example, by providing the vendors with an application programming interface (API) or by letting the vendors customize the menu and navigation options through the store portal discussed with reference to FIG. 42. Item-dependent views are also provided. Based on the content that is being viewed, an appropriate viewing method is used. For example, the method of displaying cosmetics may be different from that of displaying clothes. The chat window enables the user to chat with a selected user (who could be on our website or on any other social networking site like Facebook or on a chat application such as msn or via email or on a cell phone communicating via text such as through SMS or via voice by employing text to speech conversion, in exemplary embodiments) or with all members of a selected shopping trip. The panel on the right in FIG. 41C (but to the left of the chat window 390) provides various options and controls to the user as described earlier. The "My Friends Views" box in the panel is similar to 244 described earlier. It enables the user to select a view which could be the user's own view or any of the user's friend's views and interact with friends in the modes of operation discussed with reference to FIG. 7A-D, and described next in an exemplary embodiment. In the synchronous mode (which is the default mode), clicking on a friend's name in the "My Friends Views" displays the view 243 as seen by that friend in the current user's view 243. In the common mode (which can be initiated by clicking on a 'common' icon next to the friend's name), the view of the current user including navigation options becomes interactable/controllable by all the friends who have been marked as 'common'. In the asynchronous mode, (which can be entered by clicking on the "shared items" icon on the top menu as described below with reference to FIG. 41D), clicking on a friend's name lists items that are being shared asynchronously by that friend. The view 243 is undockable/dockable/movable/dragable to allow multiple views simultaneously and can also be minimized/maximized/resized. One way to do this is to drag out the view 243 which opens it in a new window that can be placed elsewhere. Multiple views may be opened at any given time. As shown in FIG. 41C in an exemplary embodiment, the multiple views are shown by numbers next to "My View", or the user's friends' names in 244. This is particularly useful when viewing multiple items collaboratively. For example for mixing and matching; friends may find a skirt that they like and may need to search for a top to go with it. An interface similar to that described with reference to FIG. 45 can also be used here for mixing and matching. The panel is also undockable/dockable and can be moved/dragged around and also be minimized/maximized/resized based on the users' preference. Under "My Friends Views", users can also see which of the user's friends are online or are actively browsing. This is indicated by the color of a 'person' icon next to each name. A shortcut is also located next to each of the friends' names to quickly slide out the chat box 390 and chat with the friend. Users can also click on a phone icon that lets the user talk to a friend or all members of a shopping trip. In an exemplary embodiment this is done either over VoIP (Voice over Internet Protocol) or by dialing out via a telephone/cellular line through a modem. Users can also engage in a video chat with their friends. Clicking on the radio on the left, brings up options for the radio (such as a title to play, a playlist, volume, play individually, play the same music for all members of the shopping trip, etc.) in the view 243. These options can be set using the various modes of interaction as described above, Clicking on the "shared items" icon on the top menu brings the "My Shared Items" and "My Friends Shared Items" boxes in the panel as shown in FIG. 41D in an exemplary embodiment. These boxes list the items that are posted by the user or by the user's friends for sharing with others asynchronously. Clicking on the "My Wardrobe" icon on the top menu brings up a "My Wardrobe" box in the panel as shown in FIG. 41E in an exemplary embodiment. This box lists the items that the user has in his/her wardrobe. In an exemplary embodiment, items get added to the wardrobe once the corresponding real items are purchased. Users can drag and drop items from the "My Wardrobe" box to the view 243 or can mark the items in "My Wardrobe" for sharing. Clicking on the "Consultant" icon brings up a "Chat with a consultant" box in the panel as shown in FIG. 41F in an exemplary embodiment. Users can add consultants from a list. Recommendations on style consultants by friends are also displayed. Users can share views and engage in an audio/video/text chat with consultants similar to the way they interact with their friends as described above. Consultants can also participate in collaborative decision making through votes described as described in this document. Upon clicking on the "Check Out" icon, users are presented with the SPLIT-BILL screen as discussed with reference to FIG. 21. Clicking on the "Logout" icon logs the user out of the system. The user's friends can see that the user has logged out as the colour of the icon next to the name of the user under "My Friends Views" changes. The user may join the shopping trip later and continue shopping. The user can exit from a shopping trip by clicking on the shopping trip icon, which brings up the screen shown in FIG. 40 or 41B, and then clicking on the "exit" icon next to the name of the shopping trip. The interface and system described here can also be used to browse external websites and even purchase items.

Store feeds (which could be videos on the latest items in the store or the items on sale in a store, or could also be streaming videos from live webcams in stores displaying items on sale) as described in this document are also viewable in the screen 243. Users of the shopping trip can not only access products offered by various stores but also services. For example, a movie ticket purchase service is offered that works as follows in an exemplary embodiment: Suppose a bunch of friends want to go out to watch a movie. These friends can go on our site. On selecting the name of a cinema from a services menu, the users are presented with a screen that displays the available locations for the cinema. Users can choose the location they want to go, or assign a head to decide on the location or let the system propose a location to go to. If they chose a location themselves, a majority vote is taken and the location corresponding to this majority is proposed as the location that they should go to. If all the users agree to go to the voted location, they can proceed to checkout/booking. Otherwise, the system proposes alternatives. If any of the users assigns a head, the choice of the head is taken as the choice of the user too. The system can also propose locations. For example, it may calculate the location of a theater that minimizes the travel for all the users on a shopping trip such as a location that falls close to all the users. The system may also identify locations where there is a special promotion or a sale or something to do in the proximity. It can make statements such as, "You can go to Blah Theater and then go for dinner at DinnerTime Restaurant which is only five minutes away and food there is at half price today". In an exemplary embodiment, this can be done by evaluating conditional probabilities that are constructed based on data from several users. After selecting the location, the users are presented with another screen that lets them choose the movie that they would like to watch and the show time. Trailers for each of the movies currently playing may be shown on this page and the users. The selection of movie titles and show time proceeds in a similar manner to that of the location of a theater. Upon selection of a location, movie and time, the users proceed to checkout at which point they have the option of using Split-Bill features if desired. (Users may simply state a movie they would like to watch and the system may propose the nearest location that plays the movie and that works with all the members of the shopping trip). This method works with any of the modes of operation of the shopping trip. In an exemplary embodiment, users can also watch the movie for which tickets have been purchased online collaboratively. Further details are discussed with reference to FIG. 44. Shopping trips can also work on mobile devices.

Users of the shopping trip can also collaboratively pick and choose designs, styles, colours, and other aspects of apparel, and share their user model or user data 111 to build customized apparel. Similarly, users can design a room and purchase furniture, or design, build and buy furniture or other items. Collaboration during shopping (using the modes of operation of a shopping trip) can be used not only for product or catalog or mall browsing but with any shopping facility or shopping tool such as the shopping cart, fitting room, wardrobe, user model, consultant, etc. Tools present in toolbar 239 such as editing zooming, panning, tilting, manipulating view, undo, etc, as described with reference to FIG. 20 can also be used during a shopping trip.

Figure 42:
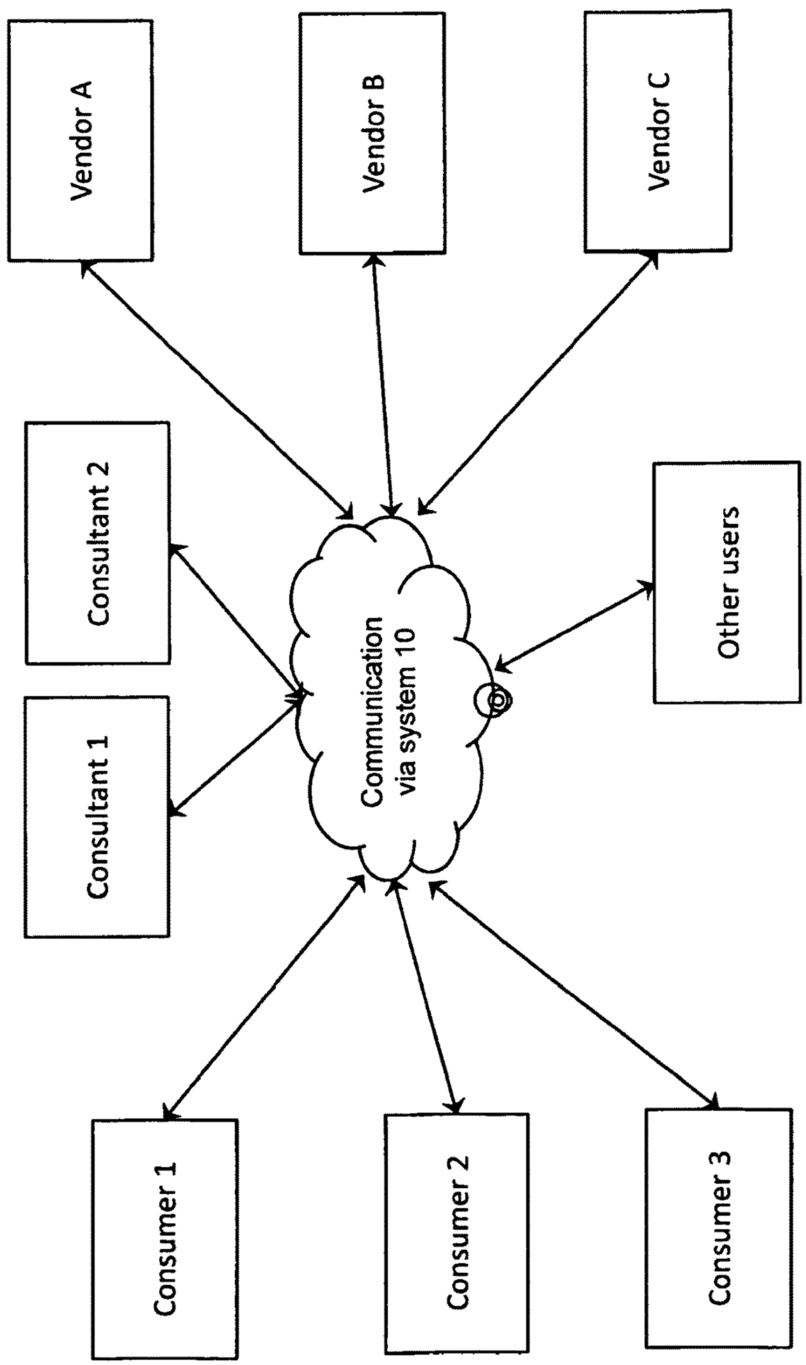
FIG. 42 illustrates a sample interaction between various parties using system 10.

Reference is now made to FIG. 42 where one form of interaction between various parties with system 10 is shown in exemplary embodiment. Consumers can interact with their various computing devices 14, 16 not shown in the image. Other users may include shipping and handling users, administrative staff, technical support, etc. Consumers browse products, interact together and shop. When a purchase order is received at the portal server 20, vendors selling the product are notified. They then approve the purchase order, upon which the payment received from the customer is deposited in the corresponding vendor's account. The shipment order is placed through shipping and handling users. Alternatively, the customer may pick up order at a store branch using a 'pick up ID' and/or other pieces of identification. The store the customer is interested in picking up the order at can be specified through the system. The system may find the vendor store closest in proximity to the customer's location (customer's home, office etc.). An interface exists for interaction between any type of user and system 10, and between different groups of users via system 10. For instance, customers may interact with each other and with store personnel/vendors, and with fashion consultants via a webpage interface. Vendors may interact with customers, consultants and other businesses via a 'MyStore' page available to vendors. Vendors can upload store feeds (in audio, video, text formats etc.), product information and updates via this page, as well as interact with customers. Vendors can see (limited information on) who is entering their store in real time and also offline. For example, they can see if a set of users entering their store are on the same shopping trip, the age group of users (arbitrary noise may be added to the age), the gender of the user. This allows the vendor to make comments like, "Hello boys, can I help you with anything?". Users can set the privacy level they are comfortable with through the preferences panel. Fashion consultants can upload relevant information through pages customized to their need. They can upload the latest fashion tips, magazines, brochures, style information etc. They can easily pull up and display to the user product information, dress 'how-tos', style magazines and related information as appropriate. They can also interact via various forms of interaction (such as audio/video/text chat etc.) described in this document.

Figure 21A:
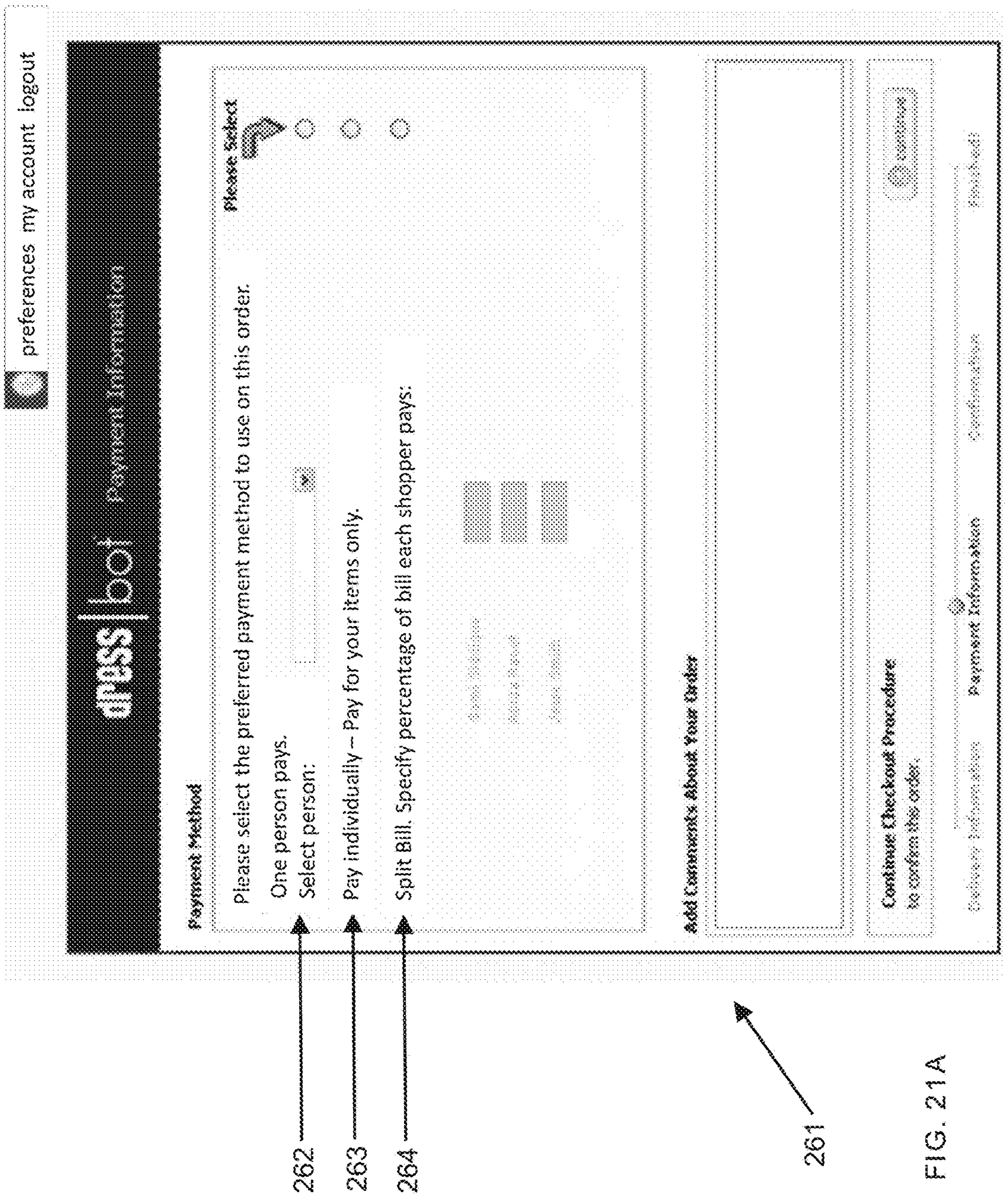
FIG. 21A-G are images illustrating Split-Bill features.
Figure 21B:
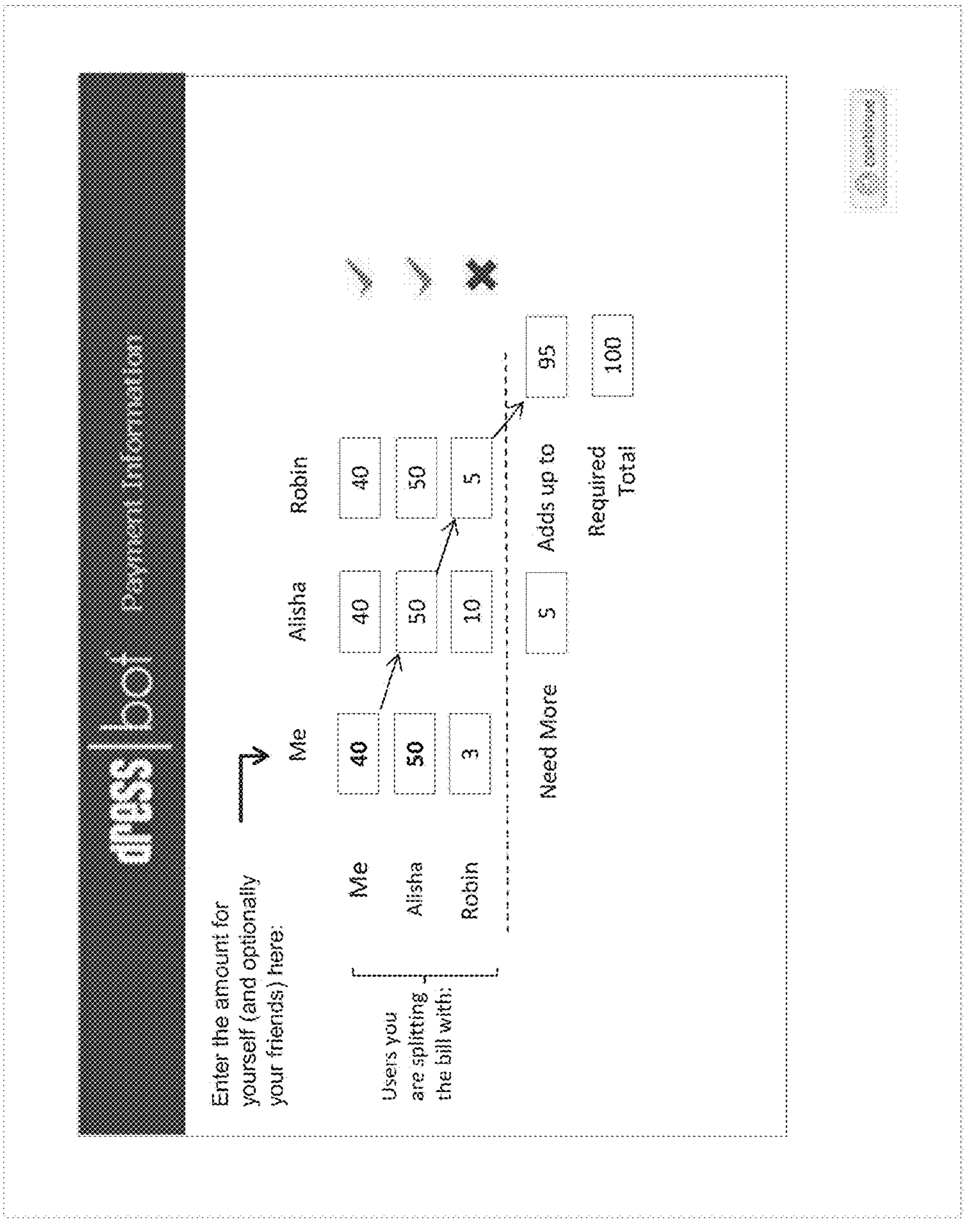

Users on a shopping trip have the opportunity to use the Split-Bill™ feature to make payments for purchases. Split-Bill is a feature that enables users to share the cost of a purchase or the amount of a transaction by allocating some or all of the cost or amount to be paid by each of the users. Optionally, a subset of users that are party to the transaction may be allocated the entire cost or amount of the transaction. This feature also calculates the portion of taxes paid by each individual in a transaction and can be used in conjunction with the receipt management system discussed with reference to FIG. 48D. Split-Bill also enables users to claim their portion of an expense when claiming reimbursement for expenses (for example, expenses incurred on part of an employee for the purposes of work). There are many options for ways of operation of the Split-Bill feature. Most of these ways can be thought of as similar to the modes of operation of a shopping trip as described with reference to FIG. 7A-D. Some of these methods are described next in exemplary embodiments: FIG. 21A demonstrates an exemplary embodiment of Split-Bill 261. Different payment schemes are available to the users of a shopping trip. A member of the shopping trip may pay for the entire bill using option 262 or each member pay for his/her individual purchases using option 263. Alternately, the bill may be split between members by amount or percentage (as illustrated in FIG. 21A) or other means of division using option 264. Such a service would also be applicable to electronic gift cards available through system 10. More than one user may contribute to an electronic gift card and the gift card may be sent to another user via system 10. The recipient of the gift card would be notified by an email message or a notification alert on his/her profile page or other means. The senders of the gift card may specify the number of people contributing to the gift card and the exact amount that each sender would like to put in the gift card or the percentage of the total value of the gift card that they would like to contribute to. In one exemplary embodiment, the Split-Bill method works as follows: When a user decides to split a bill on a supported website or application, they choose the friends that they wish to split the bill with and the portions of the bill that each friend including themselves will pay. After that, they confirm their order as usual and get sent a payment processing gateway to make payment. Once they have paid their portion of the bill, the other participants are notified of the split bill payment. These other users accept the split bill notification and are sent to the confirmation page for an order where they confirm their portion of the bill and are sent to the payment processing gateway. Once each member of the split bill group has made their payment, the order's status is changed to paid and becomes ready for fulfillment. A hold may be placed on authenticated payment until all other participants' payments have been authenticated at which point all the authenticated payments are processed. If a participant declines to accept a payment, then the payments of all other participants may be refunded. Users can also split a bill with a friend (or friends) who is offline. In this case, a user or users come to the Split-Bill screen and indicate the name of the user(s) that they would like to split a portion or all of the bill with. That user(s) is then sent a notification (on our website or on any other social networking site like Facebook or on a chat application such as msn or via email or on a cell phone communicating via text such as through SMS or via voice by employing text to speech conversion, in exemplary embodiments). That user(s) can then decide to accept it in which case the transaction is approved and the payment is processed, or deny it in which case the transaction is disapproved and the payment is denied. This mode of operation is similar to the asynchronous mode of operation as discussed with reference to FIG. 7B.

Figure 21C:
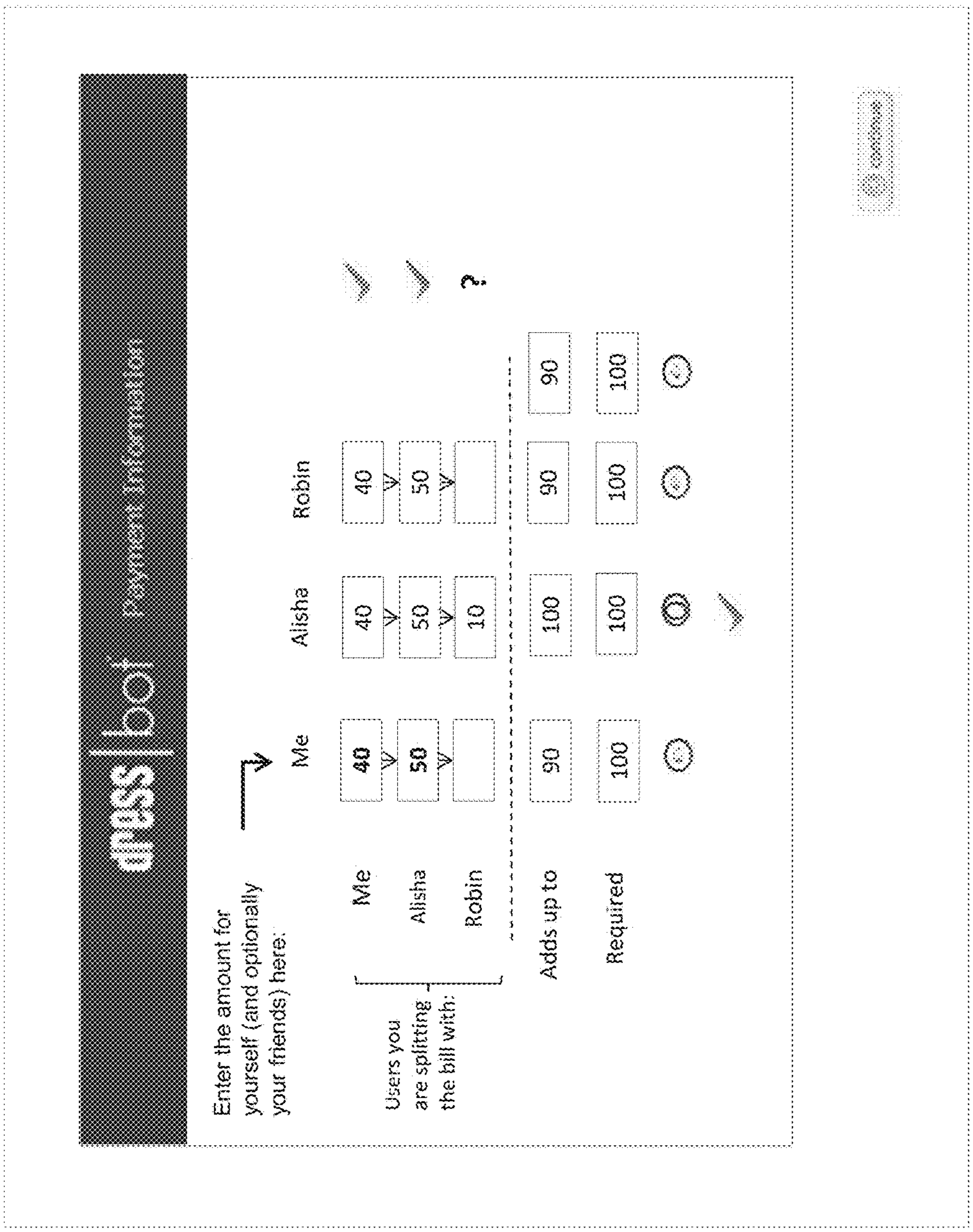
Figure 21D:
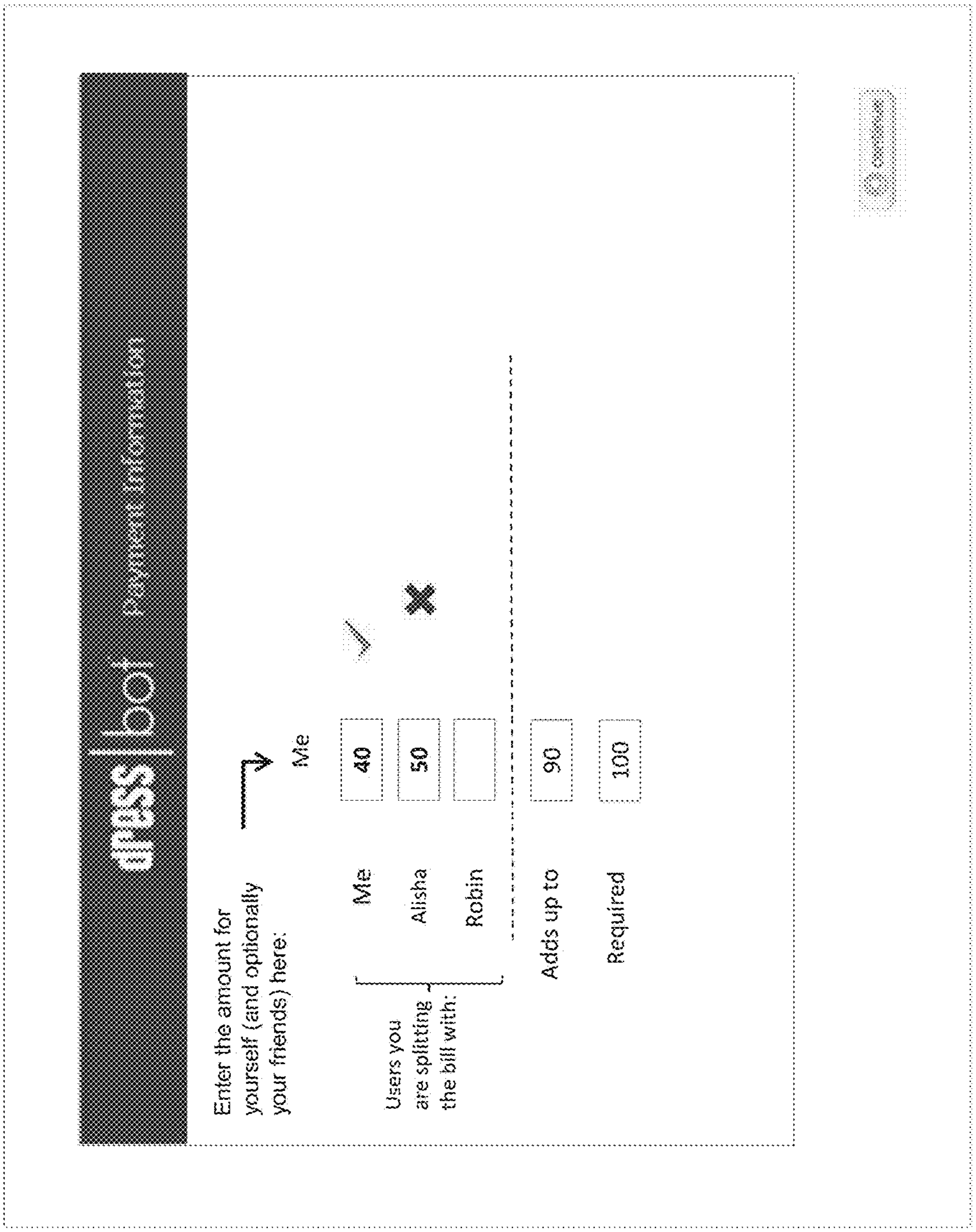

In another exemplary embodiment, the Split-Bill method works as follows: When members of a shopping trip decide to split a bill on a supported website or application, each of them is presented with a screen such as the one shown in FIG. 21B in an exemplary embodiment. In the first (left-most) column, the user enters the amount that he/she would like to pay (top row) of the total amount. Other users are shown similar screens. As the user enters this amount, it is "flooded" (viewable) to the other users' screens. The user can also enter the amount that he/she would like other members to pay in the first column. The other columns indicate the amounts that others have entered. For example, in FIG. 21B it is shown that Alisha has entered "50" as the amount that she would like to pay. In the 3-by-3 matrix shown, each column is for entering the amount that a member of the trip would like the members of the trip to pay. A user (user A) can optionally override the amount that another user (user B) should pay in their (user A's) column in the row that corresponds to the user's (user B) name. If the amounts entered by all the members for any given row are consistent, a check mark appears. In an exemplary embodiment, a user must enter the value in at least their field and column to indicate approval. The user cannot override the values in the grayed out boxes as these boxes represent the values entered by other users. If there is inconsistency in the values entered in any row, a cross appears next to the row to indicate that the values entered by the users don't match. As the users enter their amounts an "Adds up to box" indicates the sum of the amounts that the users' contributions add up to. In an exemplary embodiment, the amounts along the diagonal are added up in the "Adds up to box". Another field indicates the required total for a purchase. Yet another field shows how much more money is needed to meet the required total amount. If all rows are consistent, the users are allowed to proceed with the transaction by clicking on the "continue" button. The amounts entered can be the amounts in a currency or percentages of the total. In an exemplary embodiment, users can also view a total of the amounts that each of the users is entering, as shown in FIG. 21C in an exemplary embodiment. Users can also select a radio button or a check box below the column corresponding to a user to indicate that they would like that user's allocation of amounts across friends. For example, as shown in FIG. 21C the user has chosen Alisha's way of splitting the bill. If all members chose Alisha's way of splitting the bill, then a check mark appears below Alisha's column and the users are allowed to proceed by clicking on the "continue" button. The user whom other members are choosing for splitting the bill may also be communicated for example using colours. This mode of operation is similar to the synchronous mode of operation as discussed with reference to FIG. 7C.

In another exemplary embodiment, the Split-Bill method works as follows: When members of a shopping trip decide to split a bill on a supported website or application, each of them is presented with a screen such as the one shown in FIG. 21D in an exemplary embodiment. Users can enter the amount that they would like to pay in a field next to their name. If the amount adds up to the required total, the users are allowed to continue with the purchase.

In another exemplary embodiment, the Split-Bill method works as follows: When members of a shopping trip decide to split a bill on a supported website or application, each of them is presented with a screen such as the one shown in FIG. 21D in an exemplary embodiment. Users can enter the amount that they would like to pay in a field next to their name. In this case, the users can enter an amount in any of the fields next to the members names simultaneously using the communication protocol described with reference to FIG. 7D. The users also share the same view. Each user also gets to approve his/her amount by checking a box next to their name. If the amount adds up to the required total and each of the users has approved his/her amount, the users are allowed to continue with the purchase. This mode of operation is similar to the common mode of operation as discussed with reference to FIG. 7D.

Figure 21E:
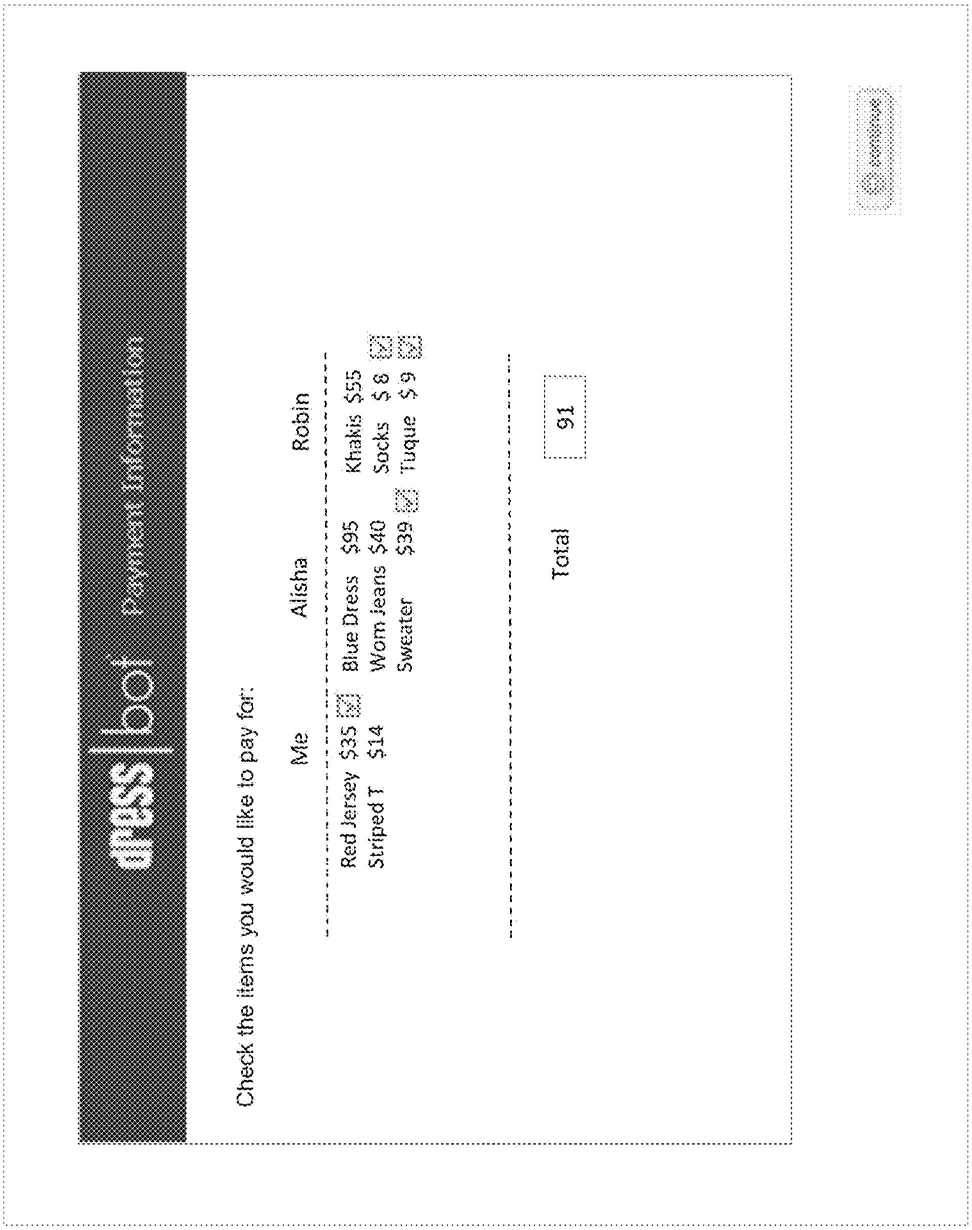
Figure 21F:
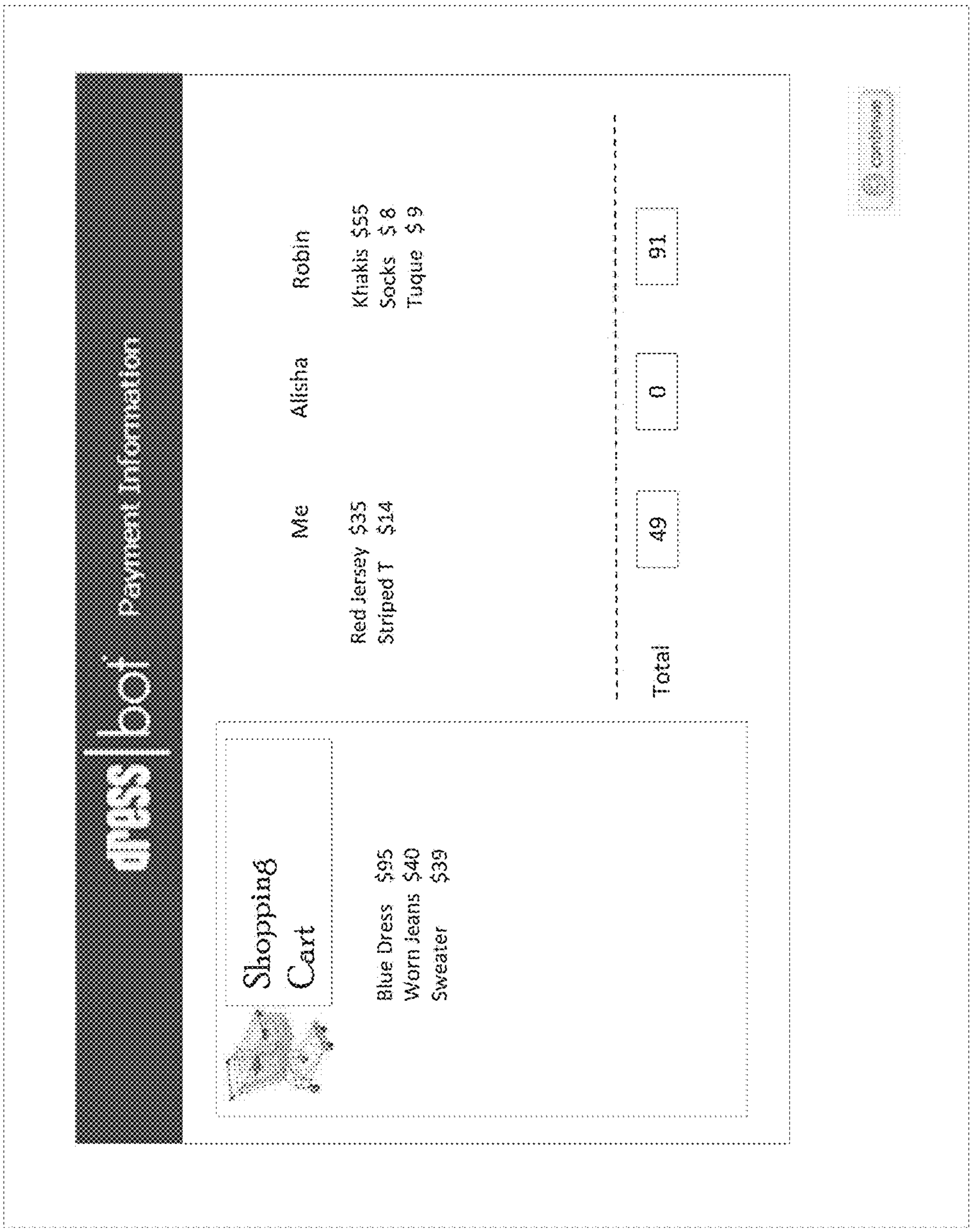
Figure 21G:
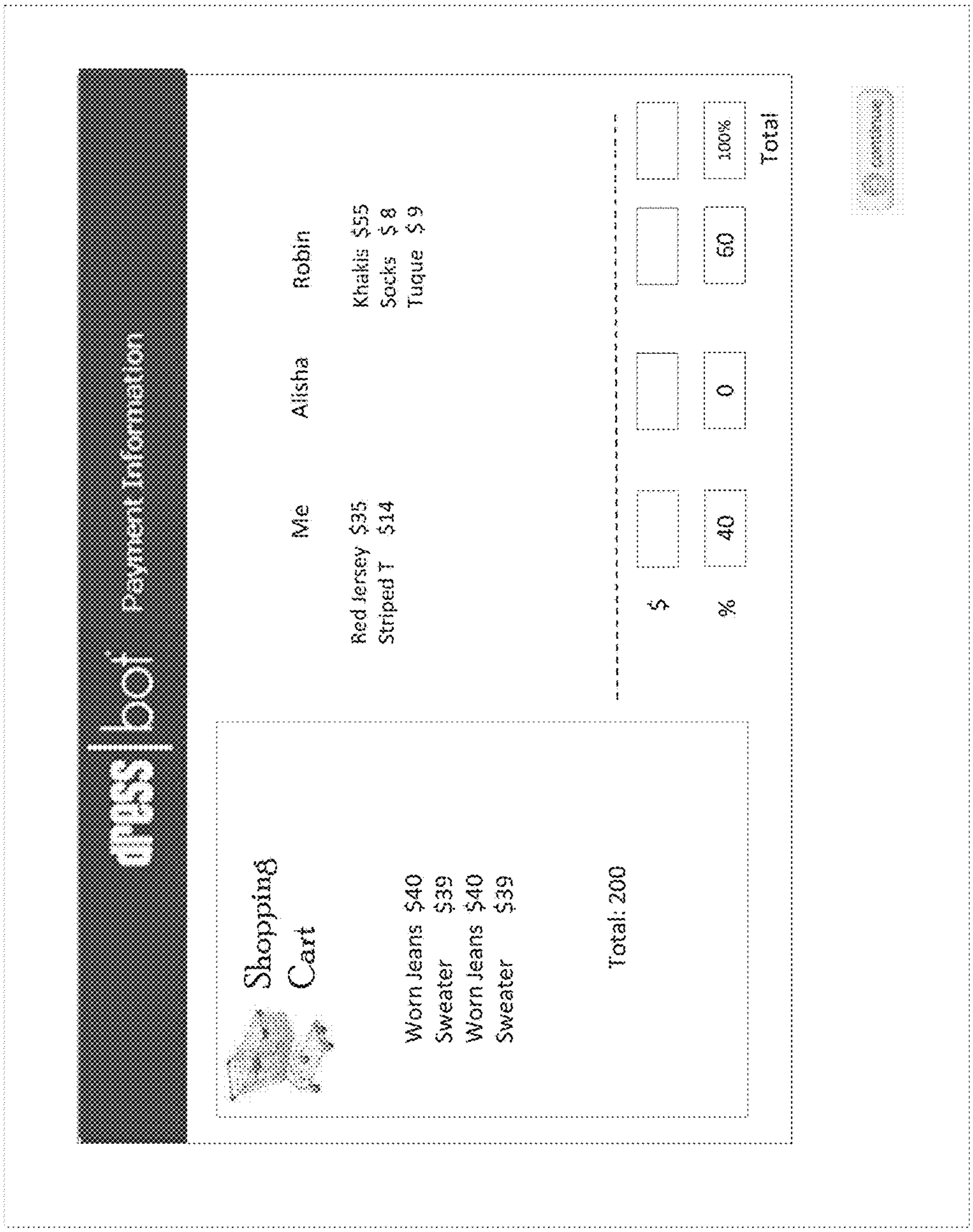

During a shopping session, individual shopping carts as well as shared shopping carts are available. In an exemplary embodiment, changes made by a user of the shared shopping cart are synchronized across all users of the shared shopping cart. An alternative option would be to make the shopping cart only viewable to others (read-only). Split-Bill also enables product-wise division. Users can also pick and choose which items from each of the members shopping carts they would like to pay for. An exemplary embodiment of such a method is illustrated in FIG. 21E. As shown in this figure, a user has chosen to pay for his "Red Jersey", Alisha's sweater, and Robin's socks and tuque. The user's total is also shown. Items that are paid for are shipped to the respective users (shopping cart owners) or can be shipped to a common address (common to all users). Reference is now made to FIG. 21F where another exemplary embodiment of Split-Bill is shown. Users can drag and drop items from a shared shopping cart into a list under their name. The list indicates the items that the user would like to pay for. At the bottom of the list the total of each user is also shown. Reference is now made to FIG. 21G where another exemplary embodiment of Split-Bill is shown. Users can drag and drop items from a shared shopping list into a list under their name and indicate the amount of the total bill that they would like to pay. This could be an amount in a currency or a percentage of the bill. In another exemplary embodiment, users can state an amount or a maximum amount (which could even be zero) that they can afford to pay. Other users can make payments on behalf of this user.

The Split-Bill feature can also work in any combination of the methods described above. In the above embodiments of Split-Bill, options are also available to split a bill evenly between users or to split the outstanding or remaining amount evenly between users. The above embodiments of Split-Bill can also be used in conjunction with multiple shopping trips. A trip leader may also be assigned to decide on how the bill is split. Reoccurring or monthly payments may also be shared between friends using the above methods. This can also take place in a round Robin fashion where one user pays the first month, a second user the second month and so on. The Split-Bill feature allows processing of credit, debit, points cards and/or other supported payment options. Payments can be made using any combination of these options. For example, a product that is about to be purchased may be paid for partially from a debit/bank account, partially via a credit card, partially using a gift card, and partially using points or store credits. Points or credits may come from stores or from a user's friends. Also supported is the borrowing/lending of money and points between friends. This can be used in conjunction with contract management system. The Split-Bill feature enables currency conversion. Users in different countries can view the amount to be shared in their local currency or other currencies of their choice. The Split-Bill feature also enables users to request money or points from their friends (including those on social networks such as Facebook) or other users. This can be done when the user from whom money is being requested is online or offline similar to the method described above. Upon approval money or points get transferred to the account of the user who requests funds. This can then be transferred to the user's debit account, credit account, points account, etc. The amount of a transaction may also be split between companies and other groups. For sites that do not support the Split-Bill feature, two or more parties can deposit to an account using the Split-Bill service on a supported site, upon which a debit or a credit or a points card or an electronic money voucher is created. This account can then be used on a third party site for a shared purchase. In an exemplary embodiment, the Split-Bill method is also available as an independent component on a website for people to share the amount of a translation. Users can collaboratively buy products/services and send them as a gift to other users. Users can also ship gifts to users based on their location as specified in social networking sites or on our site or based on their mobile device location. This allows users to send gifts to an up-to-date address of the users' friends.

Investments may be made through Split-Bill. Other financial transactions may be conducted in a collaborative manner, including currency exchange. Currency may be exchanged, in exemplary embodiment, with a friend or someone in a friend's network so that the user may ensure that the transaction is being carried out through a trusted reference. A person traveling to another country may exchange money with a relative or friend in that country. In another exemplary embodiment, shares and stocks may be traded collaboratively, for example through a split bill interface. Tools may be available for investors to collaboratively make investments and assist them in making decisions.

Figure 35:
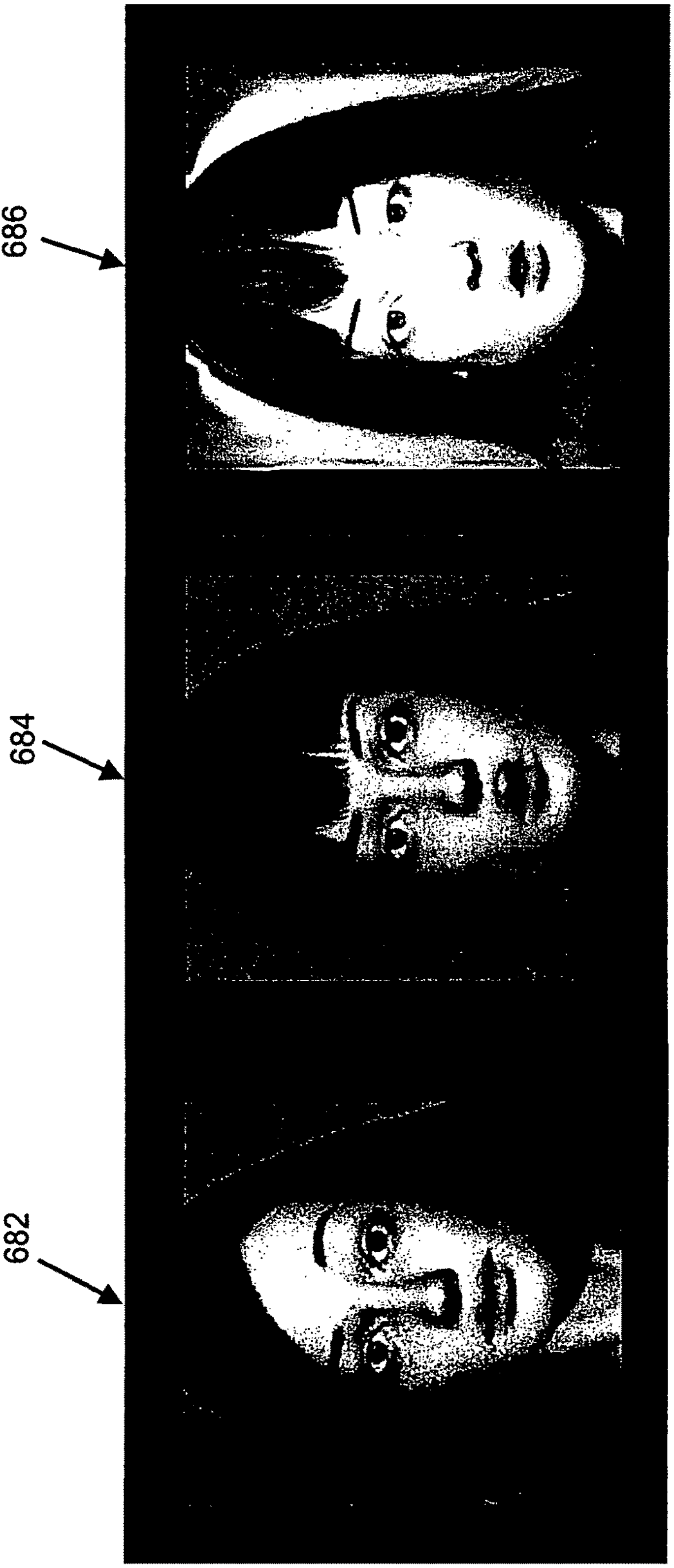
FIG. 35 is an image showing sample manipulations of a user model's expressions and looks.

Reference is now made to FIG. 35 where a virtual model is shown in display windows illustrating examples of how a user can animate their character model's expressions/movements/actions and/or change their model's look. The expressions/actions/dialogue/movements of the character model can be synchronized with the user's own expressions/actions/dialogue/movements as tracked in the image/video (in an exemplary embodiment using a method similar to [52]) of the user or these can be dictated by the user through text/speech and/or other command modes or through pre-programmed model expression/action control options provided through system 10. The display window 682 shows the virtual model 'raising an eyebrow'; display window 684 shows the model with a surprised expression sporting a different hairstyle; display window 686 shows the virtual model under different lighting conditions with a different hair colour. The exemplary embodiments in the figure are not restrictive and are meant to illustrate the flexibility of the virtual models and how a user can animate and/or control their virtual model's looks, expressions, actions, background/foreground conditions etc. Facial expressions may be identified or classified using techniques similar to those used in [53]. The virtual model can be thus manipulated even when the user uses it to communicate and interact with other users, for example, as in a virtual chat session. In another exemplary embodiment of collaborative interaction involving a user's model, stylists and friends of the user can apply makeup to the user model's face to illustrate make up tips and procedures. The makeup may be applied to a transparent overlay on top the content (user model's face) being displayed. The system allows the user to save the animation and collaboration sessions involving the user model.

Figure 36:
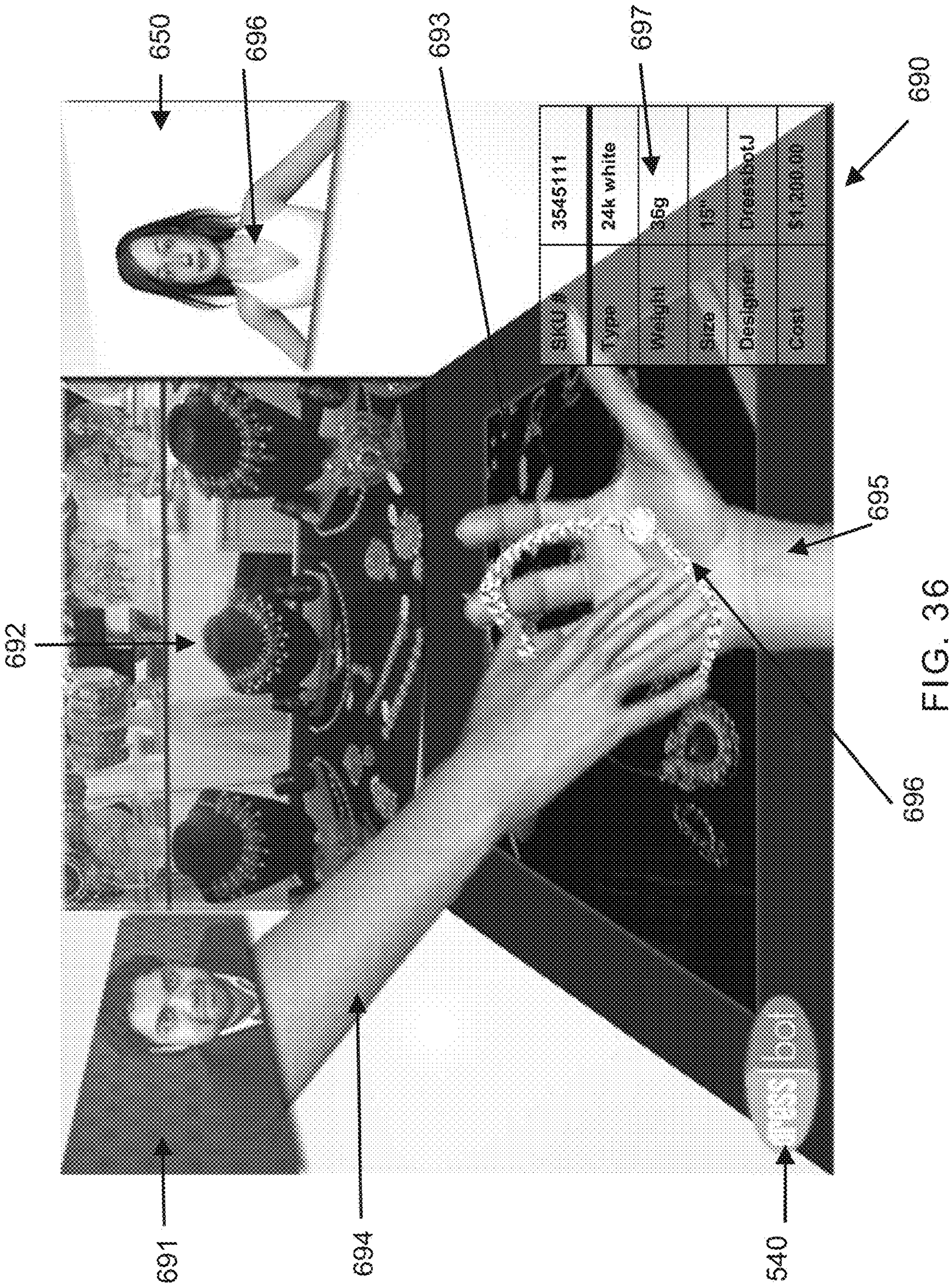
FIG. 36 is an image of a sample virtual store window showing virtual interaction between a user and a sales service representative.

Reference is now made to FIG. 36. This figure, in an exemplary embodiment, shows a sample virtual store window 690 involving virtual interaction between the user and a sales service representative in a real jewelry store, and incorporating augmented reality elements as described next. In this example, a sales representative 691 interacts with the user in real-time via streaming video (acquired by a webcam or some other real-time video capture device). The user in this instance interacts with the sales personnel via the user model 650 which is lip-syncing to the user's text and speech input. Panoramic views of the displays 692 in the real jewelry store appear in the store window 690. An 'augmented reality display table' 693 is present on which the sales representative can display jewelry items of interest to the user. Virtual interaction takes place via plug and play devices (for example I/O devices such as a keyboard, mouse, game controllers) that control the movement of simulated hands (of the user 694 and sales personnel 695). Additionally, a device that functions as an 'articulated' control i.e., not restricted in movement and whose motion can be articulated as in the case of a real hand, can be used to augment reality in the virtual interaction. Store personnel such as sales representatives and customer service representatives are represented by virtual characters that provide online assistance to the user while shopping, speak and orchestrate movements in a manner similar to real store personnel and interact with the user model. The augmented reality display table is featured by system 10 so that vendors can display their products to the customer and interact with the customer. For example, a jewelry store personnel may pick out a ring from the glass display for showing the user. A salesperson in a mobile phone store may pick out a given phone and demonstrate specific features. At the same time, specifications related to the object may be displayed and compared with other products. Users also have the ability to interact with the object 696 in 2D, 3D or higher dimensions. The salesperson and customer may interact simultaneously with the object 696. Physics based modeling, accomplished using techniques similar to those described in [54], is incorporated (these techniques may be utilized elsewhere in the document where physics based modeling is mentioned). This display table can be mapped to the display table in a real store and the objects virtually overlaid. A detailed description 697 of the object the user is interested in is provided on the display while the user browses the store and interacts with the store personnel. A menu providing options to change settings and controls is available in the virtual store window, by clicking icon 540 in an exemplary embodiment. The above example of a virtual store illustrates features that make the virtual store environment more realistic and interaction more life-like and is described as an exemplary embodiment. Other manifestations of this virtual store may be possible and additional features to enhance a virtual store environment including adding elements of augmented reality can be incorporated.

Figure 22:
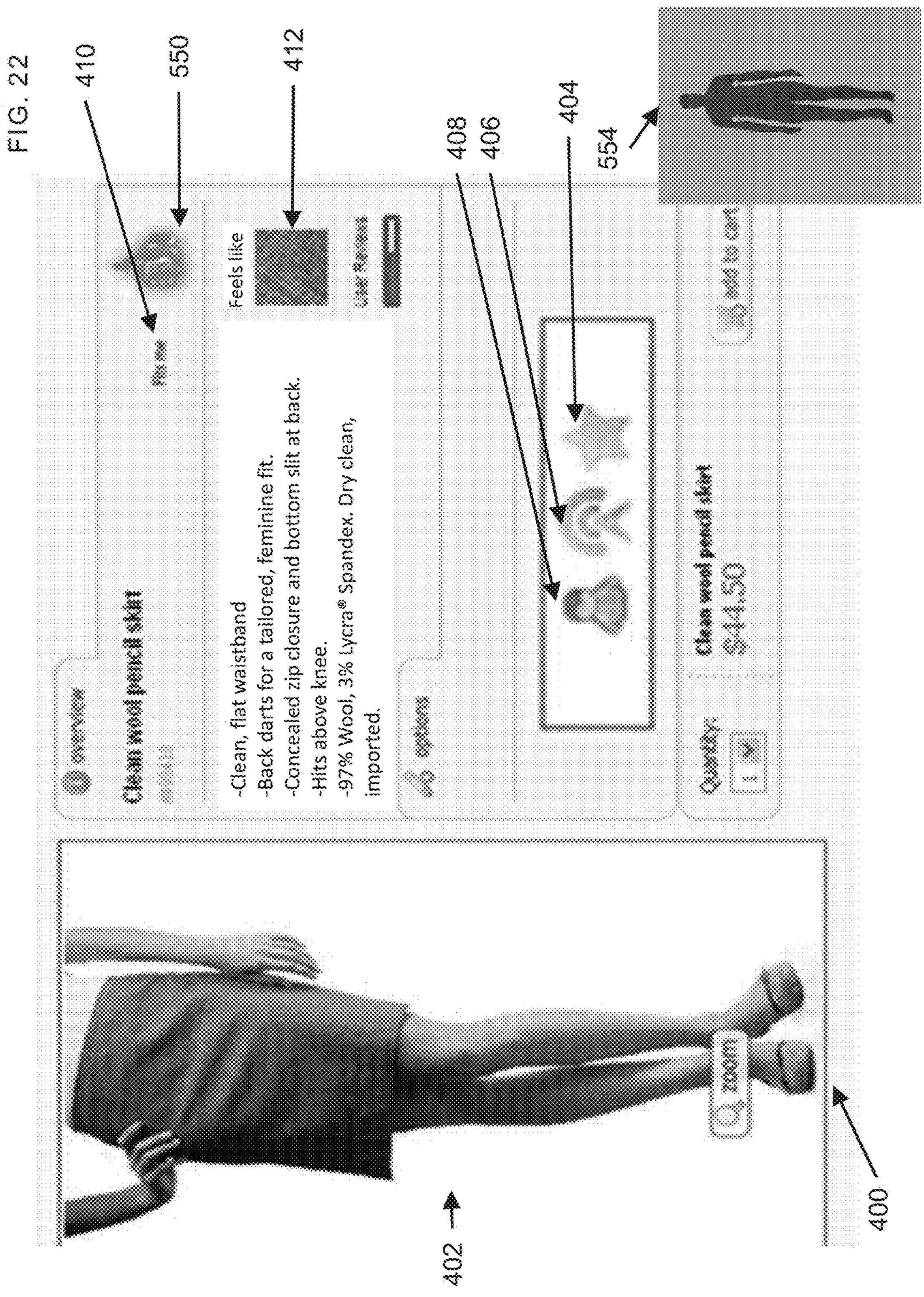
FIG. 22 is an image of a sample apparel display window.

Reference is now made to FIG. 22, where an apparel display window 400 is shown in an exemplary embodiment. The display windows provide visual representations of the apparel items that are available to model/purchase to the user. The display window 400 comprises a visual representation 402 of the apparel item. In the example provided herein, a visual representation of a skirt is provided. Further information regarding the pricing, and ordering information, should the user desire to purchase this item is available. The user is able to view reviews of this apparel items that have been submitted by other users by engaging the review icon 404 in an exemplary embodiment. The user is able to further share this particular apparel item with friends by engaging the share icon 406 in an exemplary embodiment. If the user is browsing in the regular mode of operation (not on a shopping trip with friends), clicking on this icon presents the user with a screen to select a mode of operation. If the synchronous mode or the common mode of interaction are chosen, the user is presented with a shopping trip window as described with reference to FIG. 40. If the user chooses the asynchronous mode of operation, the item gets added to the "shared items" list. The user can manage shared items through an interface as described with reference to FIG. 23. If the user is engaged in the synchronous or common modes of interaction, clicking on the icon 406, adds the item to the "shared items" list. The user can also send this item or a link to the item to users of social networking sites. The user is able to try on the apparel items on their respective user model by engaging the fitting room icon 408 in an exemplary embodiment. The method by which a user may try on various apparel items has been described here for purposes of providing one example of such a method. Suitability of fit information may be displayed next to each catalog item. In an exemplary embodiment, this is done by stating that the item fits ('fits me') 410 and/or placing an icon that conveys the fit info (for eg. icon 550). Further details of displaying the goodness of fit information is described with reference to FIG. 30. A 2D or 3D silhouette 554 may also be placed next to catalog items to visually show goodness of fit. Information on how the apparel feels is also communicated to the user. This is done in an exemplary embodiment, by displaying a zoomed in image of the apparel 412 ("Feels Like") illustrating the texture of the apparel. The sound that the apparel makes on rubbing it may also be made available.

Models of products (photorealistic 3D models or NPR models) for use in catalogs may also be constructed by using images submitted by users. Images contributed by several users may be stitched together to create models of products. Similarly, images from several users may also be used to create a user model for the users' friend. Holes or missing regions, if any, present in the constructed models may be filled with texture information that corresponds to the most likely texture for a given region. The most likely texture for any given region can be estimated, in an exemplary embodiment, using Naïve Bayes or KNN. This can be done as described earlier, using statistics drawn from regions in images surrounding the holes as the input and the texture in the missing region as the output.

Figure 24:
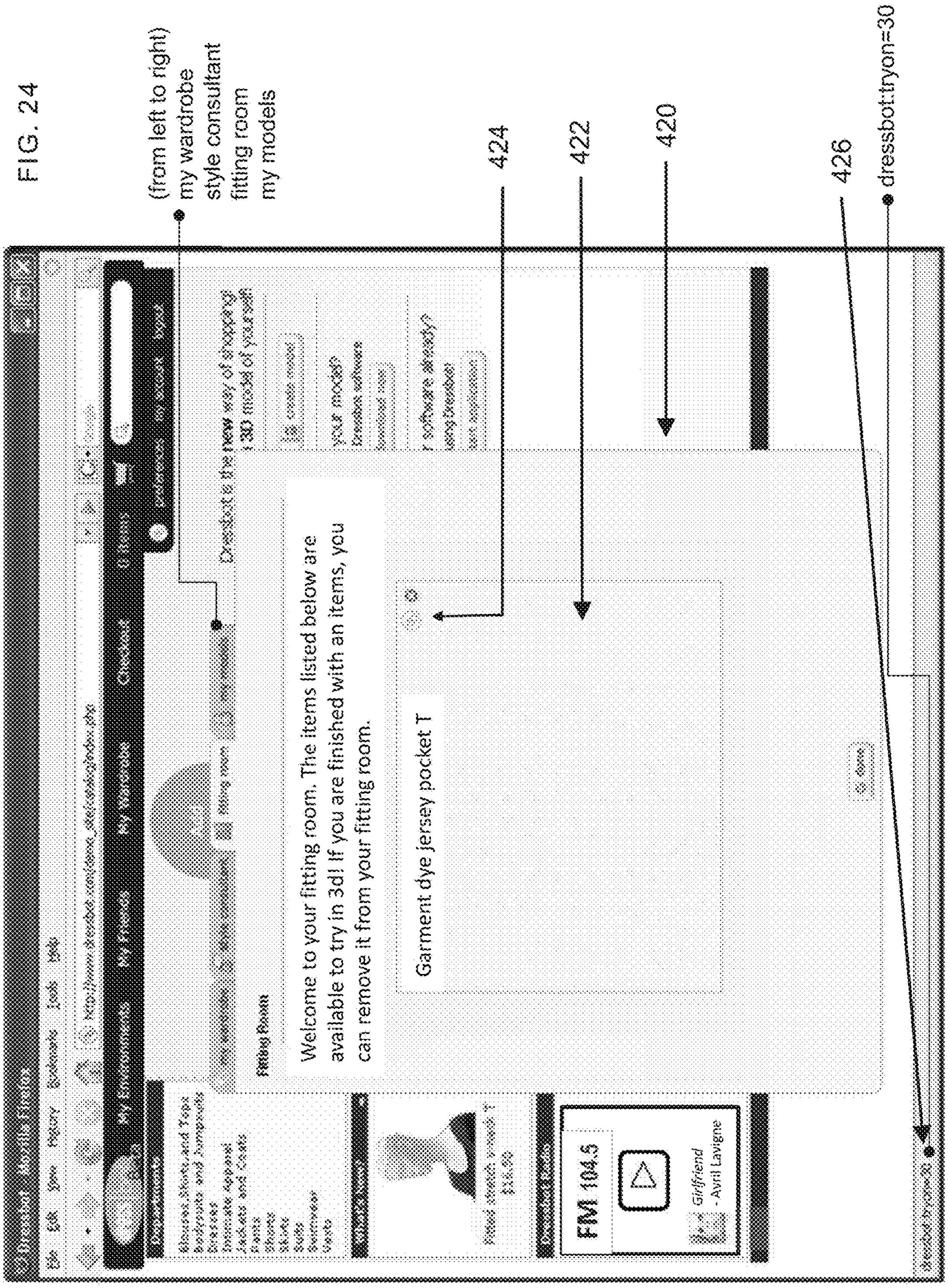
FIG. 24 is an image of a sample fitting room window in a browser window.

When a user has chosen to try on an apparel items, the user is presented with a list of the various apparel items that have selected to try on in an exemplary embodiment. Reference is now made to FIG. 24, where a sample fitting room window 420 is shown in an exemplary embodiment. The fitting room window 420 lists the various apparel items that the user has selected to try on. Each apparel item has an identification number assigned to it by system 10 for purposes of identification. By selecting one of the items from the selection window 422, and clicking on icon 424, the user requests that the system 10 fit and display the apparel item on the user model. The status bar 426 displays the command that is executed—"dressbot:tryon=30" indicating that the item with ID (identification number) equal to 30 is being fitted on the user model.

Figure 29A:
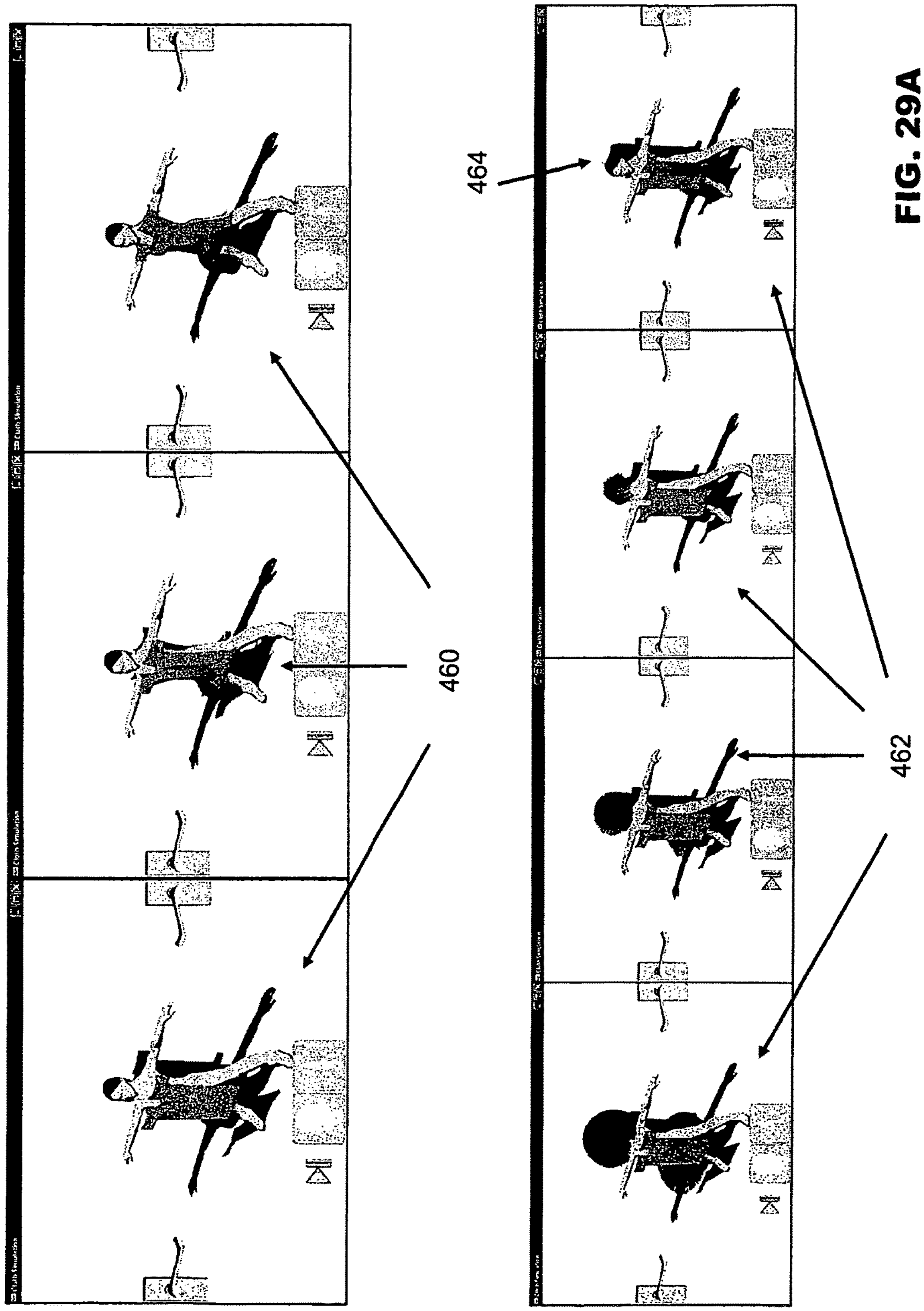
FIG. 29A is an image showing sample visual sequences displayed to a user while the apparel and hair is being modeled and fitted on the user model.
Figure 37:
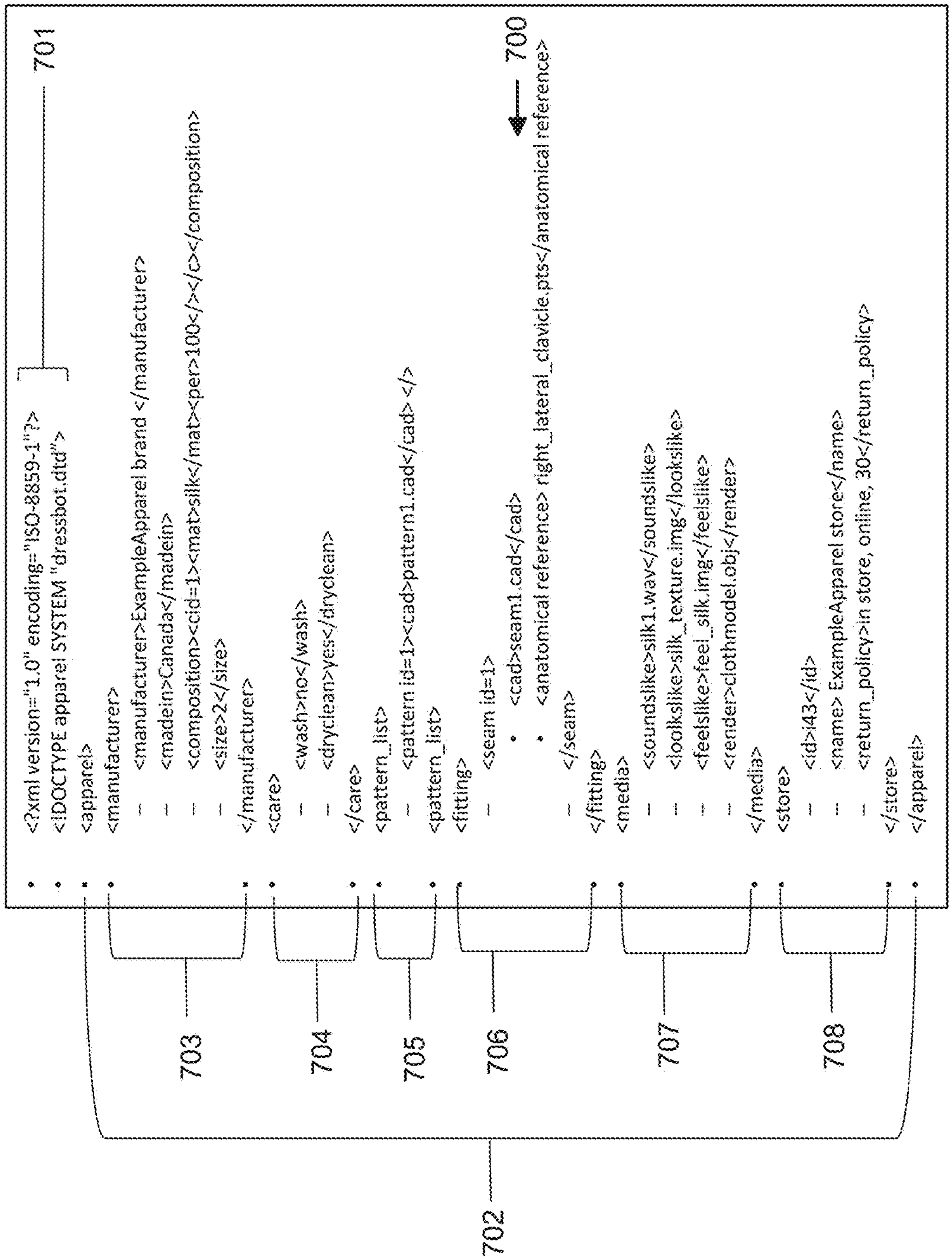
FIG. 37 is an outline of a sample ADF file in XML format.
Figure 38:
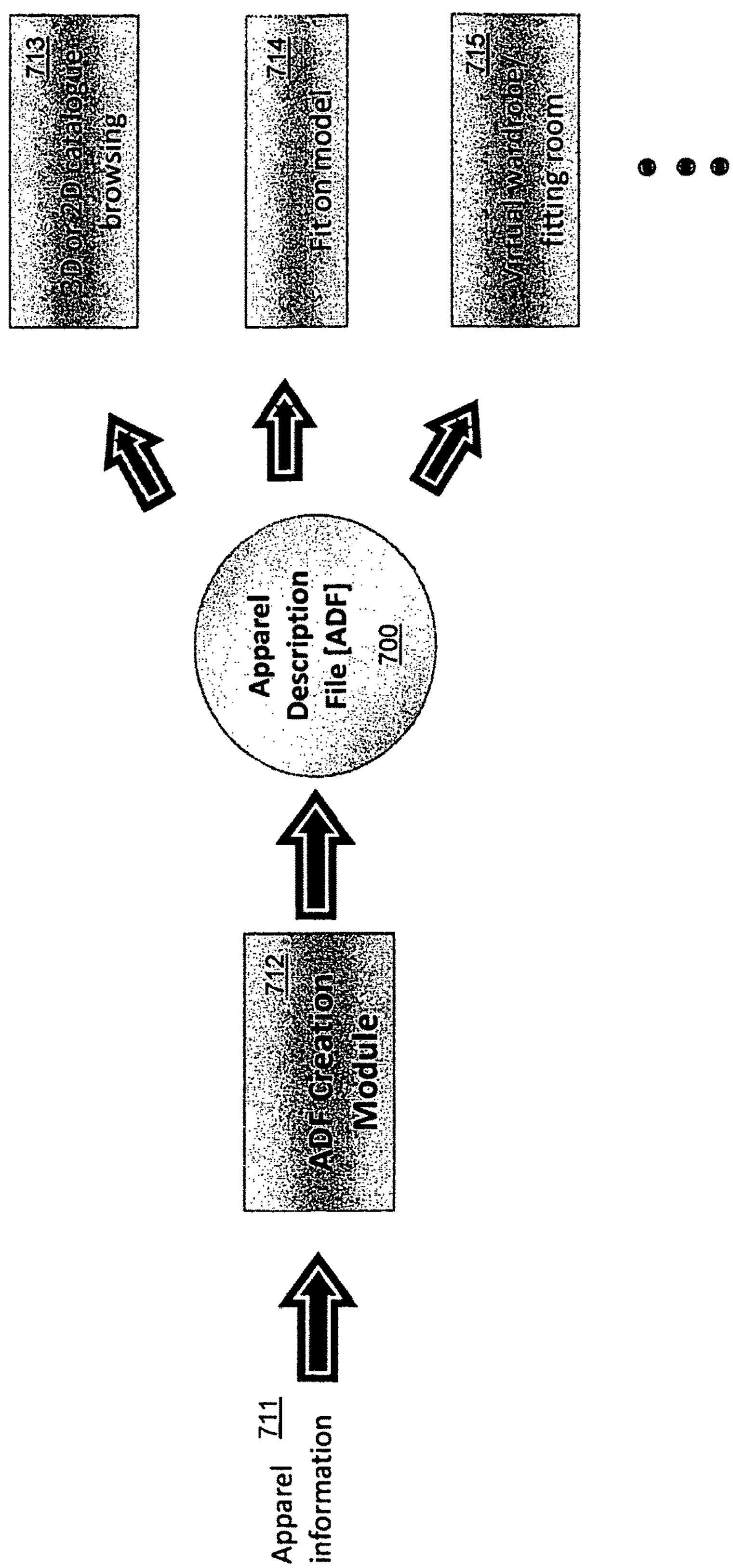
FIG. 38 is a flowchart diagram that provides an overview of ADF file creation and use.

An item of apparel is comprised of patterns (tailoring, stitch-and-sew terminology). All items of apparel are described that are associated with the system 10 have an apparel description file (ADF) associated with them. In exemplary embodiment, the ADF file can be in XML format and the CAD file provided to system 10 by the retailer module 58 can be encapsulated within this ADF file. The apparel description file contains all information regarding the apparel including information necessary to model and display the apparel and to determine its fit on a model. This includes, for example, the pattern information for a given apparel; how the individual components of the apparel are stitched together; material properties such as composition, texture, etc; cloth care instructions; source information (country, manufacturer/retailer); optical properties including BDRF (Bidirectional Reflectance Distribution Function), bump map etc; microscopic images to reveal texture; location of where each piece goes with respect to anatomical landmarks on models. Any and all information related to the actual apparel and any and all information needed by system 10 to create the virtual apparel, display and fit it on a model is contained within the ADF file. An ADF file in XML format is presented in FIG. 37 in an exemplary embodiment, The ADF file 700 contains header information 701 followed by information describing a specific apparel. The apparel tags 702 indicate the start (<apparel>) and end (</apparel>) of apparel description. Specific tags are provided within this region for describing different aspects of the apparel. For instance, the manufacturer description 703 includes the name of the manufacturer, the country source, the composition and size information in this file. The care information 704 provides details on whether the apparel can be washed or dry-cleaned; the pattern tags 705 enclose the CAD filename containing the details on apparel pattern data; the fitting information 706 that describes how a virtual manifestation of the apparel fits on a virtual human model is encapsulated by the fitting tags 706; the media tags 707 enclose filenames that provide visual, audio and other sense (such as feel) information about the apparel, as well as the files and other data containing display information about the specific apparel (the 3D display data for the apparel model lies within the <render> tag in this example). Further store information 708 such as the unique store ID in the system 10, the name of the store and other details relating to a specific store such as the return policy is provided in the ADF file. The ADF file 700 in FIG. 37 is presented for purposes of illustration and is not meant to be restricted to the XML format or the tags given in the file. Other manifestations of the ADF are possible and other tags (descriptors) may be included to describe a given apparel. Much of the information describing the apparel is contained in the CAD file obtained from the retailer 58, while the information necessary to model, display and fit the apparel is augmented with the CAD file to form the ADF. Reference is now made to FIG. 38 where a quick overview is provided of ADF file creation and use, in an exemplary embodiment. Apparel information 711 described previously, as well as information associated with the specific apparel in its CAD file is packaged by the ADF creation software 712 to form the ADF file 700. This ADF file information is then subsequently used in modeling the apparel digitally for purposes of display in electronic catalogues and displays 713; for fitting on 3D user models 714; for displaying and listing in the virtual wardrobe and fitting room 715 as well as other forms of digital apparel viewing and interaction. Pattern information comprising the apparel is extracted. This information is contained in the CAD and/or ADF files and is parsed to form the geometric and physics models of the apparel. In forming the geometric model, a mesh is generated by tessellating 3D apparel pattern data into polygons. This geometric model captures the 3D geometry of the apparel and enables 3D visualization of apparel. The physics model is formed by approximating the apparel to a deformable surface composed of a network of point masses connected by springs. The properties of the springs (stiffness, elongation, compressibility etc.) are adjusted to reflect the properties of the material comprising the apparel. The movement of the cloth and other motion dynamics of the apparel are simulated using fundamental laws of dynamics involving spring masses. Cloth dynamics are specified by a system of PDEs (Partial Differential Equations) governing the springs whose properties are characterized by the apparel material properties. The physics model enables accurate physical modeling of the apparel and its dynamics. Reference points on the apparel specify regions on the apparel corresponding to specific anatomical landmarks on the human body. The information concerning these points and their corresponding landmarks on the body will be contained in the CAD and ADF files. The reference points on the geometric and physics based models of the apparel are then instantiated in 3D space in the neighbourhood of the corresponding anatomical landmarks of the character model. From these initial positions, the reference positions are pushed towards the target anatomical positions. At the same time, springs interconnecting seams are activated to pull together the simulated apparel at the seams. FIG. 29A illustrates an example of the visual sequences 460, from left to right, displayed to the user in a window while the apparel is being fitted on a non photorealistic rendering of the user model. An example of the visual sequences 462, from left to right, presented to the user in a window during hair modeling on the non photorealistic rendered user model is also shown in FIG. 29A. The hair 464 on the user model is animated using physics-based techniques which permit realistic simulation of hair look and feel, movement and behavior.

Figure 29B:
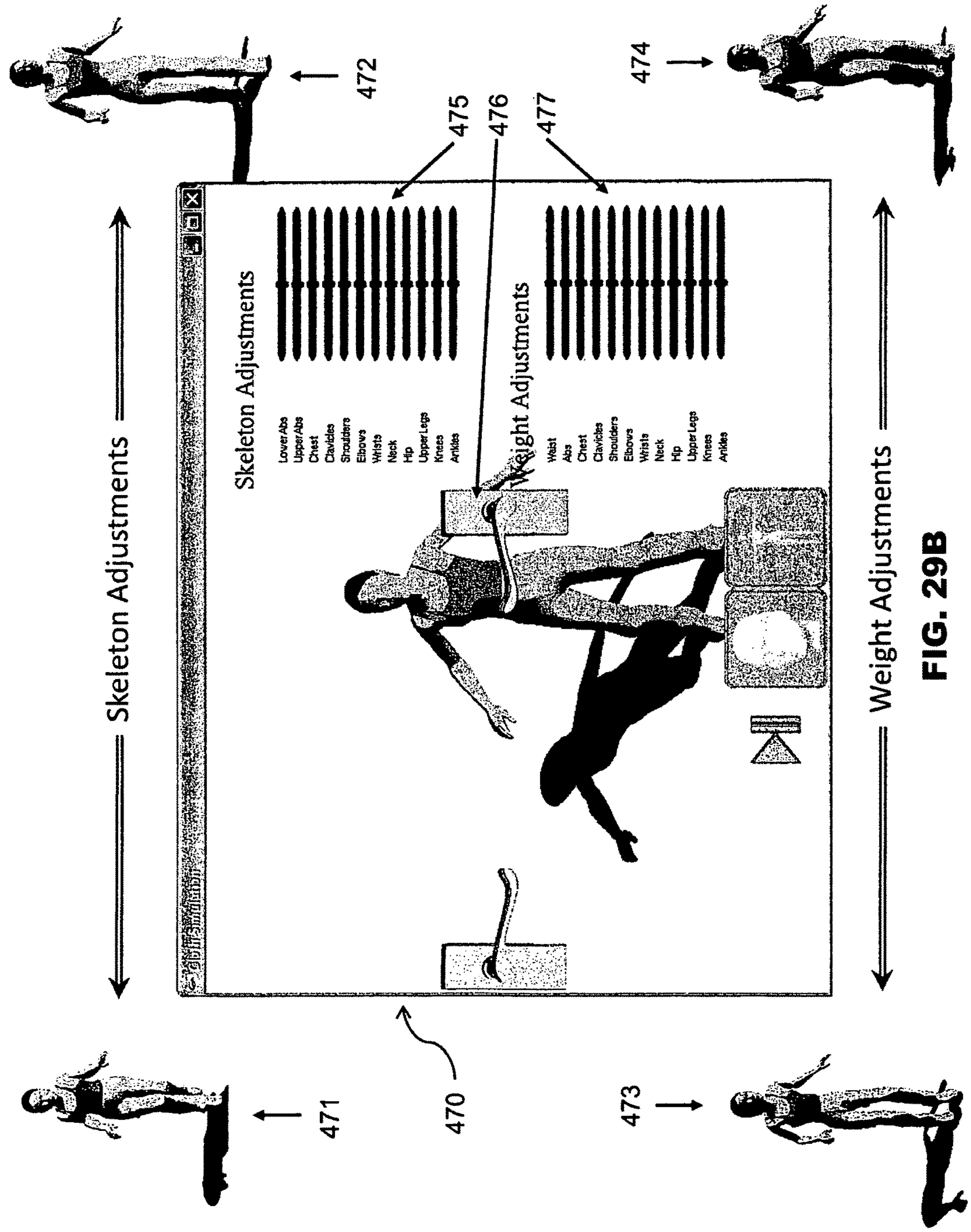
FIG. 29B is an image illustrating sample mechanisms available to the user for making body adjustments to their user model.

Reference is now made to FIG. 29B where a user model adjustments interface 470 is shown in an exemplary embodiment, containing a non photorealistic rendering of a user model. Options to make body adjustments are displayed upon clicking the menu display icon 476. A sample mechanism is shown for making adjustments to the body. Slider controls 475 and 477 can be used to make skeleton and/or weight related adjustments to the user model. Skeleton adjustments allow modifications to be made to the generative model of the skeletal structure of the user model. This renders anatomically accurate changes to be made to the user model. In an exemplary embodiment, upon moving some of the skeleton adjustment controls 475 to the right, a taller user model (with elongated bones) 472 is obtained whereas, by moving some of the skeleton adjustment controls 475 to the left, a petite user model 471 is obtained. In another similar exemplary embodiment, weight adjustment controls 477 can be used to obtain a heavier user model 474 or a slimmer user model 473. In an exemplary embodiment, manipulating the skeletal adjustment controls increases or decreases the distance between a joint and its parent joint. For example increasing the value of the length of a shin increases the distance between the ankle joint and its parent joint, the knee joint. In an exemplary embodiment, manipulating the weight adjustment controls increases or decreases the weight assigned to the corresponding vertices and moves them closer or farther from the skeleton. For example, increasing the weight of a selected portion of the shin places the vertices corresponding to that region further from the skeleton. Continuity constraints (a sigmoid function in an exemplary embodiment) are imposed at the joints to ensure plausible modifications to the user model. Users can also deform the user model by nudging the vertices corresponding to the user model. Users can also specify the body muscle/fat content which sets the appropriate physical properties. This is used, for example, to produce physically plausible animation corresponding to the user.

Figure 29C:
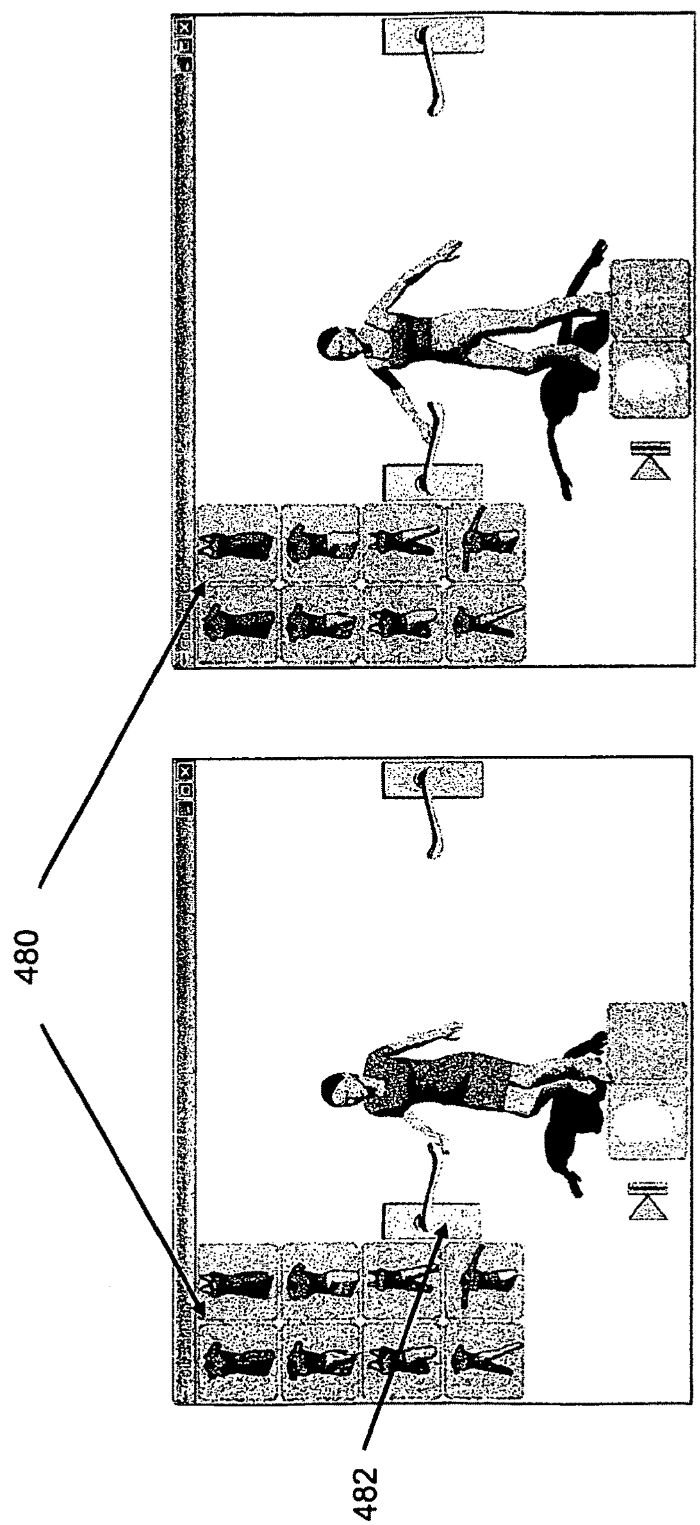
FIG. 29C is an image showing sample product catalogue views available to the user and a sample mechanism for trying on a product in the catalogue on the user model.

Reference is now made to FIG. 29C where a sample window is shown demonstrating product catalogue views available to the user from which apparel may be selected for fitting onto their user model. A product catalogue 480 may be displayed by clicking a menu display icon 482. The user may then select a given outfit/apparel/product from the catalogue upon which it will be fit and displayed on the user model. In exemplary embodiments, product catalogues are available in the local application 271 or within the browser or a combination of both as described with reference to FIG. 10 and FIG. 31.

Figure 30:
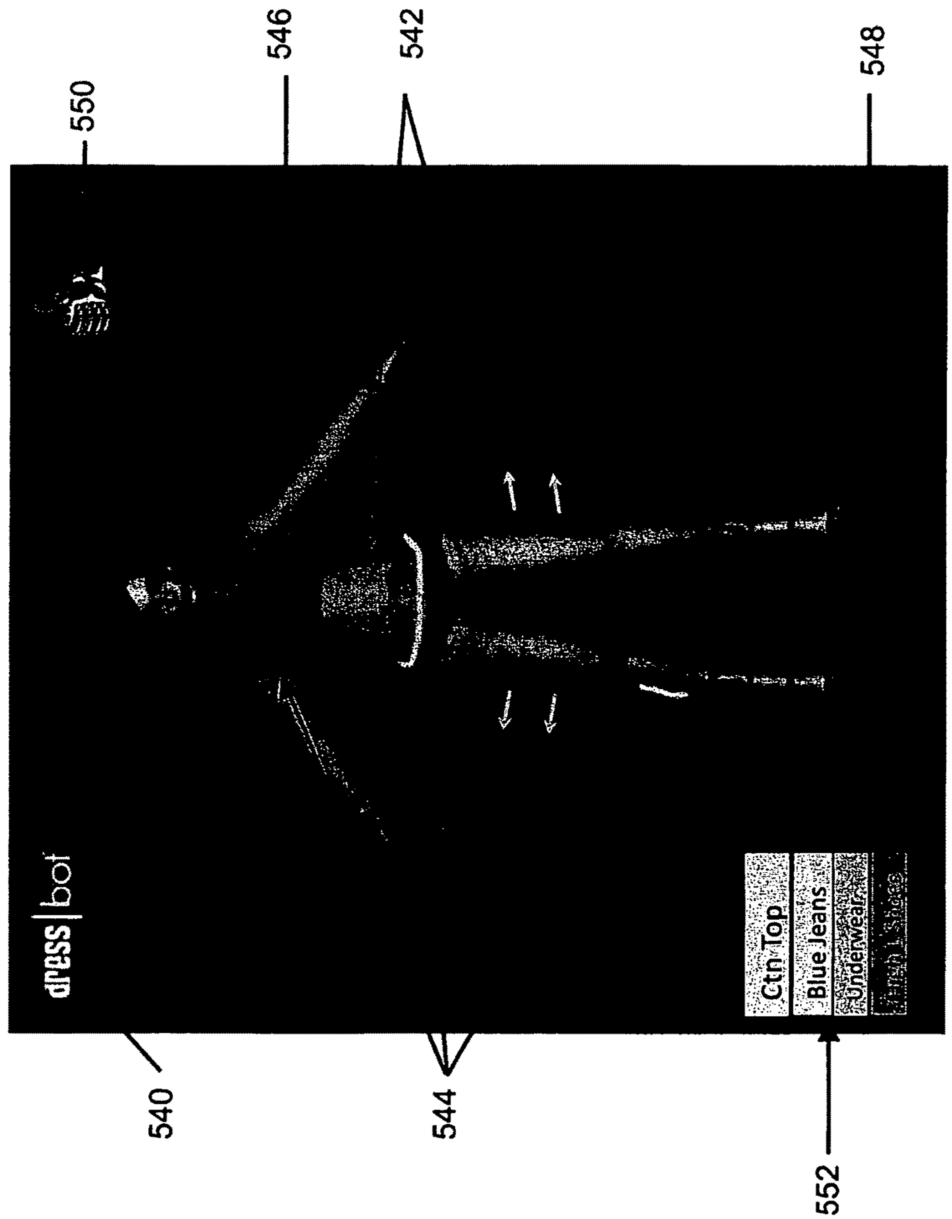
FIG. 30 is an image showing sample visualization schemes for fit information with respect to the body surface.

By clothing the user's model with apparel chosen by the user, the user is able to visualize and examine the appearance of the apparel on their body from an external perspective and also get an approximate idea of how the apparel fits. In order to communicate fit information to the user in more exact terms, metrics are used that define the suitability of apparel not just based on size information but also as a function of body type and fit preferences. The system will relay suitability of fit information to the user using aspects that are, but not limited to, quantitative and qualitative in nature. For example, goodness of fit is a quantitative metric. In exemplary embodiment, for determining apparel goodness of fit on a user model, the convex hull of the model is compared with the volume occupied by a given piece of clothing. As mentioned previously, apparel can be modeled as springs by system 10. In order to determine regions of tight fit in this case, in exemplary embodiment, physical stress and strain on the apparel and/or model can be computed using the spring constant of the apparel material. Regions of loose fit may be determined by evaluating normals from the surface. The distance between the body surface and the apparel surface can be ascertained by computing the norm of the vector defined by the intersection of the surface normal to the model's surface with the cloth surface. This process can be made computationally efficient by sampling surface normals non-uniformly. For instance, regions of high curvature and greater importance may have many more normals evaluated than regions of low curvature. In assessing suitability of fit, qualitative aspects are also incorporated by system 10. These include, but are not limited to, user preferences. An example of this is the user preference for loose fitting clothes. On their user model, users can visualize suitability of fit through various visualization schemes provided by system 10. In exemplary embodiment, regions of different fit on the apparel may be colored differently. Visual indicators include, but are not limited to, arrows on screen, varying colors, digital effects including transparency/x-ray vision effect where the apparel turns transparent and the user is able to examine fit in the particular region. Some examples are illustrated in FIG. 30. The visualization options are provided to the user via a menu available by clicking the icon 540, in exemplary embodiment. In this figure, different fit regions are depicted using coloured arrows 542, highlighted regions 544 as well as transparency/x-ray effects 546. Transparency/x-ray effects 546 allow fit information to be visualized with respect to body surface. In FIG. 30, the apparel on the 3D body model is made transparent in order for the user to visually examine overall apparel fit information—regions of tight/proper/loose fit. With reference to FIG. 30, regions of tight fit are shown using red coloured highlight regions (armpit region). Loose fitting regions are shown via green arrows (upper leg) and green highlight (hips). Comfort/smug fitting is depicted using orange arrows (waist) and yellow highlight (lower leg). Users may also define the numerical margins that they consider 'tight', loose' and so on for different apparel. For example, the user may consider a shirt to be proper fitting around the arms if the sleeves envelope the arm leaving between 1-2 cm margin. The user may specify these margins and other settings using the options menu 540 available to the user. The transparency/x-ray effect also provides visual information with regards to layers of clothing. The users may wish to select particular items for visualization on the model. In one exemplary embodiment, they may select from the itemized list 552 which lists all of the apparel items the user has selected to fit on the user model as part of an ensemble for instance. Accordingly, the items that are not selected may disappear or become transparent/light in colour (i.e., recede or fade) in order to make more prominent the selected items of apparel. Thus, the transparency effect emphasizes certain items visually while still preserving other layers of clothing so that the highlighted apparel may be examined with respect to other items it will be worn in combination with. The layers worn by the model in FIG. 30 may be examined from different perspectives of the model (cross-sectional view for example). This page also provides the user with the menu (available by clicking icon 540) described previously for setting/manipulating the model and environment as well as setting view options, share options (for example, sharing model views with friends in specific apparel). Other purposes for which visual indicators may be applied includes, but is not limited to, relaying the user with information regarding the quality or make of an apparel. For example, different colours may be used to outline or highlight a shoe sole in order convey whether the given shoe is hard-soled or soft-soled, Separate icons may also be provided such as 548 provided to interact and/or manipulate model as shown in FIG. 30. Additionally, an icon summarizing suitability of fit may be provided 550. This will incorporate all the quantitative and/or qualitative aspects assessing goodness of fit and give the overall consensus on whether the apparel will fit the user (thumbs up) or not (thumbs down) in an exemplary embodiment. The 'summary' icon may be programmed by default, for example, to give a 'thumbs up' if two qualitative and quantitative aspects are satisfied. This default setting may be changed to suit the user's suitability of fit requirements. More details on the fit are available to the user by clicking on or hovering over the icon 550. The user can also choose to display portions of these details next to the icon through the preferences page. In an exemplary embodiment, the user can see the fit information by taking an item to the fitting room (eg. by dragging and dropping a catalog item into the fitting room). In another exemplary embodiment, the user can see all the items that the user is browsing with the fit information without the need to place the item in the fitting room. All instances of features shown in FIG. 30 are illustrative examples and are not meant to be restricted to these and can embody and encompass other forms, illustrations and techniques.

Figure 23:
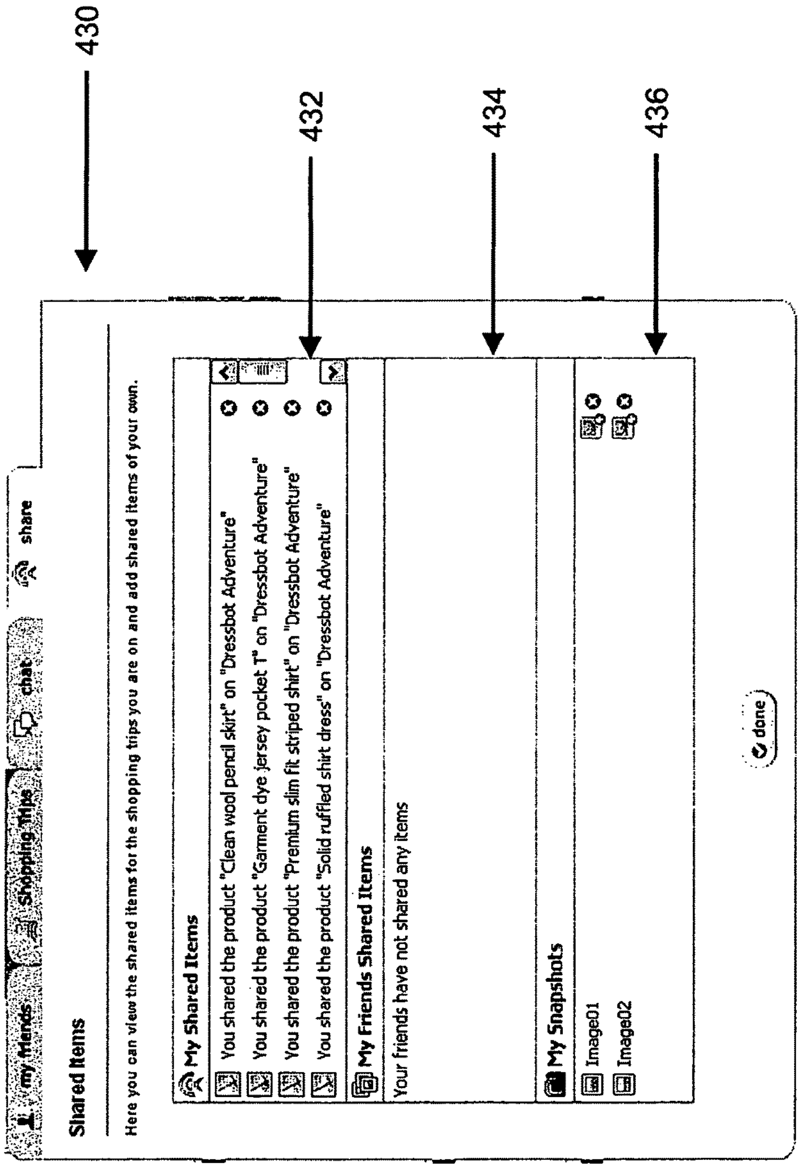
FIG. 23 is an image of a shared item window.

Reference is now made to FIG. 23, where a sample shared item window 430 is shown in an exemplary embodiment. The shared item window 430 displays the various items that the user has shared, in a shared list 432, and a list of items that friends have shared in a friend shared list 434. The snapshots lists 436 allow a user to share various images that they have captured of their user model with other users. When viewing and interacting with the user model, the user is provided the ability to capture an image or snapshot of the image, and share the respective snapshot or image with other users. These features illustrate one exemplary embodiment of the asynchronous mode of operation of a shopping trip.

Figure 25:
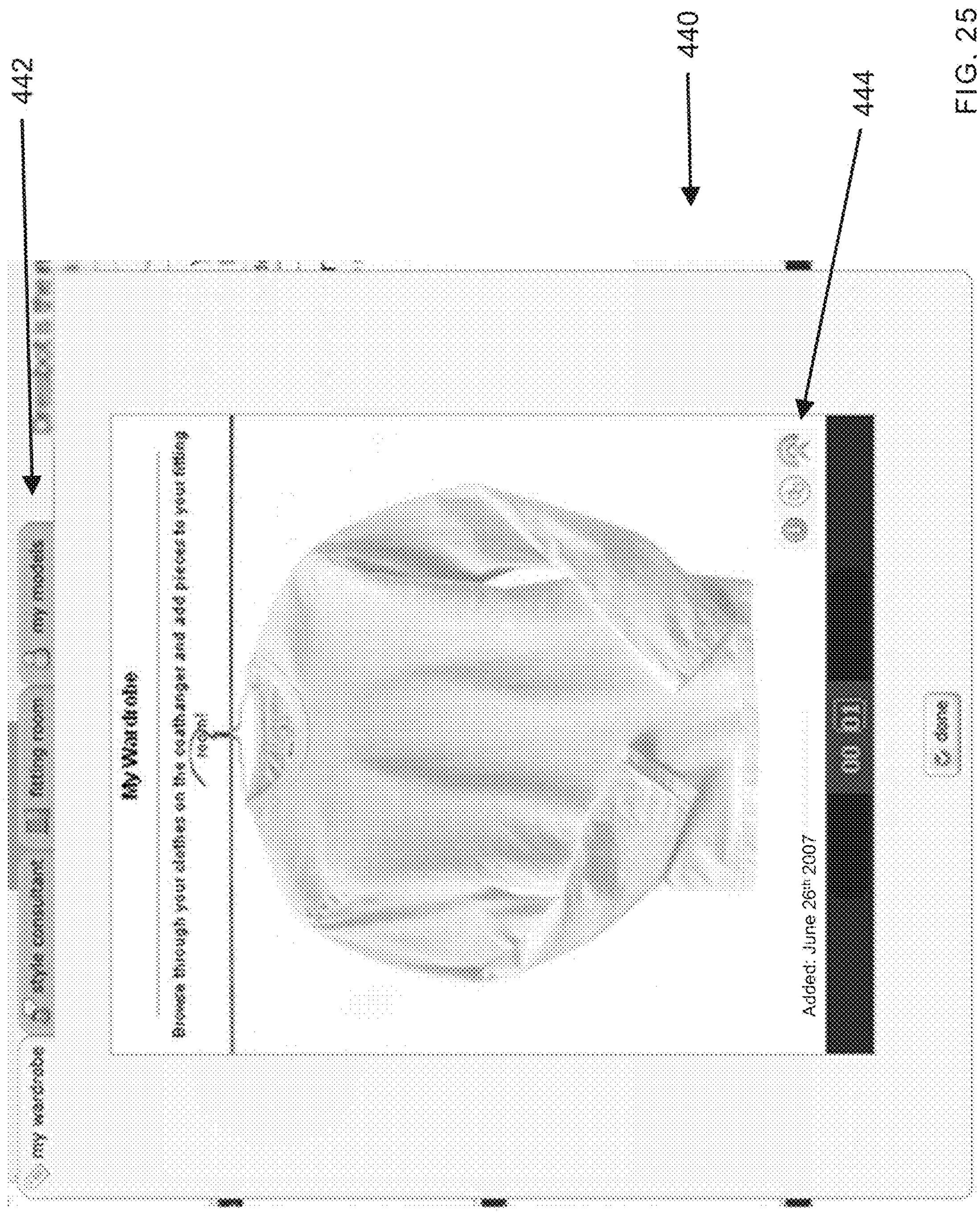
FIG. 25 is an image of a sample wardrobe item.
Figure 26:
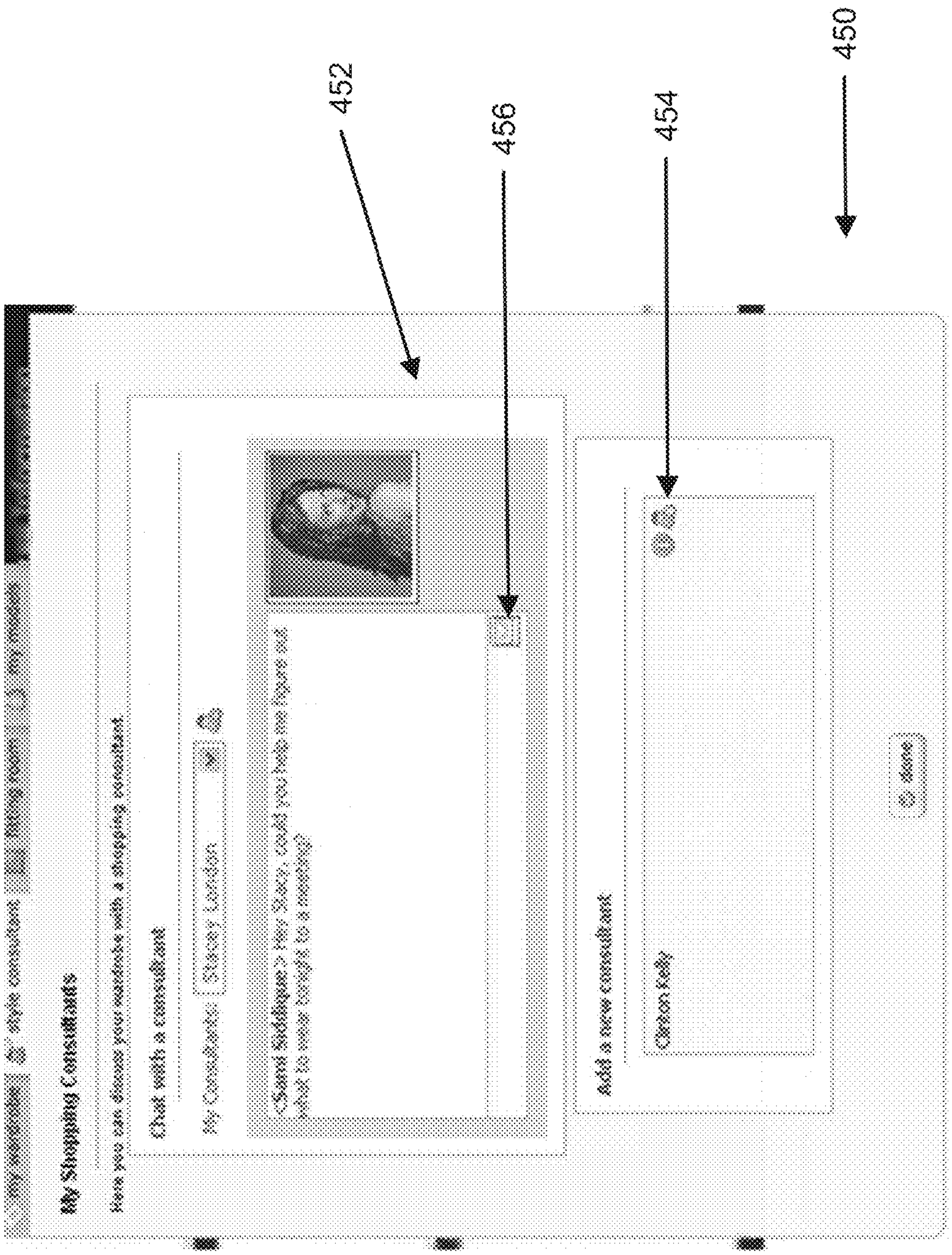
FIG. 26 is an image of a sample wardrobe consultant window.
Figure 28:
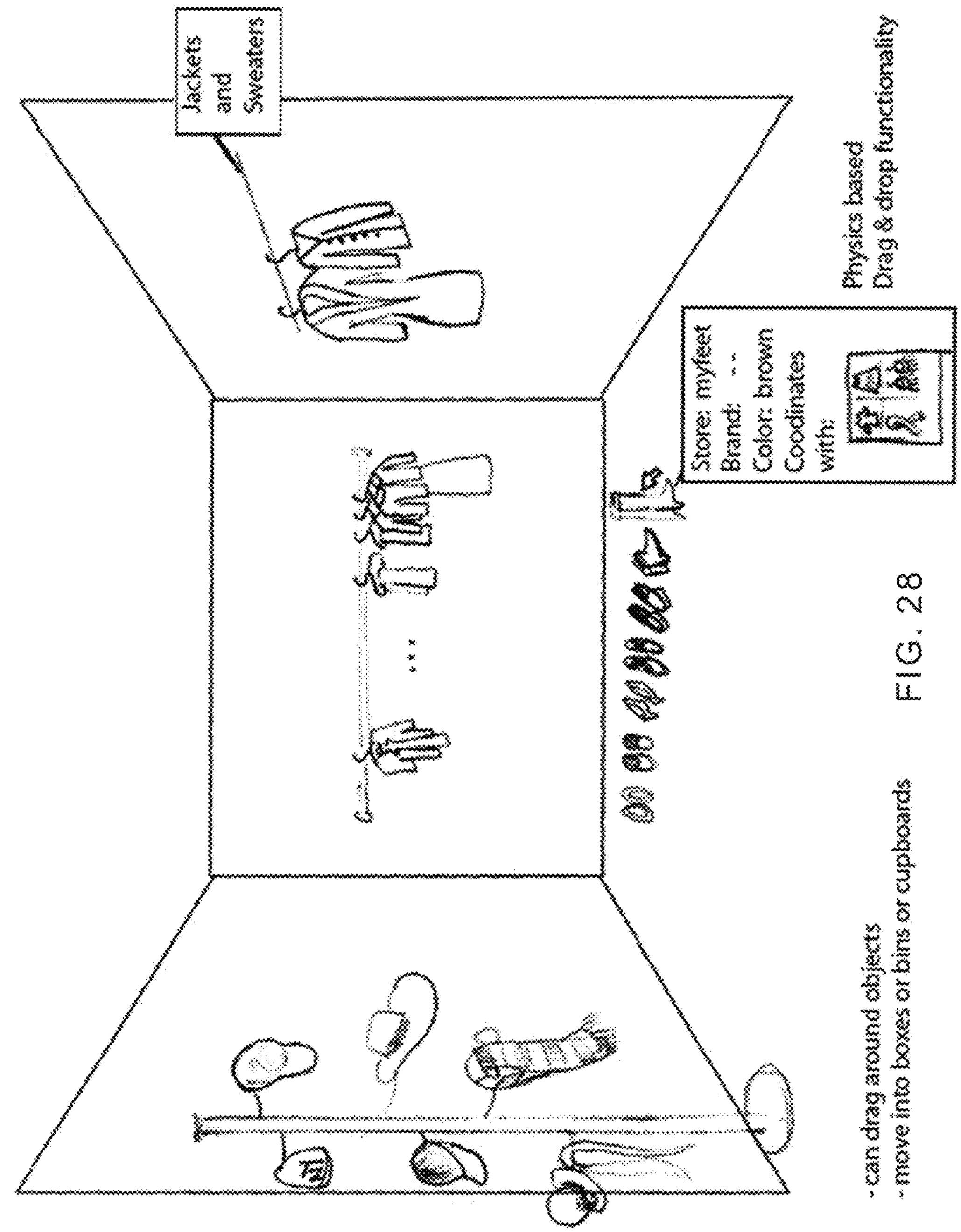
FIG. 28 is an image of a sample 3D realization of a virtual wardrobe.

Reference is now made to FIG. 25, where a sample wardrobe image 440 is shown in an exemplary embodiment. Wardrobe images 440 are used in an exemplary embodiment to display to the user the apparel items that a user has added to their wardrobe. A user may browse all of the items that are in their virtual wardrobe, and may request that they receive comments regarding items in their wardrobe from a consultant. The user is presented with options as in the tabbed menu 442 shown in exemplary embodiment, so that they can quickly navigate and browse the apparel in their wardrobe and fitting room; try on apparel on their model as well as get feedback regarding apparel and dressing style options from the style consultant. From left to right, the icons 444 available to the user in their wardrobe include: (1) the icon that displays to the user apparel information such as the make and manufacturer details, care instructions, store it was bought from, return policy etc. as well as user tagged information such as who gifted the apparel, the occasion to wear it for, etc.; (2) the icon to fit selected apparel on the user model; (2) the icon to share selected apparel with other users. The icons shown have been presented as examples and may include icons that perform other functions. The icons shown may be represented with different symbols/pictures in other manifestations. Reference is made to FIG. 28 where a drawing of a 3D realization of a virtual wardrobe is shown. This wardrobe can be incorporated with physics based animation functionality so that users can drag around objects; arrange and place them as desired in the wardrobe;

move them into boxes or bins or hangers or racks etc. Users will be able to visualize articles of clothing and other apparel in their wardrobe; tag each item with a virtual label that may contain apparel specific information as well as user specified information such as the date the apparel was bought; the person who gifted the apparel; upcoming events on which it can be worn as well as links to other items in the wardrobe and/or fitting room with which that item can be coordinated or accessorized with etc. Reference is made to FIG. 26, where a sample style consultant window 450 is shown in an exemplary embodiment. The style consultant 452 is able to comment on the user's items in the wardrobe, upon request of the user. The icons 454 shown from left to right include: (1) the icon to obtain information on the specific style consultant; (2) the icon to add/remove style consultants from the user's personal list. Icon 456 provides the user with options to engage in communication with the style consultant either via email or chat which may be text/voice/video based or may involve augmented reality, in exemplary embodiments.

Reference is now made to FIG. 27 where a sample diagram is presented illustrating the actions involving the fitting room 420 and wardrobe 440 that the user may engage in while browsing for apparel. While browsing for apparel displayed as in example window 400, the user can add an item to their fitting room by clicking on an icon 424 next to the item they wish to virtually try on. Once an item has been added to the fitting room 420, that item will become available to the user in the local application 271 for fitting on their model. Once the item has been added to the fitting room, the user may model the apparel item on their user model, and/or decide to purchase the item, in which case the apparel item can be added to the virtual wardrobe 440. Alternately, the user may decide not to purchase the item in which case the item will stay in the fitting room until the user chooses to delete it from their fitting room. The user may choose to keep a purchased item in their wardrobe 440 or delete it. If the user decides to return an item, that item will be transferred from the user's wardrobe 440 to the fitting room 420. The user may also decide to conduct an auction or a garage sale of some or all of the real items in their wardrobe. Users with access to the virtual wardrobe can then view and purchase items on sale of interest to them via system 10. The virtual items in the fitting room and wardrobe can also be purchased for use in other sites that employ virtual characters/models. The virtual apparel items in the fitting room and wardrobe may be exported to external sites or software involving virtual characters/models such as gaming sites, 'virtual worlds' sites and software.

Figure 46A:
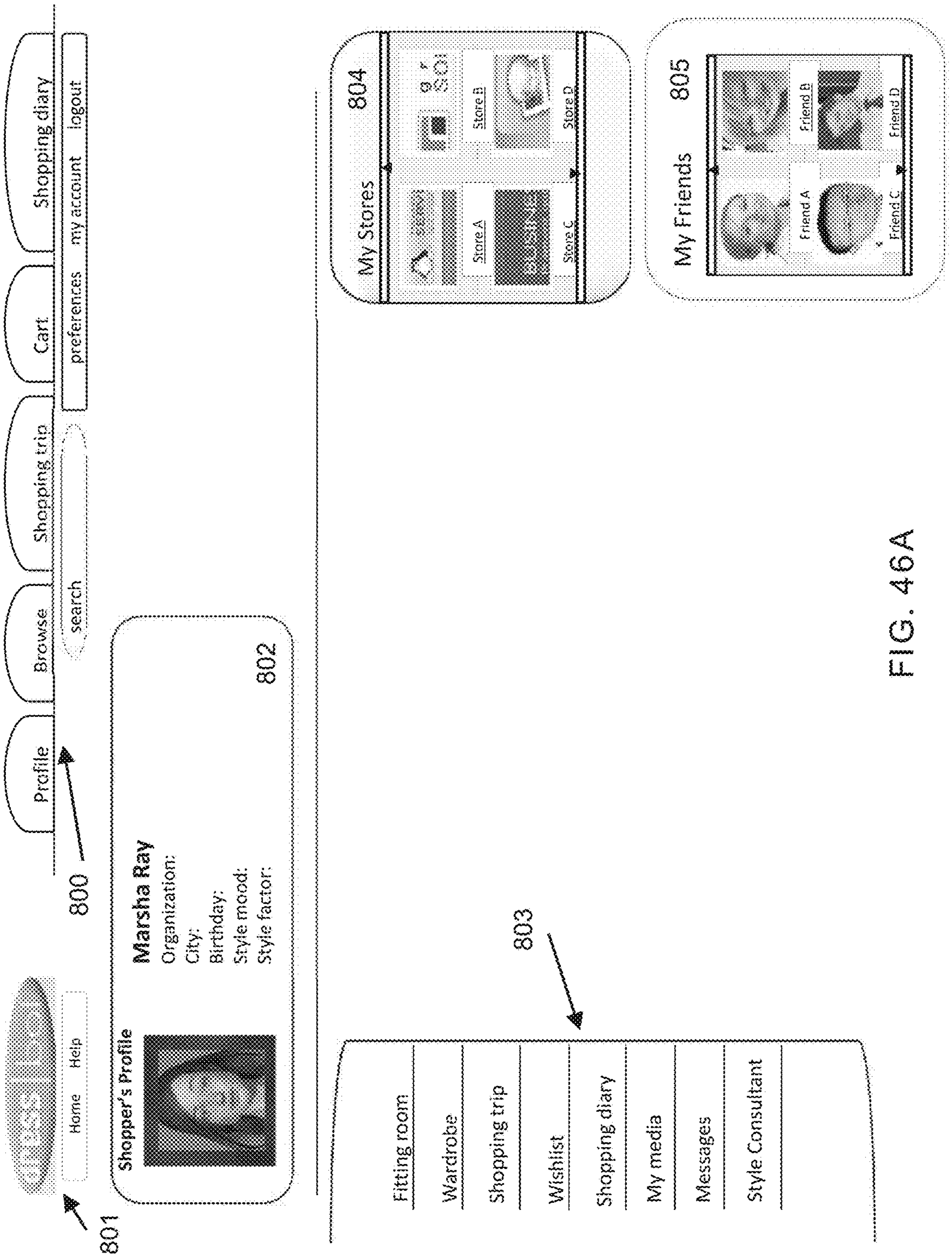
FIG. 46A is an image of another sample main page for shopping.

Reference is now made to FIGS. 46A to 46H where other exemplary embodiments of the features described in this patent have been presented. FIG. 46A shows a profile or home page of a user registered with system 10. The user can grant access to this page to other users by setting permissions. A master menu 800 with option tabs—'profile', 'browse', 'shopping trip', 'cart', 'shopping diary' is shown at the top of the page. These tabs navigate to pages which allow the user to respectively, access their profile page; browse stores and products; manage collaborative shopping trips; view and manage items in cart; access personalized shopping and other miscellaneous features. Icon 801 displays the logo of system 10 and provides the user with a menu containing certain options such as home page access and help with features available to the user on system 10. Display box 802 represents the information card providing profile details of the user. Display box 804 contains hyperlinks to all stores subscribing to system 10 or just the favourite/most frequently visited stores by the user. Additionally, users may engage display box 805 for adding friends they would like to collaborate with. In an exemplary embodiment, users may add friends they normally like to acquire feedback from or go out with for shopping. The user may also add other users registered with system 10 whose fashion/style sense they like and follow (the user would be that person's 'style fan' in that case). Another menu 803 is provided in FIG. 46A as an exemplary embodiment which permits the user to access more features available on system 10.

Figure 46B:
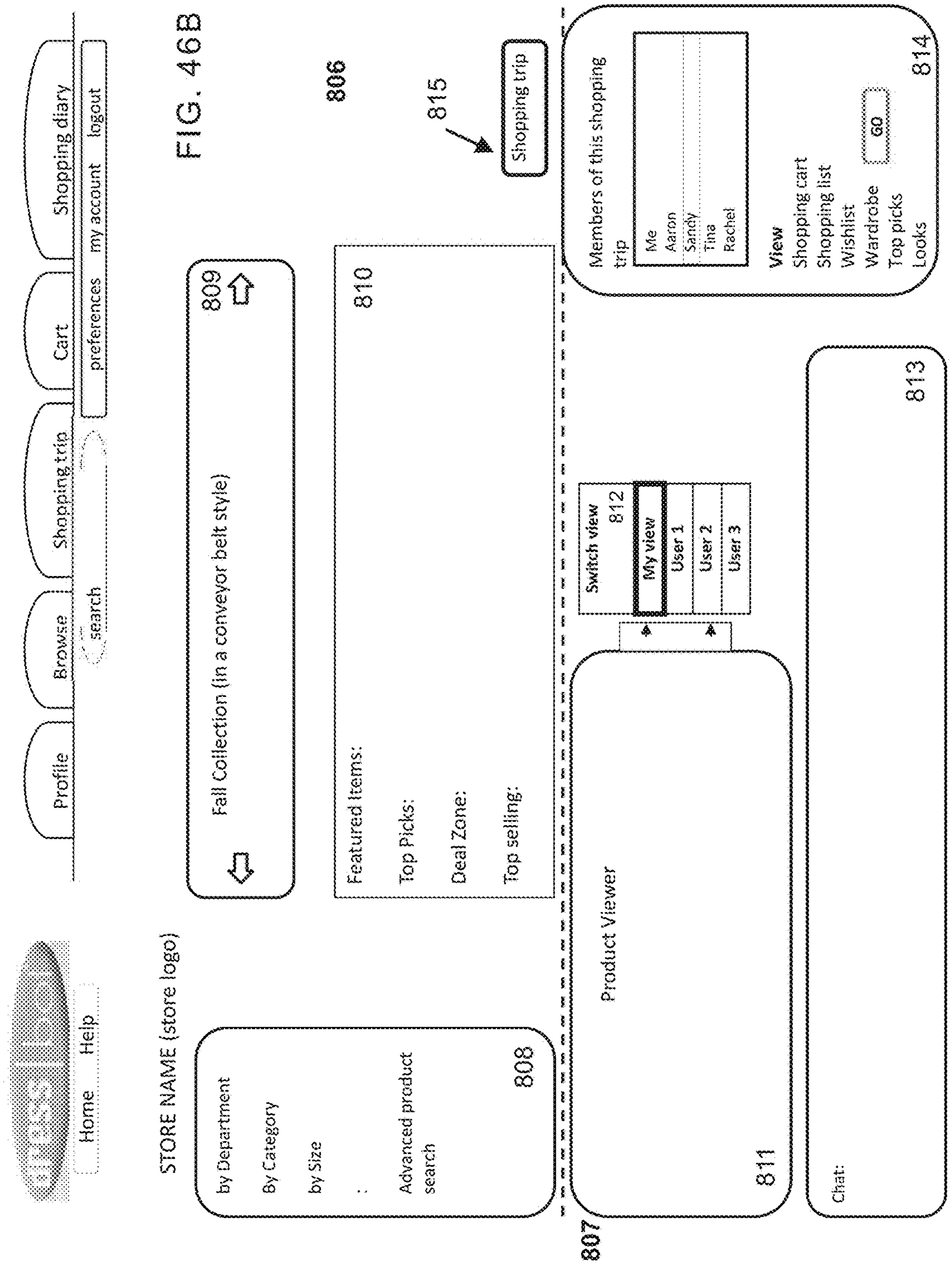
FIG. 46B is an image of a sample store window.
Figure 46C:
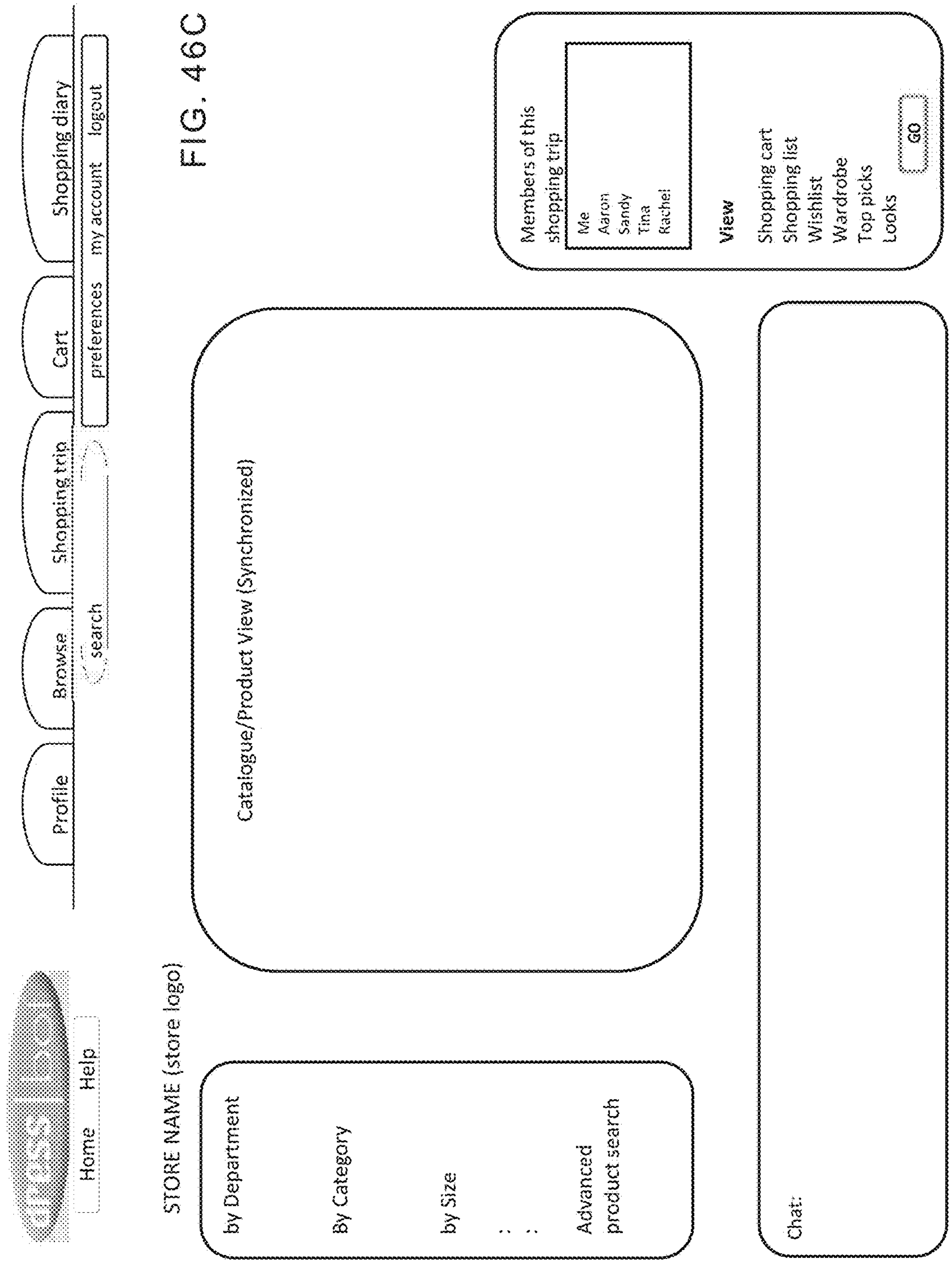
FIG. 46C is an image of another sample store window.
Figure 46D:
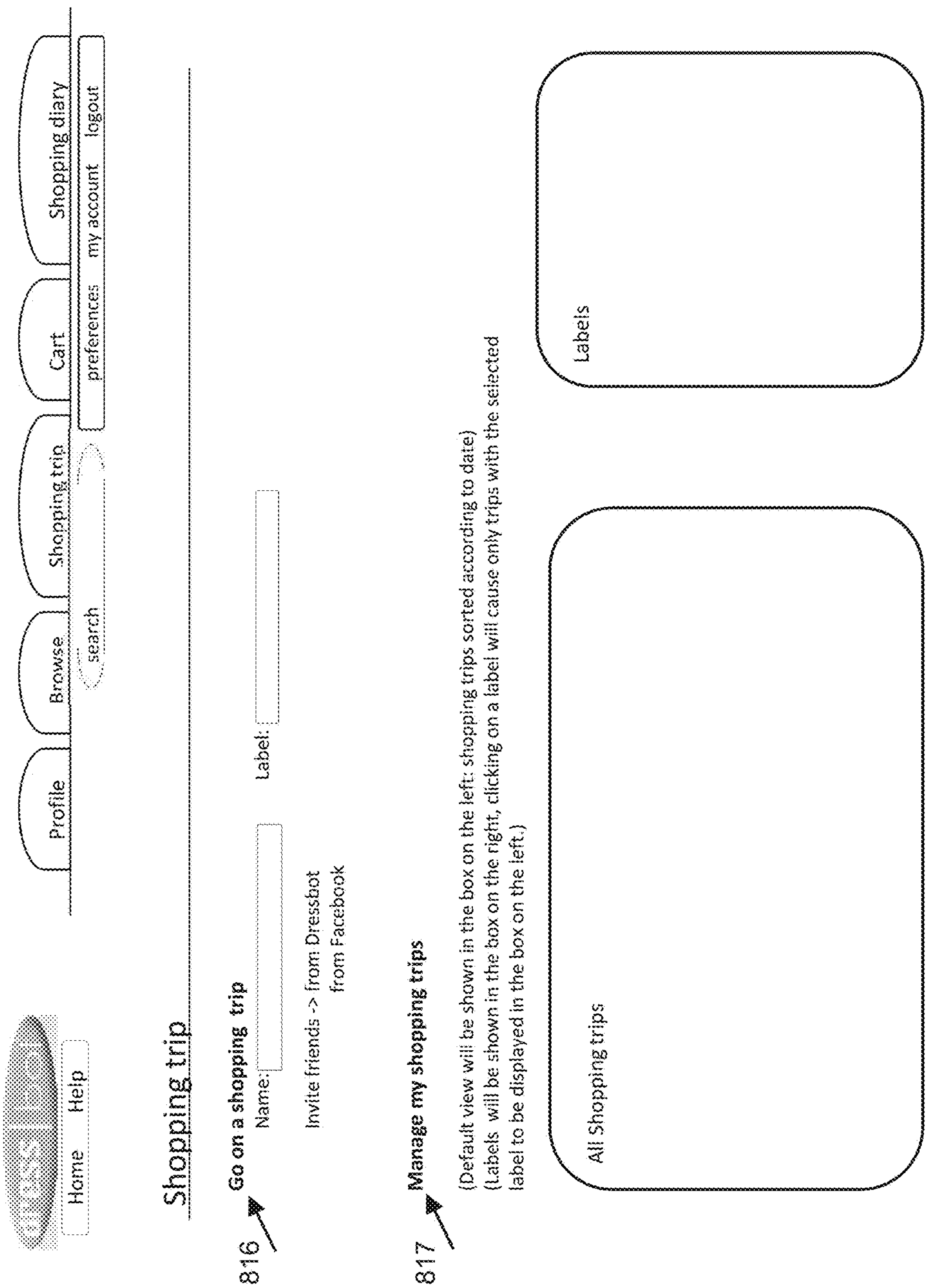
FIG. 46D is an image of sample shopping trip window.

Reference is now made to FIG. 46B where a store page 806 is shown. The products available in the store 808 may be categorized according to different fields such as department, category, size etc. Users may also be able to search for products in the store. Stores have the option of personalizing their store pages. In an exemplary embodiment, the season's collection may be displayed in a product display window 809. Items featured by the store and other item collections may also be displayed in another window 810. FIG. 46B also displays a collaborative shopping trip window 807 on the same page. The shopping trip window may be launched by clicking on icon 815. The shopping trip dialog 807 containing collaborative shopping features may open up in a separate window or in the same window/page being viewed by the user. Some collaborative shopping features are illustrated in the shopping trip dialog 807 as exemplary embodiments. A synchronized product viewer 811 enables collaborative shopping between members of that shopping trip displayed in window 814. Products being browsed by other users of the shopping trip may be viewed in the product viewer 811 via menu 812. By selecting a given user in window 814, the user can browse the shopping cart, shopping list, wishlist, wardrobe, and other personalized shopping features shown in 814 of the selected user, if that user has granted permission, by clicking on the 'GO' button in window 814. A chat window 813 and/or other synchronous or asynchronous means of communication may be available to enable communication with other users while shopping. Reference is now made to FIG. 46C which illustrates another layout in exemplary embodiment. This layout combines some store page features with collaborative shopping trip features on the same page. A regular store page 806 shown in FIG. 46B may convert to a page as in FIG. 46C upon activating the shopping trip. Reference is now made to FIG. 46D where a sample shopping trip manager window/page is shown. Users can create new shopping trips 816; categorize trips by labeling them and invite friends on shopping trips. Users can view and sort shopping trips 817 according to labels.

Figure 46E:
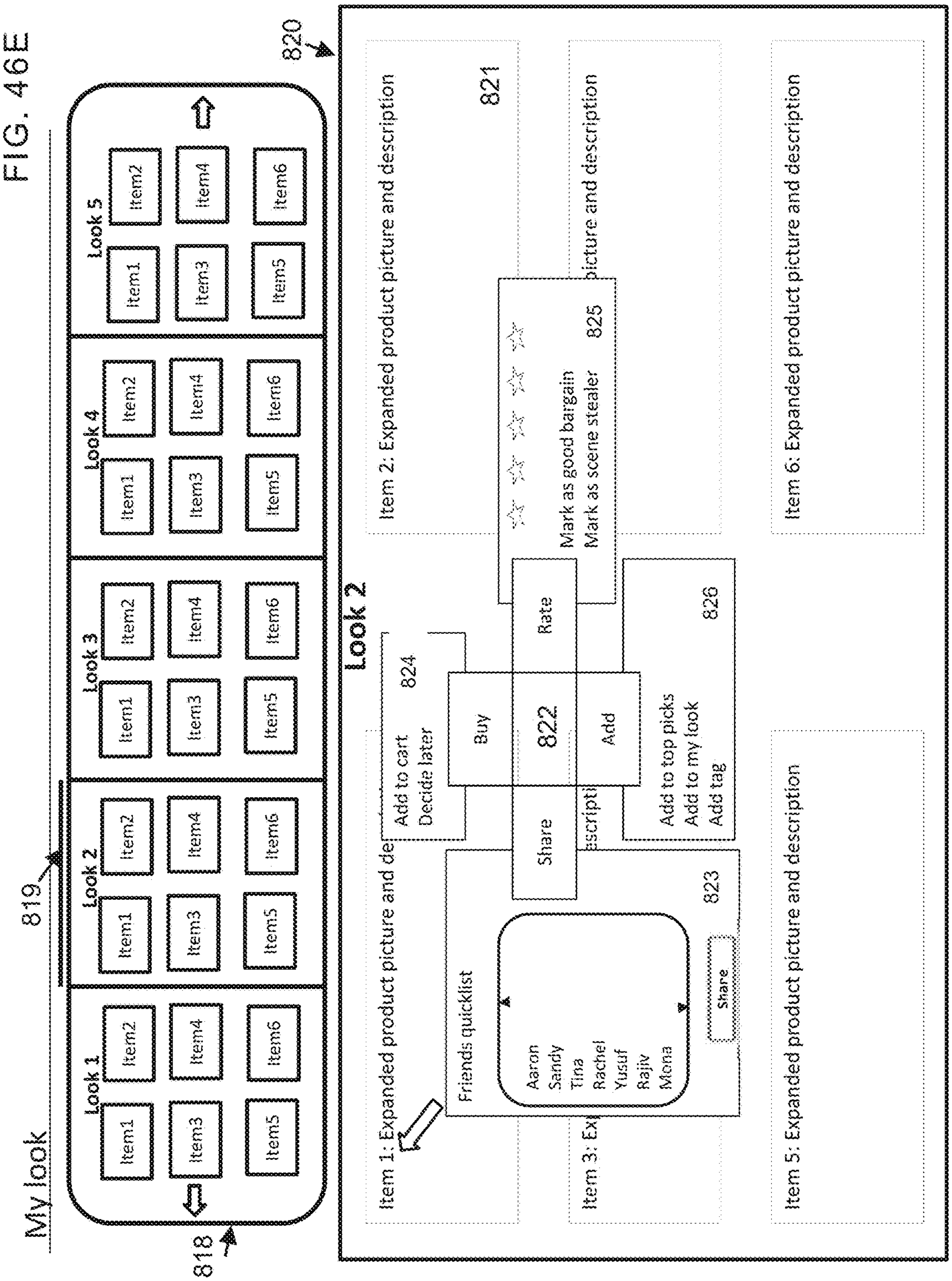
FIG. 46E is an image of a user's sample personalized looks window.

Reference is now made to FIG. 46E where a user's personalized 'looks' window/page is shown in exemplary embodiment. A 'look' in this context is defined as a collection of products put together by the user from different product catalogues to create a complete ensemble or attire defining a suggested 'look'. Other users may gauge a user's fashion sense or style by browsing through the given user's looks page. A browser window 818 allows the user to browse looks they created. Each look 819 is composed of several items put together by the user. In an exemplary embodiment, a look 819 may contain a blazer, a blouse, a skirt, a pair of shoes, a handbag and other accessories to complement the given look. A user may obtain expanded views of products comprising a given look by highlighting a look 819, upon which another dialog or window 820 is launched containing expanded views 821 of items composing 819. Upon selecting an item in the expanded view 820, a product options menu 822 appears which is comprised mainly of the four option boxes outlined in red. The other sub-menus 823-826 appear upon clicking the respective main product menu options besides which they appear. The product options menu 822 is shown in exemplary embodiment and it enables tasks such as product purchase 824, product sharing with other users 823, rating the product according to different criteria 825 and addition of the product to various personalized user lists 826.

Figure 46F:
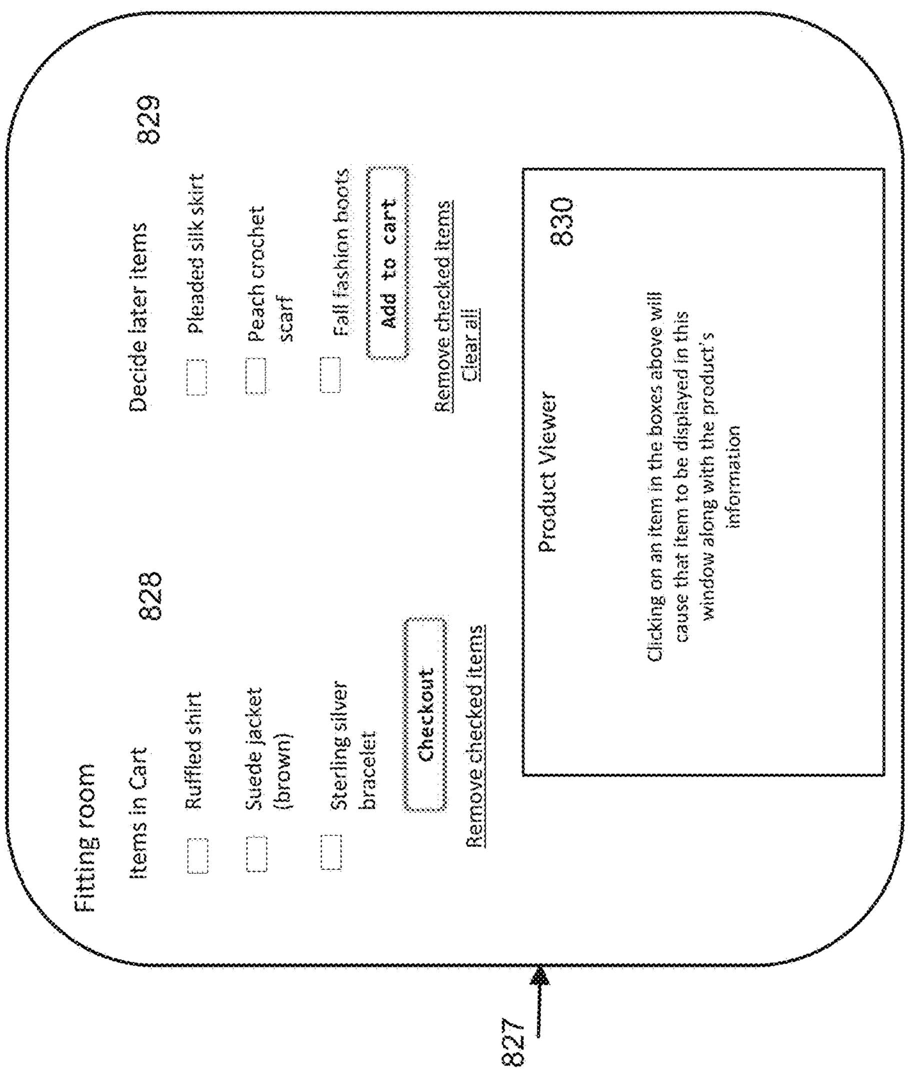
FIG. 46F is an image of a sample fitting room window.
Figure 46G:
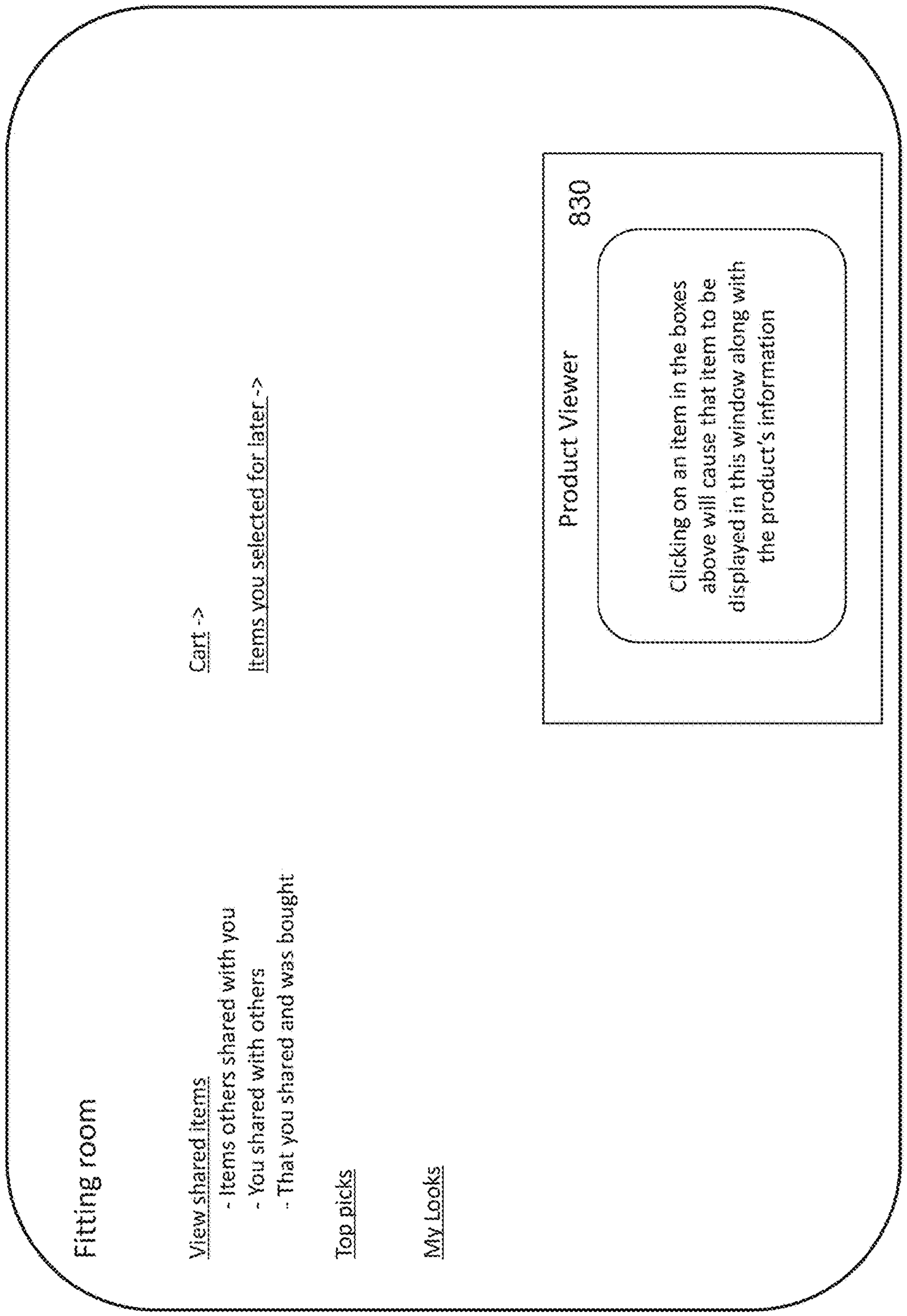
FIG. 46G is an image of another sample fitting room window.

Reference is now made to FIGS. 46F-G where other exemplary embodiments of the fitting room window have been shown. FIG. 46F shows some features comprising the fitting room 827. These may include the shopping cart 828, or items that the user has selected but is undecided about purchasing 829, and the product viewer 830 which provides product views of the item selected from the shopping cart or the 'decide later' cart. Another version of the fitting room is shown in FIG. 46G which incorporates the product viewer 830, the shopping cart, 'decide later' items as well as other customized user lists such as shared items, top picks, my looks and others.

Figure 46H:
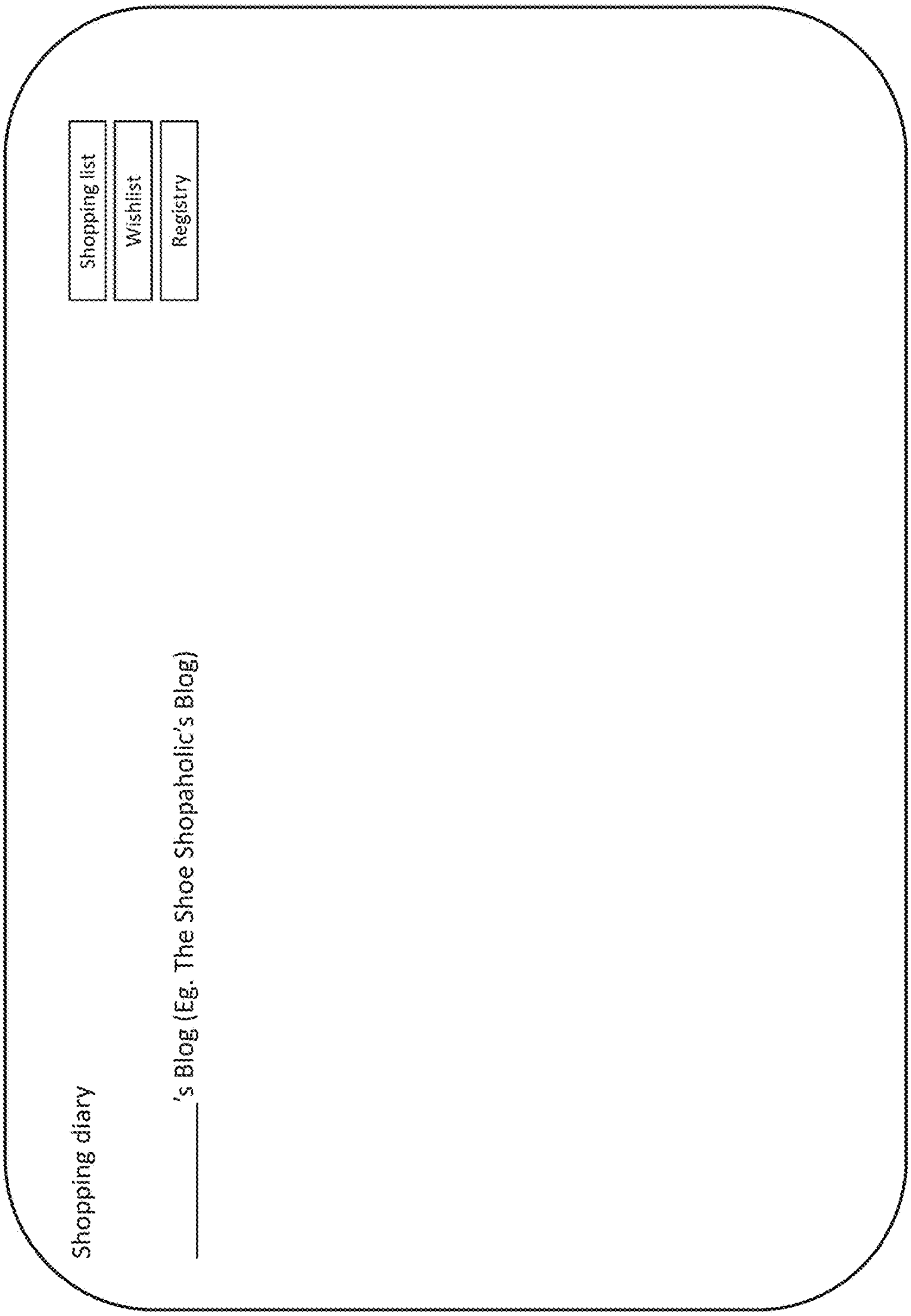
FIG. 46H is an image of a sample shopping diary window.

Reference is now made to FIG. 46H where a shopping diary window/page and its features are shown in an exemplary embodiment. The shopping diary is comprised of personalized user lists such as shopping lists, wishlists, gift registries, multimedia lists and others. Additionally it may incorporate a shopping blog and other features.

Figure 46I:
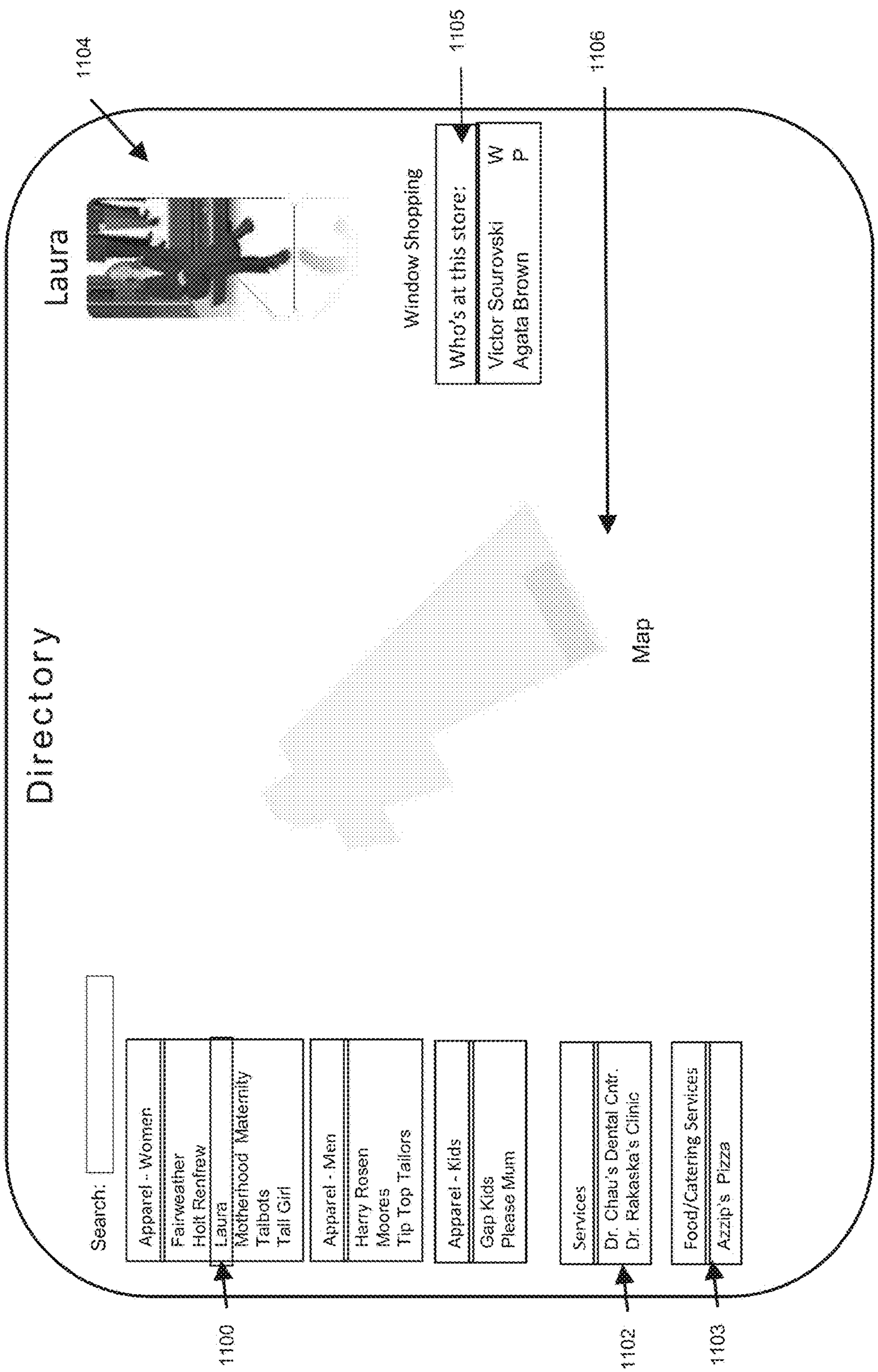
FIG. 46I is an image of a sample directory page.

Reference is now made to FIG. 46I where a layout or directory of the mall comprising stores subscribing to system 10 is shown in an exemplary embodiment. This can be customized to form a user-specific directory that lists businesses and people that a user is associated with in a community. Stores are listed on the left and categorized by gender and age group. A map or layout 1106 of the virtual mall is presented to the user where the stores on system 10 may additionally be shown graphically or using icons. Upon selecting a store 1100 from the list, a store image 1104 may be displayed. A 'window shopping' feature permits users to get live feed from the store including information 1105 such as other users browsing the store. The user may be able to identify contacts in their friends list who are browsing the store via this feature and also identify the contact's category (i.e., work—W, personal—P etc.). Additionally, other services 1102 may be listed such as dental and other clinics. Users may be able to book appointments online via a clinic appointment system available through system 10. Users may also make use of a 'smart check' feature that checks the user's calendar for available slots and suggests potential dates to the user for booking appointments and/or proceeds to book the appointment for the user by providing the clinic with the user's availability dates. Once the clinic confirms a booking, the smart check calendar feature informs the user of the confirmed date via SMS/email/voicemail/phone call. Users may set their preferred method of communication. It may additionally suggest to the clinic the best dates for scheduling an appointment by cross-referencing both the patient/client's schedule and the clinic's schedule. Users may mark other appointments in their digital calendar. The calendar may send appointment reminders via SMS, email, phone call to the user depending on user preferences and the user will be presented with options to confirm, cancel or postpone the appointment upon receiving the appointment reminder. The calendar would notify the user of the duration after which the appointment is scheduled, for example—'your dentist appointment is in 15 minutes'. Furthermore, the smart-check feature could also cross-reference the dentist clinic's electronic schedule in real time and inform the user whether their appointment is delayed or postponed because the clinic is not running late or for some other reason. Other services such as food/catering 1103 may be available permitting the user to order online. Another feature available on system 10 is an 'electronic receipt manager'. This feature allows the user to keep track of all receipts of products purchased through system 10 and other receipts that the user may want to keep track of. This may prove useful to users for purposes such as exchanging or returning merchandise, tax filing, corporate reimbursements and others. Users would be able to categorize receipts (example, business, personal etc.); import and export receipts to other places such as the user's local computer or a tax filing software and other places; conduct calculations involving amounts on those receipts. Stores on system 10 may also find it useful to have and store these electronic receipts in order to validate product purchases during a product return or exchange. (Receipts for purchases made at the physical stores can also be uploaded to the electronic receipt manager. This can also be done at the point of sale (POS)). An interface for the Electronic Receipt Manager and further details are described with reference to FIG. 48D. The store and services layout 1106, and store and services listing may also be customized by the user to comprise favourite stores and services of the user i.e., stores and services such as the dentist, mechanic, family physician, hair salon, eateries etc. most frequently visited by the user (may be entitled 'My Business' section in exemplary embodiment). This would permit the user to create their own virtual mall or virtual community providing quick and easy access to stores and services most beneficial to the user as well as their contact and other information. (Users can search for businesses and add them to their 'community' or contacts list. On searching for a business using a name, a list of businesses with that name or similar names may be shown and may be displayed in ascending order of the distance from the user's home, office, city, or current location). A user can also visit other users' virtual malls and communities. Alternatively, a virtual mall may be mapped to a real mall and contain stores and services that are present in the real mall. In exemplary embodiment, the 'My Business' concept described above may be integrated with social networking sites. Tools may be available to businesses to communicate with the user clients and customers, such as via the clinic appointment system described above. Tools may be available to customers to manage receipts, product information and also to split bills. The system described with reference to FIG. 46I may be integrated with the VOS and/or VS described in this document.

Figure 47A:
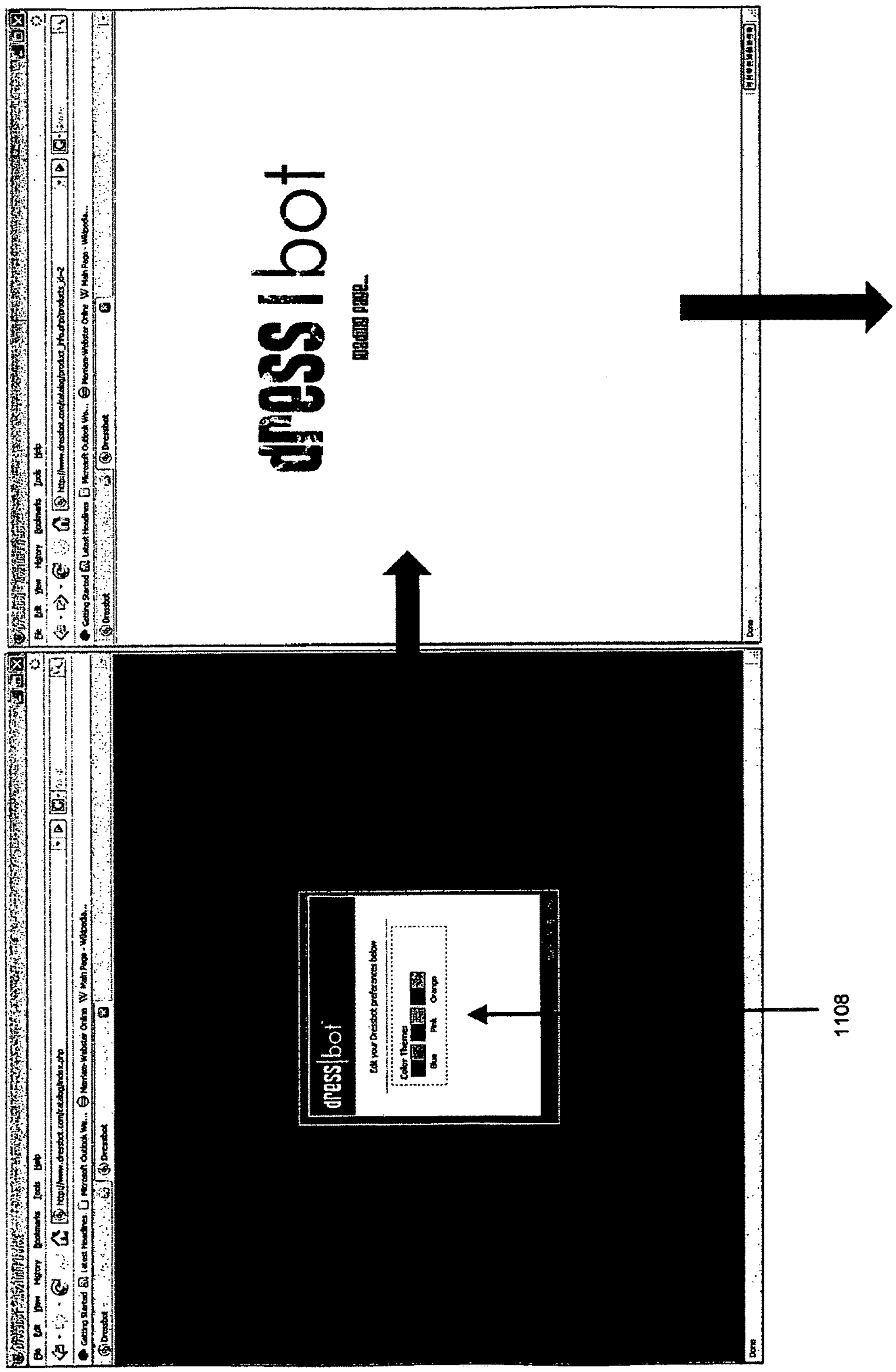
FIG. 47A-B are sample images illustrating a feature that allows users to customize the look and feel of the browser application.
Figure 47B:
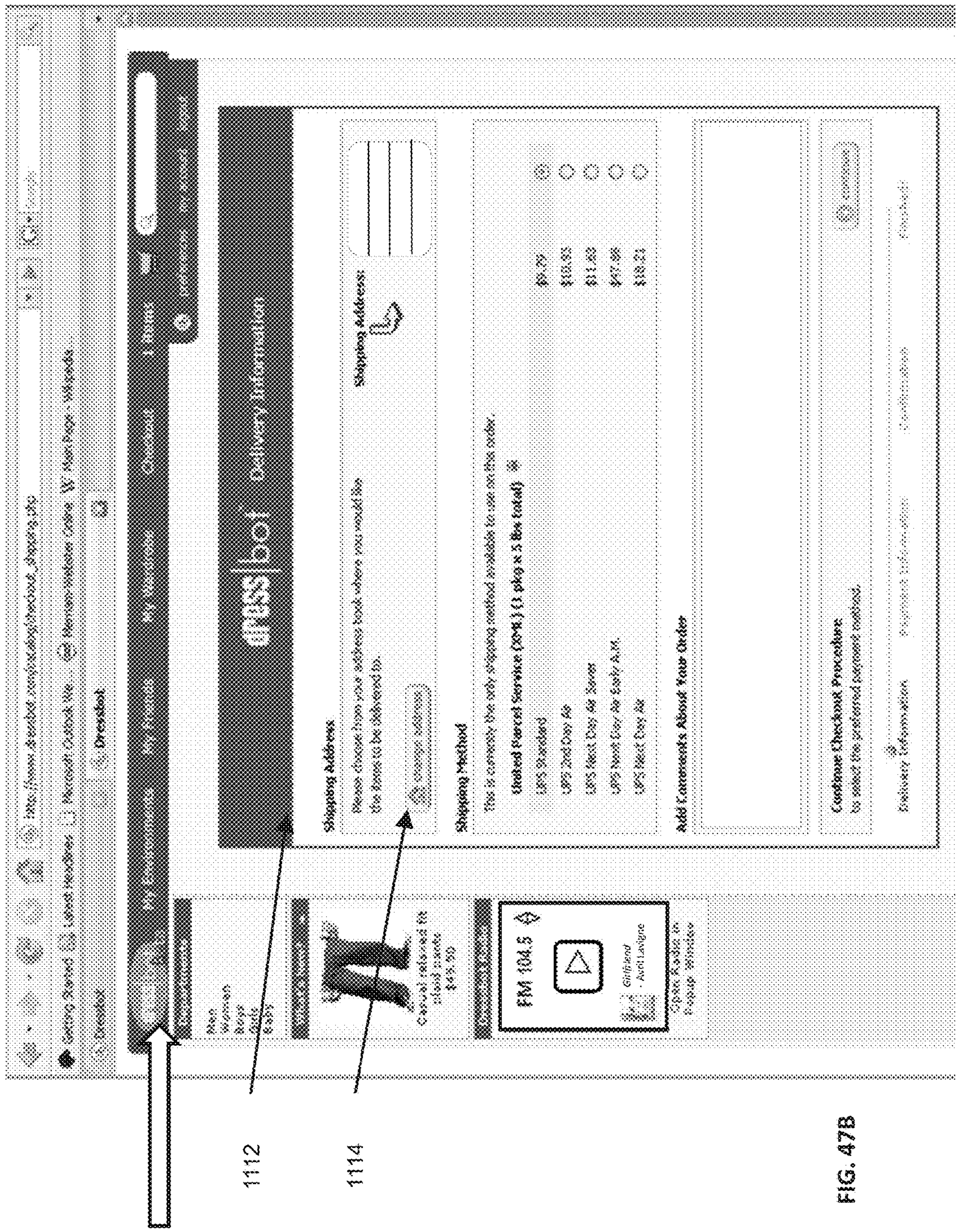

Reference is now made to FIGS. 47 A-B which illustrate features that allow the user to customize pages on system 10; to set the theme and other features that allow the user to personalize the browser application's and/or local application's look and feel. FIG. 47A shows a theme options menu 1108 where a user can choose and set the colour theme of the browser pages that they will be viewing during their session on system 10. In the instance shown in FIGS. 47A and 47B, the user has chosen 'pink'. Accordingly, the theme changes as shown via the windows in FIGS. 47A-B. FIG. 47B also shows features available to the user for specifying the delivery information 1112 of a product upon purchase. Users may specify a friend from their address book or friends' list and also specify the delivery location type (i.e., work, home etc.). The system would then directly access the latest address information of that friend from their user profile. This address would subsequently be used as the delivery address.

Reference is made to FIGS. 48A-F, where some features and layout designs of system 10 are illustrated in exemplary embodiment. These features and designs can be used with the local application or a web browser or a website in exemplary embodiments. The description of these figures is provided with respect to the local application but it also holds in the case of a browser implementation or a website implementation of the same.

Figure 48A:
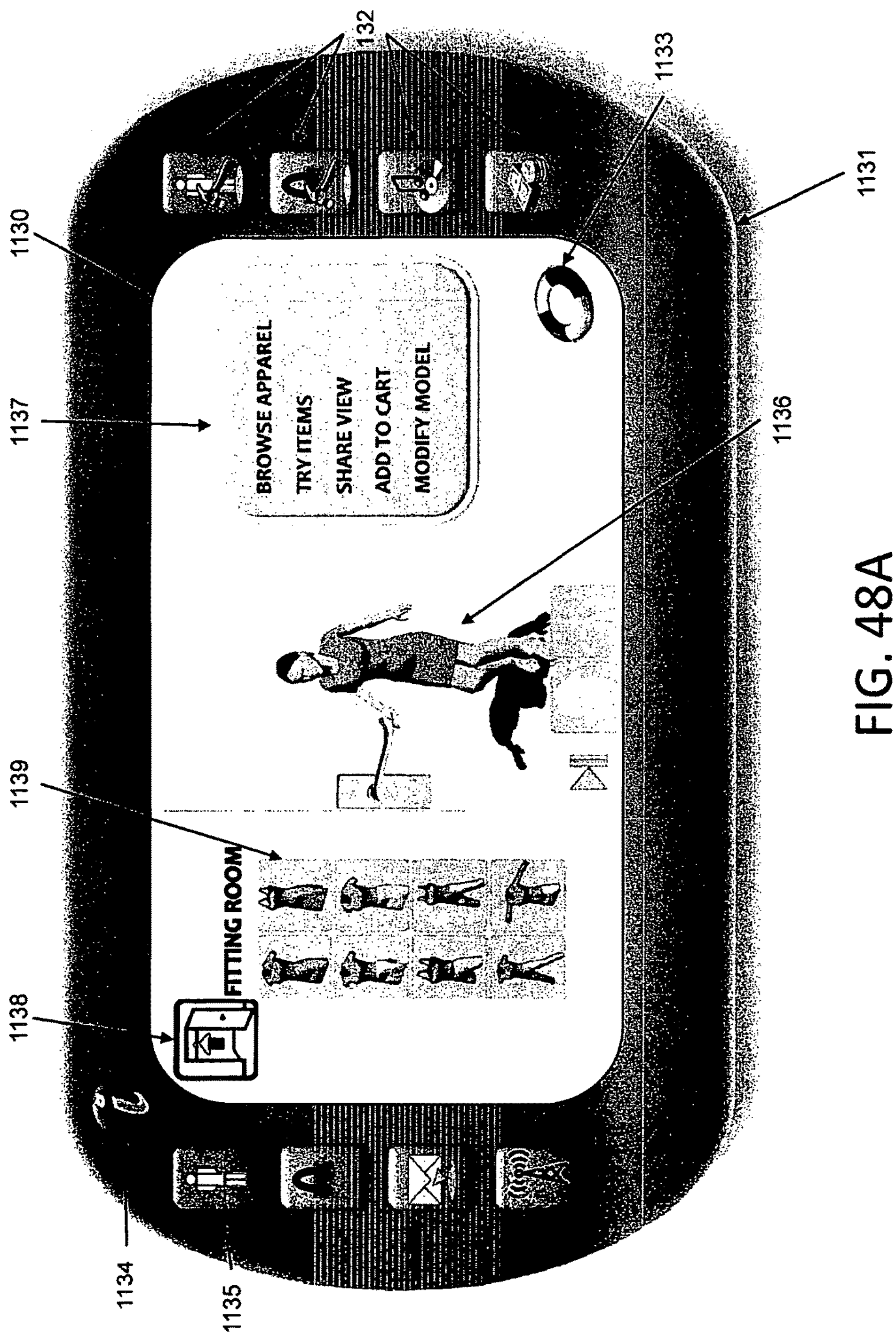
FIGS. 48A-F, are images illustrating sample layout designs and select features of system 10.

Reference is now made to FIG. 48A. The display screen 1130 is encased by an outer shell 1131, henceforth referred to as the 'faceplate' of the local application. The faceplate can be changed by a user by selecting from a catalogue of faceplates with different designs and configurations, which will be available under menu options.

On the faceplate are navigation links represented by buttons with icons 1132, in an exemplary embodiment. The lifesaver icon 1133 serves as a link for the help menu. Button 1134 represents the user account navigation link which directs the user to their account or profile space/section on the local application, consisting of the user's personal information, account and other information; settings and options available to the user to configure their local application or browser application; information and links to tools and applications that the user may add to their local or browser application. Navigation link 1135 on the faceplate is discussed with reference to FIG. 48A. Other navigation links on the faceplate will be discussed with reference to the figures that follow. Button 1135 directs the user to the user model space/section of the local application (button 1135 is highlighted with a red glow here to show that it is the active link in this figure i.e., the screen 1130 displays the user model space). In this space, users can access their 3D model 1136. Menu options 1137 for viewing, modifying and using the 3D model are provided on this page. Other features may be present in this space that can be utilized in conjunction with the 3D model. For instance, the fitting room icon 1138 is provided as an exemplary embodiment. Upon activating this icon (by clicking it for example), the fitting room contents are displayed 1139 (in the form of images here) enabling the user easy access to the apparel they would like to fit on their user model 1136.

Figure 48B:
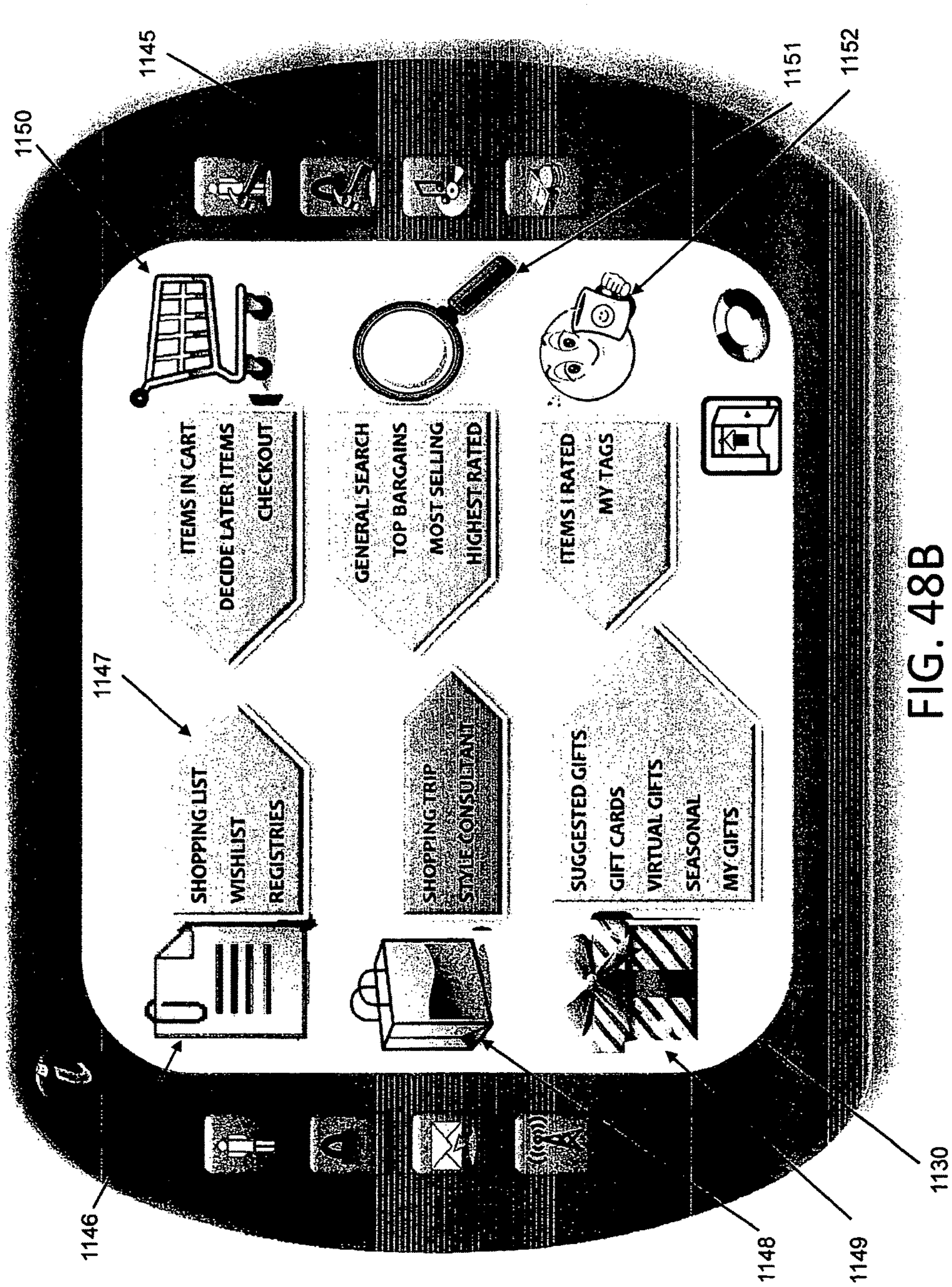

Reference is now made to FIG. 48B. In this figure, navigation link 1145, which represents 'shopping tools' is shown as being active. Hence, in this figure, the display screen 1130 displays the shopping tools space of the local application. This space provides the user with applications and options that assist in shopping online and/or electronically via the local application software. Most of these features have been described previously in this document and are discussed here mainly to illustrate an exemplary embodiment of the local application's layout. Icon 1146, when activated (by hovering over icon with mouse or by clicking icon, as examples) displays a menu of user lists 1147 (shopping list, wishlist, registries etc.), which may be used to document shopping needs. This menu 1147 subsides/is hidden when the icon is deactivated (i.e., by moving the mouse away from the icon or by clicking the icon after activating it, as examples). Icons 1148-1152 in FIG. 48B function in a similar way in terms of activation and deactivation. Icon 1148 provides a menu with features to assist in shopping and in making the shopping experience immersive. As shown in the figure, these features include the collaborative shopping trip feature, consultation (online or offline) with a style or fashion expert among others. Feature 1149 provides the user with access to gift catalogues, gift cards/certificates, as well as information on gifts received and sent. Icon 1150 provides the shopping cart menu listing items that the user has chosen for purchase; that the user has selected for making a decision to purchase or not at a later date. It also directs the user to the checkout page. Feature 1151 assists the user in making shopping related searches and also in seeking out products in specific categories such as 'top bargains', 'most selling, 'highest rated' etc. Icon 1152 provides features customizable by the user and/or user specific tools such as item ratings, product tags or labels etc.

Figure 48C:
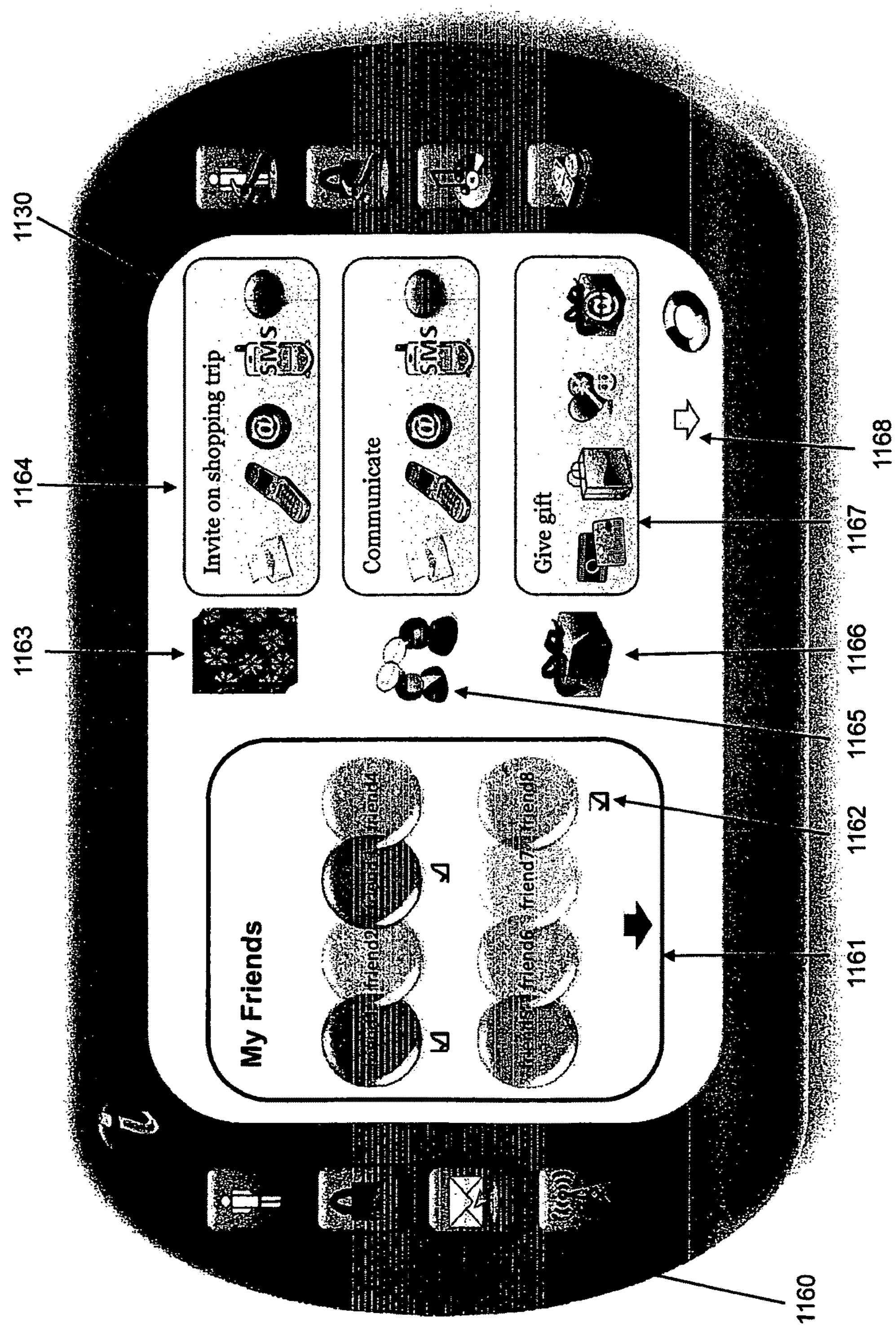

Reference is now made to FIG. 48C. Navigation link 1160, which represents the 'connect' feature is shown as being active. This link directs the user to the social networking space of the local application. The list box 1161 provides the user with a listing of the user's friends and other contacts. It may contain contact names, contact images, web pages, personal and other information relating to each contact. Feature 1162 provides the user with the facility to select multiple contacts (in this case, feature 1162 appears in the form of checkboxes as an exemplary embodiment). On the right side of the display screen 1130, social networking features are provided i.e., applications that provide the facility to shop, communicate, interact online, virtually and/or electronically and perform other activities electronically with contacts. Some of these features are illustrated in FIG. 48C as an exemplary embodiment. Icons 1163, 1165, 1167 can be activated and deactivated in a fashion similar to icons 1146, 1148-1152 in FIG. 48B. Upon activating icon 1163, a shopping trip invite menu 1164 appears, providing the user with options to send an automated or user-customized shopping trip invitation message to all or selected contacts from the list 1161. These options are symbolized by the icons in the menu 1164. From left to right, these icons allow the user to send invitations via 'instant notification', 'phone', email', 'SMS' or 'text message', and 'chat'. Feature 1165 provides a menu with options to communicate with all or selected users in 1161. These options are similar to the ones in menu 1164. Feature 1166 provides the user with gift giving options available on system 10. Users can select friends in 1161 via 1162 and choose the from the gift options available in menu 1167. From left to right in menu 1167, these icons represent the following gift options: 'gift cards', 'shop for gifts', 'donate with friends', 'virtual gifts'. This list can contain other gift options such as the ones provided by 1149 in FIG. 48B. The arrow 1168 allows the user to navigate to other applications in this space that are not shown here but maybe added later.

Figure 48D:
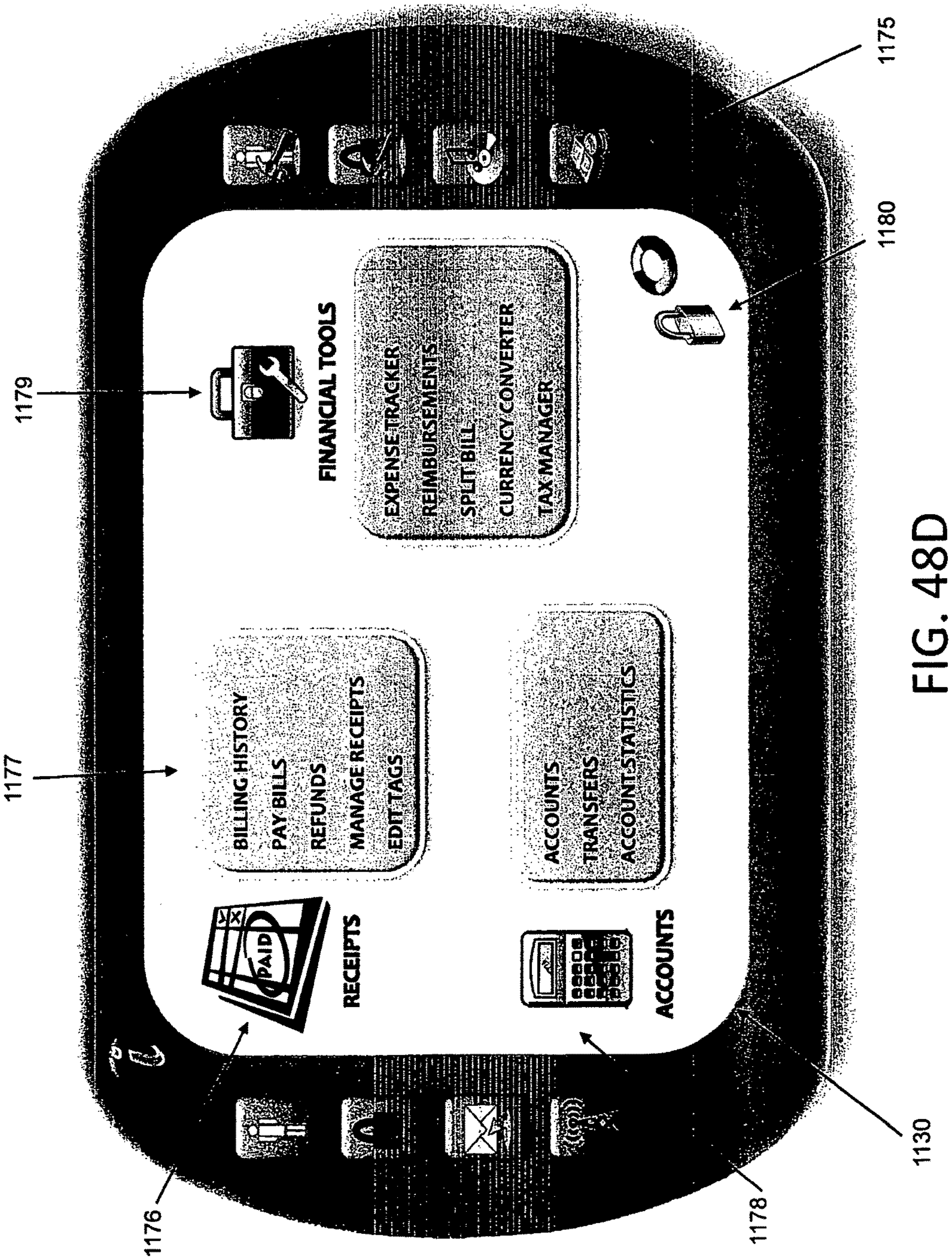

Reference is now made to FIG. 48D. In this figure, the 'financial tools' link 1175 is shown as active and the corresponding space that the user is directed to is shown in the display screen 1130. Some of the features accessible by the user in this space are described next. Feature 1176 and other icons in this space can be activated and deactivated in a manner similar to icons in other spaces of the local application, as explained previously. Upon activating icon 1176, options menu 1177 appears displaying options that can be used to view, manage and perform other activities related to purchase receipts, refunds and similar transactions. Some of these are shown in 1177—'billing history' allows the user to view the complete listing of financial transactions conducted through system 10; 'pay bills' allows the user to pay for purchases made through system 10 via a credit card provided for making purchases at stores on system 10; 'refunds' assists in making and tracking refunds; 'manage receipts' allows the user to organize, label electronic receipts, and other housekeeping functions involving their receipts, perform calculations on receipts; 'edit tags' allows users to create, modify, delete receipt/bill tag or labels. These could include 'business', 'personal' and other tags provided by the system or created by the user. The accounts feature 1178 provides options that allow the user to view and manage accounts-balances, transfers and other account related activities, account statistics and other account specific information. These accounts can be mapped to a user's banking accounts, which may be at multiple financial institutions; these could include credit/debit card accounts; accounts for credit cards provided for conducting financial transactions on system 10; gift card accounts. Feature 1179 provides other tools that assist the user in managing financial transactions conducted on system 10, as well as financial accounts, and other personal and business finances. Some of these are shown in the figure and include—'expense tracker', 'split bill' which was described previously in this document, 'currency converter', tax manager' etc. Since this is a space requiring stringent security measures, icon 1180 details the user on security measures taken by system 10 to protect information in this space. The electronic receipts may be linked with warranty information for products from the manufacturer/retailer, so that users may track remaining and applicable warranty on their products over time. For the manufacturer and retailer, the electronic receipt information on a user's account may serve useful for authenticating product purchase and for warranty application terms. Since the receipt is proof of product purchase, it may also be used to link a user's account containing the receipt for a product, with the user manual, product support information and other exclusive information only available to customers purchasing the product. Other information such as accessories compatible with a product purchased may linked/sent to the user account containing the product's receipt.

Figure 48E:
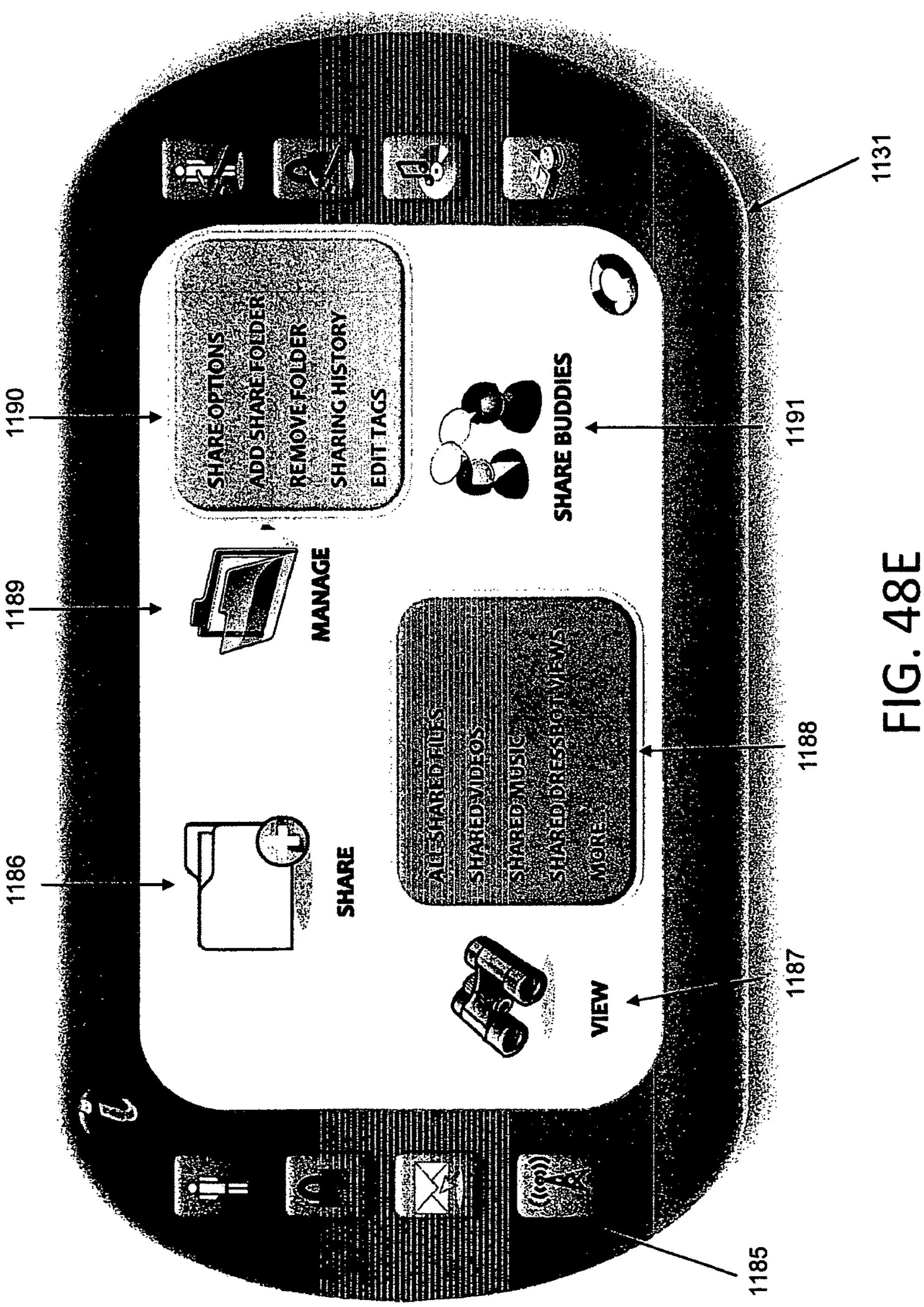

Reference is now made to FIG. 48E where the 'share manager' space (1185) on the local application is described. User files on a local machine or on in the user account on system 10 can be shared by activating a share icon similar to 1186. Items may be shared in other spaces as well but this space provides a comprehensive list of features for sharing items, managing shared items, users and activities involving shared items. Users can keep track of items they have shared with other users (1187, 1188). Users may change share settings and options, view their sharing activity history, tag shared items, add/remove files/folders and perform other actions to manage their sharing activity and items (1189, 1190). Users may maintain lists of other users they share items with, subscribe to and send updates to sharing network on items shared, and maintain groups/forums for facilitating discussion, moderating activities on shared items (1191).

Figure 48F:
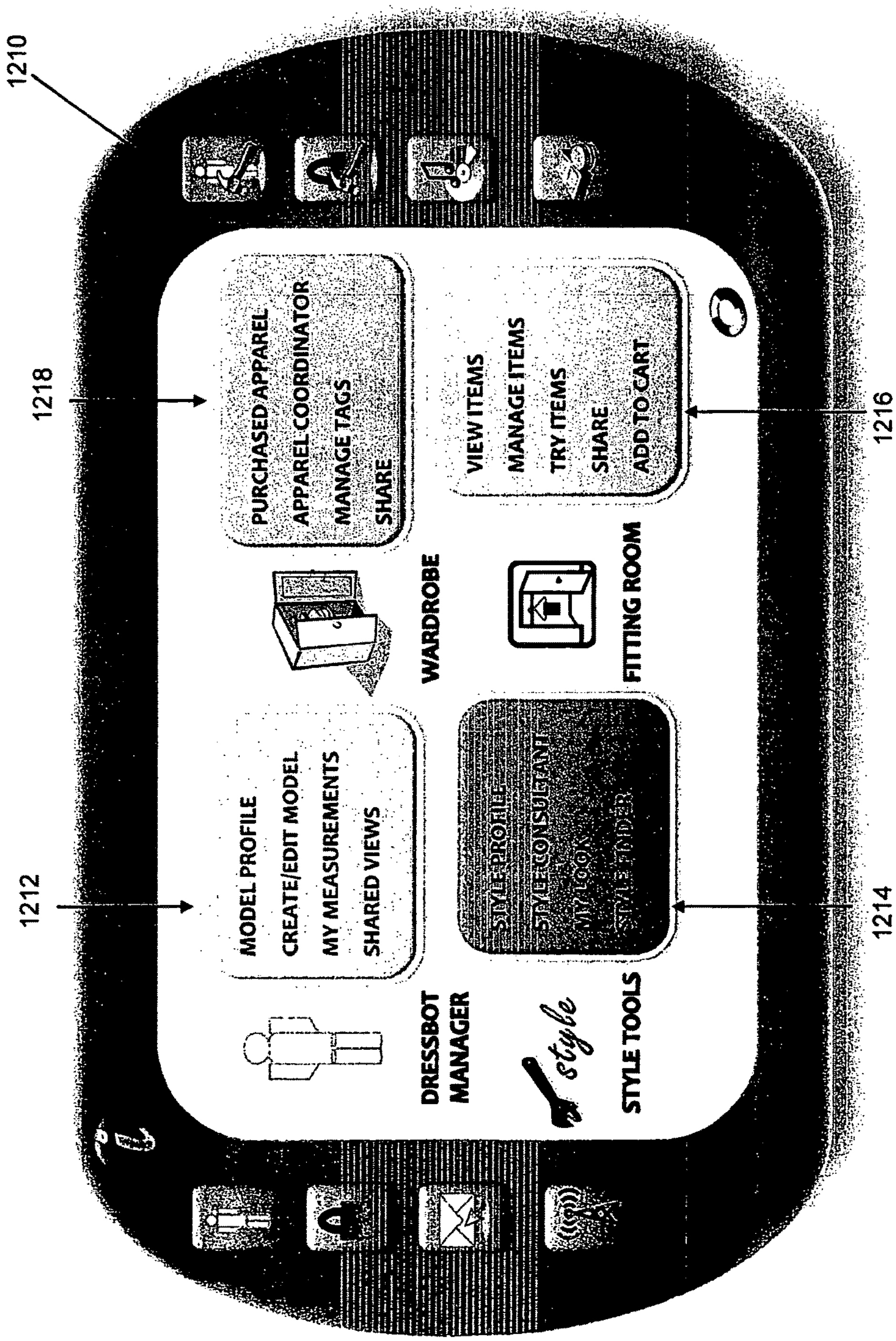

Reference is now made to FIG. 48F where the 'user model tools' space is described. Here the user can access make changes and manage their 3D simulated user model and model profile information (1212). Style tools are available to assist users in making better fashion choices while shopping for clothes and apparel (1214). These tools include consulting or acquiring fashion tips/advice from a fashion consultant, constructing a style profile which other users or fashion experts may view and provide appropriate fashion related feedback. A 'my look' section is also present in this space where users can create their own ensembles/looks by putting together items from electronic clothing and apparel catalogues (available from online stores for example). Further, users may manage browse or search for outfits of a particular style in store catalogues using style tools provided in this space (1214). A virtual fitting room (1216) is present to manage apparel items temporarily as the user browses clothing stores. Apparel in the fitting room may be stored for trying on/fitting on the user model. A virtual wardrobe space (1218) also exists for managing purchased apparel or apparel that already exists in the user's physical wardrobe. The simulations/images/descriptions of apparel in the wardrobe may be coordinated or tagged using the wardrobe tools (1218). The fitting room and wardrobe feature and embodiment descriptions provided earlier also apply here.

Throughout the FIGS. 48A-F, the application has been referred to as a 'local application'. However, this application may also be run as a whole or part of a web application or a website or a web browser or as an application located on a remote server.

Figure 49A:
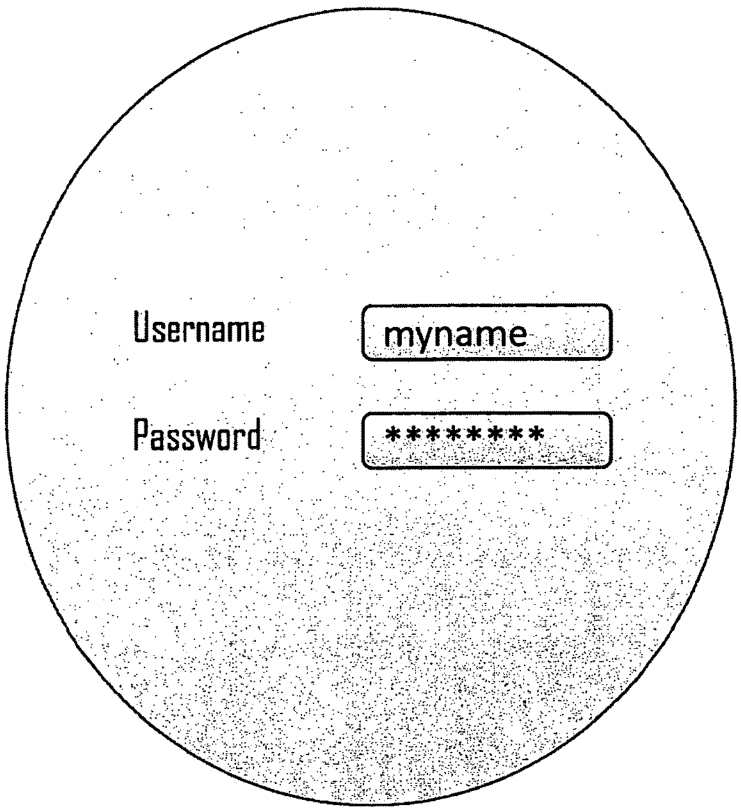
FIGS. 49A-O are images illustrating sample features of the AFMS/VOS.

Operating systems need to be redefined to incorporate collaborative environments and functions. Reference is now made to FIGS. 49A-0 where an immersive Application and File Management System (AFMS) or Virtual Operating System (VOS) and its features are described. This AFMS/VOS system or a subset of its features may be packaged as a separate application that can be installed and run on the local or network machine. It can also be implemented as a web browser or as part of a web browser and/or as part of an application that is run from a web server and can be accessed through a website. It can also be packaged as a part of a specialized or reconfigurable hardware or as a piece of software or as an operating system. This application may be platform independent. It may also take the form of a virtual embodiment of a computing device shown in FIG. 2.

An exemplary embodiment of AFMS system and its features are described in FIGS. 49A-L. FIG. 49A is a login window that provides a layer of security which may or may not be present when an application using this system is accessed depending on the security level selected.

Figure 49B:
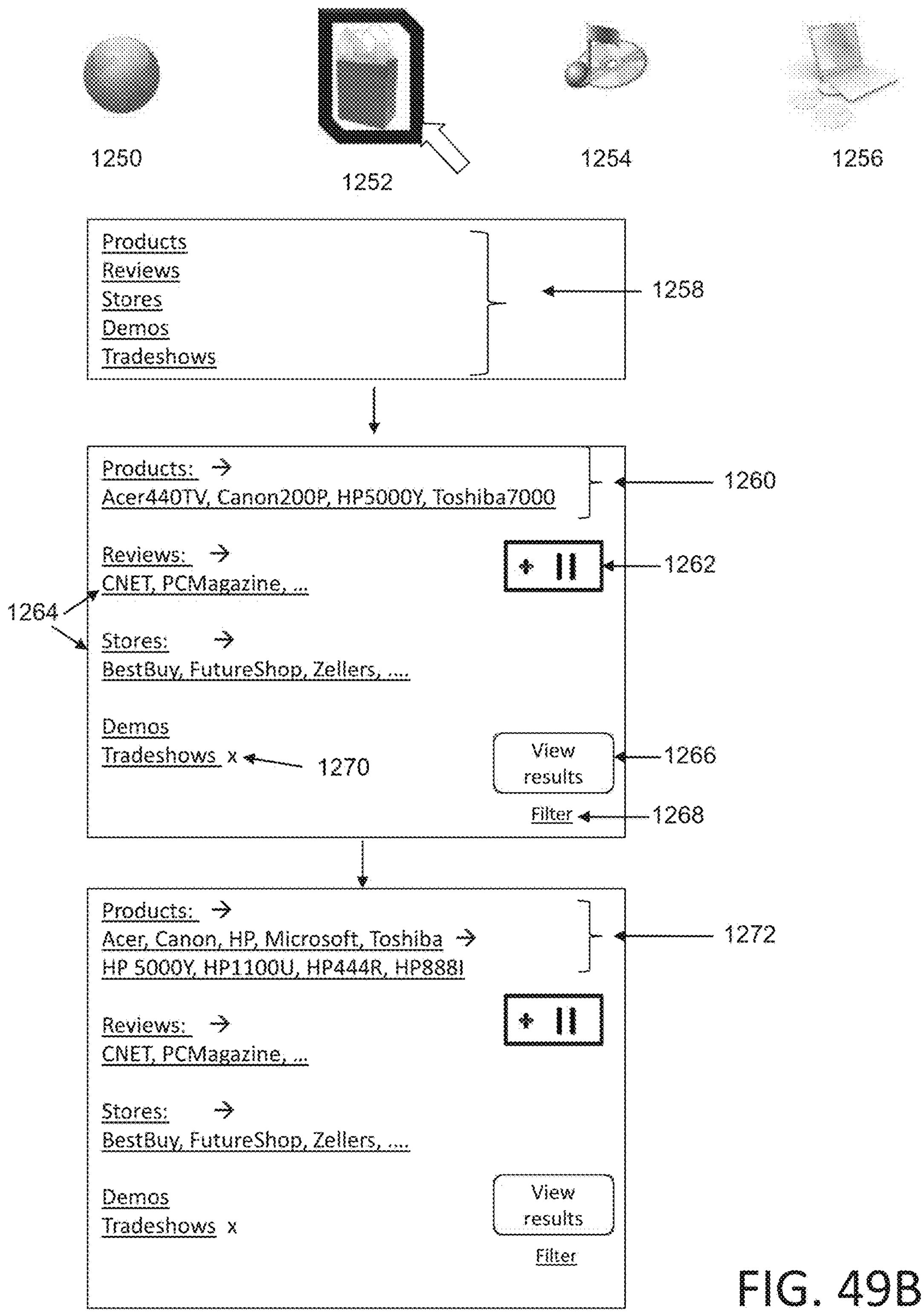
FIG. 49L is an image of the sample storage structure of the AFMS/VOS.
FIG. 49M is an image of a sample user accounts management structure within the AFMS/VOS.
FIG. 49N is an image that shows sample abstraction of a search query that is fed into the search engine that is a part of the AFMS/VOS.
FIG. 49P is an image of a sample application management structure within the AFMS/VOS.
FIG. 49Q is an image of an exemplary embodiment of file tagging, sharing, and searching features in the VOS/AFMS.
FIG. 49R is a sample image of a user interface for filtering search data.
FIG. 49S is a sample image of an interface to the object oriented file system.

Reference is now made to FIG. 49B where some file category and search level features are demonstrated, in an exemplary embodiment. Default file categories may be provided with the system and are some are shown in the figure in an exemplary embodiment. These are folders to store web links (1250), shopping related content (1252), multimedia related content (1254) and data files (1256). Users may create their own folders or remove any of the default folders provided, if they wish. In this figure, the shopping related folder is selected. It contains the categories or tags 1258, which are shown in exemplary embodiment. The user can create new tags, remove tags, create sub-level tags/categories and so on. The user can also conduct tag-keyword specific files searches within the system. For instance, the user can go the product tag and access the sub-tags (1260) within this category. The user can select the keyword Canon200P (highlighted in orange in the figure). Other tags/sub-tags (1264) can be similarly selected to be used in combination in the keyword specific search. An operator menu 1262 is provided so that the user can combine the tags using either an 'OR' or 'AND' operator in order to conduct their search, the results of which can be obtained by clicking the search operator 1266. The user may also choose to filter certain results out using the 'filter' function 1268 which allows the user to set filter criteria such as tag keywords and/or filename or and/or subject, content or context specific words and other criteria. The user may also choose to filter out tags and/or sub-tags by using a feature that allows the user to mark the tag as shown (in this case with a 'x' sign 1270 as shown in exemplary embodiment). User can create multiple levels of tags and sub-tags as shown by 1272.

In the description above, a file categorizing system has been defined in terms of tags that can be created and linked/associated with files and folders. Users can view tags, as shown in FIG. 48B, instead of filenames and folder names as in a standard file system. The tagging method can also be used to tag websites while browsing. Tags can be used with documents, images, applications, and any other type of data. Files and folders can be searched and the appropriate content retrieved by looking up on one or a combination of tags associated with the files and folders. Users may also simply specify tags and the AFMS would identify the appropriate location to store/save/backup the file. In exemplary embodiment, if a user is trying to save an image with the tag, 'Ireland'. The AFMS would identify the file as an image file and the tag 'Ireland' as a place/destination that it identifies as not being in the user's vicinity i.e., (not in the same city or country as the user). Then, the AFMS would proceed to store the file in an image space/section/file space in the subspace/subsection entitled or tagged as 'My Places' or 'Travel'. If a subspace does not exist that already contains pictures of Ireland, it would create a new folder with the name/tag 'Ireland' and save the image in the newly created subspace, else it would save the image to the existing folder containing pictures of 'Ireland'. In another exemplary embodiment, the user may want to save a project file tagged as 'Project X requirements'. The AFMS determines that there are associate accounts, as described later, that share files related to Project X on the owner user's account. The AFMS proceeds to save the file in the space tagged as 'Project X' and sets file permissions allowing associate accounts that share Project X's space on the owner user's account to access the newly saved file (Project X requirements). Thus, the AFMS/VOS not only determines the appropriate load/save location for files, but also the permissions to set for any new file on the system. Additionally, the file and folder content may be searched to retrieve relevant files in a keyword search. Users may be provided with the choice of viewing and searching for files according to the standard mode i.e., file and folder names or they may opt for using tagged content. This would offer greater control to users in terms of visualizing, managing and using their files and data. Data and files that are tagged provide the user with more flexibility in terms of organizing and accessing data. In exemplary embodiment, a user may tag a photo showing the user as a child with his mom on the beach, with the term 'childhood memories'. The user may tag the same photo with the phrase 'My mommy and me' and 'beach'. Anytime the user searches for any of the tags, the photo is included in the collection of photos (or album) with the given tag. Thus, a single photo can comprise multiple albums if it is tagged with multiple keywords/phrases.

Applications are designed that make use of the tag concept. In exemplary embodiment, one such application is a photo mixer/slideshow/display program that takes as input a tag name(s), retrieves all photos with the specified tag, and dynamically creates and displays the slideshow/photo album containing those photos.

Figure 49C:
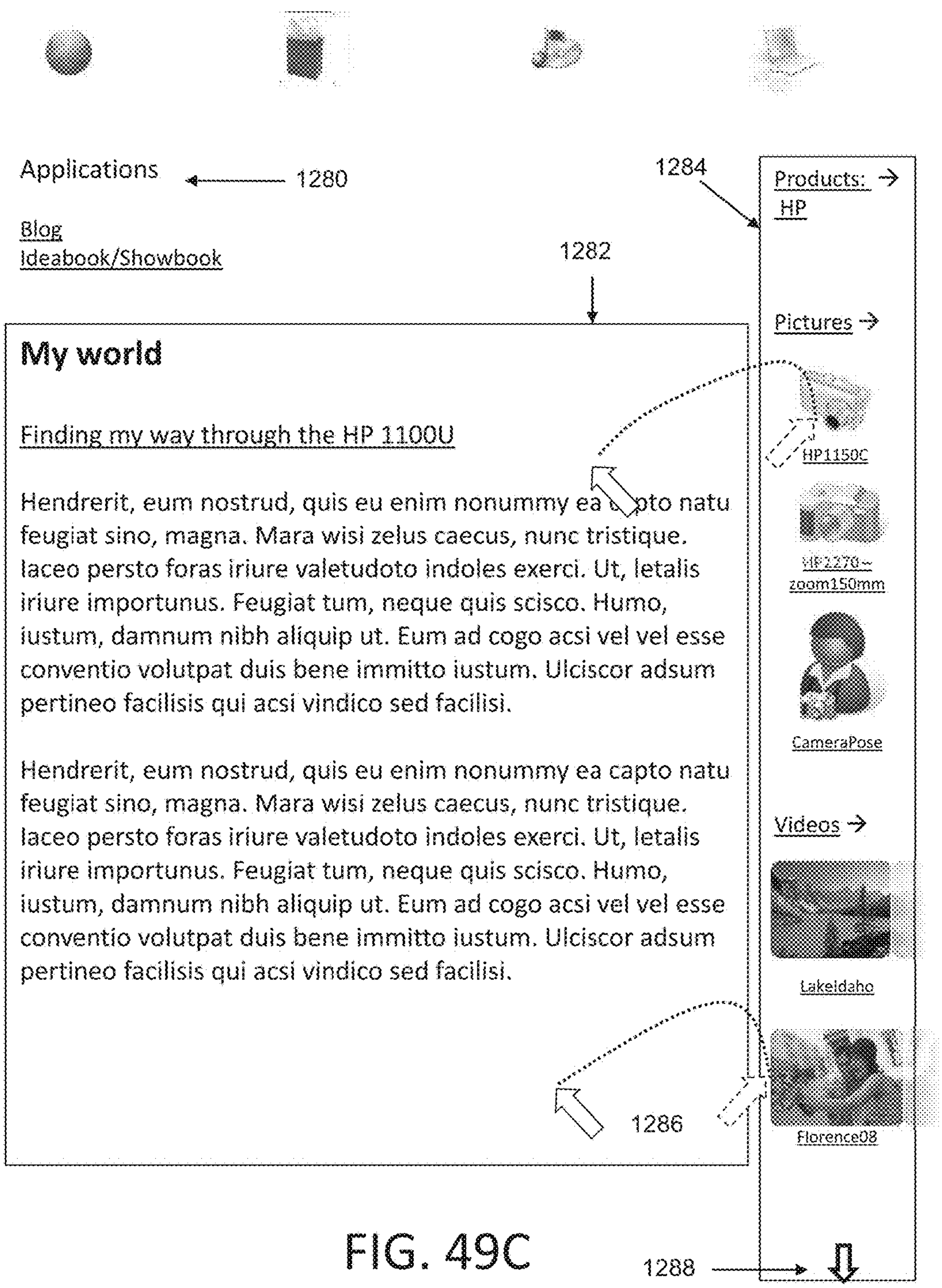
Figure 49D:
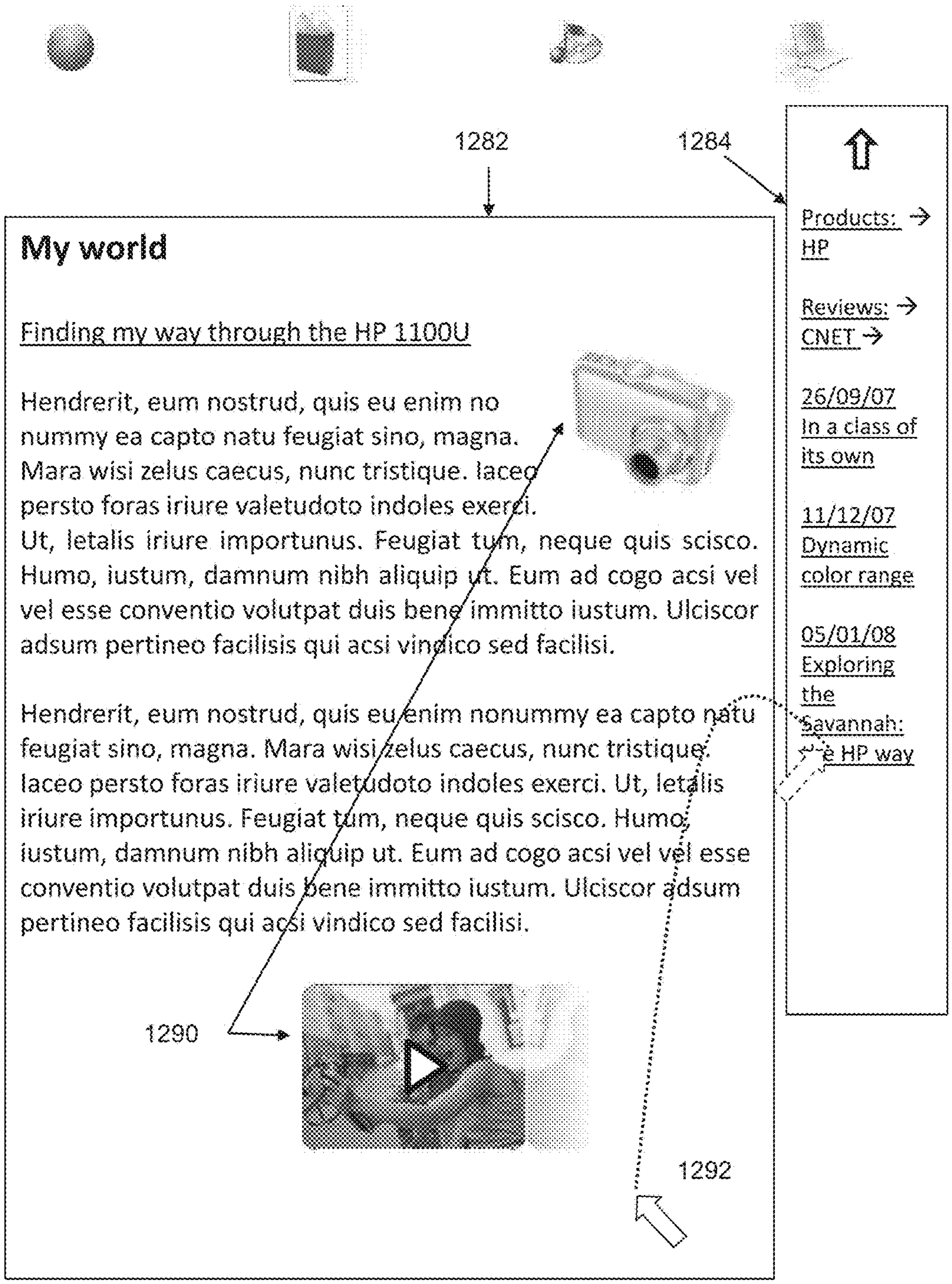

Reference is now made to FIG. 49C. Applications 1280 may be provided by the AFMS/VOS system. Alternatively, external applications may be added to it. In the following figure, examples of two applications are shown in context in order to describe the immersive features of this system. The first application is a blog 1282. This application can be instantiated (i.e., opens up) within the AFMS itself, in an exemplary embodiment. If the blog exists on a website, then the user would navigate to that site and edit its contents from within AFMS. Users can then add multimedia content to their blog with ease. The AFMS provides an interface 1284 for viewing and using files that may be located either on the user's local machine or in the AFMS or on a remote machine connected to the web. The file viewer/manager may open up in a sidebar 1284 as shown in exemplary embodiment, or in a new dialog window or take some other form which allows concurrent viewing of both the application 1282 and files. Snapshots of files can be seen within this file manager as shown by 1284. The user can then simply drag and drop files for use in application 1282. Examples of this are shown in FIG. 49C. The user can drag and drop images or videos 1286 for user with the blog application 1282. The following figure FIG. 49D shows the resulting effect. Further, the complete file repository may be accessed by using a navigation scheme 1288 within the manager to view contents. Here a cursor scheme 1288 is used to navigate within the file manager.

Figure 49E:

Reference is now made to FIG. 49D where the blog application 1282 is shown with the image and video files 1290 that were uploaded by dragging and dropping from their respective file locations using the file manager window 1284. The file manager window 1284 in FIG. 49D shows files that include the tags 'Products: HP' and 'Reviews: CNET'. Web links are shown sorted by date. The figure shows that hyperlinked content can also be embedded within applications via the file manager. Here the link is dragged and dropped 1292 demonstrating ease of use even in such cases. Reference is made to FIG. 49E where the result is shown. The hyperlinked content appears with the title, source and a summary of the content. The way this content appears can be modified by hovering with the mouse over this content, in an exemplary embodiment. This causes a window 1296 to appear which shows options that the user can select to show/hide entire hyperlinked article content, or summary and/or the source of the content.

Figure 49F:
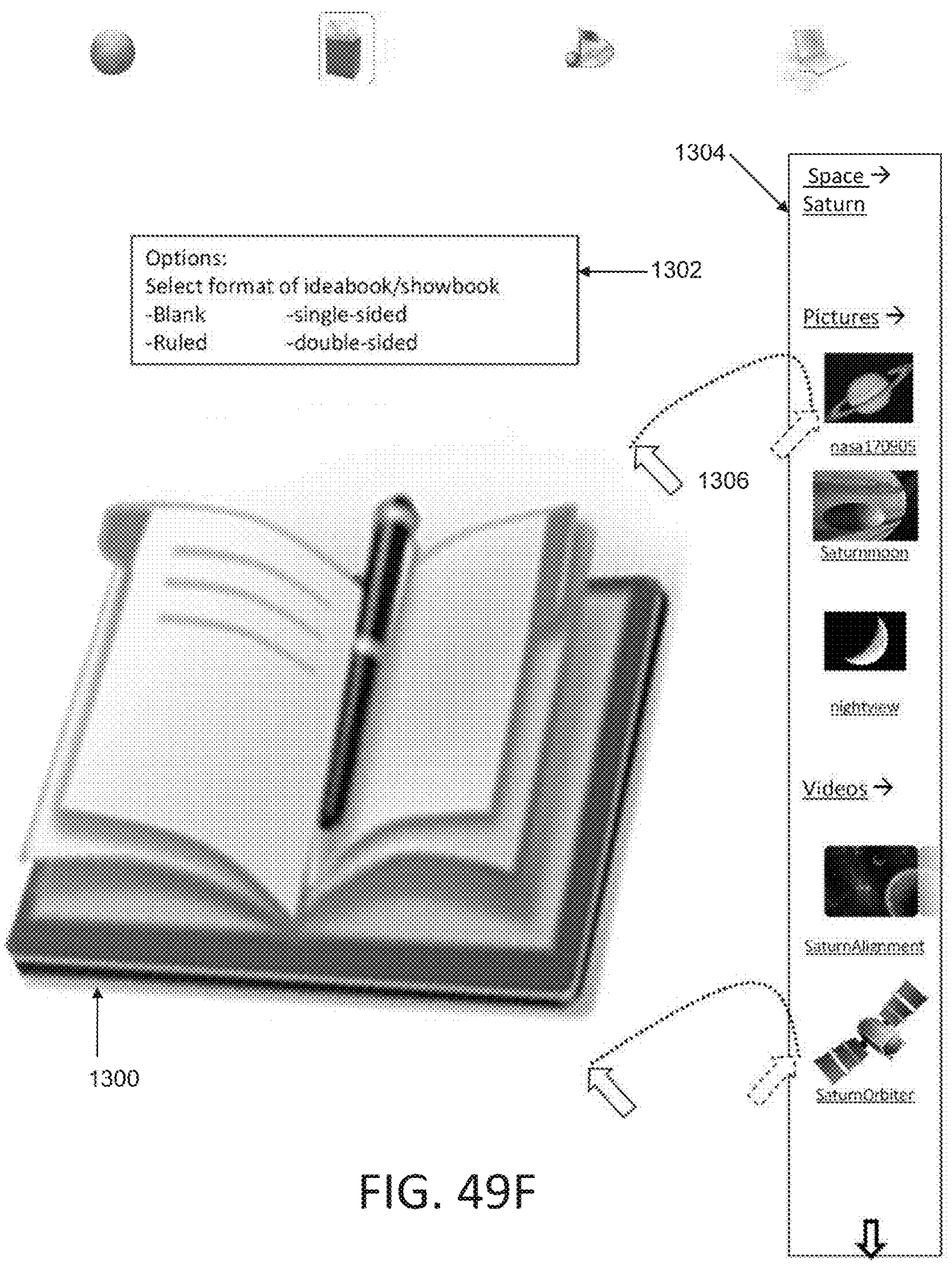
Figure 49G:
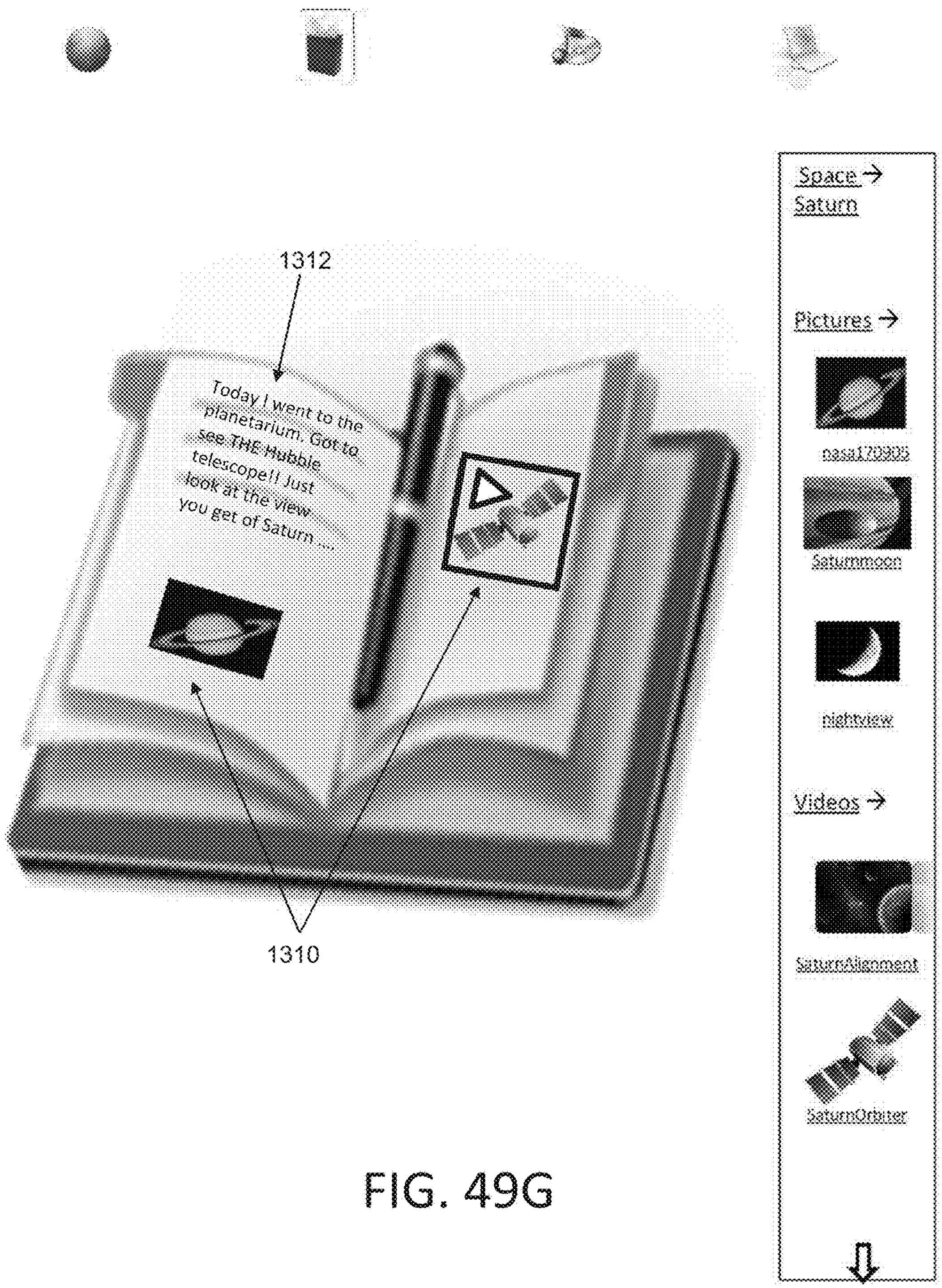

Reference is now made to FIGS. 49F-G where an example of immersive file features comprising the AFMS/VOS is given with reference to another application. In this case, it is a notebook/scrapbook application 1300 as shown in FIG. 49F. Options 1302 for customizing applications and/or changing application settings will be present in the AFMS. Here too is shown the file manager window 1304 from which files under the relevant tags can be dragged and dropped 1306 to the appropriate location in the application 1300. FIG. 49G shows the results 1310 where the selected multimedia files have been uploaded to the application by a simple move of the mouse from the file space to the application space within the AFMS. Content 1312 in the application may be edited or uploaded from the file space right within the AFMS where the users have readily available their file space, applications, the web and other resources.

Figure 49H:
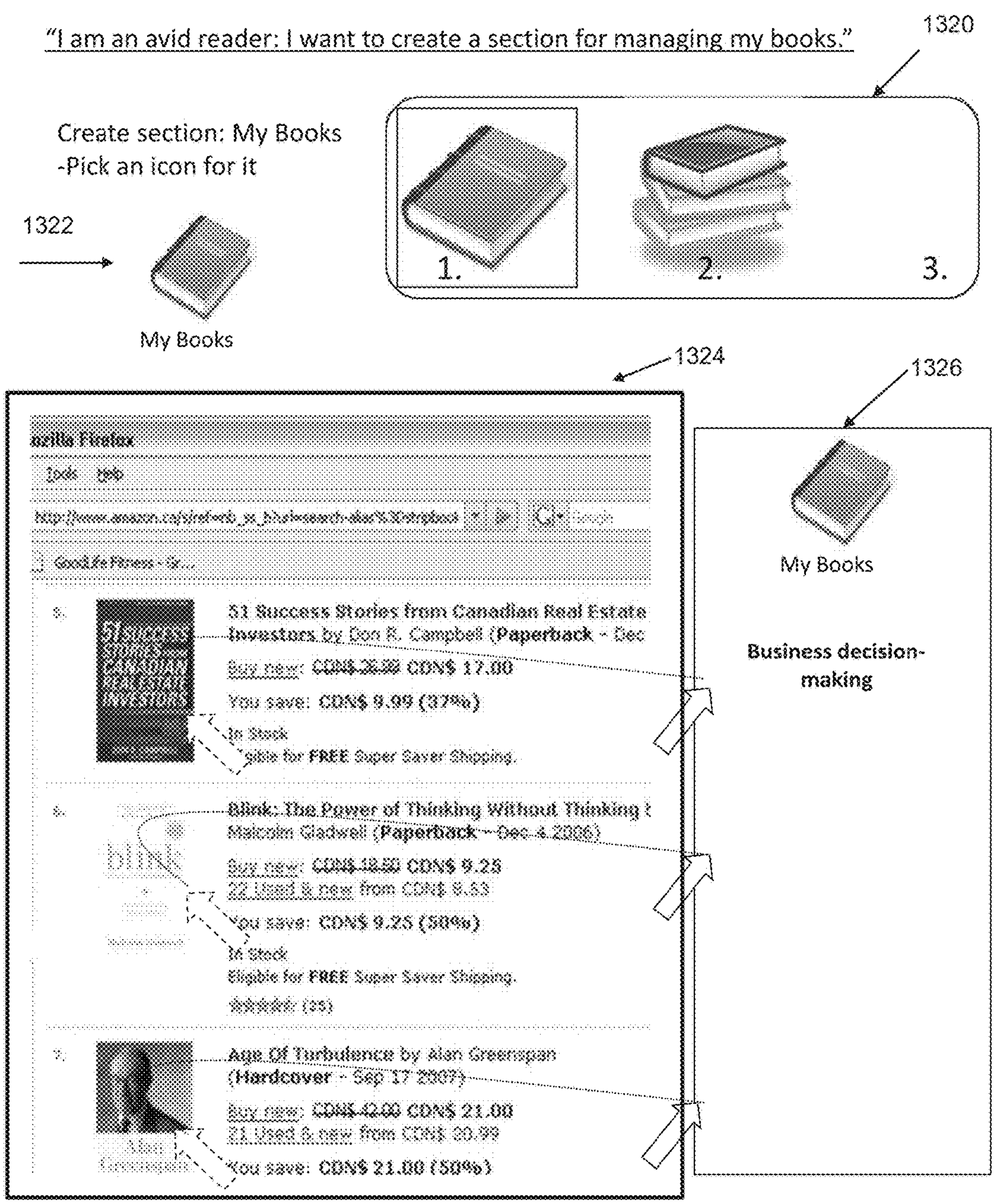
Figure 49I:
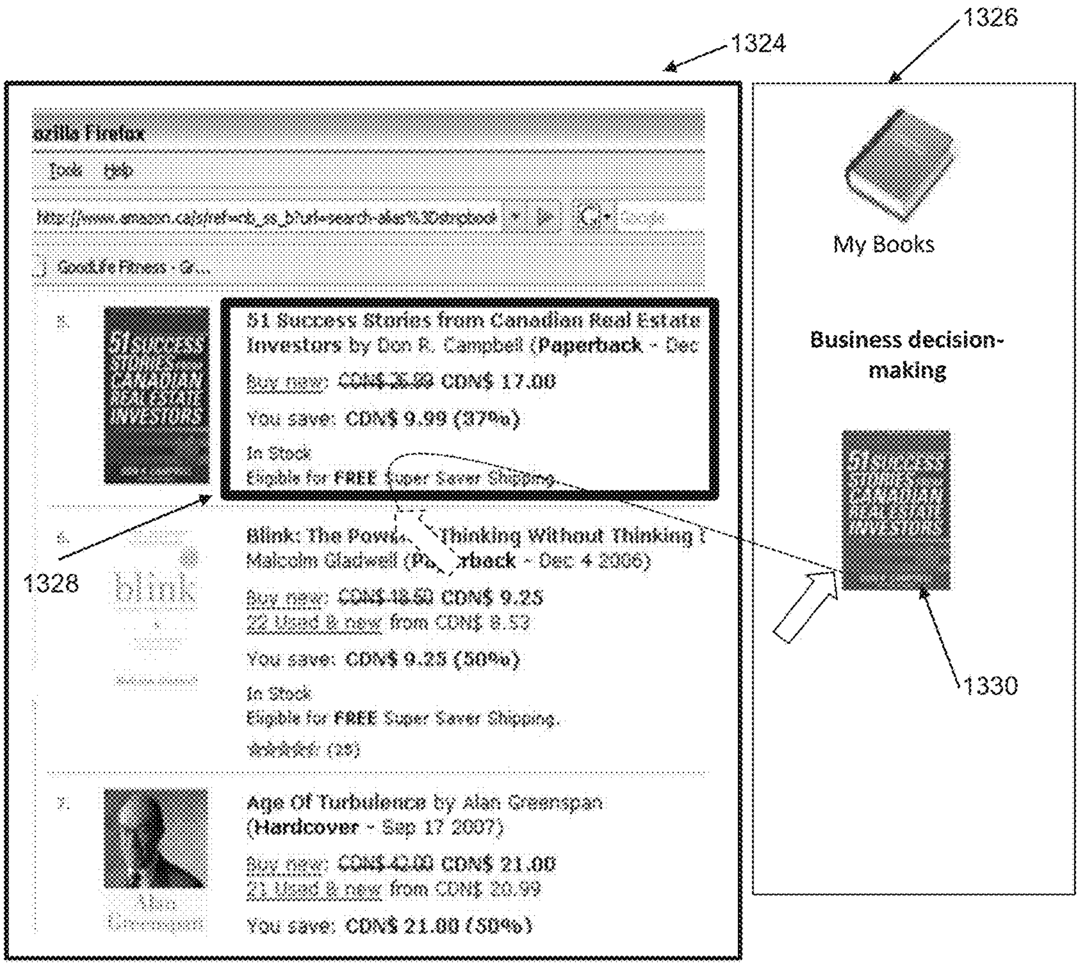

Reference is now made to FIGS. 49H-L where the flexibility of file spaces and their content within the AFMS/VOS is described with reference to an example. FIG. 49H presents the example at the top in terms of a user need. A user may want to create an exclusive file space (also called 'smart file spaces') for books where they can store and manage a variety of file types and content. The AFMS/VOS allows the user to create such a section. The procedure starts off by creating and naming the section and picking an icon for it which will be provided in a catalogue 1320 to users. Users may also add their own icons to this catalogue. The result is the user's very own book space 1326 which can be referenced by the iconic section caption 1322. The user may decide to add folders or tags in this space. One such tag/category is shown in 1326 as: 'Business decision-making'. As the user browses websites in the webspace 1324 provided by the AFMS/VOS, the user can easily upload/copy appropriate content from the website/URL location into their custom-built file section 1326. FIG. 49H shows the user dragging and dropping images of books that the user is interested in, into the books section 1326. The image content thus gets uploaded into the user's customized file space. Images and other content uploaded/copied from a site in this manner into a user's file space may be hyperlinked to the source and/or be associated with other information relating to the source. Users can add tags to describe the data uploaded into the file space. The AFMS/VOS may automatically scan uploaded object for relevant keywords that describe the object for tagging purposes. In the case of images, the system may use computer vision techniques to identify objects within the image and tag the image with appropriate keywords. This is equivalent to establishing correspondence between images and words. This can be accomplished using probabilistic latent semantic analysis [55]. This can also be done in the case of establishing correspondence between words (sentences, phonemes) and audio. FIG. 49I illustrates that textual content/data may also be copied/uploaded into the user's customized file space by selecting and copying the content in the space. This content may be stored as a data file or it may be 'linked' to other objects that the user drags the content over to, in the file space. For instance, in FIG. 49I, the user drags the selected content 1328 from the webspace 1324 over the image 1330. Hence the copied content gets linked to this image object 1330. The linked content may be retrieved in a separate file or it may appear alongside the object, or in a separate dialog or pop-up or window when the user selects the particular object, for instance, by clicking on it.

Figure 49J:
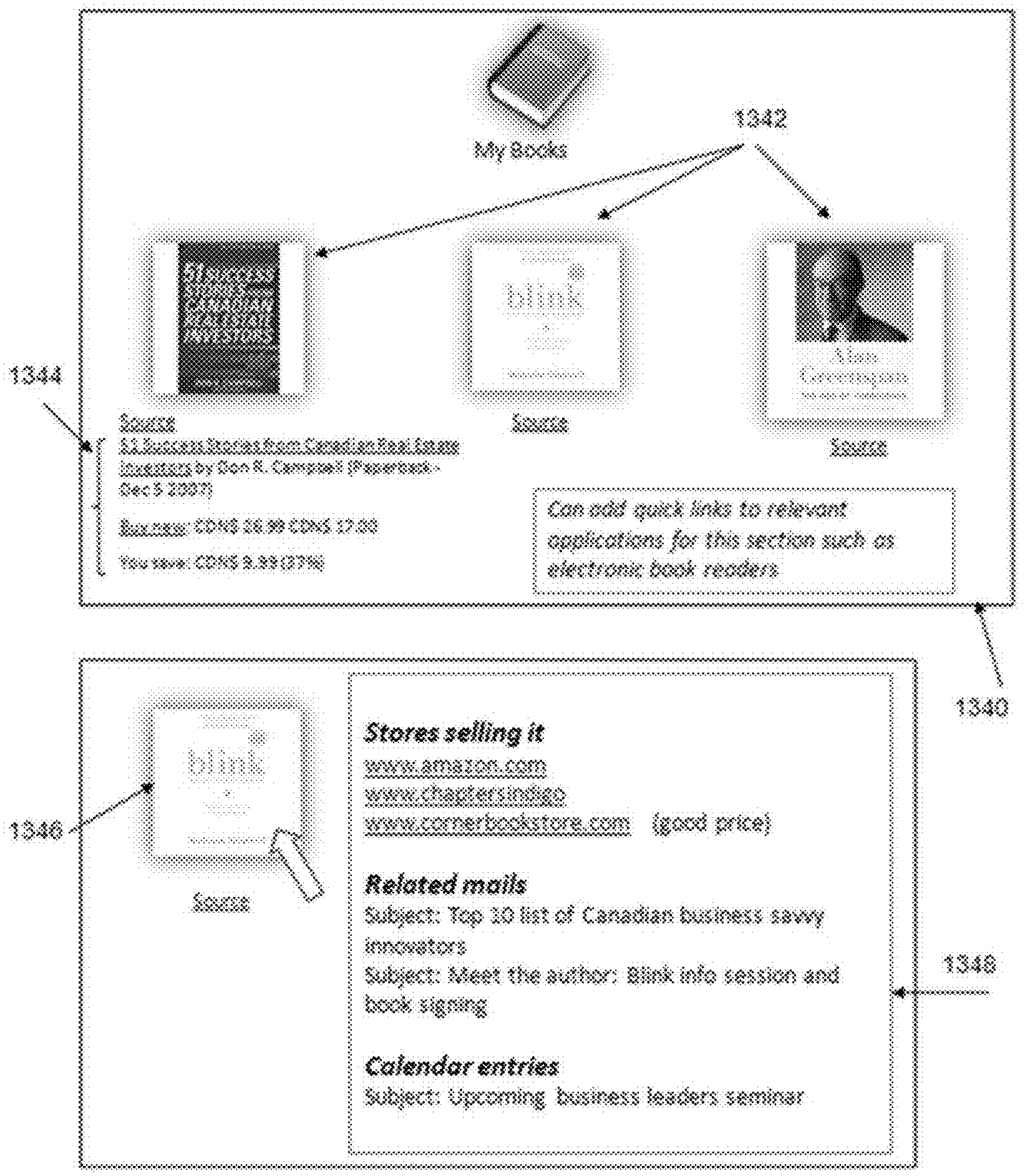

FIG. 49J shows the file space 1340 after content from the website has been uploaded. The image objects 1342 along with their source information are present. The content 1344 (corresponding to the selected text 1328 in FIG. 49I) can be viewed alongside the linked image in the file space 1340. Thus, the AFMS/VOS allows for creation and management of 'context specific file spaces' where the user can easily load content of different types and organize information that appears to go together best, from a variety of sources and locations, in a flexible way, and without worrying about lower layer details.

Organization of information in these file spaces is not tied to data type or file format or application being used, but instead all objects that appear to the user as belonging together can be tied together as a single 'information unit'. These information units can then organized as bigger information units and so on. In the current example the image of the book, its source and the content it is linked with together comprise one information unit. The book objects together (1342) comprise a higher information unit comprising the 'My Books' section. These information units stand apart from standard data files and folders because they contain data of multiple types that is linked or associated together, and hence are flexible. Further, data and content of different types from multiple sources can be assimilated together by the system which will handle the lower layer functionality to create these information units in a manner that is easy to access, view and manage, thus enhancing the value of the information to the user.

In FIG. 49J, additional examples are given to demonstrate other ways of combining data with information units. An object in a file space can be cross-referenced with information or data from other applications that is of relevance or related to that object. For instance, the book object or information unit 1346 can be cross referenced with web links, related emails and calendar entries as shown in 1348 and categorized using relevant tags. In this example, the user has added web links of stores that sell the book, emails and calendar entries related to the subject matter and events involving the book. Thus, the user can easily reference different types of files and objects that are related to the same subject matter or object using the features of this file system. The information in any given smart file space can be used by the AFMS/VOS to answer user queries related to objects in the file spaces. For instance, in the present example, the user may query the AFMS for the date of the 'blink' book signing event in the 'My Books' file space 1340 in FIG. 49J. The AFMS identifies the 'blink' object 1346 in the file space and looks up appropriate information linked to or associated with 1346. In this case since the query deals with 'date', the AFMS searches for linked calendar entries and emails associated with 1346 related to 'book signing', by parsing their subject, tags and content. In this case, the AFMS would identify and parse the email entry on book signing in 1348 in FIG. 49J and answer the query with the relevant date information.

In an exemplary embodiment of the smart file space implementation, each file space may be associated with an XML file. When an object or content (image, text, etc.) is dragged and dropped, the code underlying the content is parsed and the appropriate information and properties are identified. This information includes type of content or data, content source, location, link information (for example, this is a link to an image of a house), content description/subject. Other information that the AFMS/VOS determines includes, the application needed to view or run the object being saved into the file space. For instance, when an image is dragged and dropped into a file space from a web page, the HTML code for the web page is parsed by the AFMS in order to identify the object type (image) and its properties. Parsing the image source tag (<src>) in the HTML file for the web page provides the source information for the image, in exemplary embodiment.

Figure 49K:
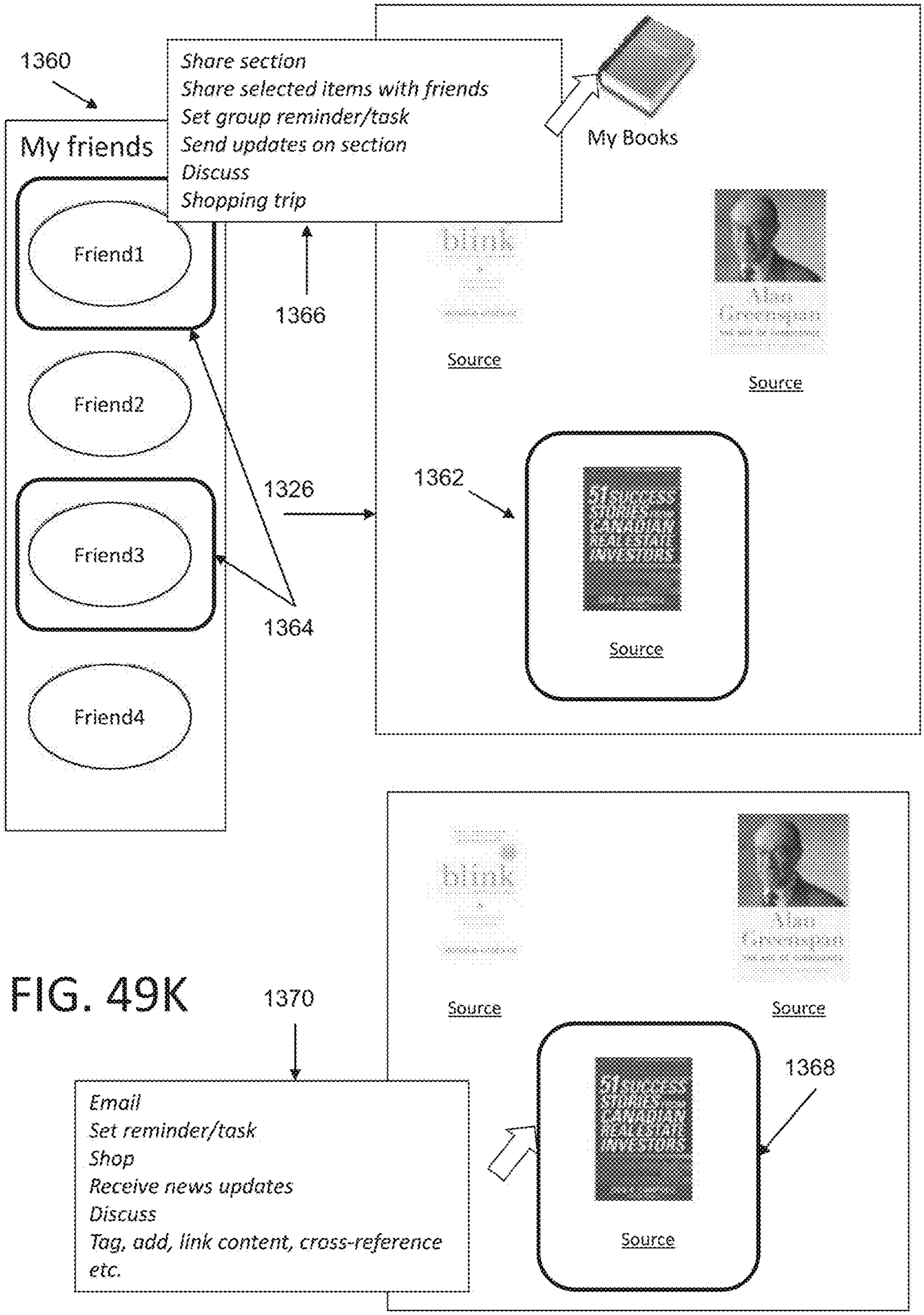

In FIG. 49K, collaborative features of the AFMS/VOS and its associated file management features are described. Users can maintain a list of friends 1260 and their information in the AFMS/VOS. These friends can have limited access accounts on this system (called 'associate' accounts described later) so that they can access and share the primary user's resources or interact with the primary user. Users can set options to share information units/objects in their file spaces, such as book object 1362 in the 'My Books' section 1326 in FIG. 49K, with their friends. Users can drag and drop objects directly onto a friend's image/name in order to share those objects with the friend. Another feature in this file system is that when an object 1362 in the file space 1326 and friends 1364 from the friends list 1360 are selected concurrently, a special options window 1366 pops up that presents features relevant to the 'sharing' scenario. The AFMS/VOS recognizes that selections from both the friends list and file space have been made and presents users with options/features 1366 that are activated only when such a simultaneous selection occurs and not when either friends or file space objects are exclusively selected. Some of these options are shown in 1366 in exemplary embodiment. For instance, users can set group tasks for themselves and their friends involving the selected object, such as attending the author signing event for the book 1362. Other options include turning on updates, such as the addition of objects, for a section to the selected friends; going on a shopping trip for the object with selected friends.

Owners may be able to keep track of physical items they lend to or borrow from their friends. An object in a file space may be a virtual representation of the physical item. Users can set due dates or reminders on items so that items borrowed or lent can be tracked and returned on time. A timestamp may be associated with a borrowed item to indicate the duration for which the item has been borrowed. This method(s) to keep track of items can serve as a Contract Management System. This service can be used to set up contracts (and other legal documents) between users using timestamps, reminders and other features as described. Witnesses and members bound to a contract may establish their presence during contract formation and attestation via a webcam or live video transmission and/or other electronic means for live video capture and transmission. Members bound to a contract and witnesses may attest documents digitally (i.e., use digital signatures captured by electronic handwriting capture devices for example). Users may also create their WILL through this system. User authenticity may be established based on unique pieces of identification such as their Social Insurance Number (SIN), driver's license, passport, electronic birth certificate, retinal scans, fingerprints, health cards, etc. and/or any combination or the above. Once the authenticity of the user has been verified by the system, the system registers the user as an authentic user. Lawyers and witnesses with established credibility and authenticity on the system may be sought by other users of the system who are seeking a lawyer or witness for a legal document signing/creation for example. The credibility of lawyers, witnesses and other people involved in authenticating/witnessing/creating a legal document may further be established by users who have made use of their services. Based on their reliability and service, users may rate them in order to increase their credibility/reliability score through the system. Thus, group options involving data objects and users is a unique file management feature of the AFMS/VOS that allows for shared activities and takes electronic collaboration to a higher level. The Contract Management System may be used/distributed as a standalone system.

FIG. 49K shows options/features 1370 that are presented for managing an information unit upon selecting the particular object or information unit 1368 in a file space. These options allow users to send an email or set tasks/reminders related to the object; tag the object, link other objects; receive news feeds related to that object; add it to another file space; and perform other tasks as given in 1370.

In another exemplary embodiment of AFMS/VOS usage for information lookup, a user may want to look up information on the last client meeting for a specific project. The file space for the project, created by the user, would contain the calendar entry for the last meeting, the email link containing the meeting minutes as an attachment, and other related objects and files. The user may also share the project file space with other users involved in the project by adding them as ‘friends’ and sharing the file space content, in exemplary embodiment. Thus, the smart file space saves the user time and effort as the user no longer has to perform tedious tasks in order to consolidate items that may ‘belong together’ according to a user's specific needs. For instance, in this case the user does not need to save the meeting minutes or the email content separately; just dragging and dropping the appropriate email from the email application to the project's file space suffices and the email and attachment are automatically linked to/associated with the project. The user does not have to open the calendar application and tediously browse for the last calendar entry pertaining to the meeting. Also, sharing the project space with colleagues is easy so that project members can keep track of all files and information related to a project without worrying about who has or doesn't have a particular file. Other information may be available to users sharing a file space such as the date and time a particular file was accessed by a user, comments posted by shared users etc. Additionally, tools to ease file sharing and collaboration may be available via the VOS as described below with reference to FIG. 20.

Figure 49L:
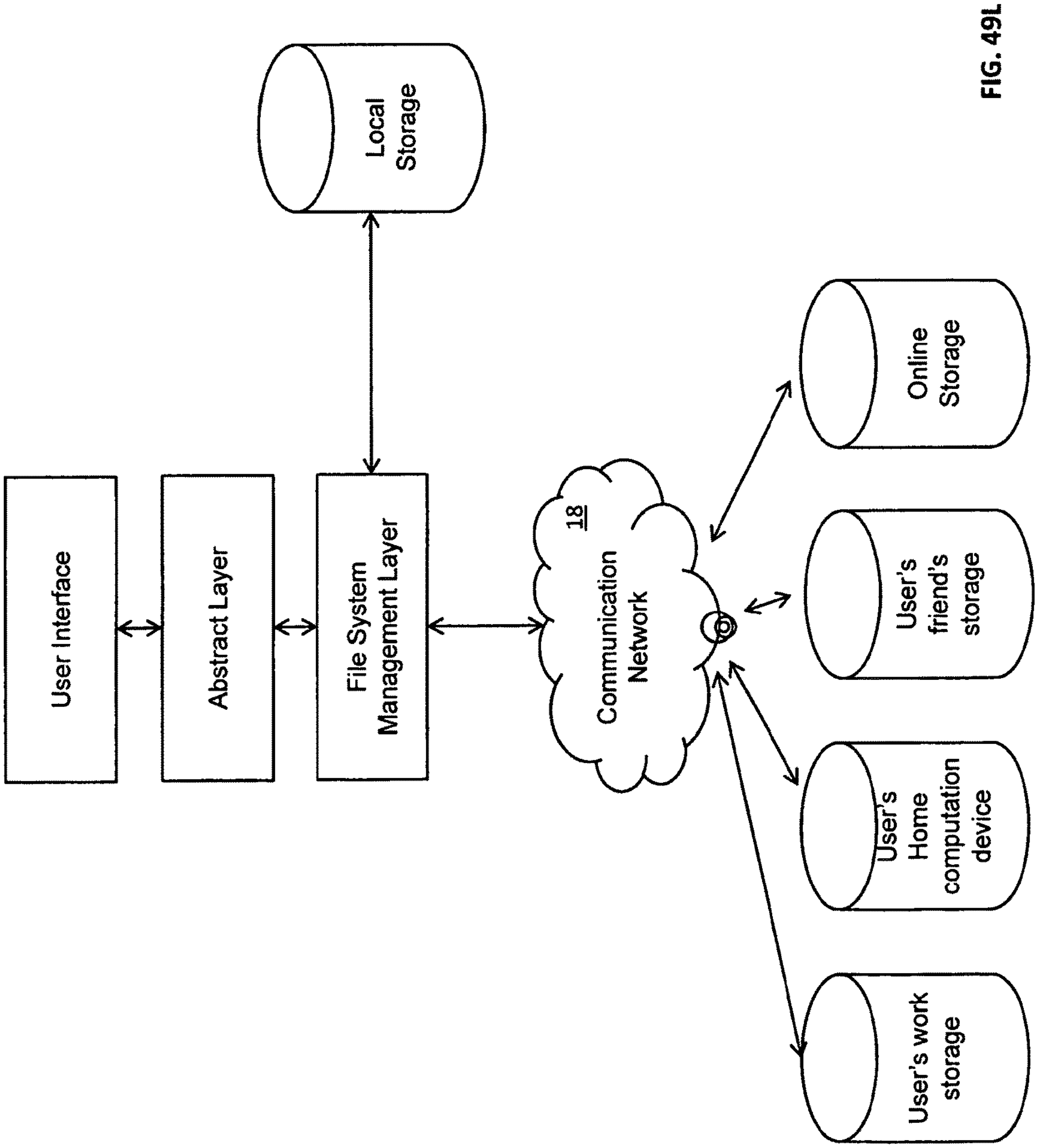

FIG. 49L represents an exemplary embodiment of the storage structure of the AFMS/VOS. Data stored on a user's local machine or remote sites or servers such as a user's work machine, or online storage, and data of user's friends on the system is managed by the file management layer. The file management layer handles conflict analysis, file synchronization, tagging, indexing, searching, version control, backups, virus scanning and removal, security and fault protection and other administrative tasks. Data (modification, updates, creation, backup) in all user and shared accounts on local or remote machines, on web servers, web sites, mobile device storage and other places can be synchronized by this layer. A property of the file system is that it caches files/and other user data locally when network resources are limited or unavailable and synchronizes data as network resources become available, to ensure smooth operation even during network disruptions. Backups of data conducted by AFMS may be on distributed machines. An abstract layer operates on top of the file management system and provides a unified framework for access by abstracting out the lower layers. The advantage of this is that the VOS offers location transparency to the user. The user may log in anywhere and see a consistent organization of files via the VOS interface, independent of where the files/data may be located or where the user may be accessing them. The VOS allows users to search for data across all of the user's resources independent of the location of the data. Another feature of this file system is the option of storing a user's information, profile and other account resources on the user's resources (for example, the user's home or work computer) instead of a web server to ensure privacy of a user's data and account information. FIG. 49P demonstrates an exemplary embodiment of an application execution protocol run by the Application Resource Manager ARM (which is a part of the virtual operating system). Once a user requests an application 1400, the ARM checks to see whether this application is available on the portal server 1402. If so, then the application is run from the portal server 1404. If not, then the application plug-in is sought 1406. If the plug-in exists, the application is run from the local machine 1412. If a plug-in for the application does not exist, a check for the application on the local machine is conducted 1410. If available, the application is executed from the client's local machine 1412. If not, the application is run from a remote server on which the user has been authenticated (i.e., has access permission) 1414, 1416. If all the decision steps in the algorithm in FIG. 49P yield a negative response, the ARM suggests installation paths and alternate sources for the application to the user 1418. The user's data generated from running the application is saved using the distributed storage model.

Another feature of the AFMS is that the user may store files in a “redirect” folder i.e., files moved/saved to this folder are redirected by the AFMS to the appropriate destination folder based on the file's tags and/or content. The user may then be notified of where the file has been stored (i.e., destination folder) via a note or comment or link in the “redirect” folder that directs the user to the appropriate destination. An index file may automatically be generated for folders based on titles/keywords/tags in the documents and/or the filename. This index may display titles/keywords/tags along with snapshots of the corresponding files.

Figure 49M:
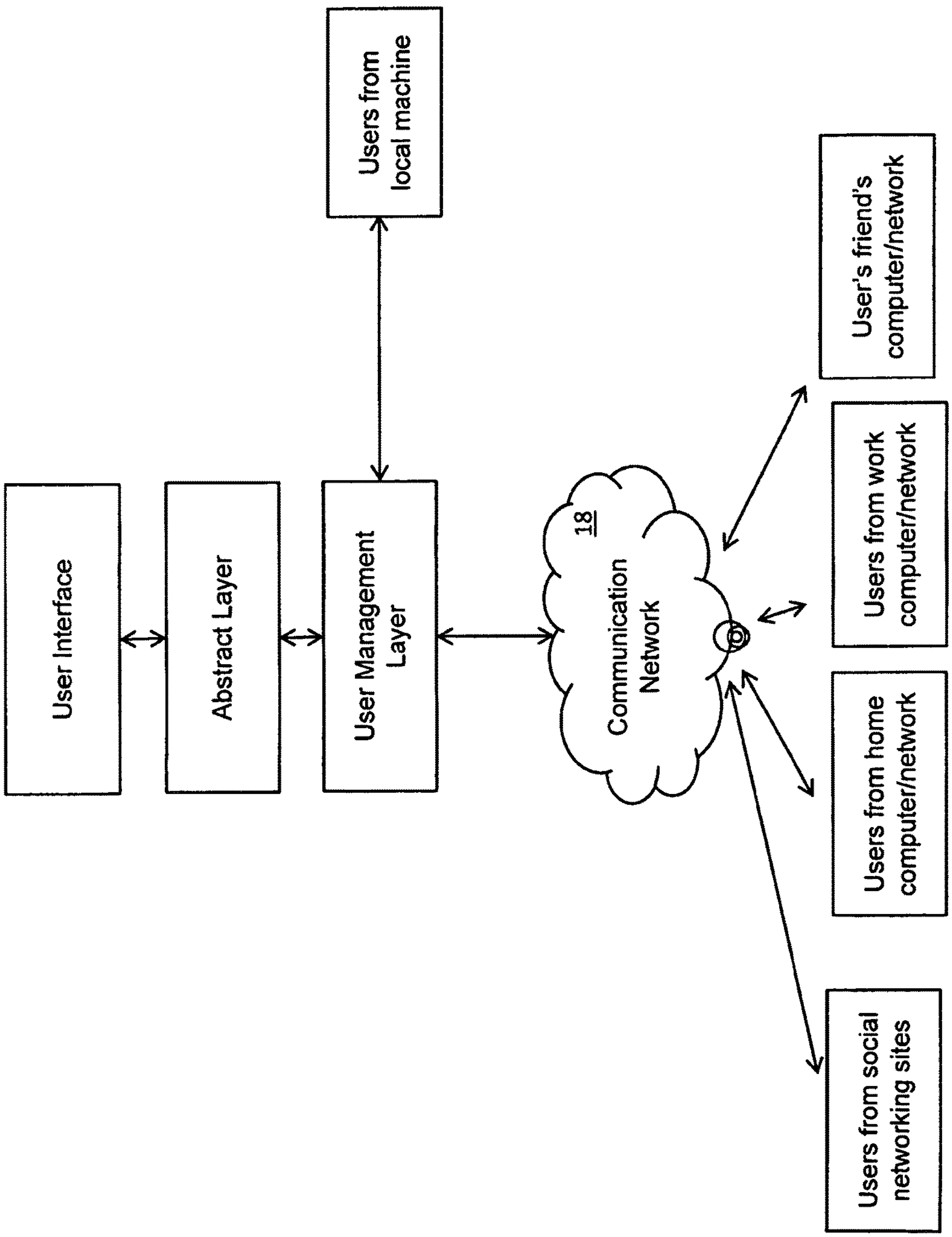

Reference is now made to FIG. 49M where a user accounts management structure is shown. Central to this system is a user management layer that manages a given 'owner' user's accounts as well as 'associate' accounts, which would include accounts of all other friends, users and groups (the owner would like to associate with). Associate accounts would be created to give access to the owner account resources and data. The owner account would have all administrative rights and privileges (read, write, execute, for example) and can set permissions on associate accounts to grant or restrict access to the owner's account and resources. An associate account may be viewed as 'the set of all owner resources that the associate user has access to, and the set of all activities that the associate user can engage in with the owner user'. An associate account would be linked to and accessible from the associate user's primary/owner account. The owner account may be accessible to and from the owner user's computer, to and from a machine at remote locations such as the office, to and from accounts at social networking sites, and through a web browser/web sites. Account information such as usernames and passwords for the user's accounts on websites and other servers that the user accesses from the VOS may be stored on the system so that the user bypasses the need to enter this information every time the user accesses their external account. The owner may set group policies for the associate accounts so that they have access to specific resources and applications for specific time periods on the owner's account. Owner users have the option of classifying associate users into categories such as acquaintances from work, school, family, strangers etc. As described before, users may share information and files with their friends, and also engage in shared activities such as games, edit documents collaboratively etc., through the VOS. Another feature of the VOS is that over time it allows the user to specify automatic changes in access privileges/permissions of associate accounts on the user's network. In exemplary embodiment, a user may want to let associates accounts, starting out with limited access/privileges, have access to more resources over time. Through the VOS, the user is able to specify the resources that associate accounts may automatically access after a certain period of time has elapsed since their account was created or since their access privileges were last changed. The user may also be able to grant greater access privileges automatically to associate accounts after they demonstrate a certain level of activity. After the specified period of time elapses or the level of activity of an associate account increases/decreases or is maintained, the VOS automatically changes the access privileges of the associate users who have been granted access to increased/decreased resources as pre-specified by the user through options provided by the VOS. This is the 'Growing Relations' feature of the VOS where access privileges rules of associate accounts are specified by a user and are changed accordingly by the system, as and when specified by the user. The VOS is able to regulate resource use and change access privileges automatically in the absence of user specified access privilege rules, in another exemplary embodiment. The VOS may monitor activity levels of associate accounts and interactivity between user and associate users and automatically determine which associate users may be allowed greater access privileges. If there is greater interactivity over time between the user and a certain associate user, then the system may deem this associate user as a 'trusted associate'. It may also use other means of determining the 'trustworthiness' of an associate user. The system may seek permission of the user before changing access privileges of the trusted associate user. As the 'trust score' (the method used by the system to keep track of the activity levels of an associate account) of an associate user increases, the system would promote the status of the associate account progressively by assigning status levels such as: Stranger, Acquaintance, Friend, Family—in that order from first to last. The higher the status of an account, the more access privileges are granted to that account. In a similar manner, if the VOS detects that there is little interactivity of an associate account over time, or determines lower resource needs of an associate account or assesses that an associate account is less 'trustworthy' based on usage patterns of associate account users, then the VOS would regress the status of the account and grant less privileges accordingly. The system may again seek the permission of the user before modifying access privileges of any associate account.

The VOS allows password synchronization across websites, networks and machines. For example, if a user changes a password for logging onto a local machine, say a home computer, the password change is synchronized with a password the user may use to login to their account on a webpage. Various levels of access privileges may be granted by the VOS to users, including but not limited to that of a root user, administrator, regular user, super user, guest, limited user, etc., in exemplary embodiment. The VOS also allows execution of shell commands. VOS also provides a software development kit for users to write applications for the VOS.

Figure 49N:
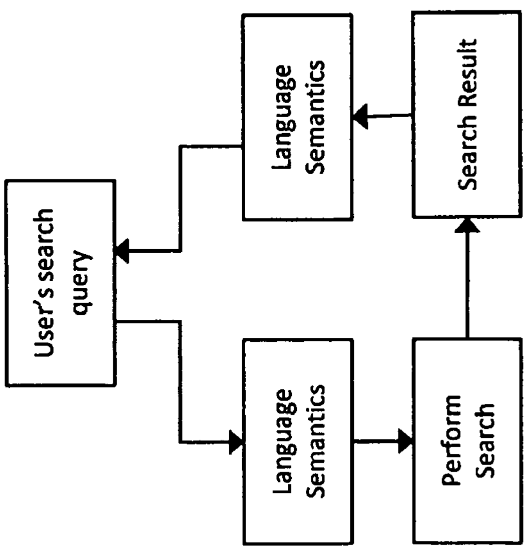
Figure 49O:
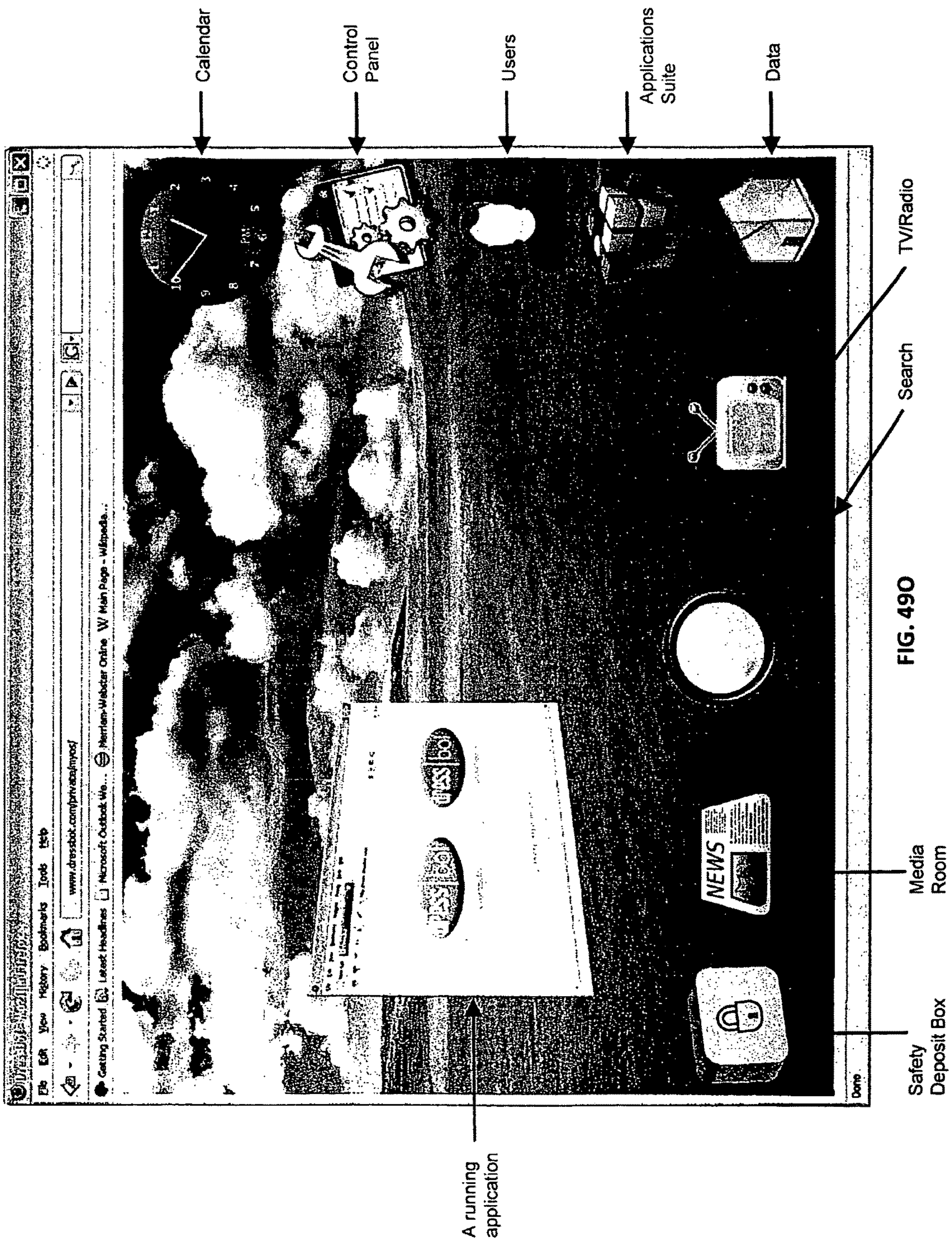
Figure 49P:
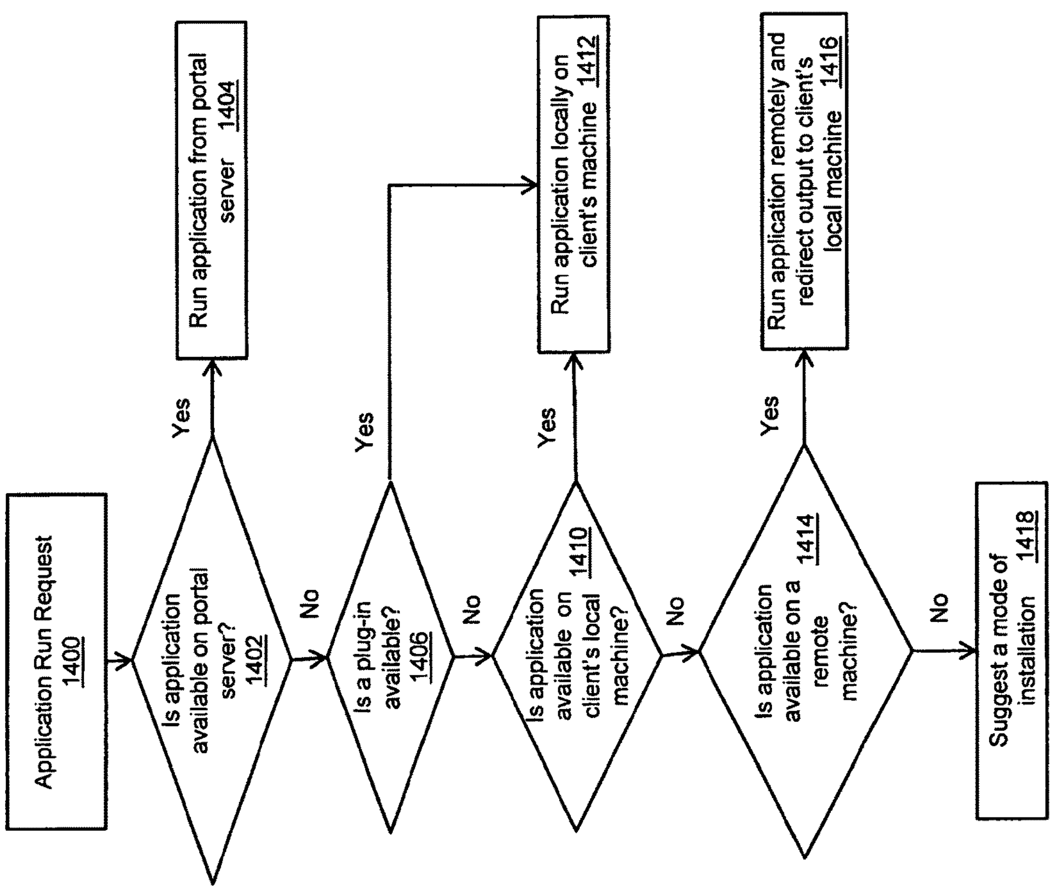

The system may also contain an immersive search engine application that performs searches on queries presented to it. The search engine may be available as a standalone feature for use with browsers and/or network machine(s) or local machine browsing applications. It may be available as part of a VOS browser, containing one or more of the VOS's features. Some of the features unique to this immersive search engine are described next. Reference is made to FIG. 49N where abstraction of a search query is demonstrated in exemplary embodiment. When a user performs a search, the input is not limited to typing text and using a keyboard. Instead a new approach is proposed, where the input could be speech to text, or mouse gestures or other data. In another example, a user may be able to drag and drop content from a newsfeed into the search query field. Context level searches may be performed by the search engine. In an exemplary embodiment, when a user comes across an image while browsing the web, the user may be able to simply drag and drop the image into the search field and the browser would retrieve search results that pertain to the image objects, theme or subject. The user may quote a sentence and the search engine would retrieve searches related to the underpinning of that statement in a context related search, in another exemplary embodiment. Thus, this method effectively provides a layer of abstraction for the conventional search. The search engine can also retrieve search results in the form of lists where each lists contains the results that fall under a specific category or context. Categories and sort criteria may be user specified. In an exemplary embodiment, the user may want to search for cars of a particular year and want them categorized according to color, most selling, safety rating and other criteria. The search engine then retrieves search results of cars of that year sorted according to the specified criteria in different lists. It also keeps track of user information so that it can provide contextual information specific or relevant to the user's life. For example, if a user's friend has a car with the specifications that the user is searching for, then the search engine indicates to the user that the user's friend has a car with the same or similar specifications. The search engine mines the information units present in a user's directory in order to present relevant contextual information along with search results. For instance, the user may be interested in six cylinder engine cars as inferred by the system based on information objects in the user's directory. The search engine then indicates to the user as to which of the search results pertain to six cylinder engine cars. This type of contextual data mining can be done as discussed in reference to FIG. 6E. Additionally, this search engine can present to the user information in a variety of formats, not necessarily restricting the search output to text. For instance, the results may be converted from text to speech.

Users can save sites and bookmark sites using tags while browsing web pages. In exemplary embodiment, this can be done using the VOS browser or any other browser that supports tagging and saving. The tags can then be used by web crawlers to rank pages for use in search engines. Conventionally, web crawlers used by search engines rely primarily on the keywords provided by authors of websites, as well as content on web pages. The method described here also utilizes tags provided by ordinary users browsing websites. This method also allows sites to be searched which are not registered with the search engine.

Reference is now made to FIG. 49 O where an exemplary embodiment of the VOS is shown running as a website. The user may be presented with this screen upon logging in. There are many applications available for use in the VOS. An API is also available for developers to build applications for the VOS. Any of the applications such as text editors, spreadsheet applications, multimedia applications (audio/video, photo and image editing), white board can be used collaboratively with other users through an intuitive interface. Collaborative application sharing may be accomplished using techniques discussed with reference to FIG. 7A, B, C, D. Shared users may include friends/family members/other associates from social networking sites or work or home computer accounts. Any changes made to data or applications and other resources can be viewed by all users engaged in the collaboration of these resources and accounts. Users can customize i.e., change the look and feel of the VOS including the background, theme etc. The VOS may also provide an interface that allows for text, video and audio overlay. The calendar feature in FIG. 49 O cross-checks calendars of all users for scheduling an event or an appointment or a meeting and suggests dates convenient for all users involved. A time-stamping feature is also available that lets users timestamp documents. This feature also has an encryption option that allows users to encrypt documents before uploading, acquire a timestamp for the document and retrieve it for future use, keeping the confidential all the while. This might serve useful where time-stamping documents serves as proof of ownership of an invention, for example. Encryption may be accomplished using two encryption keys in exemplary embodiment. One key would be available only to the user and the system would maintain the other key. Remote technical assistance is also provided for this interface. FIG. 49 O also incorporates advanced search (described previously with reference to FIG. 49N), distributed data access (FIG. 49L), advanced user management (FIG. 49M), safety deposit box, media room, launch pad, library, TV/radio and other features as shown in FIG. 49 O. The 'safety deposit box' would contain sensitive materials such as medical records, legal documents, etc. These contents are encrypted and password protected. In an exemplary embodiment, data is encrypted at the source before backing it up on machines. The files may also be accessible or linked to commercial and other public or private large-scale repositories. For instance, medical records of a user could be linked to or accessible from hospital repositories to which a user has been granted limited access. Application layers may be added that mine the contents of the safety deposit box in order to present information to the user in functional and relevant manner. In exemplary embodiment, a 'calendar alert' application may remind the user of pending actions. For instance, based on their medical record, the application would alert the user that a vaccination is due, or a dentist appointment is due. In another instance, the application would alert the user based on financial records that their taxes are due. Similar scenarios may exist for legal documents. The 'media room' would include all files and folders and content that the user wishes to publish or make public such as web pages, videos (such as YouTube videos) etc. The launch pad is a feature that allows users to place objects in a region and take appropriate actions with those objects. It provides an interface for programming actions that can be taken with respect to objects in a variety of formats. The launch pad includes community users who can contribute their applications and other software for use. In exemplary embodiment, a user may move 2D onto a "3D-fy" application widget in the launch pad section in order to transform the 2D images into their corresponding 3D versions. In another exemplary embodiment, a user may add an application in the launch pad area that allows document sharing and editing through a webcam. The library section may include e-documents such as e-books, electronic articles, papers, journals, magazines etc. This section will be equipped with the facility whereby electronic magazines, e-papers etc. to which the user may have subscriptions would be 'delivered' by the subscribed service and made available in this section. The TV/radio feature allows users to browse and view channels in a more traditional sense online. The channels may be browsed using the keyboard or mouse. It may also be combined with the user interface discussed with reference to FIG. 54D. The output of cable TV could also be viewed via this facility. In exemplary embodiment, this can be done by redirecting output from the user's TV or cable source to the user's current machine via the internet or network. The channels can be changed remotely, for example via the interface provided by the VOS or a web interface independent of the VOS. In exemplary embodiment, this may be done by connecting a universal TV/radio/cable remote to a home computer and pointing the device towards the object being controlled via the remote, if necessary (if it's an infrared or other line-of-sight communication device). A software on the computer communicates with the remote to allow changing of channels and other controls. The audio/video (NV) output of the TV or cable is connected to the computer. The computer then communicates with the remote device over the Internet, for display/control purposes in exemplary embodiment. The TV/radio content may include files, and other media content on the user's local or remote machine(s), and/or other user accounts and/or shared resources. The radio may play live content from real radio stations. The system may also allow recording of TV/radio shows. On logging off the VOS, the state of the VOS including any open applications may be saved to allow the user to continue from where the user left upon logging in again. Any active sessions may also persist, if desired.

Figure 49Q:
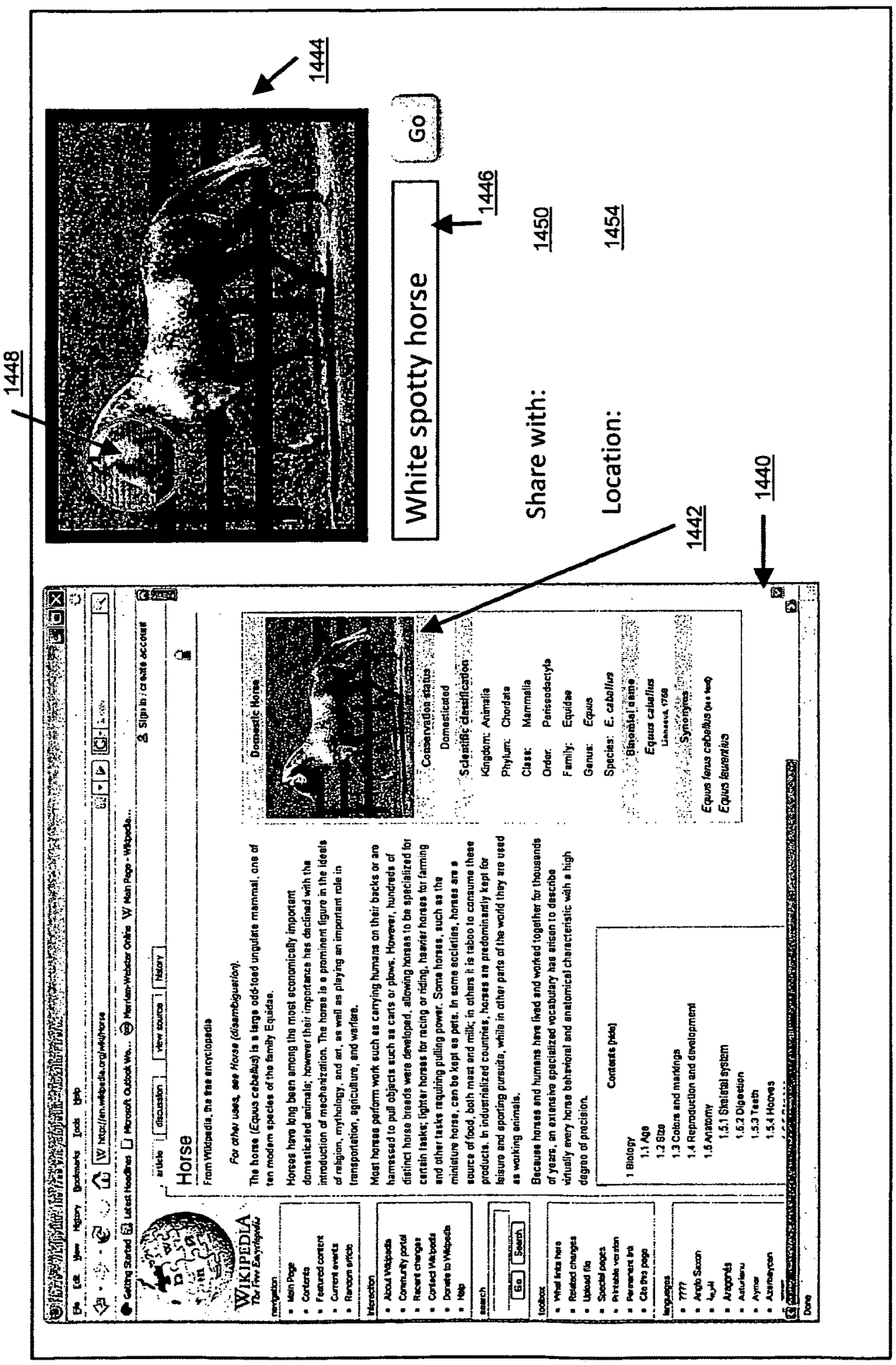

FIG. 49Q provides an additional exemplary embodiment of file tagging, sharing and searching features in the VOS/AFMS. As a user browses web pages in a web browser 1440, which may be the VOS browser, the user may choose to save web page content such as an image 1442. The user would be able to choose the format to save it in, and also edit and save different versions of the image. Here the image 1444 is shown with a border around it. The user can tag images to be saved using keywords 1446. Parts of the image can also be labeled as 1448. The user can specify friends and associate users to share the image with 1450. The location 1454 of the image/file can be specified in abstract terms. For instance, the user can specify the location where the file is saved such as the home or office machine, or 'mom's computer'. Owing to the distributed file storage nature of the VOS, the lower layers can be abstracted out if the user chooses to hide them. The VOS is based on a language processing algorithm. It can recognize keywords and sort them according to grammatical categories such as nouns, verbs, adjectives etc, by looking up a dictionary in exemplary embodiment. It can learn the characteristics of the associated word based on the image. More specifically, the user may be able to train the algorithm by selecting a keyword and highlighting an object or section of the image to create the association between the keyword and its description. For instance, the user may select the keyword 'horse' and draw a box around the horse in the image, or the user may select 'white' and click on a white area in the image. In this way, the system can be 'contextually' trained. Similar training and associative learning can occur in the case of audio and video content. Based on the image keywords, labels and associated characteristics learnt, the system would be able to make contextual suggestions to the user. In exemplary embodiment, the user may search for a 'black leather purse'. The VOS would remember search terms for a period of time and make suggestions. So for instance, if an associate user or someone on the user's friend list bought a leather purse, the system would notify the user of this fact and the source/store/brand of the purse and check the store catalogue from which the purse was bought, for similar or different purse in 'black' and/or 'leather'. In another exemplary embodiment, the system would inform a user 'A' of photos that an associate user 'B' has added containing user A's friend whom the user A wishes to receive updates on. The VOS presents search results in a 'user-friendly' manner to the user. Some aspects may be pre-programmed, some aspects may be learned over time by the VOS with regards what constitutes a user-friendly presentation, whether it involves displaying images, videos, audio, text, and any other file or data in any other format to the user. In exemplary embodiment, a user may search for a friend's photos and the VOS would display images found of the user's friend after properly orienting them, by applying affine/perspective transformations for example, before displaying them to the user. The user's friend may also be highlighted by using markings or by zooming in, as examples in order to make it easier for the user to identify their friend in a group, for instance. User may conduct search using filters or terms that are adjectives such as 'dark', 'purple', 'thick', 'lonely' etc., as well as any class of words that can be used to describe or characterize a noun/object. The VOS searches for relevant information matching these search terms/filters based on tags associated with files and objects. Additionally, computer vision techniques can be used to characterize whole images/video sequences, and objects and components within images/videos.

If the user is listening to a soundtrack, the system can make comments, based on user's mined data, such as 'it's your friend's favourite music track'. It can analyze the soundtrack and find tunes/music similar to the one the user is listening to. It can identify other soundtracks that have been remixed by other users with the track the user is listening to or find soundtracks compatible with the user's taste etc. Extraction of familiar content can be done by the system in exemplary embodiment using a mixture of Gaussians [56] or techniques similar to those in [57]. The user would be able to specify subjective criteria and ask the system to play music accordingly. In exemplary embodiment, the user can specify the mood of the music to listen to, for instance—sad, happy, melodramatic, comical, soothing, etc. Mood recognition of music can be performed via techniques specified in [58]. The system can also monitor user activities or judge user mood through a video or image capture device such as a webcam and play music accordingly or make comments such as 'hey, you seem a little down today' and play happy music or suggest an activity that would make the user happy or show links that are compatible with the user's interests to cheer the user up. The tracks can be played either from the user's local machine or from online stores and other repositories or from the user's friends' shared resources. Detecting the mood underlying a soundtrack and content similar to a soundtrack can be detected using techniques specified in [59].

The VOS can make recommendations to users in other areas by incorporating user preferences and combining them with friend's preferences, as in the case of a group decision or consult i.e., 'collaborative decision-making or consulting'. In exemplary embodiment, users may specify their movie preferences such as 'action, 'thriller', 'drama', 'science fiction', 'real life', etc. They may specify other criteria such as day and time of day they prefer to watch a movie, preferred ticket price range, preferred theatre location, etc. In an online collaborative environment, such as that shown in FIG. 20 in exemplary embodiment, users may consult with each other or plan together. For example, a group of friends may want to go and watch a movie together. Every user has their own movie preference, which the system may incorporate to suggest the best option and other associated information, in this case the movie name, genre, show time etc. Other tools and features to facilitate group decisions include taking votes and polls in favour or against the various options available to the users. The system would then tally the votes and give the answer/option/decision that received the maximum votes. The system may also incorporate general information about the subject of decision in order to make recommendations. For instance, in the movie example, the system may take into account the popularity of a movie in theatres (using box office information for example), ticket deals for a movie, etc. in order to make recommendations. Users can also use the modes of operation described with reference to FIG. 7 for collaborative applications on the VOS. For example, when editing a file collaboratively, as a user edits a document, he/she can see the additions/modifications that are being made by other users.

Figure 49R:
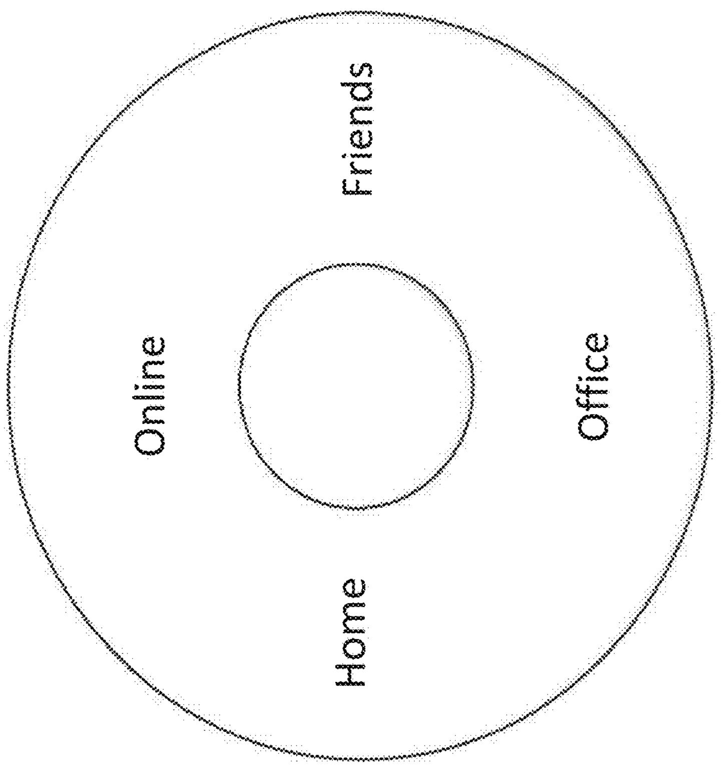

Reference is made to FIG. 49R where an example of a user interface for filtering search data is shown. Users can filter files on the basis of location, file types or by file author(s).

Figure 49S:
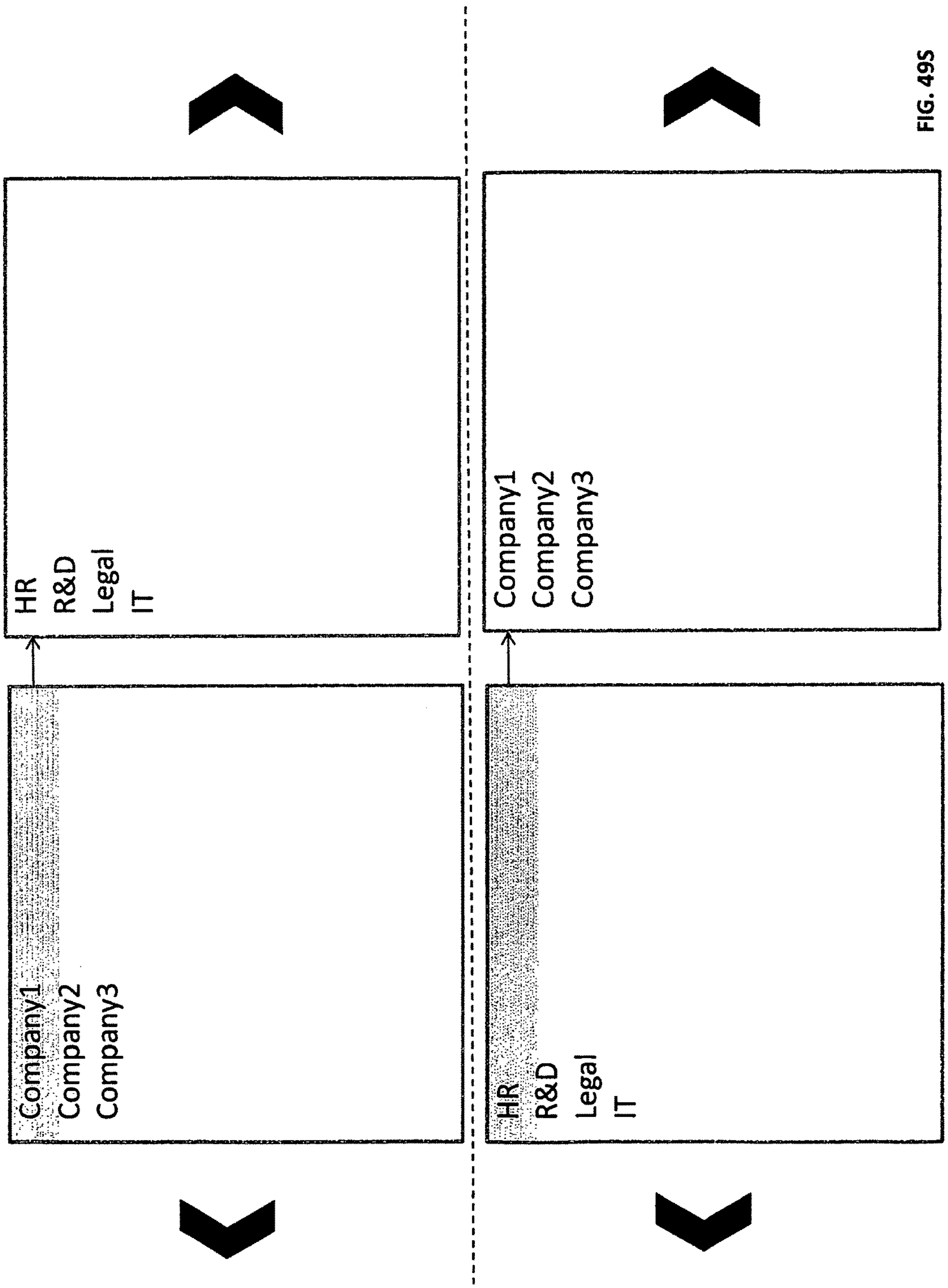
Figure 50:
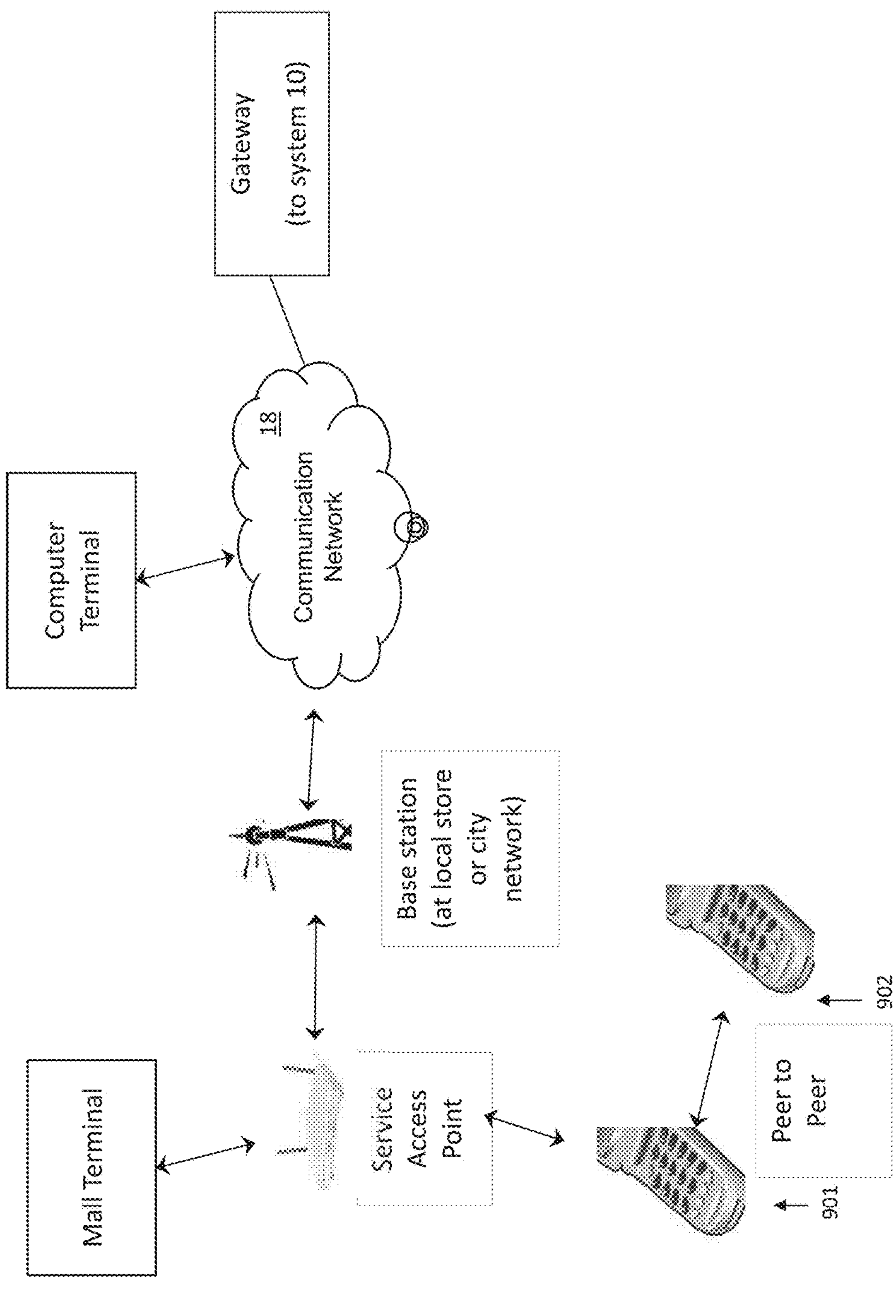
FIG. 50 illustrates a sample mobile communication system when a user is in a store.

Reference is now made to FIG. 49S where an exemplary embodiment of an object oriented file system is shown. Users can specify the structure of a folder (used for storing files on a computer). For example, as shown in the figure, a user can create of folder of type "company" in which the user specifies a structure by creating entries for subfolders of type "HR", "R&D", "Legal", and "IT". Regular folders may also be created. Each of the created folders can have its own structure. The user can have a folder listing all the folders of type "company" as shown in the box on the left in the top row of FIG. 49S. The content of a selected folder is shown in a box on the right in the top row. The user has options to view by "company" or by the structures that constitute that folder, say by "HR". In FIG. 49S, the top row shows an example of viewing by "company". If the user chooses to view by "HR", the view on the right (as shown in the bottom row of FIG. 49S) displays the all the HR folders organized by "company". Other filters are also available to the users that search according to the desired fields of a folder. Arrows are available on the right and left of the views to go higher up or deeper into folders. In another exemplary embodiment, instead of having a structure, the folders and files can have tags that describe the folder and the files. The proposed object oriented file system simplifies browsing and proves the advantages of a traditional file system and a fully fledged database.

Reference is now made to FIG. 20. The collaborative interface shown in FIG. 20 for a shopping trip may be used in the case of other collaborative activities such as application, file, document and data sharing. A generic version of the interface FIG. 20 is now described in exemplary embodiment to illustrate this extension. Panel 241 lists friends involved in the collaboration. An application panel replaces the store panel 242 and displays shared applications of users involved in the collaboration. Panel 247 lists the user's documents, data files and other resources. Panel 248 lists the user's friends' documents, data files and other resources. Window 243 would facilitate collaborative sharing of applications, documents, data, other files and resources between users of a collaboration. Users can direct any signal to 243—video, audio, speech, text, image, including screen capture, i.e., they may specify a region of the screen that they wish to share in 243, which could include the entire desktop screen. (A perspective correction may be applied to documents that are being shared. For example, if a video of a talk is being shared and the video of the slides of the presentation is being shot from an angle (as opposed to the camera being orthogonal to the screen), a perspective transform may be applied so that lines of text on the screen appear horizontal to ease viewing) Users may be able to drag and drop applications, files, documents, data, or screenshots as well as contents/files captured by the screenshots and other resources into window 243 during collaborative sharing. Instances of collaboration include shared use of applications; viewing, creating, editing, saving documents or image files etc. Window 243 has a visual overlay for users to write or draw over to permit increased interactivity during collaborative discussions. This is analogous to whiteboard discussions except that here the overlay may be transparent to permit writing, scribbling, markings, highlighting over content being shared in 243. All this content may be undone or reversed. The overlay information can be saved without affecting the original content in 243 if the user chooses to do so. Overlay information can be saved in association with the original content. The system also allows a 'snap to object' feature which allows users to select and modify objects in the view. The toolbar 239 provides overlay tools and application and/or document and file specific tools for use with the specific application and/or file or document or data being shared in 243. View 243 also supports multiple layers of content. These layers could be hidden or viewed. The screen size of 243 is resizable, movable, dockable, undockable. All sessions and content (viewed, edited, text, speech, image, video, etc.), including collaborative content and information may be saved including all environmental variables. When editing a file collaboratively, as a user edits a document, he/she can see the additions/modifications that are being made by other users. Collaborative environments such as these can be specialized to cater to occupation, age group, hobby, tasks, and similar criteria. In an exemplary embodiment, a shared environment with features described above may exist for students where they can collaborate on homework assignments and group projects as well as extracurricular activities such as student council meetings, organization of school events etc. Specialized tools to assist students collaborate on school related activities is provided with toolbar 239. This environment would also contain applications specific to the context. For instance, in the students' collaborative environment, students would be able to provide reviews on courses or teachers using the application provided for this purpose.

Furthermore, the whiteboard may be integrated with a 'convert to physical model' feature that transforms a sketch or other illustration or animation on the whiteboard to an accurate physical model animation or video sequence. This may be accomplished via techniques similar to those described in [3]. In exemplary embodiment, a user may draw a ball rolling on a floor which then falls off a ledge. The physics feature may convert the sketch to an animation sequence where the floor has a friction coefficient, and the ball follows Newton's Laws of Motion and the Laws of Gravitation while rolling on the floor or free-falling. In addition, voice to model conversion may occur where the semantics underlying speech is analyzed and used to convert to a physical model. This may be accomplished by converting speech to text and then text to picture [60] and then going from picture to model [3]. Objects seen in a webcam may be converted to a model [3]. Users can then be allowed to manipulate this object virtually. The virtual object's behaviour may be modeled to be physically plausible. Based on the content of the whiteboard deciphered through OCR optical character recognition techniques or sketch to model recognition [3] or speech to model recognition, related content (for example advertisements) may be placed in the proximity of the drawing screen and/or related content may be communicated via audio/speech, and/or graphics/images/videos.

The interface shown in FIG. 20 may be used for exhibitions, where different vendors can show their product offerings.

Figure 51A:
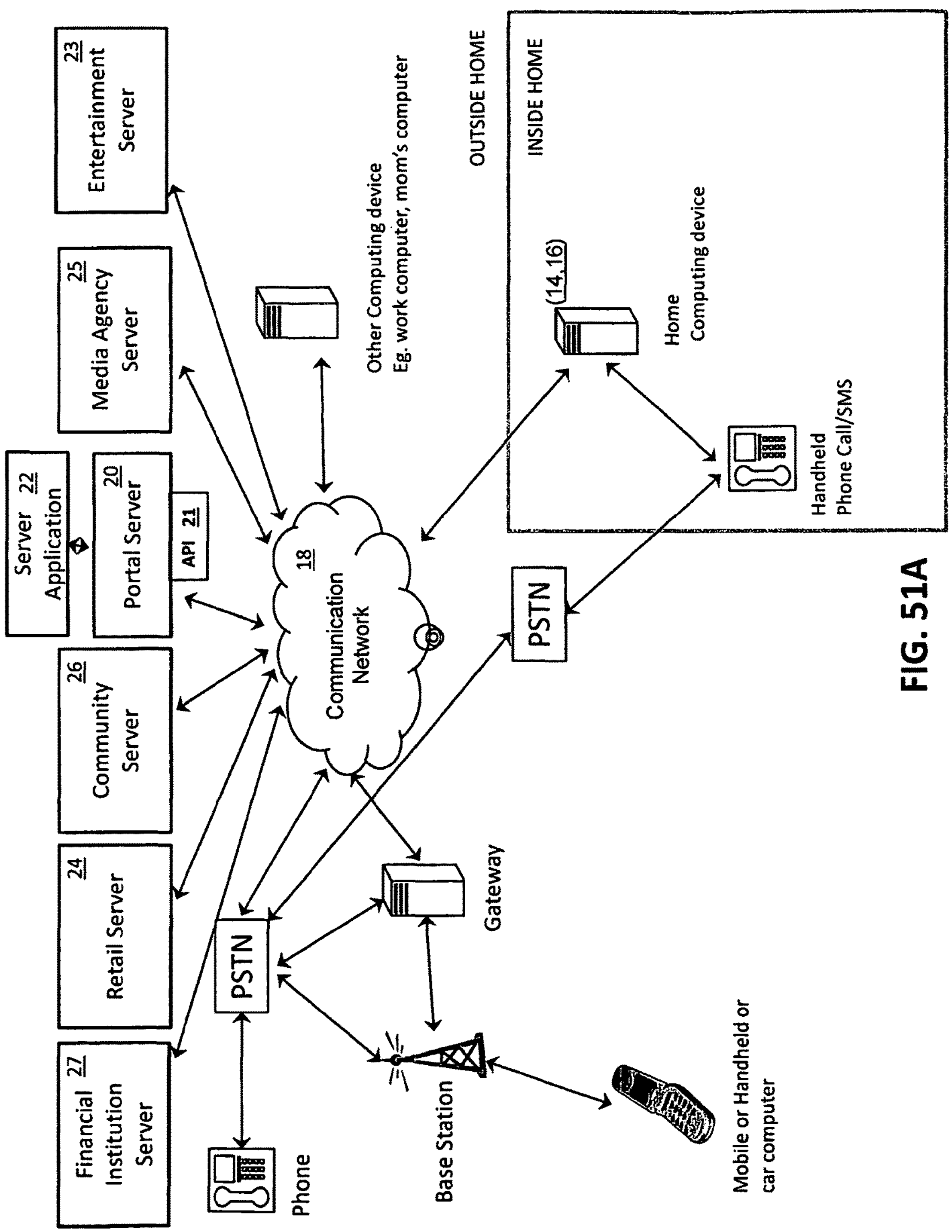
FIG. 51A illustrates a sample communication network demonstrating external connections to system 10.

Reference is now made to FIG. 51A where a communication network demonstrating external connections to system 10, is shown in exemplary embodiment. FIG. 51A shows devices, systems and networks that system 10 can be connected to, in exemplary embodiment. System 10 is connected to the Public Switched Telephone Network (PSTN), to cellular networks such as the Global System for Mobile Communications (GSM) and/or CDMA networks, WiFi networks. The figure also shows connections of system 10 to exemplary embodiments of computing applications 16, and exemplary embodiments of computing devices 14, such as a home computing device, a work computing device, a mobile communication device which could include a cell phone, a handheld device or a car phone as examples. The AFMS/VOS may be connected to external devices, systems and networks in a similar manner as system 10. The AFMS may additionally be connected to system 10 itself to facilitate shopping, entertainment, and other services and features available through system 10.

In the following discussion, a 'Human Responder Service', its functionality and application is described. This service makes use of the data, and applications connected to the network shown in FIG. 51A. This service may be available on the portal server 20 as part of system 10, or it may be implemented as part of the virtual operating system, or it may be available as an application on a home server or any of the computing devices shown in FIG. 51A and/or as a wearable device and/or as a mobile device. The Human Responder Service or Virtual Secretary is a system that can respond to queries posed by the user regarding user data, applications or services. The system mines user data and application data, as well as information on the Internet in order to answer a given query. An exemplary embodiment of a query that a user can pose to the system through a mobile communication device (cell phone or handheld in an exemplary embodiment) includes "What is the time and location of the meeting with Steve?" or "What is the shortest route to the mall at Eglinton and Crawford road?" or "Where is the nearest coffee shop." Further refinements in the search can be made by specifying filters. An exemplary embodiment of such a filter includes a time filter in which the period restriction for the query may be specified such as "limit search to this week" or "limit search to this month". The filters may also be as generic as the query and may not necessarily be restricted to time periods. The input query may be specified in text, voice/audio, image and graphics and/or other formats. In an exemplary embodiment, the user can send a query SMS via their mobile device to the Virtual Secretary (VS) inquiring about the location of the party the user is attending that evening. On receiving the SMS request, the VS looks up the requested information on social networking sites such as Facebook of which the user is a member, the user's calendar and email. After determining the requested information, the VS then responds to the user by sending a reply SMS with the appropriate answer. If multiple pieces of information are found, the VS may ask the user which piece of information the user would like to acquire further details on. The user may also dictate notes or reminders to the VS, which it may write down or post on animated sticky notes for the user.

In an exemplary embodiment, the VS may be implemented as an application 16 on a home computing device 14 that is also connected to the home phone line. Calls by the VS can be made or received through VoIP (Voice-over-Internet-Protocol) or the home phone line. The VS can also be connected to appliances, security monitoring units, cameras, GPS (Global Positioning Systems) units. This allows the user to ask the VS questions such as "Is Bob home?" or "Who's at home?" The VS can monitor the activity of kids in the house and keep an eye out for anomalies as described with reference to FIG. 52B. Prior belief on the location of the kids can come from their schedules which may be updated at any time. Other services are available to the user include picking up the home phone and asking the VS to dial a contact's number, which the VS would look up in the user's address book on the user's home computer or on a social networking site or any of the resources available through the VOS. The user may click on an image of a user and ask the VS to dial the number of that user. The user may point to a friend through a webcam connected to the VS and ask the VS to bring up a particular file related to the friend or query the VS for a piece of information related to the friend. The VS may also monitor the local weather for anomalies, and other issues and matters of concern or interest to the user. For instance, if a user is outside and the VS system is aware of a snowstorm approaching, it sends a warning notification to the user on their mobile phone such as, "There is a snow-storm warning in the area John. It would be best if you return home soon." Other issues that the VS may monitor include currency rates, gas prices, sales at stores etc. This information may be available to or acquired by the VS via feeds from the information sources or via websites that dynamically update the required information.

Figure 51B:
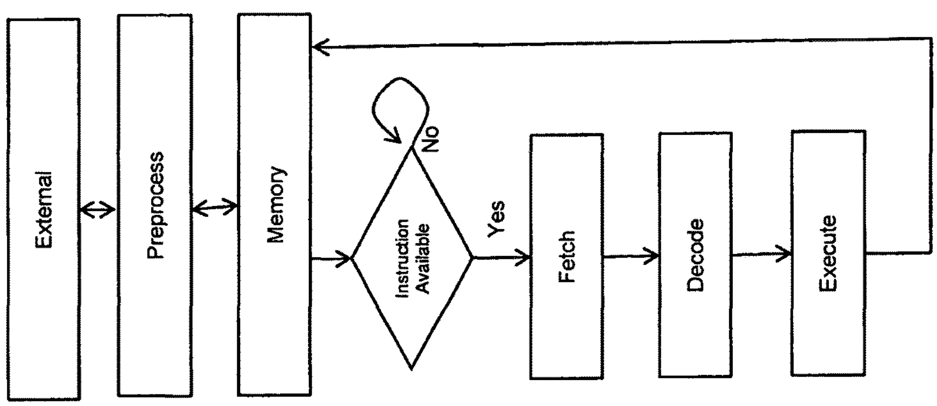
FIG. 51B illustrates a sample flowchart showing the operation of the VS.

One exemplary embodiment of the VS is described in FIG. 51B. The system waits for external user commands. Commands can come via SMS, voice/audio/speech through a phone call, video, images. These commands are first pre-processed to form instructions. This can be accomplished using speech-to-text conversion for SMS, voice/audio/speech; parsing gestures in videos; and processing images using methods described with reference to FIG. 52A. These instructions are then buffered into memory. The system polls memory to see if an instruction is available. If an instruction is available, the system fetches the instruction, decodes and executes it, and sends it back to memory. The response in memory is then preprocessed and communicated to the external world.

The VS answers queries by looking up local information—user, application data on the local machine, and then proceeds to look up information in other networks to which the user has access, such as web-based social networks, and the internet. It may also automatically mine and present information where applicable. In exemplary embodiment, when a user receives a phone call, the VS searches address books on the local machine and/or the Internet and/or social networks such as web-based, home or office networks to look up a person's name, phone and other information, including pictures, and display the appropriate information during an incoming phone call. If the information is not on any of the user's networks, the VS may look up public directories and other public information to identify caller and source. The VS may also look up/search cached information that was previously looked up or that is available on the local machine. Additionally, the VS gives information about the type of caller and relation between caller and user. For instance, the VS informs the user whether the call is from a telemarketing agency or from the dentist or from Aunt May in San Francisco etc. The VS may also specify location of the caller at the time of the call using GPS and positioning and location techniques. The VS may make use of the colloquial language to communicate with the user. The call display feature can be used as a standalone feature with cell phones and landlines and VoIP phones. A user may query the VS with a generic query such as 'What is an Oscilloscope?' The VS conducts a semantic analysis to determine the nature of the query. In this case, it determines that the query is related to a definition for a term. In this case, it would look up a source for definitions such as an encyclopaedia, based on its popularity and reliability as a source of information on the internet, or as specified by the user. As an example, it may look up Wikipedia to answer the user's query in this case.

Services based on identifying users' location are available through the VS. The VS may also be linked to, accessible to/by mobile phones or handheld devices of members in the user's friends' network, businesses in the user's network and other users and institutions. Location can be computed/determined using mobile position location technologies such as the GPS (Global Positioning System) or triangulation data of base stations, or a built in GPS unit on a cell phone in exemplary embodiment. The VS can inform the user if friends of the users are in the location or vicinity in which the user is located at present; and/or indicate the position of the user's friend relative to the user and/or the precise location of a given friend. In exemplary embodiment, if the user is at a grocery store, and the VS detects that a friend (George) of the user is around the corner, then the VS may point this out to the user saying, "Hey, George is at the baked goods aisle in the store." In order to establish location in the store, the VS may establish a correspondence between the GPS location coordinates on the store map available via the retail server 24. The VS may additionally overlay the location coordinates on a map of the store and display the information on the user's handheld device. The VS may display a 'GPS trail' that highlights the location of a user over time (GPS location coordinates in the recent past of a user being tracked). The trail may be designed to reflect age of data. For example, the colour of a trail may vary from dark to light red where the darker the colour, the more recent the data. The users may communicate via voice and/or text and/or video, and/or any combination of the above. The content of the conversation may be displayed in chat boxes and/or other displays and/or graphics overlaid on the respective positions of the users on the map. Also, the user can query the VS to identify the current geographic location of a friend at any given time. Therefore, identification of a friend's location is not necessarily restricted to when a friend is in the user's vicinity. Users may watch live video content of their friend on their mobile device from their location. They may interact with each other via an overlaid whiteboard display and its accompanying collaborative tools as described with reference to FIG. 20. In exemplary embodiment, with reference to FIG. 56, 'User A' may be lost and he may phone his friend, 'User B' who can recognize the current location of User A based on the landmarks and video information User A transmits via his mobile. User B may also receive GPS coordinates on her mobile via the VS. User B can then provide directions to User A to go left or right based on the visual information (images/video) that is transmitted to User B's mobile via User A's mobile. User B may also scribble arrows on the transparent overlay on the video, to show directions with reference to User A's location in the video, which would be viewable by User A. Based on the content of the whiteboard deciphered through OCR optical character recognition techniques or sketch to model recognition [3] or speech to model recognition, related content (for example advertisements) may be placed in the proximity of the drawing screen or anywhere else on the mobile's screen and/or related content may be communicated via audio/speech, and/or graphics/images/videos.

Users may request to appear invisible or visible to friends and/or other users, so that they cannot be located by the user they appear invisible to. Businesses may use location data for delivery purposes in exemplary embodiment. For instance, pizza stores may deliver an order made via the VS to the user placing the order, based on their GPS coordinates. Users can request to be provided with exact 'path to product' in a store (using the communication network and method described with reference to FIG. 50 previously), upon which the VS provides the user with exact coordinates of the product in the store and directions to get there. The product location and directions may be overlaid on a store/mall map. Also, in virtual stores/malls/tourist locations and other virtual places described in this document, users may request 'path to products', and they will be provided with product location information and directions overlaid on a map of the virtual world. Alternatively, they may be directed to their destination by a virtual assistant or they may directly arrive at their virtual destination/product location in the virtual world.

Order placements and business transactions can also be conducted via a user's mobile device. A user may view a list of products and services on their mobile device. The user may place an order for a product or service via their mobile device via SMS or other services using the WAP protocol or through a cell phone based browser in exemplary embodiment. The vendor is informed of the order placed through a web portal and keeps item ready for pick up or delivers the item to address specified by user or the current location of user, which may be determined using a cell phone location technique such as GPS and cell-phone triangulation. Users may pre-pay for services or make reservations for services such as those provided in a salon via their mobile device and save waiting time at the salon. Vendors may have access to 'MyStore' pages, as described in exemplary embodiment previously with reference to FIG. 42. Once the order and transaction is approved, a confirmation is sent to the user. Electronic receipts may be sent to the user on their cell phone via email, SMS, web mail, or any other messaging protocol compatible with cell phones. Other information can be linked to the cell phone based on electronic receipts such as warranty and other information as described previously with reference to electronic receipts.

In an exemplary embodiment, a user 'Ann' may be a tourist visiting Italy for the first time, and would like to find out which restaurants have good ratings and where they are located. The user can query the system to determine which restaurants 'Jim' (a friend who visited Italy recently) ate at, their locations, and the menu items he recommends. The system, in this case, looks up Ann's friend's network on a social networking site, in exemplary embodiment, to access and query Jim's account and acquire the appropriate information. Jim has a virtual map application where he has marked the location of the restaurants he visited when he was in Italy. The restaurants each have a digitized menu available (hyperlinked to the restaurant location on the map) where items can be rated by a given user. Given that Ann has permission to access Jim's information, the information pertaining to location of the restaurants that Jim visited and liked and the ratings of menu items of those restaurants will be made available to Ann on her mobile device. Alternatively, Jim's travel information may be available from a travel itinerary that is in document or other format. In this case, the restaurant location information may be overlaid onto a virtual map and presented to Ann. The menu items that Jim recommended, along with their ratings may be hyperlinked to the restaurant information on the map in document, graphics, video or other format. Other files such as photos taken by Jim at the restaurants, may be hyperlinked to the respective restaurant location on the map. Thus, in this example, the VS utilized information on a friend's account that may be located on a user's machine or other machine on the local network, or on the community server 26 or on a remote machine on the internet; a map application that may be present on the local machine, or on the portal server 20 or other remote machine; and restaurant information on the retail server 24 or other machine. In this manner, the VS can combine information and data and/or services from one or more storage devices and/or from one or more servers in the communication network in FIG. 51A.

Users may utilize the VS for sharing content 'on the fly'. A website or space on a web server may exist where users can create their 'sharing networks'. Alternatively, sharing networks may be created via a local application software that can be installed on a computing machine. A sharing network comprises member users whom the user would like to share content with. A user may create more than one sharing network based on the type of content he/she would like to share with members of each network. Members may approve/decline request to be added to a sharing network. A space is provided to each sharing network where the members in the sharing network may upload content via their mobile communication device or a computing machine by logging into their sharing network. Once the user uploads content into the sharing space, all members of that particular sharing space are notified of the update. Sharing network members will be informed immediately via an SMS/text message notification broadcast, as an example. Members may change the notification timing. They may also alternatively or additionally opt to receive notification messages via email and/or phone call. In exemplary embodiment, a user may upload videos to a sharing space. Once the video has been uploaded, all the other members of the sharing network are notified of the update. Members of the network may then choose to send comments 'on the fly' i.e., members respond to the video update by posting their comments, for which notifications are in turn broadcast to all members of the sharing network. In another exemplary embodiment, the VS may directly broadcast the uploaded content or a summary/preview/teaser of the uploaded content to all members of the sharing network. Real-time communication is also facilitated between members of a sharing network. Chat messages and live video content such as that from a webcam can be broadcast to members of a sharing network in real-time. The sharing network feature may be available as a standalone feature and not necessarily as part of the VS.

The tourism industry can make use of the VS to provide users with guided tours as the user is touring the site. Instructions such as 'on your right is the old Heritage building', and 'in front of you are the Green Gardens', may be provided as the user browses a site and transmits visual and/or text and/or speech information via their mobile and/or other computing device to the VS. In exemplary embodiment, a user may transmit site information in the form of images/videos to the VS, as he browses the site on foot. Alternatively or additionally, the VS can provide tour guide information based on the GPS coordinates of a user. Instructions may be provided live as the user is touring a site. The user may transmit their views via a webcam to the tour application, which is part of the VS. The tour application then processes the images/videos in real-time and transmits information on the what is being viewed by the user (i.e., 'guided tour' information). Users may ask the VS/tour application queries such as 'What is this' and point to a landmark in the image or ask 'What is this white structure with black trimmings to my left?'. Thus, the VS tour application may decipher speech information and combine the query with image/video and any visual information provided to answer the user. The tour instructions/information can be integrated with whiteboard features so that landmarks can be highlighted with markings, labels etc., as the user is touring the site. The VS may alternately or additionally transmit site information/tour instructions based on the GPS coordinates and orientation of the user. Orientation information helps to ascertain the direction in which the user is facing so that appropriate landmark referencing may be provided such as 'to you left is . . . ', 'turn right to enter this 14th century monument' etc. Orientation may be determined by observing two consecutive coordinates and computing the displacement vector. Tour information/instructions may be registered with existing map applications and information and/or street view applications and information (for example Google Street View). Computationally intensive tasks, such as registration of the user's view with maps or other views in a database, may be transmitted to a remote server and the results may be transmitted back to the user's mobile device. Advertisement information may be overlaid/linked to relevant sites on user views on a mobile in exemplary embodiment.

Data from the user's mobile device may be used to reconstruct a 3D model of the scene, and may be available for viewing remotely. The reconstruction, if too intensive' may occur on a remote machine.

Instructions may also be catered to users on foot (instead of in a vehicle for example), via the handheld. These include instructions specific to a person on foot, such as 'turn around', 'look up', in exemplary embodiment. In the case of directions to a location as well, users may be provided alternate instructions to arrive at a destination when traveling by foot (thus, directions are not limited to driving directions).

The VS may be integrated with a map application where users can directly or mark recommended places to visit. These marked places may be hyperlinked with to-do lists that specify the activities or events the user can engage in at those places; or blogs that catalogue user experiences. Photos, videos and other graphics and multimedia content may be linked to a place on the map describing the place, its significance and its attractions. These may also be pictures/videos taken by friends, virtual tours etc. A user may add or request to see specific feeds for a given place. In exemplary embodiment, the local news headlines corresponding to a selected place on the map may be displayed. Areas of interest such as general news, weather, science or entertainment, may be selected by the user to filter and display news and other information of interest. Event feeds that display events or activities on a particular month or week or day of the year at a place may be requested. Generic user videos capturing user experience or travel content at a place may be displayed. These may be videos that are extracted from a video uploading site such as YouTube, based on keywords such as place or other default keywords or keywords specified by the user. Local shopping feeds containing information about the places with the most popular or cheap and other categories of shopping items may be linked or associated with the places on the map. Most popular local music and where to buy information may be associated with a place. Other local information such as car rentals, local transit, restaurants, fitness clubs and other information can be requested by the user. Thus, local information is made easily available on any computing or mobile or display device. In addition, map overlays and hyperlinks to appropriate sources/places are used in order to make information presentation as user-friendly as possible. The user can also request the VS to display itineraries that include cities, places, events, attractions, hotels that the user chooses. In addition, the user may specify filters such as price range and time period to include in forming the itinerary. The VS would scan the appropriate databases detailing places, events, attractions and hotels and their associated information such as prices, availability, ticket information etc. in order to draw up a suggested itinerary accommodating user requirements as best as possible. The user may make all reservations and purchases of tickets online. The VS would direct the user to the appropriate reservation, purchasing and ticketing agents. Alternatively, the VS may be equipped with a facility to make hotel, event bookings and ticket purchases (for events, attractions etc.) online.

The VS may be used to connect to the services in a local community as well. Users can request an appointment at the dentist's office, upon which the system will connect to a scheduling software at the dentist's end (service's end), in exemplary embodiment. The scheduling software would check for available slots on the day and time requested by the user, schedule an appointment if the slot is available and send a confirmation to the VS. The VS then informs the user of the confirmation. If the available date and time is already taken or not available, the scheduler sends the user a list of available slots around the day and time the user has requested. The VS provides this information to the user in a user-friendly format and responds to the scheduler with the option the user has selected.

A facility is a 'Centralized Communication Portal' (CCP) which provides users with access to all emails (work, home, web based, local application based), voice messages, text messages, VoIP messages, chat messages, phone calls, faxes and any other messages/calls available through electronic messaging services. The CCP may take the form of a web based software or a mobile device software and/or both and/or local application for use on a computing machine or a mobile device or a landline phone. The CCP is equipped with text-to-speech and speech-to-text conversion so that it is possible for users to access emails in the form of voice messages, and voice messages in text format, in exemplary embodiment. The user can set the display name and number or email address of outgoing phone calls, emails, SMS or the system can determine these automatically based on factors such as who the message is for or what the context of the message is, etc. The system only lets the users set the phone number or email address of outgoing messages if the user owns these phone numbers and email addresses. In an exemplary embodiment, the owner ship of a phone number or email address is established by posing a challenge question to the user the answer to which is sent to the phone number or email address.

While a person is on a call, the CCP can simultaneously make a recording of the conversation, if access is granted by the participants of the call; convert the call recording into text; reformat the message if necessary and provide the user with options to do something with the recording such as email or save call recording, in an exemplary embodiment. The CCP can keep track of a call or message duration and/or size. This may be useful in case of professional services that charge per call or message for their services provided via phone or email or other messaging service(s). The CCP allows users to program features. In an exemplary embodiment, users can program the CCP to respond in a certain way to an incoming call. For example, the user may program the CCP to ignore call or forward the call to an answering machine, if the incoming call is from a specific number or person, for instance. In another exemplary embodiment, a user (Ann, for example) may program the CCP to respond to calls by automatically receiving the call after two rings, for example, and playing a message such as 'please state your name', or 'please wait until Ann picks up', or playing audio tracks from a certain folder available on the user's local machine or a remote machine or through a web page. If the caller user is logged into their CCP account, available through a web page or a local application on their computer or mobile device, then they may be able to view videos that the receiver user (i.e., the user receiving the call) has programmed the CCP to play before they pick up the call (the video may play via a visual interface provided by the CCP). In another exemplary embodiment of programming options, users may be able to set forwarding options for incoming calls and emails. For example, the user may program the CCP to forward all incoming emails (chat or text messages) or incoming emails (chat or text messages) from specific users to a mobile handheld/phone; forward incoming calls to a mobile phone to an email address or to another cell phone(s), in exemplary embodiments. Images in emails/text/chat messages may be converted to text using computer vision techniques such as those described with reference to FIG. 52 and FIG. 6. Text to speech conversion may then be carried out and, thus image information in text/email/chat messages can also be made available via voice messages or voice chat. PBX (Private Branch eXchange) systems may be integrated with the CCP.

An easy-to-use visual interface may be provided by the CCP. When a call is made, the interface may display the status of the receiver user. In exemplary embodiment, the status of a user may be: busy, back in 10 minutes, not in, hold/wait, leave message, attending another call, call another number: #####, etc. In another exemplary embodiment, a virtual character may greet the caller via the visual interface and inform the caller of the receiver's status, and instruct the caller to leave a message or direct the caller to another phone number or provide alternate directions. In another exemplary embodiment, a video recording of the receiver user may greet the caller user and provide status information and/or instructions to leave a message, call another number, hold/wait etc. Image to text conversions may also be useful to convey visual elements of a conversation (in addition to the audio/speech elements), in the case that users would like to view webcam/video conversations in text message form or in audio/voice format. Text to image conversion can be carried out using techniques similar to those described in [60]. This conversion may be utilized when users opts to see email/chat/text/SMS messages via the visual interface. In this case, in addition to displaying text information, image information obtained via text-to-image conversion may be displayed. Alternatively, this converted image information can be displayed as a summary or as a supplement to the actual messages.

Users may additionally connect to each other during a call or chat or email communication via webcam (s) whose output is available via the CCP's visual interface. Any or all of the collaborative tools, and methods of interaction discussed with reference to FIG. 20 may be made available to users by the CCP for collaborative interaction between participants during a call or chat or email communication via the CCP's visual interface. Users may be able to organize their messages, call information and history in an environment that allows flexibility. In exemplary embodiment, users may be able to create folders and move, add, delete information to and from folders. They may tag messages and calls received/sent. They may organize calls and messages according to tags provided by the system (such as sender, date) or custom tags that they can create. Call and message content and tags are searchable. Spam detection for phone calls, chat, text and voice messages (including VoIP) is integrated with the CCP, in addition to spam detection for email. In an exemplary embodiment, this is accomplished using a classifier such as a Naïve Bayes classifier [7, 61]. In addition, spam feature lists may be created using input from several users as well as dummy accounts. In an exemplary embodiment, if a user's friend who receives the same or similar email, phone call, SMS, etc. marks it as spam then the probability of that message being spam is increased. Dummy accounts may be setup and posted on various sources such as on the internet and messages collected on these accounts are also marked with a high probability of being spam. Users also have the option to unmark these sources/numbers as spam. A signature may be used by the CCP to confirm the authenticity of the source of the message. In an exemplary embodiment, this signature is produced when the user's friend logs into the system. In another exemplary embodiment, this signature may be produced based on the knowledge of the user's friend available to the CCP. Additionally, the CCP may inform the user that a particular number appears to be spam and if the user would like to pick up the phone and/or mark the caller as spam. The CCP may additionally provide the user with options regarding spam calls such as: mute the volume for a spam call (so that rings are not heard), direct to answering machine, respond to spam call with an automated message, or end call, block caller etc. Users may arrange meetings via the CCP. A user may specify meeting information such as the date, time and location options, members of the meeting, topic, agenda. The CCP then arranges the meeting on behalf of the user by contacting the members of the meeting and confirming their attendance and/or acquiring alternate date, time, location and other options pertaining to the meeting that may be more convenient for a particular member. If any of the users is not able to attend, the CCP tries to arrange an alternate meeting using the date/time/location information as specified by the user that is not able to attend and/or seeks an alternate meeting date/time/location from the user wishing to arrange the meeting. The CCP repeats the process until all users confirm that they can attend or until it synchronizes alternate date, time and location parameters specified by all members of the meeting. Users may specify the best mode such as email, phone, fax, voice, chat, text message via which the CCP may contact them to arrange a meeting. Users can also confirm whether they would be attending a meeting in person or via video/phone conferencing etc. Instead of providing only a binary classification ("spam" or "not spam"), the spam detector may provide more levels of spam detection; it may provide several levels of classification. If desired by the user, it can automatically sort emails, phone calls, SMS, etc. based on various criteria such as importance, nature (eg. social, work related, info, confirmation, etc.) etc. This may be done in an exemplary embodiment by learning from labels specified by users and/or attributes extracted from the content of the email, phone call, SMS etc. using Naïve Bayes. In an exemplary embodiment, a technique similar to that used in [62] is used for ranking.

The CCP may assign users a unique ID similar to a unique phone number or email address, which may consist of alphanumeric characters and symbols. In exemplary embodiment, it may assume the form 'usernarne#company'. It may be tied to existing top-level domains (TLDs), for example, the '.com' domain. When someone dials or types this ID, a look up table is used to resolve the intended address which could be a phone number or email/chat address or VoIP ID/address or SMS ID. Users may specify whether they would like to use the CCP ID as the primary address to communicate with any user on their contact list. Users may also use the CCP ID as an alias.

The CCP may be integrated with the VS and/or incorporates one or more features of the VS, and vice versa.

An example of a "Job Application and Resume Management Service" (JARMS) is described next. This application may be available on the portal server 20. Users can create their "Job Profile" via this service. Forms and fields will be available for users to document their background and qualifications including their personal history, education, work and voluntary experience, extra-curriculars, affiliations, publications, awards and accomplishments, and other information of relevance to their careers. This service would provide questionnaires that may be useful to record or test skill subsets of the user. Hiring managers may find this additional information useful to assess a given job applicant's skills. Furthermore, commonly asked questions by Human Resources (HR) personnel may be made available for users to post answers to. This would assist the employers in further reducing application processing times. The skill and HR questions may be posted in text, audio, video and any other multimedia format. The user responses to those questions may also be posted in text, audio, video and any other multimedia format. A "Portfolio" section is available that assists the user in developing, preparing and uploading documents and other files of relevance to their career, for example, resumes, posters, publications, bibliographies, references, transcripts, reports, manuals, websites etc. This service will make it convenient for the user to upload documents in a variety of formats. Also, the user can design different resumes for application to different types of jobs. A tools suite assists the user in document uploading, manipulation and conversion. In exemplary embodiment, a PDF (Portable Document Format) conversion tool, document mark-up, and other tools are provided to the user. Users can upload transcripts directly from their University Registrar/Transcript offices, or websites through this service. The transcripts may be authenticated by the Universities or certified electronically. In this manner, the employers can be assured of the validity of the transcript uploaded through this service. References and their contact information is provided by the user via this service. Links to the accounts of the referees on JARMS or social networking sites such as LinkedIn may also be provided on the user's profile. Videos from YouTube or other sources that document user accomplishments or work such as a conference presentation or an online seminar or a product demonstration and other examples may be uploaded.

JARMS is equipped with additional security features so that information is not easily viewed or captured by third party individuals or software etc. Employers to which users are interested in submitting their application to may be provided with access to the user's job profile. Users may also select the account resources they would like to make accessible to the employer.

Figure 53:
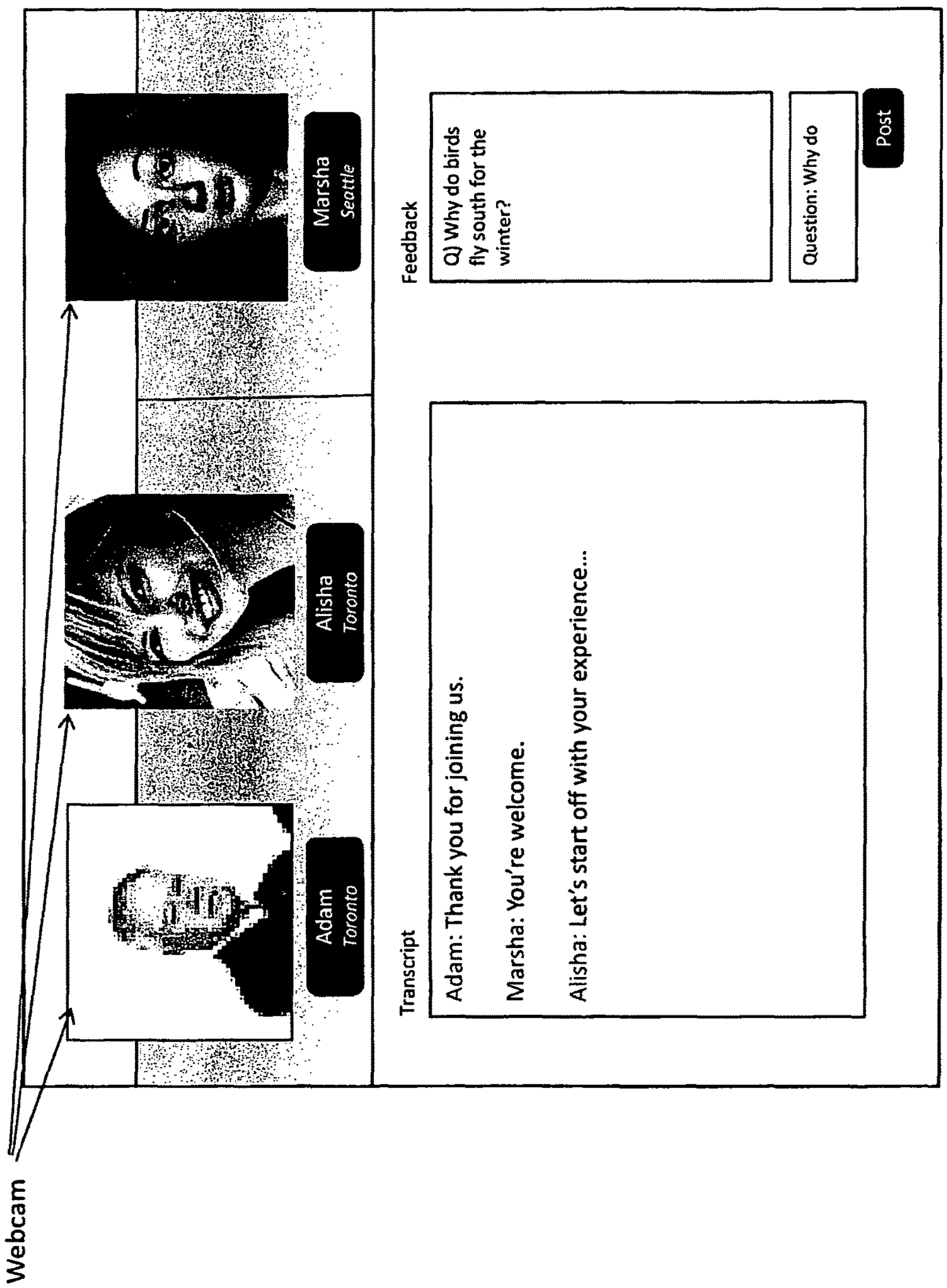
FIG. 53 illustrates a sample interface for broadcasting and collaborative communication.

An "Interview Room" facility is available through JARMS which is an online space where real time interviews can be conducted. Visual information along with audio and other content from a webcam, camcorder, phone etc. may be broadcast and displayed in windows that assume a configuration as shown in FIG. 53, so that all users in an interview session can be seen simultaneously. The interview room may be moderated by personnel from the institution or company that is conducting the interview. This session moderator can allow or disallow individuals from joining the session. The interviewee and interviewers can view each other simultaneously during the interview session in the display windows in FIG. 53, by using video capture devices at each end and broadcasting the captured content. The interview may involve video and audio content only or it may be aided by speech to text devices that convert audio content to text and display content as in the 'Transcript' display box FIG. 53. Alternately, text input devices such as a keyboard/mouse may be used to enter text. JARMS sessions may be private or public. These sessions may be saved or loaded or continued or restored. The session content including video content may be played, paused, rewinded, forwarded.

The collaborative broadcasting and viewing of content in windows arranged as in the configuration given in FIG. 53 may occur during an online shopping session or during a news coverage session online or a technical support session and during other collaborative communication and broadcast sessions online. In exemplary embodiment, during a news broadcast session, questions posed by viewers of the news story will appear in a 'Live Viewer Feed' (Feedback) box. Another feature, "Live Image Retrieval" looks up/searches for images corresponding to the words relayed in the broadcast in real-time, either on the local machine or the internet or a file or folder specified by one or more of the users involved in the collaborative session, and displays the appropriate images during the session to the viewers in another display window. The system may look up image tags or filename or other fields characterizing or associate with the image in order to perform the image search and retrieval corresponding to words in the collaborative conversation or broadcast. In exemplary embodiment, this can be accomplished as shown in [60]. The Live Image Retrieval (LIR) application can be used with other applications and in other scenarios. In exemplary embodiment, a user may specify an object in text or voice or other audio format, during online shopping. The LIR would retrieve images corresponding to the specified word from the retail server 24. The user can then select the retrieved image that best matches the user's notion of that object. For instance, the user may specify black purse and the LIR would retrieve images of many different types of black purses from different sources such as a black leather purse, brand name/regular black purses, black purses in stores in proximity of the user's location, fancy/everyday use black purses, etc. When the user's selects the purse meeting characteristics that the user is looking for, system 10 or the VS directs the user to the source of that purse, which may be an online store.

Another application ('Social Bug'—SB) in the portal server 20 is described next that lets users upload content conveying information of interest to the general public such as activities, restaurants, shopping, news etc. These topics may be linked to specific geographical areas, so that users can look up information that pertains to a specific region of interest, such as the local community they reside in. So, in exemplary embodiment, users may look up or search content related to activities and events in their local community. The content may be uploaded by common users or business owners. Such video content will provide more information related to a topic in the form of reviews, user experiences, recommendations etc. The content is as dynamic and topics as wide-ranging as the users' interests. The uploaded content may assume the format of videos in exemplary embodiment. Moderators for each region may filter the content uploaded by users and choose the most relevant videos. The content may be organized or categorized according to fields such as 'activities', 'events', 'businesses', 'shopping item/store', 'news area' etc. Users can also specify the kind of information they would like to receive more information on via feeds, in an exemplary embodiment. Users may opt to receive feeds on a particular tag/keyword or user or event or business or subject.

The user can indicate specific filters like 'video author', 'reviewer', 'subject', 'region/locality', 'date created', 'event date', 'price range', and videos, video feeds and related content will be presented grouped according to the filters and/or filter combinations and keywords specified. Users can also specify objects in videos they are looking for, for example, 'Italian pasta', or a particular chef, in videos about restaurants. Video tags and other information describing a video (such as title, author, description, location etc.) may be used in order to find and filter videos based on criteria specified by the user. Additionally, video content (for instance, image frames, music and speech content) is mined in order to filter or find videos according to the user specified criteria.

This application allows users to indicate whether they liked a given video. Users can specify what they like about a video using keywords. Users may specify what kind of content they would like to see more of. A section/field titled 'More of . . . " would assist users in specifying preferences, suggestions about content they like or would like to see more of.

Relevant links and applications would be provided to users via this service depending on the content being viewed. In exemplary embodiment, if users are viewing restaurant related content, links would be provided allowing users to send a query to the restaurant, call up the restaurant, or book reservations via SMS, phone, email or chat. Similarly, if the user is viewing news items, news feed items and polls related to the content the user is viewing will be provided in the form of summaries or links. Top rated or most viewed response videos posted by viewers to news stories may also be posted on the same page. Videos may be pre-filtered by moderators. In exemplary embodiment, organizations working for social causes can post response videos to news stories covering issues such as poverty or human rights. They may conduct campaigns or provide information online through the use of videos. Such response videos will help to target specific audiences interested in the issues the organization is working/campaigning for. Since news videos are more popular, traffic can be directed to other videos relaying similar content but which may not necessarily belong to the same genre (for instance, two videos may both talk about poverty, but one may be a news story and the other an advertisement or documentary produced by an NGO). These videos may be posted as response videos to more popular videos, which may not necessarily be news videos.

Objects in videos and/or frames may be hyperlinked and/or tagged. In exemplary while browsing a jewelry store advertisement or infomercial, a user may click or hover or select an item of interest (a necklace, for example) and be provided with details on the make, model, materials of the necklace, pricing information etc. on the same or different frame/page. Alternatively/additionally, while a user is browsing the video, tags/comments/links may appear automatically. Users may also be provided with additional information such as deals available at the store; other users browsing the video and user's friends, if any, that are browsing/have browsed the same video or shopped at the store; where similar products or items may be found; store/business ratings/comments/reviews; how the store compares with other stores with reference to specific criteria such as bargains, quality, service, availability of items, location accessibility. Additional features such as those discussed with reference to FIG. 36 may be available. In another exemplary embodiment, tagged/hyperlinked objects within videos/images/simulations (which may be live or not) may be used for providing guided tours. In another exemplary embodiment, videos/image frames may be tagged/hyperlinked. As a video plays and a tagged frame appears, the corresponding tag is displayed to the user. The tags/hyperlinks/comments described above are searchable. On searching for a tag or browsing through tags the corresponding videos are shown.

Users can also avail of the translation feature that enables translation of videos in different languages either in real-time or offline. Text, audio and/or video content is translated and presented as audio/speech, text (subtitles for example). Shared viewing of videos between friends is possible. When shared viewing or broadcasting occurs, the same video may be simultaneously viewed by users sharing it, in different languages. The same feature is available in any/all of the chat applications mentioned in this document i.e., text typed in a certain language in a chat application may be translated to multiple languages and made available in real-time or offline to the different users of a chat session in audio/ speech, text (subtitles for example). The video presentation/content may be interactive i.e., users watching the videos may interact with each other via the collaborative tools described with reference to FIG. 20 and modes referenced in FIG. 7. Additionally the video may be a live broadcast where the presenter or video author(s) or video participants may interact with the audience watching the broadcast via the collaborative tools described with reference to FIG. 20 and modes referenced in FIG. 7.

Summaries of video content may be provided in addition to video lists. Conferences or seminars or news stories or documentaries or movies may be summarized and provided to users. Users may be able to obtain a real-time summary of a given video before choosing to view the complete video. Composite summaries of related videos or videos grouped by subject, tags or title or author or keyword or any other criteria may be provided to users. This involves providing a summary of all videos in the group in one video. As the composite video plays, individual links to the corresponding video being shown in the summary at any given moment, are displayed. Video summarization (VSumm) techniques may involve tracking of most popular keywords. These include most commonly used search terms, and tags of most viewed videos in exemplary embodiment. VSumm may also keep track of important keywords via phrases implicitly referencing them such as 'important point to be noted is . . . ' in a video, in order to identify important regions/content in videos (i.e., these regions are namely those audio/video signal sequences in a video in which important keywords are embedded).

Additionally, users may specify summarization parameters, such as the length of the summarized video and/or filters. Users can employ filters to specify scenes (video, audio, text content/clips) to include in the summaries. These filters may include keywords or person or object name contained in the video clip to be included in the summary. In exemplary embodiment, a user may specify an actor's name whose scenes are to be contained in the summary of a movie. Other filters may include the kind of content the user would like to pre-filter in the video such as 'obscene language' in exemplary embodiment.

Figure 55:
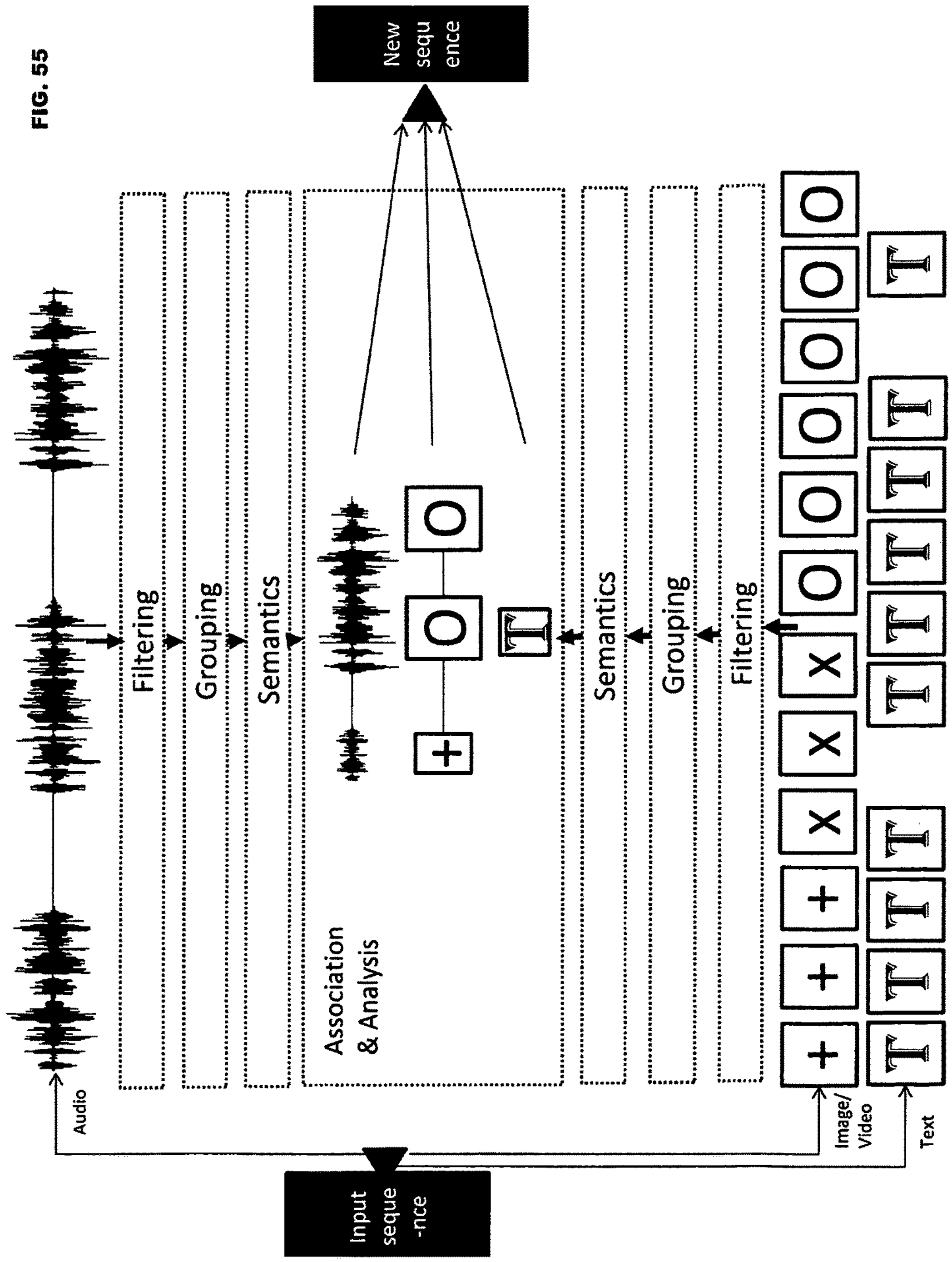
FIG. 55 illustrates an exemplary embodiment of a method for audio/video/text summarization.

Given a video/audio/text sequence, the sequence can be summarized according to the procedure illustrated in FIG. 55 and described next, in exemplary embodiment. Given an audio-visual A/V (or audio, or image or video, or text or any combination thereof) sequence, it may be broken down (split) into audio, video, image and text streams, while maintaining association. In exemplary embodiment, if a PowerPoint presentation is the input, then the audio-video-image-text content on any given slide is associated. If an audio-video sequence is being analyzed, then audio and video signals at any given time are associated. Different processing techniques are then applied in different stages as shown in FIG. 55 to carry out the input sequence summarization.

At the optional Filtering step, pre-processing is carried out using digital signal processing techniques. In an exemplary embodiment, a transformation is applied to an image sequence to convert it into the corresponding signal in some pre-defined feature space. For example, a Canny Edge detector may be applied to the frames of an image sequence to obtain an edge space version of the image. Multiple filters may be applied at this step. Subsequences can be identified not just over time, but also over frequency and space. The resulting pre-processed data sequences are passed on to the Grouping stage.

At the Grouping stage, subsequences are identified and grouped based on their similarity. Distance metrics such as Kullback-Leibler divergence, relative entropy, mutual information, Hellinger distance, L1 or L2 distance are used to provide a measure of similarity between consecutive images, in exemplary embodiment. For instance, when mutual information is computed for consecutive data frames, and a high value is obtained, the data frames are placed in the same group; if a low value is obtained, the frame is placed in a new group. Motion information is also extracted from an image sequence using optical flow for example. Subsequences exhibiting similar motion are grouped together. Frequencies corresponding to different sources, for example different speakers are identified and may be used during synopsis formation. For instance, a script may be composed based on users identified and their spoken words. In exemplary embodiment, frequencies corresponding to different sources are identified using expectation-maximization (EM) with Mixture of Gaussians (MoG). This method may also be used in the context of interviews (as described with reference to FIG. 53), live broadcasts, and other video and data sequence summaries.

Semantic analysis is then carried out on the data sequence to identify and localize important pieces of information within a subsequence. For text information, for instance, large-font or bold/italicized/highlighted/underlined and other specially formatted text, which generally indicates highlighted/important points, is identified. Significant objects and scenes within an image or video sequence, may be identified using object recognition and computer vision techniques. Significant speech or audio components may be identified by analyzing tone, mood, expression and other characteristics in the signal. Using expectation-maximization (EM) with Mixture of Gaussians (MoG) for example, the speech signal can be separated from background music or the speech of a celebrity can be separated from background noise.

If the input information is associated with a tagged file, such as an XML file for example or the file shown with reference to FIG. 37, then tags may be analyzed to identify important components. In exemplary embodiment, in the case of a text file, the associated tagged file describing the text may contain tags indicating bold/italicized points i.e., important content in the file. From subsequences determined to be significant, exemplars may be extracted. Exemplars may be a portion of the subsequence. For example, in the case of text, it could be a word or a sentence; for an image sequence it could be a frame or a portion of the frame or a set of frames or a composite of frames/frame portions in the subsequence; for an audio signal it could be a syllable(s), or a word, or a music note(s) or a sentence (this system also enables music to text conversion. Notes corresponding to the music may be output as a text file. For example, it may contain C-sharp, A-minor). The subsequences may additionally be compressed (lossless or lossy compression may occur) using Wavelet transform (for example), composited, shortened, decimated, excised or discarded. This summarization procedure is also useful for mobile applications where bandwidth, graphics and memory resources are limiting.

In another exemplary embodiment, an image can be divided in space into different regions and the most significant components can be extracted based on an evaluation of the significance of the information in these regions. In yet another exemplary embodiment, significant components can be extracted from a sequence of images, and these significant portions can then be composited together within a single image or a sequence of images, similar to a collage or mosaic.

In exemplary embodiment, in FIG. 55 the sequence represents an input data sequence (each square represents a single frame or data unit in the input information sequence). The sequence may consist of different scenes. For example, a given scene could be one that represents the inside of a car; another could be an office scene shot from a particular viewpoint; another could be a lecture slide. At the Grouping step, subsequences are identified based on similarity measures described before. The different subsequences that are identified by the algorithm are shown with different symbols in this figure. Subsequences can be of variable length as illustrated in FIG. 55. The Semantic analysis step then extracts exemplars from each group (in this case +, O). In this case, the algorithm picks out a + frame from the subsequence it labeled as '+', and a portion (O, O) of the subsequence it identified as 'O'.

The associated data—audio, video sequence data are reformatted. In exemplary embodiment, reformatting is based on significance. For instance, if an image is larger, it may occupy a larger portion of the screen. Audio content may be renormalized if necessary. The audio, video and text channels may be merged to produce a new sequence or they may be provided to the user separately without merging.

The AFMS, VS, LIR, JARMS, SB systems may be used within a local area network such as a home or office network. Users who wish to share each other's data may be added to the network permitting sharing of applications within the network and restricting access to the data of the shared network users. The AFMS, VS, LIR, JARMS, SB systems and/or the features and methods described with reference to system 10 and/or a combination of any of the above may be used in conjunction with each other or independently. One or more features and methods of the AFMS, VS, LIR, JARMS, SB systems and/or the features and methods described with reference to system 10 and/or any combination of the above may be used as standalone features as part independent systems or as part of other systems not described in this document.

The shopping trip feature may be incorporated as a feature that is part of a browser or that may be installed as a browser plug in. This would allow activation of the shopping trip upon visiting almost any site accessible by the browser. All of the features described as part of this invention can also be incorporated as such i.e., as part of a browser or as a browser plug in, making it possible to use these features on any site.

This invention further illustrates the 3D browser concept. This browser would incorporate web pages and websites with the depth component in addition to 2D elements. Users will be able to get a sense of 3D space as opposed to 2D space while browsing web pages and websites via the 3D browser.

This invention incorporates additional features available on a mobile device such as a mobile phone or a personal digital assistant (PDA) to assist the user while shopping in a physical store. When users enter a store, the mobile device will detect and identify the store by receiving and processing wireless signals that may be sent by a transmitter in the store, and will greet users with the appropriate welcome message. For example, if the store is called 'ABC', the user will be greeted with the message 'welcome to ABC' on their wireless device. The user may be uniquely identified by the store based on their mobile phone number for example. The store may have a unique ID that will identified by the cell phone and used to also keep track of stores/places visited by the user. Additionally, store specials and offers and other information may be presented to the user on their mobile device (in the form of visual or audio or other forms of relaying digital input on a mobile device). Instead of automatic store identification, the mobile may instead accept user input (text, speech and other forms) for identifying store and then present relevant store information to the user. Users will be able to search for items in the store using their mobile device and will be able to identify the location (such as the department, aisle, counter location etc.) of the product they wish to buy. They will receive an indication of whether they are approaching the location of or are in the vicinity of the product in the store and/or if they have reached or identified the correct location. The user may see a 'path to product' as described elsewhere in this document. The mobile device is equipped with a barcode scanner and can be used for checking inventory, price and product information by scanning the barcode on a product. The mobile device may also process the user's shopping list available on the mobile device and automatically generate availability, inventory, location, discounts, product description, reviews and other relevant information pertaining to the product and display it to the user. In an exemplary embodiment, this may be accomplished as follows with reference to FIG. 50. The mobile device 901 may transmit appropriate information request/query signals to a wireless SAP (service access point) in the store which in turn, will transmit relevant store and product information which is received and displayed by the mobile device. Depending on the specific area of the store that the user is in, the products in that area may be displayed on their mobile device. Users may also access their model on their mobile device and try-on apparel on the model, via a local application 271 version for mobile devices. A user may also go on a shopping trip (as discussed with reference to FIG. 20) using their mobile phone 901. Other members of the shopping trip may be using a mobile device 902 as well or a computer. Users will also be able to see whether their friends are in the store using their mobile device 901.

Figure 52A:
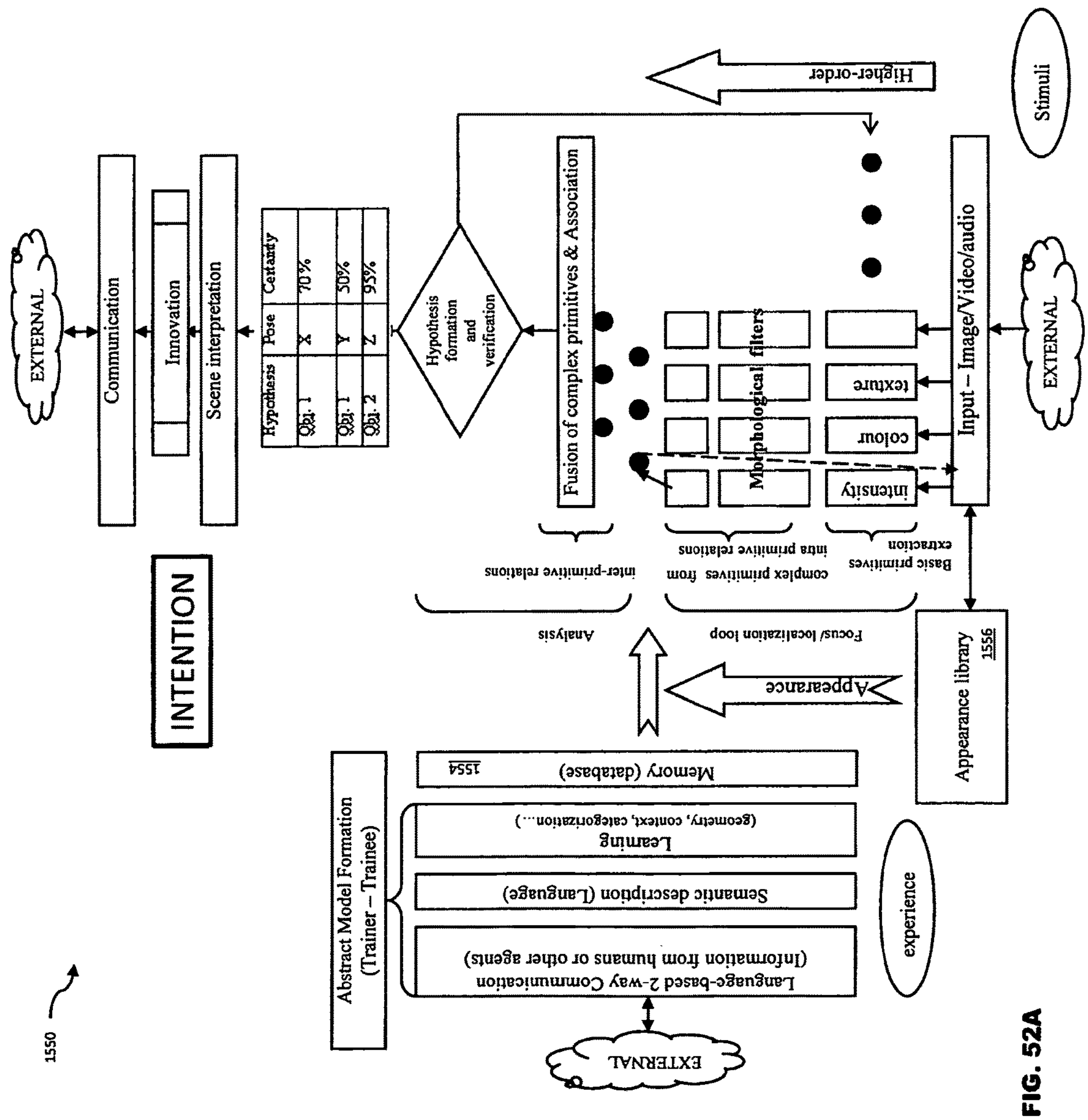
FIG. 52A illustrates an image/video/audio analysis module for generic scene analysis.

Reference is now made to FIG. 52A where an image/video/audio/text analysis module 1550 is shown in an exemplary embodiment. The image/video/audio/text analysis 1550 module outlines the steps of interaction or engagement with the outside world, i.e. external to the computer. The module 1550 may be used for generic image/audio/video/text scene analysis. In an exemplary embodiment, this module works as follows: The module is preloaded with a basic language that is stored in a "memory" database 1554. This language contains a dictionary which in turn contains words and their meanings, grammar (syntax, lexis, semantics, pragmatics, etc.), pronunciation, relation between words, and an appearance library 1556. The appearance library 1556 consists of an appearance based representation of all or a subset of the words in the dictionary. Such a correspondence between words or phrases, their pronunciation including phonemes and audio information, and appearances is established in an exemplary embodiment using Probabilistic Latent Semantic Analysis (PLSA) [55]. In an exemplary embodiment graphs (a set of vertices and edges) or cladograms are used to represent the relation between words. Words are represented by vertices in the graph. Words that are related are connected by edges. Edges encode similarity and differences between the attached words. A visual representation of the similarity could be made by making the length of the edges linking words proportional to the degree of similarity. Vertices converge and diverge as more and more information becomes available. (For example, if the system is only aware of shoes as something that is worn on feet, and it later comes across the word or a picture of sneakers, it may group it with shoes. As it learns more related words such as slippers or sandals, it groups them together but may later create separate groups for each on learning the differences between these apparel) This system also enables conversion from speech to image, image to speech, text to image, image to text, text to speech, speech to text, image to text to speech, speech to text to image or any combination thereof. The memory database 1554 and the appearance library 1556 are analogous to “experience”. The appearance library 1556 and the memory database 1554 may be used during the primitive extraction, fusion, hypothesis formation, scene interpretation, innovation, communication, and other steps to assist the process by providing prior knowledge. Shown on the right in FIG. 52A are the steps of analysis of stimuli from the external world. The stimuli can be images, video, or audio in an exemplary embodiment. It could also include temperature, a representation of taste, atmospheric conditions, etc. From these stimuli basic primitives are extracted. More complex primitives are then extracted these basic primitives. This may be based on an analysis of intra-primitive and inter-primitive relations. This may trigger the extraction of other basic primitives or complex filters in a “focus shifting” loop where focus of the system shifts from one region or aspect of a stimulus to another aspect or region of the stimulus. Associations between the complex primitives are formed and these primitives are then fused. (The primitive extraction and fusion method described here is similar to that described in reference to FIG. 6D for the case of images and video. The prior knowledge 112 is available as part of the appearance library 1556 and the memory database 1554. The method is also applicable for audio stimuli). Hypotheses are then formed and are verified. The output of this step is a set of hypotheses (if multiple hypotheses are found) that are ranked by the degree of certainty or uncertainty. For example, the output of analysis on an image of a scene containing people may be a probability density on the location of people in the scene. The modes or the “humps” in this density may be used to define hypotheses on the location of people in the image. The probability of each mode (obtained for example by computing the maximum value corresponding to the mode or the mean of the mode) may be used to define the certainty of the existence of an instance of a person at the specified location. The variance of each mode may be used to define the spatial uncertainty with which a person can be localized. The output of the hypothesis formation and verification step is passed on to a scene interpretation step at which the information makes interpretations on the scene. For example, if the system identifies a cow, some chickens, and a horse in a video, and identifies the sound of crows, it may identify the scene as a farm scene. This may be done using a classifier as described before. The output of the scene analysis step is passed on to an innovation step. At this step the system innovative remarks to the analyzed stimuli. In an exemplary embodiment, the system looks for things it has seen in the recent past, surprising things, things of interest for example gadgets and makes comments such as—“Hey, I saw this guy last week”, “That’s the new gadget that came out yesterday”, or “That’s a pleasant surprise”. Surprise is detected using the method described with reference to FIG. 52B. At the innovation step, the system also filters out things that it does not want to communicate with the outside world. This could include information that is obvious or that which is confidential. The output of the innovation model is communicated to the external world. This can be done via text, audio (using text to speech techniques), images [60] or video. The text/audio output may include expressions such as, “I am looking at a farm scene. There are many farm animals here. I am looking at the cow. It is a very tiny cow. The crows are trying to eat the corn. The dog is barking . . . ”, and so on. If the system has the capacity to perform physical activities, it may communicate by interacting physically with the environment. For example, it may pick up an object it likes and view it from other angles and weigh it. The module 1550 may be driven by an intention. The intention can be based on the user’s interest. For example, if the user likes hockey, it may pay more attention to things that are related to hockey in the stimuli. If the stimulus is a news article that mentions that a new hockey stick by the name “winstick” is out in the market, the module may perform a search on the “winstick” and extract pricing and availability information and some technical details on how the “winstick” is made to be a better hockey stick.

Figure 52B:
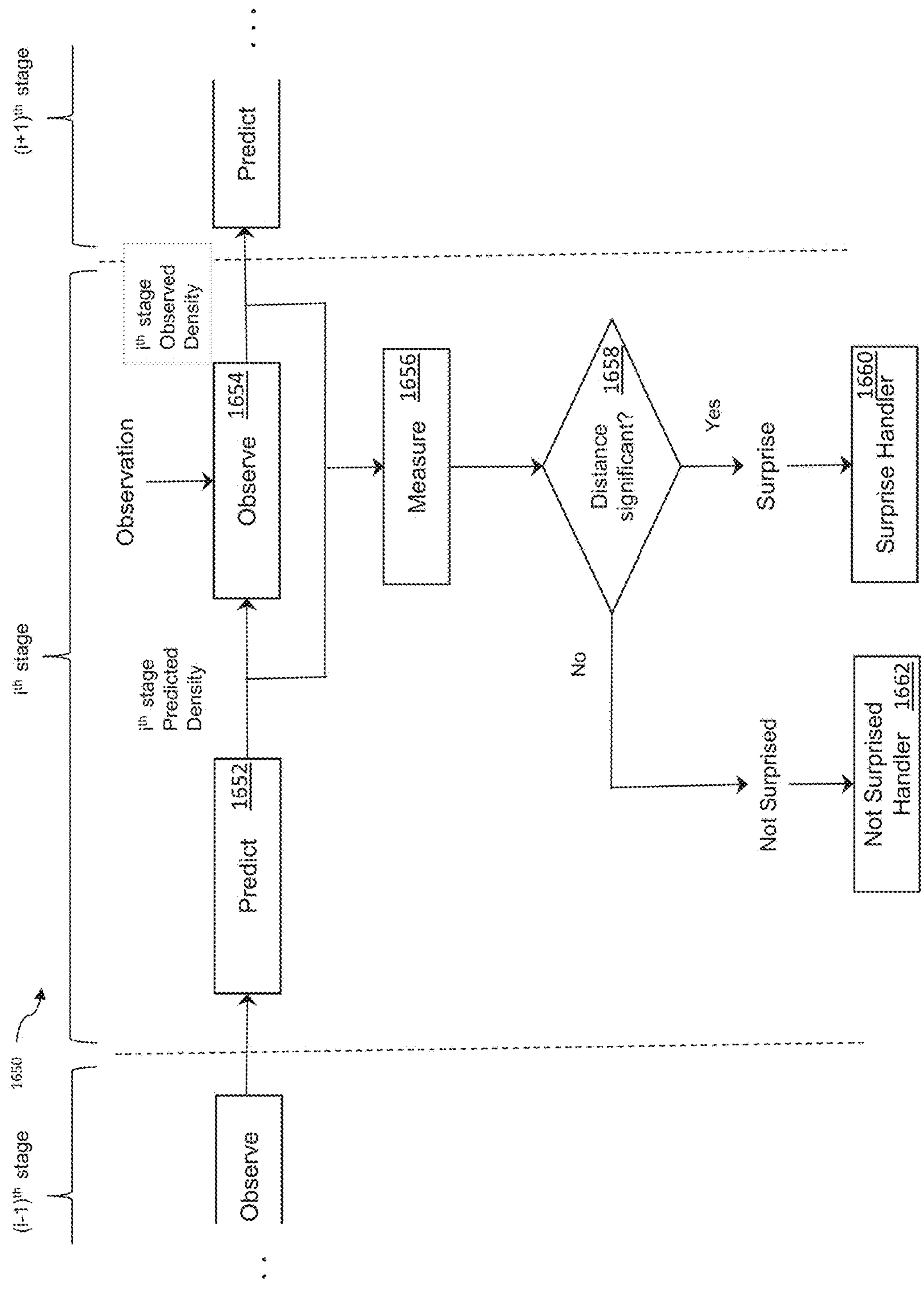
FIG. 52B illustrates a method for detecting surprise.

Reference is now made to FIG. 52B where a method 1650 for detecting surprise is shown in an exemplary embodiment. In an exemplary embodiment, the method 1650 operates as follows: The method constantly predicts the state of the system and observes the state of the system. (Alternatively, the method may predict and observe the state only as necessary). The state of the system includes variables that are of interest. For example, the state may include the state of the user which may involve the location of the user in a given camera view or the mood of the user extracted from an image or based on the music the user is listening to, or the location of the user extracted from a Global Positioning System GPS, the mood of the user’s friends, etc. Similarly, the state of the environment may include the weather, the day of the week, the location where the user is, the number of people at the user’s home, etc. One stage of the predict-update cycle is shown in FIG. 52B. At the $i^{th}$ stage, the system uses the output of the $(i-1)^{th}$ stage i.e. previous stage’s output and predicts the state of the system at the prediction step 1652. This can be done, in an exemplary embodiment, using a prediction algorithm such as Gaussian process regression for example as used in [51] or other statistical approaches such as those used in [63]. The output of the prediction stage includes a predicted probability density of the state of the system. This is passed on to an observation step 1654 together with an observation of the system. The output of the observation step 1654 includes an updated probability density called an observed density. An observation of the system, in an exemplary embodiment could be an analysis of an image taken through a webcam (eg. image-based extraction of the pose of the user) or a measurement of the temperature of the room using a thermal sensor, or any other measurement appropriate for the system. In an exemplary embodiment, an observed probability density is computed from the observation and the predicted density by computing the a posteriori density using Bayes rule. In another exemplary embodiment, the observed density is computed based on the observation alone. The difference between the predicted probability density and the observed probability density is then measured at the measurement step 1656. This is done, in an exemplary embodiment, using a distance metric such as the Kullback-Leibler divergence or relative entropy, mutual information, the Hellinger distance, or the $L_1$ or $L_2$ distance. Other statistics or functions drawn from the predicted and observed (or updated) probability densities (or distributions) could also be used. At step 1658, a test is made to determine if the distance is significant. In an exemplary embodiment, this is done based on a threshold—if the distance is over a threshold, the distance is considered significant and if it is below the threshold the distance is considered insignificant. The threshold could be assigned or could be determined automatically. In an exemplary embodiment, the threshold is chosen to be a statistic of the predicted or observed density, In another exemplary embodiment, the threshold is chosen to be a function of the degree of certainty or uncertainty in the estimate of the predicted or observed densities. In yet another exemplary embodiment, the threshold is learnt from training data. If the distance is significant, the system is enters a "surprised" state. Otherwise it remains in an "unsurprised" state. The "surprised" state and the "unsurprised" states are handled by their respective handlers. The degree of surprise may be dependent on the distance between the predicted and observed probability densities. This allows the system to express the degree of surprise. For example, the system may state that it is "a little surprised" or "very surprised" or even "shocked". (Over time if an event becomes common or occurs frequently the system may incorporate the nature of the event at the prediction step thus leading to a predicted density that is closer to the observed density and essentially getting used to the event). Such a system is used, for example, for detecting anomalies. As discussed with reference to FIG. 51A, the system may monitor the locations of kids of a home by using signals from their cell phones (for example, text messages from their cell phones indicating the GPS coordinates) using a particle filter. If a surprise is observed (for example if the location of the kid is outside the predicted range for the given time), the surprise handler may send a text notification to the kid's parents. The system may also be used in surveillance applications to detect anomalies. As another example, the system may monitor a user's location while he/she is driving a vehicle on the highway. If the user slows down on the highway, the system may lookup weather and traffic conditions and suggest alternative routes to the user's destinations. If the user's vehicle stops when the system didn't expect it to, the system's surprise handler may say to the user things such as—"Do you need a tow truck?", "Is everything ok?", "Do you want to call home for help?", etc. If a response is not heard, the system's surprise handler may notify the user's family or friends. Such a system, may also be used to predict the state of the user, for example, the mood of the user. If the system notices that the user is depressed, the surprise handler may play a comedy video or play a joke to the user to cheer him up. If the user is on a video sharing site or in the TV room for extended hours and the system sees that an assignment is due in a couple of days, the system may suggest to the user to start working on the assignment and may complain to others (such as the user's parents) if the user does not comply. Such a system is also useful for anomaly detection at a plant. Various parameters may be monitored and the state of the system may be predicted. If the distance between the predicted and observed states is high, an anomaly may be reported to the operator. Images and inputs from various sensors monitoring an inpatient may be analyzed by the system and anomalies may be reported when necessary. Another application of method 1650, would be as a form of interaction with the user. The method may be used to monitor the activities of the user which may be used to build a model of the users activities. This model can then be used to predict the activities of the user. If a surprise if found, the surprise handler could inform the user accordingly. For example, if the user's calendar says that the user has an appointment with his/her doctor and the user typically goes to the doctor on time, but on one instance is not on his/her way to the office (the system may have access o the user's GPS location and time of arrival from the current location to the doctor's office or may gather this data from indirect sources such as a chat session with the user's friends indicating that the user is going to be at a friend's party) the surprise handler may state that the user is supposed to be at the doctor's office and is getting late. The surprise handles may make similar comments on the user's friend's activities. The surprise handler may also take actions such as make a phone call, turn off the room's light if the user falls asleep and wake up the user when it's time to go to school. Method 1650 also enables a system to make comments based on visually observing the user. For example, the a system may make comments such as, "Wow! Your eye color is the same as the dress your are wearing", or "You look pretty today", based on the user's dressing patterns, method 1650, heuristics that define aesthetics and/or the method used to determine beauty described earlier in this document. The probability densities referred to above can be discrete, continuous, or a sampled version of a continuous density or could even be arbitrary functions or simply scalars that are representative of the belief of the state in exemplary embodiments. There may be cases where the system may expect a surprise, but a surprise is not found. In such situations the systems may express that it is not surprised and explain why. For example, if a tennis player loses, the system may say that it is not surprised because the wind was blowing against her direction during the match or if a football team loses, the system may express to the users that it is not surprised because the positions of the team players was consistently ill-positioned. As another example, the system may parse news and if it is found that a famous person is dead, it may express that is "shocked" to hear the news. This expression by the system can be made through a number of ways, for example through the use of text to speech conversion. The concept of surprise can also used for outlier rejection. For example, a system may employ the method described here during training to identify outliers and either not use them or assign lower weights to them so that the outliers do not corrupt the true patterns that are sought from a data.

The concept of a clique session is introduced here. A session is a lasting connection typically between a client (eg. 14) and a server (eg. 20) that is typically initiated when a user is authenticated on the server and ends when a user chooses to exit the session or the session times out. On the other hand, a clique session is one in which multiple users are authenticated and share the same session. A clique session may be initiated by any subset of the set of users who have agreed to collaborate or it may require authentication of all the users. Similarly, a clique session can be terminated if any subset or all the users of the clique session exit. The order of authentication may or may not be important. In an exemplary embodiment, all users of a clique session may have the same unique clique session ID under which the clique session data is stored. Clique sessions are useful for online collaboration applications. Clique session IDs, can also be used for accessing resources that require high security. For example, users of a joint account online may choose to have access to the online resource only if both users are authenticated and log in. As another example, a user of a bank account may have a question for a bank teller about his account. In order for the teller to view the user's account, the teller would first have to log in and then the user would have to log in to the same account to allow the teller to view the user's account and answer his question. Clique sessions may also be used for peer-to-peer connections.

Figure 54A:
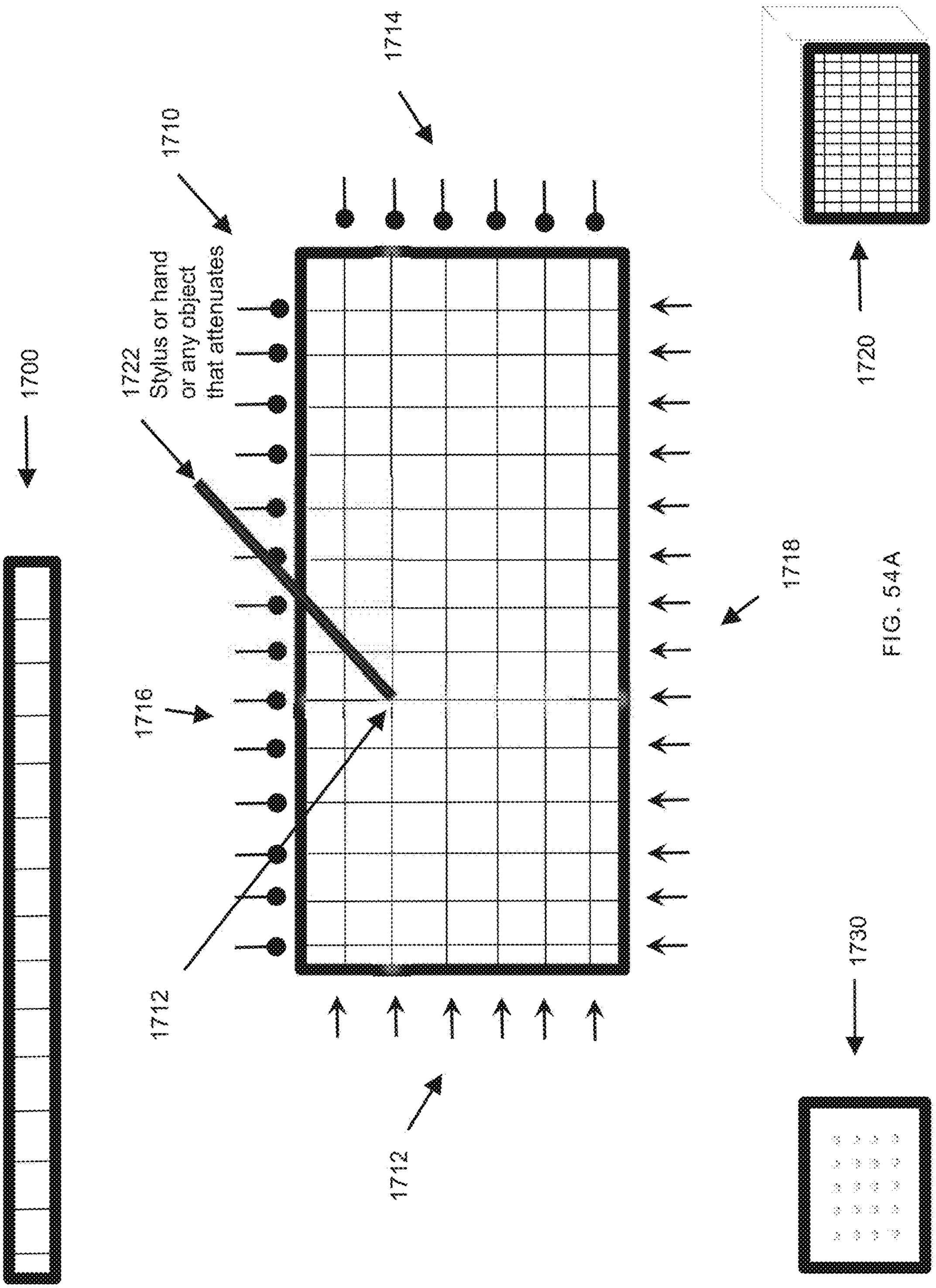
FIG. 54A-F novel devices for human-computer interaction.
Figure 54B:
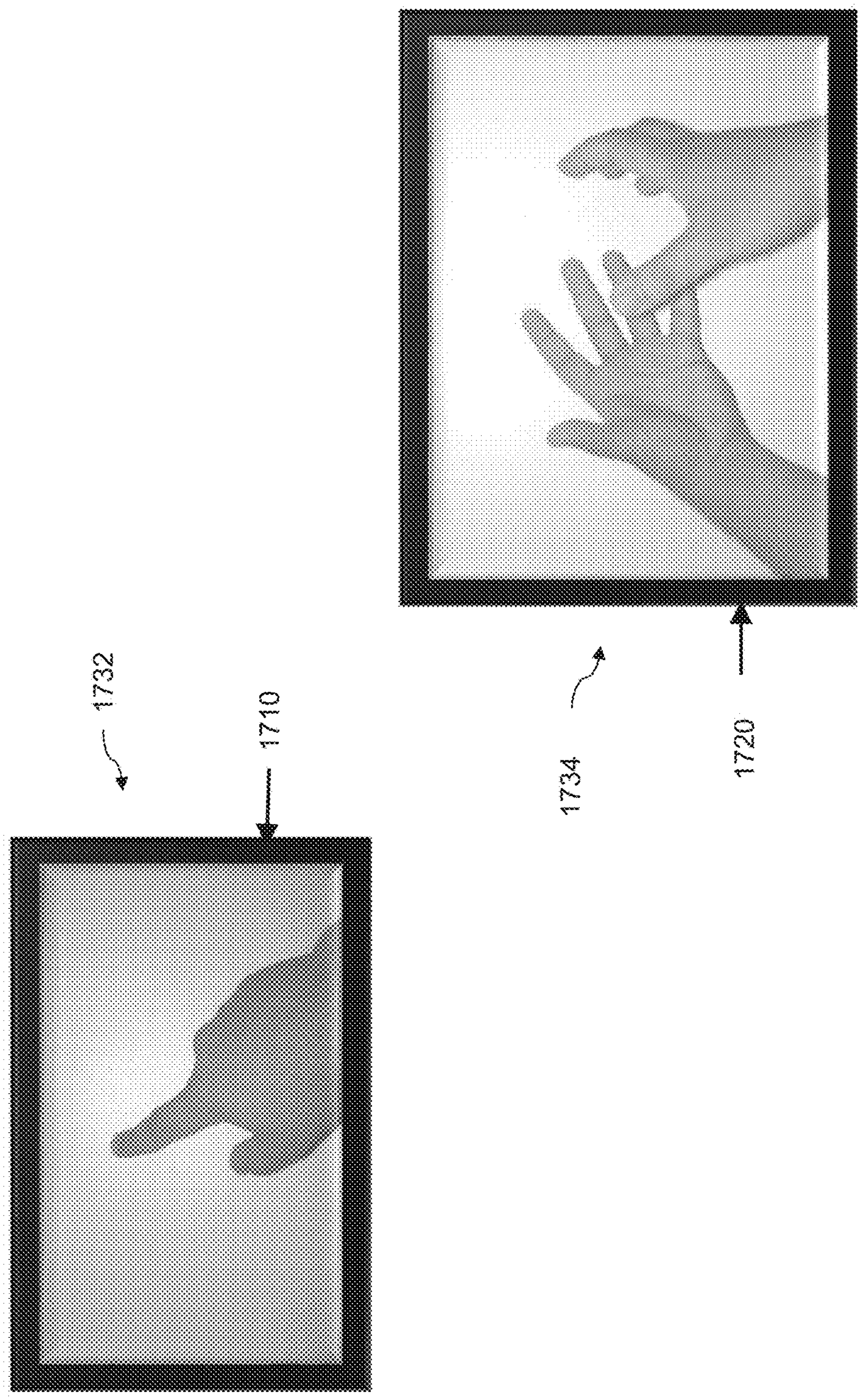
Figure 54C:
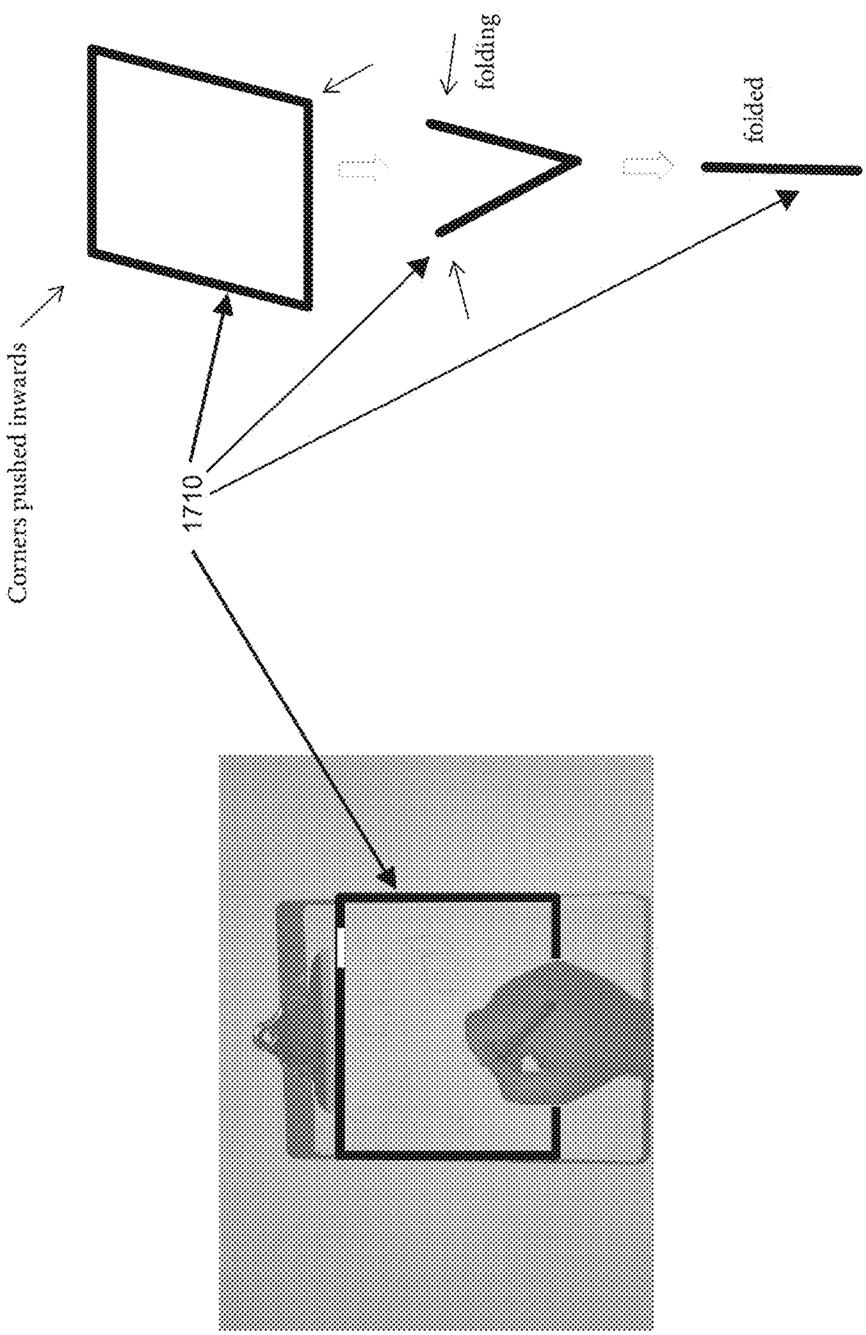

Reference is now made to FIG. 54A-F where novel devices for interaction are shown in exemplary embodiments. These devices allow another way for users to communicate with computing devices 14. Reference is now made to FIG. 54A where a novel pointing devices are shown in exemplary embodiments. This could also take a 1D form 1700, a 2D form 1710, or a 3D form 1720. In an exemplary embodiment, the 1D form 11700 works as follows: A source or a transmitter bank 1712 is located on one side of the device and a sink or sensor or a receiver bank is located on the opposite side 1714. The source may emit lasers or other optical signals, or any other directional electromagnetic radiation or even fluids. When the beam is interrupted the by an interrupting unit such as a finger or a pen, the corresponding sensor on the receiver bank is blocked from receiving the signal. This is used to define the location of the object. If lasers are used, a laser frequency different from that of typical background lighting is used. In an alternative embodiment, the interrupting unit emit instead of the source or transmitting bank. The unit also allows the use of multiple interrupting units. In this case, the multiple sensors would be blocked and this would be used to define the location of the interrupting units. In an alternative embodiment, along each side of the device, a transmitter and receiver may be used in an alternating fashion so that each side has both transmitters and receivers. In the 2D form 1710, a second set of receivers and transmitters are placed orthogonal to the first one. Similarly, in the 3D form 1720, three sets of transmitter and receiver banks are used. Reference is now made to another pointing device 1730 in FIG. 54A that is composed of a set of holes. In each of these holes, a transmitter and a receiver are located. Each of these transmitters may employ lasers or other optical signals, or any other directional electromagnetic radiation or even fluids. The transmitter and the receiver are both oriented such that they point out of the device in the direction of the hole. When a hole is covered by an interrupting unit such as a pen or a finger, the signal bounces off the interrupting device and is sensed by the receiver. This signal is then used to define the location of the interrupting unit. In all cases 1700, 1710, 1720, 1730 a sequence of blocked sensors over time can be used to define the direction of motion. Reference is now made to FIG. 54B where an illustration 1732 of the use of the 2D form 1710 is show. The user can simply drag a finger on the unit and use that to point to objects or for free form drawing. The unit may also be placed over a computer screen and used as a mouse. Also shown in FIG. 54B is an illustration 1734 of the use of the 3D form 1720. This can be used to manipulate objects in 3D. For example, this can be used with the technology described with reference to FIG. 36. This device may be used with a hologram for visual feedback or it may be used with any conventional visualizing unit such as a monitor. The device 1720 can also be used with multiple hands as shown in the illustration 1734. Reference is now made to FIG. 54C where another illustration of the use of the device 1710 is shown in an exemplary embodiment. The device 1710 may be placed on paper and the user may use a pen to write as usual on the paper. As the user writes, the device 1710 also captures the position of the pen. This is then used to create a digital version of the writing and may be stored on the unit 1710 or transferred to a computing device. The device 1710 is also portable. The corners of the device 1710 can be pushed inwards and the unit folded as shown in FIG. 54C. The compact form of this device takes the form of a pen as shown in FIG. 54C. The device 1710 can also include a palette that includes drawing tools such as a polygons, selection tools, eraser, etc. The user can also slide the device 1710 as he/she writes to create a larger document than the size of the device. This movement of the device 1710 is captured and a map is built accordingly. The motion may be captured using motion sensors or using optical flow [64] if the unit is equipped with optical sensors. The device 1710 may also be moved arbitrarily in 3D and the motion may be captured along with location of the interrupting device to create art or writing in 3D using the 2D form 1710. The device 1710 can also be used as a regular mouse. The apparatus presented in FIG. 54A-C may also be used as a virtual keyboard. Regions in the grid may be mapped to keyboard keys. In one exemplary embodiment, a user can place the apparatus on a printout of a keyboard (or a virtual keyboard may be projected using for example lasers) and use it for typing.

Figure 54D:
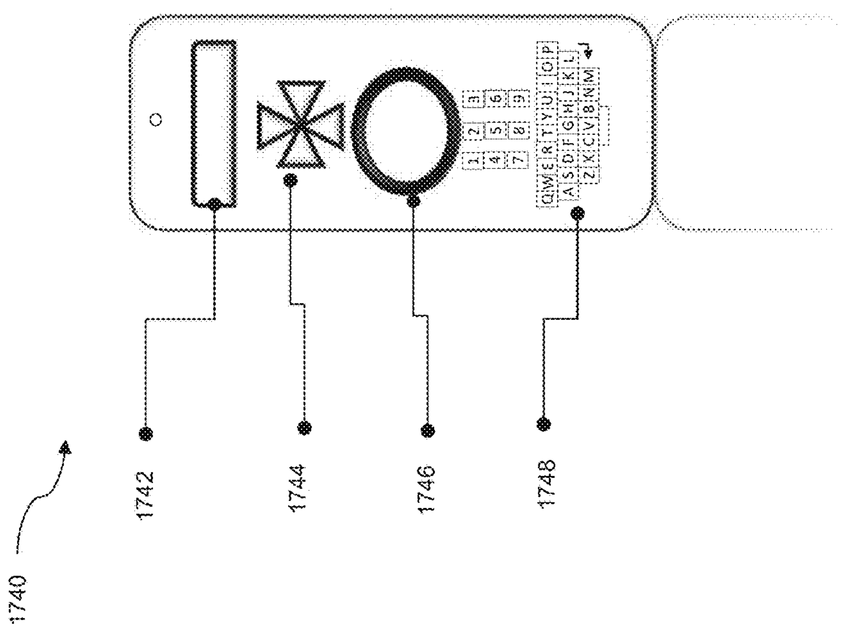
Figure 54E:
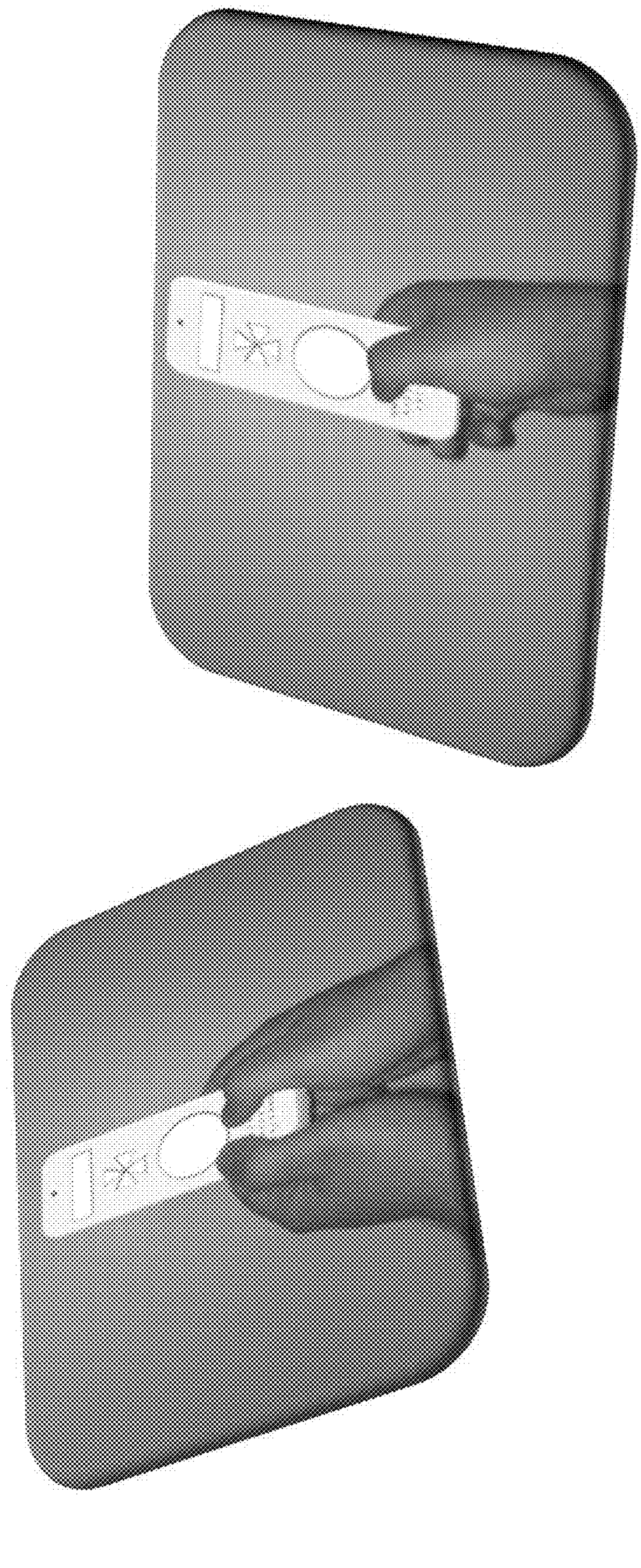

Reference is now made to FIG. 54D where a novel device 1740 for interacting with a computing device or a television in shown in an exemplary embodiment. The device 1740 includes a QWERTY keyboard or any other keyboard 1748 that allows users to enter text or alphanumerics, a mouse 1746, controls for changing the volume or channels 1744, other controls for switching between and controlling computing devices and entertainment devices such as a DVD player, a TV tuner, a cable TV box, a video player, a gaming device. The device may be used as a regular universal TV remote and/or to control a computer. The mouse may be used by rocking the pad 1746 to a preferred direction or sliding a finger over the pad. The device 1740 communicates with other devices via infrared, Bluetooth, WiFi, USB and/or other means. The device 1740 allows users to control the content being viewed and to manipulate content. For example, the device 1740 allows users to watch videos on a video sharing site. Users can use the keyboard 1748 to enter text in a browser to go to a site of their choice and enter text into a search box to bring up the relevant videos to watch. They can then use the mouse 1746 to click on the video to watch. The keyboard 1748 and the mouse 1746 can be used as a regular keyboard and mouse for use with any other application as well. The keyboard may also be used to switch TV/cable channels by typing the name of the channel. A numeric keypad may be present above the keypad, or number keys may be a part of the alpha (alphabets) keyboard and can be accessed by pressing a function key, in an exemplary embodiment. The device 1740 ma also include an LCD screen or a touch screen. The device 1740 may also be used with a stylus. The functionality of the device may be reprogrammable. The device could also be integrated with a phone. The device may be used with one hand or two hands as shown in FIG. 54E in an exemplary embodiment. The device allows easy text entry when watching videos. The device facilitates interactive television. The content of the television may be changed using this remote. The device 1740 may also include motion sensors. The motion of this device may be used change channels, volume, or control characters on a screen. The device may be used to search a video for tags and jump to tags of interest. The device may also feature a numeric keypad that allows easy placement of phone calls.

Figure 54F:
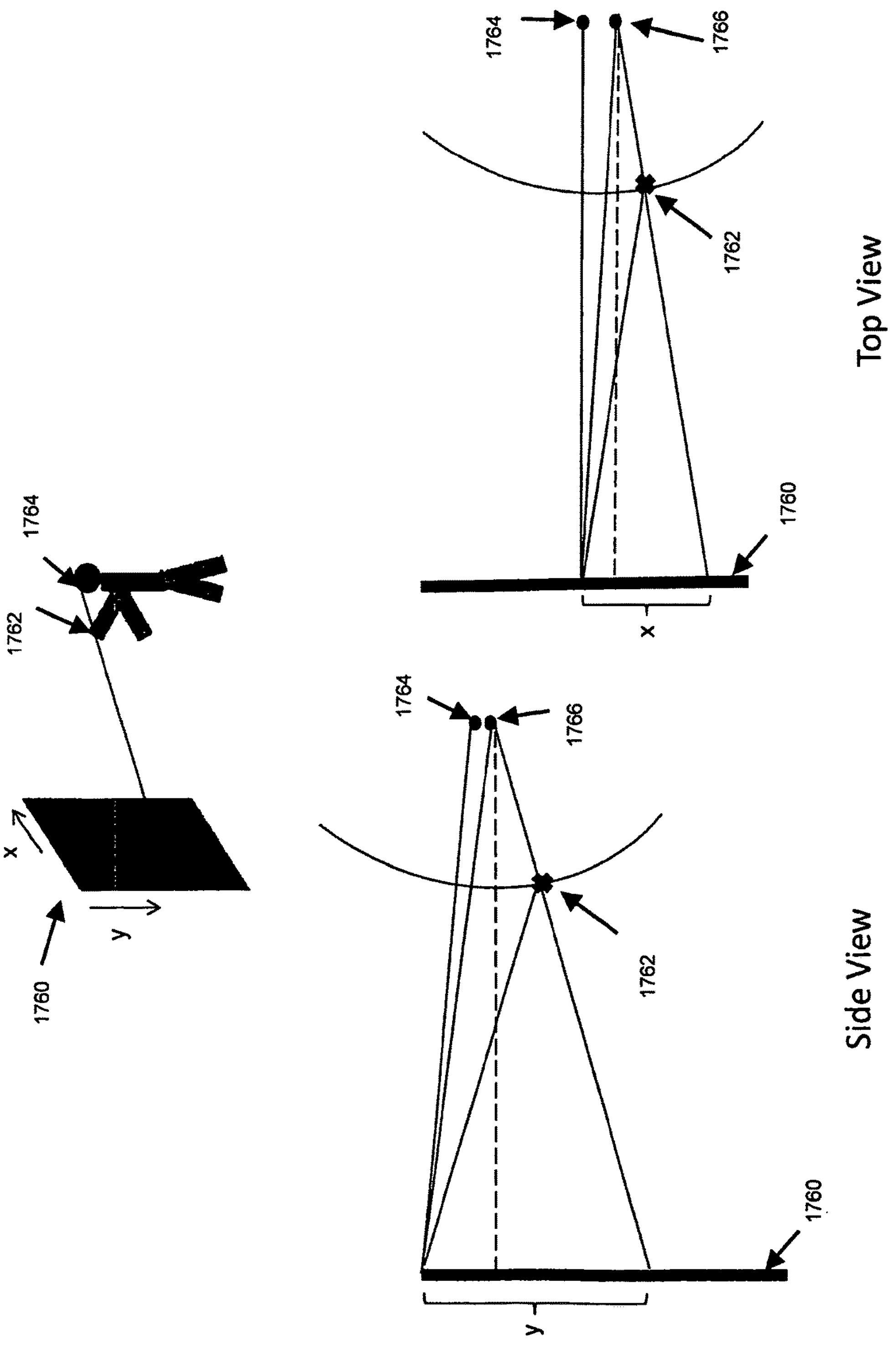

Reference is now made to FIG. 54F where of a novel human computer interface system is illustrated in an exemplary embodiment. This system makes use of a line of sight that includes two or more objects. In an exemplary embodiment, the location of the user's finger and an eye are used to determine the location where the user is pointing. The location of the user's finger(s) or hand(s) and that of one or both of the user's eyes can be used to determine where the user is pointing on the screen. The user may point to a screen 1760 using one or more finger(s)/hand(s) 1762. One or more cameras may monitor the location of 1762 and the user's right eye 1764 and/or left eye 1766. The cameras may be on top of the screen, on the sides, at the bottom or may even be behind the screen 1760. A side view and a top view of the setup are also shown in FIG. 54F. The system may make use of motion parallax to precisely determine the location pointed at by the user.

A feature to enhance user experience with documents (for example on the internet) is described below. This feature is referred to as a "quotation system". This feature allows users to quote from documents. In an exemplary embodiment, documents may be uniquely identifiable. This may be done by assigning a unique identification number to each document that is registered in a database. Documents can be indexed based on tags such as the chapter number and the line number. The tags may be inferred, or extracted or present in the underlying document. Users can embed quotes from documents. For example, a webpage may contain an embedded quote to a line from a chapter of a book. In an exemplary embodiment, hovering over the quotation or clicking on the quotation may display the corresponding quotation. In an exemplary embodiment, embedding a quotation tag with an identification number may display the quotation in the document in which the quotation is embedded. Quotations can be used for text, audio, video, or other media. A version number may be used for related documents. The system enables the user to find related quotes or verses. "Quotation chains" may also be supported. Quotation chains enable the user to quote a document that in turn quotes another document so that the source of the information can be traced.

The system 10 has been described herein with regards to being accessible only through the Internet, where a server application is resident upon a server 20. The respective applications that provide the functionalities that have been described above, may be installed on a localized stand-alone devices in alternative embodiments. The respective apparel items and other products that the user may view and or selected, may then be downloaded to the respective device upon connecting to an Internet server. The stand-alone devices in alternative embodiments may communicate with the server, where the server has access to various databases and repositories wherein items and offerings may be stored. These stand-alone devices may be available as terminals or stations at a store, which may be linked to store inventories. Using these terminals, it may be possible to search via keywords, voice, image, barcode and specify filters like price range.

While the above description provides examples of the embodiments, it will be appreciated that some features and/or functions of the described embodiments are susceptible to modification without departing from the spirit and principles of operation of the described embodiments. Furthermore, the systems, methods, features and/or functions described above may be used independently or in conjunction with other systems and/or methods; and may be applied or used in other context other than the those mentioned in this document. Accordingly, what has been described above has been intended to be illustrative of the invention and non-limiting and it will be understood by persons skilled in the art that other variants and modifications may be made without departing from the scope of the invention as defined in the claims appended hereto.

REFERENCES

[1] M. Desbrun, M. Meyer and P. Alliez, "Intrinsic Parameterizations of Surface Meshes," *Comput. Graphics Forum*, vol. 21, pp. 209-218, 2002.

[2] H. Y. Bennamoun and M., "1D-PCA, 2D-PCA to nD-PCA," *Pattern Recognition,* 2006. *ICPR* 2006. 18*th International Conference on*, vol. 4, pp. 181-184, 2006.

[3] R. Davis, "Magic Paper: Sketch-Understanding Research," *Computer*, vol. 40, pp. 34-41, 2007.

[4] O. Bimber and R. Raskar, *Spatial Augmented Reality: Merging Real and Virtual Worlds*. A K Peters, Ltd., 2005,

[5] G. L. Congdong and Li, "Collaborative Filtering Recommendation Model Through Active Bayesian Classifier," *Information Acquisition,* 2006 *IEEE International Conference on*, pp. 572-577, August 2006.

[6] T. Yoshioka and S. Ishii, "Fast Gaussian process regression using representative data," *Neural Networks,* 2001. *Proceedings. IJCNN* '01. *International Joint Conference on*, vol. 1, pp. 132-137 0.1, 2001.

[7] D. J. Hand and K. Yu, "Idiot's Bayes: Not So Stupid After All?" *International Statistical Review*, vol. 69, pp. 385-398, 2001.

[8] P. A. Flach and N. Lachiche, "Naive Bayesian Classification of Structured Data," *Machine Learning*, vol. 57, pp. 233-269, December 2004. 2004.

[9] T. Hastie, R. Tibshirani and J. H. Friedman, *The Elements of Statistical Learning*. Springer, 2001,

[10] G. Shakhnarovich, T. Darrell and P. Indyk, *Nearest-Neighbor Methods in Learning and Vision: Theory and Practice* (*Neural Information Processing*). The MIT Press, 2006,

[11] B. Froba and C. Kublbeck, "Robust face detection at video frame rate based on edge orientation features," *Automatic Face and Gesture Recognition,* 2002. *Proceedings. Fifth IEEE International Conference on*, pp. 327-332, 20-21 May 2002.

[12] A. R. Chowdhury, R. Chellappa, S. Krishnamurthy and T. Vo, "3D face reconstruction from video using a generic model," *Multimedia and Expo,* 2002. *ICME* '02. *Proceedings.* 2002 *IEEE International Conference on*, vol. 1, pp. 449-452 o. 1, 2002.

[13] L. D. Alvarez, J. Mateos, R. Molina and A. K. Katsaggelos, "High & hyphen; resolution images from compressed low & hyphen; resolution video: Motion estimation and observable pixels," *Int. J. Imaging Syst. Technol., vol.* 14, pp. 58-66, 2004. 2004.

[14] U. P. Jain and Anil K., "3D Face Reconstruction from Stereo Video," *Computer and Robot Vision,* 2006. *the* 3*rd Canadian Conference on*, pp. 41-41, 7-9 Jun. 2006.

[15] H. Zhang, A. C. Berg, M. Maire and J. Malik, "SVM-KNN: Discriminative nearest neighbor classification for visual category recognition," in *CVPR '06: Proceedings of the* 2006 *IEEE Computer Society Conference on Computer Vision and Pattern Recognition,* 2006, pp. 2126-2136.

[16] V. Perlibakas, "Automatical detection of face features and exact face contour," *Pattern Recognition Letters*, vol. 24, pp. 2977-2985, December, 2003. 2003.

[17] P. Kuo and J. Hannah, "Improved Chin Fitting Algorithm Based on An Adaptive Snake," *Image Processing,* 2006 *IEEE International Conference on*, pp. 205-208, 8-11 Oct. 2006.

[18] M. Castel and E. R. Hancock, "Acquiring height data from a single image of a face using local shape indicators," *Comput. Vis. Image Underst., vol.* 103, pp. 64-79, 2006.

[19] P. L. Worthington, "Reillumination-driven shape from shading," *Comput. Vis. Image Underst.*, vol. 98, pp. 326-344, 2005.

[20] G. Vogiatzis, P. Favaro and R. Cipolla, "Using frontier points to recover shape, reflectance and illumination,"

*Computer Vision,* 2005. *ICCV* 2005. *Tenth IEEE International Conference on*, vol. 1, pp. 228-235 o. 1, 17-21 Oct. 2005.

[21] C. H. Esteban and F. Schmitt, "Silhouette and stereo fusion for 3D object modeling," *Comput. Vis. Image Underst*., vol. 96, pp. 367-392, 2004.

[22] R. Dovgard and R. Basri, "Statistical symmetric shape from shading for 3D structure recovery of faces," *Lecture Notes in Computer Science*, vol. 3022, pp. 99-113, 2004.

[23] H. Murase and S. K. Nayar, "Visual learning and recognition of 3-D objects from appearance," *Int. J. Comput. Vision*, vol. 14, pp. 5-24, 1995.

[24] Y. Iwasaki, T. Kaneko and S. Kuriyama, "3D hair modeling based on CT data and photographs." in *Computer Graphics and Imaging,* 2003, pp. 123-128.

[25] Y. G. Zhiyong and Huang, "A method of human short hair modeling and real time animation," *Computer Graphics and Applications,* 2002. *Proceedings.* 10*th Pacific Conference on*, pp. 435-438, 2002.

[26] K. Ward, F. Bertails, TaeYong Kim, S. R. Marschner, M. P. Cani and M. C. Lin, "A Survey on Hair Modeling: Styling, Simulation, and Rendering," *Transactions on Visualization and Computer Graphics*, vol. 13, pp. 213-234, March-April 2007.

[27] A. S. Micilotta, E. Ong and R. Bowden, "Real-time upper body detection and 3D pose estimation in monoscopic images," in *Proceedings of the European Conference on Computer Vision* (*ECCV* '06)—*Volume* 3; *Lecture Notes in Computer Science,* 2006, pp. 139-150.

[28] L. Tong-Yee and H. Po-Hua, "Fast and intuitive metamorphosis of 3D polyhedral models using SMCC mesh merging scheme," *Visualization and Computer Graphics, IEEE Transactions on*, vol. 9, pp. 85-98, 2003. 2003.

[29] B. Allen, B. Curless and Z. Popovic, "The space of human body shapes: Reconstruction and parameterization from range scans," in *SIGGRAPH '*03: ACM SIGGRAPH 2003 *Papers,* 2003, pp. 587-594.

[30] V. Blanz and T. Vetter, "A morphable model for the synthesis of 3D faces," in *SIGGRAPH '*99: *Proceedings of the* 26*th Annual Conference on Computer Graphics and Interactive Techniques,* 1999, pp. 187-194.

[31] I. Baran and J. Popovic, "Automatic rigging and animation of 3D characters," *ACM Trans. Graph., vol.* 26, pp. 72, 2007.

[32] A. Hilton, J. Starck and G. Collins, "From 3D Shape Capture to Animated Models," *International Symposium on* 3*D Data Processing, Visualization and Transmission* (3*DPVT*), pp. 246-257, 2002.

[33] X. Yang, A. Somasekharan and J. J. Zhang, "Curve skeleton skinning for human and creature characters: Research Articles," *Comput. Animat. Virtual Worlds*, vol. 17, pp. 281-292, 2006.

[34] W. T. Tang and ChiKeung, "Multiresolution Mesh Reconstruction from Noisy 3D Point Sets," *Pattern Recognition,* 2006. *ICPR* 2006. 18*th International Conference on*, vol. 1, pp. 5-8, 2006.

[35] D. Anguelov, P. Srinivasan, D. Koller, S. Thrun, J. Rodgers and J. Davis, "SCAPE: shape completion and animation of people," *ACM Trans. Graph., vol.* 24, pp. 408-416, 2005.

[36] F. L. Matthews and J. B. West, "Finite element displacement analysis of a lung," *Journal of Biomechanics, vol.* 5, pp. 591-600, November, 1972. 1972.

[37] S. H. Sundaram and C. C. Feng, "Finite element analysis of the human thorax," *Journal of Biomechanics*, vol. 10, pp. 505-516, 1977. 1977.

[38] Y. Zhang, Y. Qiu, D. B. Goldgof, S. Sarkar and L. Li, "3D finite element modeling of nonrigid breast deformation for feature registration in-ray and MR images," in *WACV '*07: *Proceedings of the Eighth IEEE Workshop on Applications of Computer Vision,* 2007, pp. 38.

[39] G. Sakas, L. Schreyer and M. Grimm, "Preprocessing and Volume Rendering of 3D Ultrasonic Data," *IEEE Comput. Graph. Appl., vol.* 15, pp. 47-54, 1995.

[40] Y. Ito, P. Corey Shum, A. M. Shih, B. K. Soni and K. Nakahashi, "Robust generation of high-quality unstructured meshes on realistic biomedical geometry," *Int. J. Numer. Meth. Engng*, vol. 65, pp. 943-973, 5 Feb. 2006. 2006.

[41] S. Zhao and H. Lee, "Human silhouette extraction based on HMM," in *ICPR '*06: *Proceedings of the* 18*th International Conference on Pattern Recognition,* 2006, pp. 994-997.

[42] A. C. Kak and M. Slaney, *Principles of Computerized Tomographic Imaging*. Philadelphia, Pa., USA: Society for Industrial and Applied Mathematics, 2001,

[43] S. Linnainmaa, D. Harwood and L. S. Davis, "Pose determination of a three-dimensional object using triangle pairs," *Pattern Analysis and Machine Intelligence, IEEE Transactions on*, vol. 10, pp. 634-647, September 1988. 1988.

[44] D. Hoiem, A. A. Efros and M. Hebert, "Automatic photo pop-up," in *SIGGRAPH '*05: *ACM SIGGRAPH* 2005 *Papers,* 2005, pp. 577-584.

[45] M. Desbrun, M. Meyer and P. Alliez, "Intrinsic Parameterizations of Surface Meshes," *Computer Graphics Forum*, vol. 21, pp. 209-218, September 2002. 2002.

[46] M. C. Lincoln and A. F. Clark, "Pose-independent face identification from video sequences," in *AVBPA '*01: *Proceedings of the Third International Conference on Audio- and Video-Based Biometric Person Authentication,* 2001, pp. 14-19.

[47] I. Sato, Y. Sato and K. Ikeuchi, "Illumination from shadows," *Transactions on Pattern Analysis and Machine Intelligence*, vol. 25, pp. 290-300, March 2003.

[48] P. Rheingans and D. Ebert, "Volume illustration: nonphotorealistic rendering of volume models," *Visualization and Computer Graphics, IEEE Transactions on*, vol. 7, pp. 253-264, July 2001. 2001.

[49] A. Finkelstein and L. Markosian, "Nonphotorealistic rendering," *IEEE Computer Graphics and Applications*, vol. 23, pp. 26-27, July 2003. 2003.

[50] J. Lansdown and S. Schofield, "Expressive rendering: a review of nonphotorealistic techniques," *IEEE Computer Graphics and Applications*, vol. 15, pp. 29-37, May 1995. 1995.

[51] J. M. Wang, D. J. Fleet and A. Hertzmann, "Multifactor Gaussian process models for style-content separation," in *ICML '*07: Proceedings of the 24*th International Conference on Machine Learning,* 2007, pp. 975-982.

[52] M. D. Cordea, E. M. Petriu and D. C. Petriu, "3D Head Tracking and Facial Expression Recovery using an Anthropometric Muscle-based Active Appearance Model," *Instrumentation and Measurement Technology Conference Proceedings,* 2007 *IEEE*, pp. 1-6, 1-3 May 2007.

[53] Z. Hammal, L. Couvreur, A. Caplier and M. Rombaut, "Facial expression classification: An approach based on the fusion of facial deformations using the transferable belief model," *International Journal of Approximate Reasoning*, vol. 46, pp. 542-567, December, 2007. 2007.

[54] J. X. Chen, Y. Yang and X. Wang, "Physics-Based Modeling and Real-Time Simulation," *Computing in Science and Engg., vol.* 3, pp. 98-102, 2001.

[55] A. Shahhosseini and G. M. Knapp, "Semantic image retrieval based on probabilistic latent semantic analysis," in *MULTIMEDIA '06*: *Proceedings of the* 14*th Annual ACM International Conference on Multimedia,* 2006, pp. 703-706.

[56] H. Snoussi and A. MohammadDjafari, "Bayesian Unsupervised Learning for Source Separation with Mixture of Gaussians Prior," *J. VLSI Signal Process. Syst., vol.* 37, pp. 263-279, 2004.

[57] Y. Zhang and C. Zhang, "Separation of music signals by harmonic structure modeling," in *Advances in Neural Information Processing Systems* 18 Y. Weiss, B. Scholkopf and J. Platt, Eds. Cambridge, Mass.: MIT Press, 2006, pp. 1617-1624.

[58] Y. Yang, Y. Su, Y. Lin and H. H. Chen, "Music emotion recognition: The role of individuality," in *HCM '*07: *Proceedings of the International Workshop on Human-Centered Multimedia,* 2007, pp. 13-22.

[59] Tao Li and M. Ogihara, "Content-based music similarity search and emotion detection," *Acoustics, Speech, and Signal Processing,* 2004. *Proceedings*. (*ICASSP* '04). *IEEE International Conference on*, vol. 5, pp.-705-8 o. 5, 17-21 May 2004.

[60] X. Zhu, A. B. Goldberg, M. Eldawy, C. R. Dyer and B. Strock, "A Text-to-Picture Synthesis System for Augmenting Communication." pp. 1590, 2007.

[61] D. D. Lewis, "Naive (Bayes) at forty: The independence assumption in information retrieval," in *ECML '*98: *Proceedings of the* 10*th European Conference on Machine Learning,* 1998, pp. 4-15.

[62] H. Zhang and J. Su, "Naive bayesian classifiers for ranking," in *ECML,* 2004, pp. 501-512.

[63] D. A. Vasquez Govea and T. Fraichard, "Motion Prediction for Moving Objects: a Statistical Approach," pp. 3931-3936, April. 2004.

[64] B. K. P. Horn and B. G. Schunck, "Determining optical flow," Massachusetts Institute of Technology, Cambridge, Mass., USA, 1980.

We claim:

1. A method of collaborative information exchange between two or more users comprising:

sending via a communication network, by a first computing device, a request to a remote server to initiate an online collaborative event, wherein the remote server includes a software application providing a collaborative environment with a synchronous mode of operation;

displaying, by the first computing device, a first collaborative viewing display;

receiving, via a viewing tool on the first collaborative viewing display, a user selection of an alternative view, wherein a window of the first collaborative viewing display switches between a view controlled by the first computing device and a view controlled by a second computing device of a second participant accessing the collaborative environment;

receiving, by the first computing device, a broadcast of a browsing session of products or stores of the second computing device, from the remote server;

displaying, by the first computing device, the browsing session in the window, wherein the browsing session is synchronized with a broadcast of the browsing session sent by the remote server to the second computing device, and wherein changes to the browsing session implemented by the second participant are viewed by the first participant in real-time;

sending, by the first computing device, an electronic communication during the collaborative information exchange event; and sharing, by the computing device, account resources of the first participant with the second participant, the account resources being separate from the window and including at least one of the group consisting of: a virtual shopping cart, shopping list, wish list, virtual fitting room, user model, product of interest to a user, message, bill, audio file, image, user rating, feedback, a product page, a product image and user input regarding a product.

2. The method of claim 1, wherein the collaborative environment is a virtual shopping environment, the method further comprising:

sending a request to the remote server to view a product for sale in the window, whereby the remote server is configured to respond to all users based on the request.

3. The method of claim 1, further comprising:

accessing a tool to facilitate collaborative activities between users, the tool selected from the group consisting of:

a tool for scheduling a time to participate in the collaborative information exchange event;

a tool for proposing geographic locations for group activities;

a tool enabling a user to share group event information with the at least one other user;

a tool generating purchasing suggestions for users based on user preferences;

a tool providing activity suggestions based on user specific criteria including but not limited to users' preferences and geographic proximity of the activity event;

a tool enabling users to collaboratively design a room or other physical space virtually using virtual design elements, such as virtual furniture, and purchase real design elements corresponding to the virtual design elements; and a combination of any of the above tools.

4. The method of claim 1, further comprising:

accessing social networking data through a remote social networking site; and importing the social networking data to the first computing device.

5. The method of claim 1, wherein the first computer device includes a display and a computing application for generating a visual display including an icon depicting the second participant and an icon depicting information to be shared, the method further comprising:

selecting the icon depicting information to be shared; and dragging and dropping the selected icon into the icon depicting the second participant, whereby the computer application causes the information to be shared to be viewable remotely by the second participant through the second computing device.

6. The method of claim 1, wherein the browsing session includes a video watching event.

7. The method of claim 1, wherein the displaying the broadcast further comprises displaying freehand writing of the second user superimposed over the browsing session of the products or stores.

8. The method of claim 1, further comprising, receiving, by the first computing device, audio data from the remote server, wherein the audio data comprises the combined audio channels of the first computing device and the second computing device.

9. A method of peer-to-peer collaborative information exchange between two or more users comprising:

generating, by a first computing device connected to a communication network, a collaborative environment accessible by a second remote computing device through the communication network;

sending, by the first computing device, an invitation to the second remote computing device to access the collaborative environment;

displaying, by the first computing device, a collaborative viewing display including a window;

receiving, by the first computing device, a user selection of an alternative view, wherein the window of the collaborative viewing display switches from a view controlled by the first computing device to a view controlled by the second computing device;

displaying, by the first computing device, a browsing session of the second computing device received through a peer-to-peer connection with the second computing device, wherein the browsing session is synchronized with the browsing session displayed by the second computing device;

receiving, by the first computing device, a user selection of the alternative view, wherein the window of the collaborative viewing display switches from the view controlled by the second computing device to the view controlled by the first computing device; and sending, by the first computing device, a command to effect a change in a second browsing session displayed in the collaborative viewing display, wherein the second computing device can selectively display the change in the second browsing session in real-time through the peer-to-peer connection; and sending, by the first computing device, a communication through the communication network to the second computing device during the collaborative information exchange event.

10. A method of enabling collaborative information exchange between two or more users comprising:

generating, by a server, collaborative environment that is only accessible to a registered first user and a second user that is invited to participate in a collaborative information exchange event by the first user;

receiving, at the server, an access request from a first computer device of the first user via a communications network;

broadcasting, by the server, a first collaborative viewing display to the first computer device based on the access request, the display including an indication of other users, a window for viewing images associated with the collaborative information exchange event, and a tool enabling a user to switch window views displayed in the window between a view controlled by the first computer device of the first user and a view controlled a second computer device of the second user;

receiving, by the server, an access request from the second computer device for the second user via the communications network;

broadcasting, by the server, a second collaborative viewing display to the second computer device of the second user based on the access request from the second computer device, the display including an indication of other users, a window for viewing images associated with the collaborative information exchange event, and a tool enabling a user to switch window views displayed in the window between a view controlled by the first user and a view controlled by the second user;

receiving, at the server, a selection from the tool of the second computer device to display the view controlled by the first computer device of the first user;

broadcasting, by the server, browsing content of the first computer device simultaneously in real-time to the first computer device and the second computer device for display in the respective windows of the first collaborative viewing display and the second collaborative viewing display;

receiving, by the server, a command to effect a change in the view displayed in the window of the first collaborative viewing display; and broadcasting, by the server, a change in the view displayed in the window of the second collaborative viewing display based on the command, wherein the first user and the second user are enabled to view the change in the view displayed in real-time.

11. The method of claim 10, wherein the first collaborative viewing display and the second collaborative viewing display each further include a communications window enabling communication between the first user and the second user during the collaborative information exchange event.

12. The method of claim 10, wherein the collaborative environment is a virtual shopping environment, the server is a retail server, and the first collaborative viewing display and the second collaborative viewing display enable the display of retail information regarding a product for sale, the method further comprising:

providing, via the server, shopping information to the first user and the at least one other user in real-time via the virtual shopping environment;

providing, via the server, account resources to be displayed separate from the respective windows on both the first and second collaborative viewing displays, the account resources including at least one of the group consisting of: a virtual shopping cart, shopping list, wish list, virtual fitting room, user model, product of interest to a user, message, bill, audio file, image, user rating, feedback, and user input regarding a product.

13. The method of claim 10, further comprising:

providing, via the server, a second tool to be displayed on the first and second collaborative viewing displays, the second tool configured to facilitate collaborative activities between users, the second tool selected from the group consisting of:

a tool for scheduling a time to participate in the collaborative event;

a tool for proposing geographic locations for group activities;

a tool enabling a user to share group event information with other users;

a tool generating purchasing suggestions for users based on user preferences;

a tool providing activity suggestions based on user specific criteria including but not limited to users' preferences and geographic proximity of the activity event;

a tool enabling users to collaboratively design a room or other physical space virtually using virtual design elements, such as virtual furniture, and purchase real design elements corresponding to the virtual design elements; and a combination of any of the above tools.

14. The method of claim 10, further comprising:

importing, to the server, social networking data from a remote social networking site.

15. The method of claim 10, wherein the first and second collaborative viewing displays each further include an icon depicting at least one of the first user and the second user, and an icon depicting information to be shared, the method further comprising:

enabling, by the server, the first user to select the icon depicting information to be shared; and receiving, by the server, information indicative of the first user dragging and dropping the selected icon into the icon depicting the second user, whereby the server causes information to be shared to be viewable remotely by the at second user.

16. The method of claim 10, wherein the collaborative information exchange event includes a video watching event.

17. The method of claim 10, wherein the broadcasting the browsing content further comprises broadcasting freehand writing of the first user superimposed over the browsing content.

18. The method of claim 10, further comprising:

combining, by the server, an audio channel from the first computing device and an audio channel from the second computing device; and broadcasting, by the server, the combined audio channel to the first computer device and the second computing device.

* * * * *